US00RE45349E

(19) United States
(12) Reissued Patent
Short

(10) Patent Number: US RE45,349 E
(45) Date of Reissued Patent: *Jan. 20, 2015

(54) SYNTHETIC LIGATION REASSEMBLY IN DIRECTED EVOLUTION

(75) Inventor: Jay M. Short, Del Mar, CA (US)

(73) Assignee: BP Corporation North America Inc., Houston, TX (US)

( * ) Notice: This patent is subject to a terminal disclaimer.

(21) Appl. No.: 11/798,032

(22) Filed: May 9, 2007

Related U.S. Patent Documents

Reissue of:
(64) Patent No.: 6,605,449
Issued: Aug. 12, 2003
Appl. No.: 09/594,459
Filed: Jun. 14, 2000

U.S. Applications:
(63) Continuation-in-part of application No. 09/332,835, filed on Jun. 14, 1999, now Pat. No. 6,537,776.

(51) Int. Cl.
*C12P 21/06* (2006.01)
*C12Q 1/68* (2006.01)

(52) U.S. Cl.
USPC ..... 435/69.1; 435/6.12

(58) Field of Classification Search
None
See application file for complete search history.

(56) References Cited

U.S. PATENT DOCUMENTS

| | | | | |
|---|---|---|---|---|
| 5,023,171 | A | 6/1991 | Ho et al. | |
| 5,279,952 | A | 1/1994 | Wu | |
| 5,498,531 | A | 3/1996 | Jarrell | |
| 5,599,675 | A * | 2/1997 | Brenner | 435/6 |
| 5,605,793 | A | 2/1997 | Stemmer | |
| 5,658,727 | A | 8/1997 | Barbas et al. | 435/6 |
| 5,759,817 | A | 6/1998 | Barbas | 435/69 |
| 5,811,238 | A | 9/1998 | Stemmer et al. | |
| 5,824,485 | A | 10/1998 | Thompson et al. | 435/6 |
| 5,830,643 | A | 11/1998 | Yamamoto et al. | |
| 5,830,721 | A | 11/1998 | Stemmer et al. | |
| 5,866,363 | A | 2/1999 | Pieczenik | 435/69.1 |
| 6,096,548 | A | 8/2000 | Stemmer | |
| 6,117,679 | A | 9/2000 | Stemmer | |
| 6,165,793 | A | 12/2000 | Stemmer | 435/440 |
| 6,180,406 | B1 | 1/2001 | Stemmer | 435/440 |
| 6,277,638 | B1 | 8/2001 | Stemmer | 435/440 |
| 6,291,158 | B1 | 9/2001 | Winter et al. | |
| 6,319,714 | B1 | 11/2001 | Crameri et al. | 435/440 |
| 6,323,030 | B1 | 11/2001 | Stemmer | 435/440 |
| 6,335,160 | B1 | 1/2002 | Patten et al. | 435/6 |
| 6,337,186 | B1 | 1/2002 | Krebber | 435/6 |
| 6,344,356 | B1 | 2/2002 | Stemmer | 435/440 |
| 6,365,408 | B1 | 4/2002 | Stemmer | 435/440 |
| 6,368,861 | B1 | 4/2002 | Crameri et al. | 435/440 |
| 6,372,429 | B1 * | 4/2002 | Sharon | 435/6 |
| 6,372,497 | B1 | 4/2002 | Stemmer | 435/440 |
| 6,376,246 | B1 | 4/2002 | Crameri et al. | 435/440 |
| 6,387,702 | B1 | 5/2002 | Stemmer | 435/471 |
| 6,605,430 | B1 * | 8/2003 | Affholter et al. | 506/5 |
| 6,773,900 | B2 | 8/2004 | Short et al. | |
| 6,917,882 | B2 | 7/2005 | Selifonov et al. | |
| 7,202,086 | B2 | 4/2007 | Delcourt et al. | |
| 7,534,564 | B2 * | 5/2009 | Patten et al. | 435/6.14 |
| 2001/0039014 | A1 | 11/2001 | Bass et al. | 435/6 |

(Continued)

FOREIGN PATENT DOCUMENTS

| | | |
|---|---|---|
| AU | 703264 | 9/1995 |
| AU | 729505 | 10/1997 |

(Continued)

OTHER PUBLICATIONS

Stahl et al., BioTechniques (1993), vol. 14, No. 3, pp. 424-434.*
Rashtchian, 1995, Novel methods for cloning and engineering genes using the polymerase chain reaction, Current Opinion in Biotechnology, 6: 30-36.*
Hoheisel (1993) Analytical Chemistry vol. 209: pp. 238-246.*
Moore and Arnold (1996) Nature Biotechnology 14:458-467.
Berger et al (1993) Anal. Biochem. 214:571-579.
Söderlind et al (1995) Gene 160:269-272.
Stemmer (1995) Biotechnology 13:549-553.
Khorana, "Total Synthesis of a Gene," Science vol. 203, Feb. 16, 1979, pp. 614-625.

(Continued)

*Primary Examiner* — Suchira Pande
(74) *Attorney, Agent, or Firm* — Michael F. Kolman

(57) ABSTRACT

Harvesting the full richness of biodiversity is instantly recognized by Diversa Corporation as a powerful means to access both novel molecules having direct commercial utility as well as molecular templates that could be retooled to acquire commercial utility. A directed evolution process for rapid and facilitated production from a progenitor polynucleotide template, of a library of mutagenized progeny polynucleotides wherein each of the 20 naturally encoded amino acids is encoded at each original codon position. This method, termed site-saturation mutagenesis, or simply saturation mutagenesis, is preferably based on the use of the degenerate N,N,G/T sequence. Also, a method of non-stochastically producing a library of chimeric nucleic acid molecules having an overall assembly order that is chosen by design. Accordingly, a set of progenitor templates, such as genes (e.g. a family of esterase genes) or genes pathways (e.g. encoding antibiotics) can be shuffled to generate a sizable library of distinct progeny polynucleotide molecules (e.g. $10^{100}$) and correspondingly encoded polypeptides. Screening of these polynucleotide libraries enables the identification of a desirable molecular species that has a desirable property, such as a specific enzymatic activity serviceable for a commercial application, or a novel antibiotic. Also, a method of retooling genes and gene pathways by the introduction of regulatory sequences, such as promoters, that are operable in an intended host, thus conferring operability to a novel gene pathway when it is introduced into an intended host. For example a novel man-made gene pathway, generated based on microbially-derived progenitor templates, that is operable in a plant cell.

13 Claims, 30 Drawing Sheets

(56) References Cited

U.S. PATENT DOCUMENTS

| | | | |
|---|---|---|---|
| 2002/0086322 | A1 | 7/2002 | Yu et al. |
| 2006/0223066 | A1 | 10/2006 | Lao et al. |
| 2007/0026438 | A1 | 2/2007 | Smith et al. |

FOREIGN PATENT DOCUMENTS

| | | | |
|---|---|---|---|
| AU | 732146 | | 6/1998 |
| AU | 724698 | | 10/1998 |
| EP | 0 316 018 | | 5/1989 |
| EP | 0 316 018 | A2 | 5/1989 |
| EP | 0439182 | | 7/1991 |
| EP | 0552266 | | 7/1993 |
| EP | 0596918 | | 5/1994 |
| EP | 0633944 | | 1/1995 |
| EP | 0 703 264 | | 3/1996 |
| EP | 0911396 | | 4/1999 |
| EP | 0963434 | | 12/1999 |
| EP | 1 138 763 | | 4/2001 |
| EP | 1094108 | | 4/2001 |
| EP | 1094108 | A2 | 4/2001 |
| EP | 1103606 | | 5/2001 |
| EP | 1103606 | A2 | 5/2001 |
| EP | 1 108 781 | | 6/2001 |
| EP | 1 108 783 | | 6/2001 |
| EP | 1108782 | A2 | 6/2001 |
| EP | 1108791 | A2 | 6/2001 |
| EP | 1 130 093 | | 9/2001 |
| EP | 0876509 | B1 | 9/2001 |
| EP | 1130093 | A1 | 9/2001 |
| EP | 1 149 904 | | 10/2001 |
| EP | 1 149 905 | | 10/2001 |
| EP | 1138763 | A2 | 10/2001 |
| EP | 1149904 | A1 | 10/2001 |
| EP | 1149905 | A1 | 10/2001 |
| WO | 91/12341 | | 8/1991 |
| WO | 91/16427 | | 10/1991 |
| WO | 92/07075 | | 4/1992 |
| WO | 93/03183 | | 2/1993 |
| WO | 94/13804 | | 6/1994 |
| WO | 95/22625 | | 8/1995 |
| WO | WO 95/22625 | | 8/1995 |
| WO | WO9522625 | A1 | 8/1995 |
| WO | 96/40968 | | 12/1996 |
| WO | 97/07205 | | 2/1997 |
| WO | 97/20078 | | 5/1997 |
| WO | 97/35966 | | 10/1997 |
| WO | 97/48717 | | 12/1997 |
| WO | 98/05765 | | 2/1998 |
| WO | 98/13485 | | 4/1998 |
| WO | 98/27230 | | 5/1998 |
| WO | 9827230 | | 6/1998 |
| WO | WO9827230 | A1 | 6/1998 |
| WO | 98/38297 | | 9/1998 |
| WO | 98/58080 | | 12/1998 |
| WO | 00/42560 | | 7/2000 |
| WO | 00/42561 | | 7/2000 |
| WO | WO0042560 | A2 | 7/2000 |
| WO | WO0042561 | A2 | 7/2000 |
| WO | 00/61740 | | 10/2000 |
| WO | WO0061740 | A1 | 10/2000 |
| WO | 01/00234 | | 1/2001 |
| WO | WO0100234 | A2 | 1/2001 |
| WO | 01/23401 | | 4/2001 |
| WO | WO0123401 | A2 | 4/2001 |
| WO | 01/32712 | | 5/2001 |
| WO | WO0132712 | A2 | 5/2001 |
| WO | 01/46476 | | 6/2001 |
| WO | WO0146476 | A1 | 6/2001 |
| WO | 01/70947 | | 9/2001 |
| WO | WO0170947 | A2 | 9/2001 |
| WO | 01/73000 | | 10/2001 |
| WO | 01/75767 | | 10/2001 |
| WO | WO0173000 | A2 | 10/2001 |
| WO | WO0175767 | A2 | 10/2001 |

OTHER PUBLICATIONS

Beattie et al., "Solid-phase Gene Assembly," Nature vol. 352, Aug. 8, 1991, pp. 548-549.

Reichmann et al., "Phage Display and Selection . . . ," Biochemistry vol. 32, No. 34, Aug. 31, 1993, pp. 8848-8855.

Lutz Riechmann, et al., "Phage Display and Selection of a Site-Directed Randomized Single-Chain Antibody Fv Fragment for Its Affinity Improvement", Biochemistry, (1993), vol. 32, No. 34, pp. 8848-8855.

Vincent P. Stanton, Jr., "Definition of the Human *raf* Amino-Terminal Regulatory Region by Deletion Mutagenesis", Molecular and Cellular Biology, vol. 9, No. 2, Feb. 1989, pp. 639-647.

John Neidbardt, et al., "Different Amino Acid Substitutions at the Same Position in Rhodopsin Lead to Distinct Phenotypes", Investigative Ophthalmology & Visual Science, Apr. 2006, vol. 47, No. 4. pp. 1630-1635.

Shubba Bagrodia, et al., "A Novel Regulator of p21-activated Kinases", The Journal of Biological Chemistry, vol. 273, No. 37, Issue of Sep. 11, 1998, pp. 23633-23636.

Andreas Crameri, et al., "Molecular Evolution of an Arsenate Detoxification Pathway by DNA Shuffling", Nature Biotechnology, vol. 15, May 1997, pp. 436-438.

Schneider, et al., "Cloning Based on Efficient Tree-Fragment Assembly DNA Ligation", Biochemica, No. 3, (1998), pp. 2-3.

Arnold F. H. and Moore J.C. Optimizing industrial enzymes by directed evolution. Advances in Biochemical Engineering Biotechnology. 1997; 58:1-14. Review.

Arnold F. H. When blind is better: protein design by evolution. Nature Biotechnology. Jul. 16, 1998:617-618.

Campbell R. K. et al. Assembly and expression of a synthetic gene encoding the bovine glycoprotein hormone alpha-subnit. Molecular and Cellular Endocrinology. 1992;83:195-200.

Clackson T, et al. Making antibody fragments using phage display libraries. Nature. Aug. 15, 1991 352(6336):624-628.

Cohen J. How DNA shuffling works. Science. Jul. 13, 2001;293(5528):237.

Crameri A., et al. Molecular evolution of an arsenate detoxification pathway by DNA shuffling, Nature Biotechnology. May 15, 1997(5):436-438.

Crameri A., et al. DNA shuffling of a family of genes from diverse species accelerates directed evolution. Nature. Jan. 15, 1998;391(6664):288-291.

Crameri A., et al. Improved green fluorescent protein by molecular evolution using DNA shuffling. Nature Biotechnology. Mar. 14, 1996(3):315-319.

Crameri A., et al. Construction and evolution of antibody-phage libraries by DNA shuffling. Nature Medicine. 2(1):100-102 (Jan. 1996).

Gram H., et al. In vitro selection and affinity maturation of antibodies from a naive combinatorial immunoglobulin library. Proc. National. Acad. Sci. 89(8):3576-80, (Apr. 1992).

Griffiths A. D., et al. Isolation of high affinity human antibodies directly from large synthetic repertoires. EMBO Journal. 1994, 13: 3245-3260.

Harlow P. H., et al. Construction of linker-scanning mutations using the polymerase chain reaction. *Methods in Molecular Biology.* 31:87-96 (1994).

Hayden M.A. and Mandecki W. Gene synthesis by serial cloning of oligonucleotides. DNA. Oct. 1988; 7(8):571-7.

Higuchi R., et al. A general method of in vitro preparation and specific mutagenesis of DNA fragments: study of protein and DNA interactions. Nucleic Acids Res 16(15):7351-67 (Aug. 1988).

Ho S.N., et al. Site-directed mutagensis by overlap extension using the polymerase chain reaction. Gene 77:51-59, (Apr. 1989).

Ho S.N., et al. DNA and Protein Engineering Using the Polymerase Chain Reaction. DNA Protein Engineering Techniques 2(2):50-55, (1990).

Imamura T., et al. Identification of the domain within fibroblast growth factor-1 responsible for heparin-dependence. Biochimica et Biophysica Acta. Apr. 28, 1995;1266(2):124-30.

(56) References Cited

OTHER PUBLICATIONS

Joyce G.F. Directed molecular evolution. Scientific America. 267(6):90-7, (Dec. 1992).
Levichkin, et al. A new approach to construction of hybrid genes: homolog recombination method. Molecular. Biology. 29(5)1:572-577 (Jul.-Aug. 1995).
Melnikov A. and Youngman PJ. Random mutagenesis by recombinational capture of PCR products in *Bacillus subtilis* and *Acinetobacter calcoaceticus*. Nucleic Acids Res. Feb. 15, 1999;(27):1056-62.
Pompon D. and Nicolas A. Protein engineering by cDNA recombination in yeasts: Shuffling of mammalian cytochrome p450 functions. Gene 83(1):15-24 (Nov. 1989).
Punnonen J. Molecular breeding of allergy vaccines and antiallergic cyctokines. Int Arch Allergy Immunol. Mar. 2000;121(3):173-82. Review.
Raillard S., et al. Novel enzyme activities and functional plasticity revealed by recombining highly homologous enzymes. Chemistry Biology. Sep. 2001:8(9):891-898.
Saiki R.K., et al. Enzymatic amplification of β-globin genomic sequences and restriction site analysis for diagnosis of sickel sell anemia. Science 230(4732):1350-1354, (Dec. 1985).
Shao Z., et al. Random-priming in vitro recombination: an effective tool for directed evolution. Nucleic Acids Res. Jan. 15, 1998:26(2):681-3.
Sikorski R.S. and Boeke J.D. In vitro mutagenesis and plasmid shuffling: from cloned gene to mutant yeast. Methods Enzymol. 194:302-318 (1991).
Stemmer W.P., et al. Single-step assembly of a gene and entire plasmid from large numbers of oligodeoxyribinucleotides. Gene. Oct. 16, 1995;164(1)49-53.
Weber H. and Weissmann C. Formation of genes coding for hybrid proteins by recombination between related, cloned genes in *E.coli*. Nucleic Acids Res. 11(16):5661-69 (Aug. 1983).
Zhang J.H., et al. Directed evolution of a fucosidase from a galactosidase by DNA shuffling and screening. Proc National Academy Science U.S.A. Apr. 29, 1997:94(9):4504-9.
Zoller M.J. New recombinant DNA methodology for protein engineering. Current Opinion Biotechnology 1992. 3(4):348-54. Review.

* cited by examiner

```
                                                        100
ACACGGGCCA GGGTGATTCC GTTCTGTTTC TTCACGGCAA CCCGACGTCG
ACGTGGGAGA GGGCGACCCG ATCGTGTTCC TCCACGGAAA TCCCACGTCG
AGATGGGCGA GGGTGATCCC ATCATTTTCC AACACGGCAA TCCGACCTCA
ACGAAGGCAA GGGTGACGCC ATCGTCTTTC AGCACGGCAA CCCCACGTCG
AAGTGGGACG GGGCGACCCC ATCGTACTCT TGCACGGCAA CCCCACCTCG
ATACCGGCGA GGGAGCGCCG ATCGTGTTCC TTCACGGCAA CCCGACTTCC
GCGTCGGCGA T...CTTCCC GTCGTGTTCC TGCACGGCAA CCCCACGTCG
GACCGCGGGA TGGCACGCCT GTGCTGTTCC TGCACGGTAA CCCGACCTCG
------G--- --------C- -T--T--T-- --CACGG-AA -CC-AC-TC-
```

*FIG. 6B*

*Represents 15% of gene*

```
                                                        150
TCGTATCTGT GGAGGGGCGT AATGCCTTTT GTGACGGACG TCGCCCGATG
TCGTACCTGT GGCGGAACGT GATTCCCCAC GTTGCCGGCT TGGGACGCTG
TCGTACCTGT GGCGCAACAT CATGCCCCAT GTGCAACAGC TCGGTCGCTG
TCTTACTTGT GGCGCAACAT CATGCCGCAC TTGGAAGGGC TGGGCCGGCT
TCGTACCTCT GGCGCAACGT GTTGCCGCAC CTGGCGCCGT TAGGCCGCTG
TCCTATCTTT GGCGCAACAT CATCCCCTAT CTCGCGGATC ACGGCAGATG
TCTCACGTCT GGCGCAACGT GATCCCGCAC GTCGCTGGCC AGCACCGGTG
TCCTACCTGT GGCGCAACAT CATCCCGCAT GTAGCACCGA GTCATCGGTG
TC--A--T-T GG-G---C-T --T-CC---- -T-------- ------G---
```

*FIG. 6C*

```
            NcoI                                                                  CCGT
150am13_00  cATGATGCACG GCGATATTTC ATCGAGCAAT GACACGGTCG GCGTTGCCGT
150AM7_001  cATGCATCACG GCGACATTTC ATCGAGCAAT GACACGGTCG GCGTTGCCGT
431am7_002  cATGAGACACG GAGATATCTC CAGCAGCAAC GATTGCGTGG GCGTGGCCGT
                                                      GAG GT
150am13_00   CGTGAACTAC AAGATGCCTC GCCTTCATAC CAAGGCGGAG GTTTTAGCGA
150AM7_001   CGTGAACTAC AAGATGCCGC GGCTTCACAC CAAGGCTGAG GTGCTGGCCA
431am7_002   CGTGAACTAC AAGATGCCGC GGCTGCATAC CCGCGCGGAG GTGATGGAGA
                                                         CGG
150am13_00   ACGCCAGAAA GATCGGCGAG ATGATCGTCG GCATGAAGAC CGGCCTGCCC
150AM7_001   ACTGCCGCAA GATCGCCGAC ATGCTGGTCG GCATGAAGAG CGGCCTGCCG
431am7_002   ACGCCCGCAA GATCGCCGAC ATGGTCGTGG GCATGAAGCG CGGCCTGCCC
                                                    CCACG
150am13_00   GGAATGGATC TGGTGATCTT CCCGGAATAT TCGACCCACG GCATCATGTA
150AM7_001   GGAATGGATC TGGTGATCTT CCCGGAATAT TCCACCCACG GCATCATGTA
431am7_002   GGCATGGACC TGGTCATCTT CCCCGAGTAC TCCACCCACG GCATCATGTA
                                                      CCC GG
150am13_00   CGACTCCAAG GAAATGTACG ATACCGCGTC CGTCGTGCCC GGCGAGGAGA
150AM7_001   CGACTCCAAG GAGATGTACG ACACGGCGTC GACGGTGCCG GGTGAAGAGA
431am7_002   CGACGCCAAG GAAATGTACG AAACCGCTTC GGCCATTCCG GGCGAAGAGA
                                                        G GGG
150am13_00   CCGAGATTTT TGCCGAAGCC TGCCGCAAGG CGAAAGTCTG GGGCGTGTTC
150AM7_001   CCGAGATTTT CGCCGAGGCC TGCCGCAAGG CCAAGGTCTG GGGCGTGTTC
431am7_002   CTGCTGTGTT CGCCGACGCC TGCCGCAAGG CCAACGTATG GGGCGTGTTT
```

*FIG. 7A*

```
                                                        AAAG C
150am13_00  TCGCTCACCG GCGAACGTCA CGAGGAACAT CCGAAGAAGG CGCCCTACAA
150AM7_001  TCGCTGACCG GCGAGCGCCA CGAGGAGCAT CCCAATAAAG CGCCGTACAA
431am7_002  TCGCTGACGG GCGAGCGCCA CGAAGAGCAC CCGAACAAGG CGCCGTACAA
                                                         CAG AA
150am13_00  CACGCTGATC CTGATGAACG ACAAGGGCGA GGTGGTCCAG AAATACCGCA
150AM7_001  CACCCTGATC CTGATGAACG ACAAGGGTGA AGTCGTTCAG AAATATCGCA
431am7_002  CACGCTCATC CTGATGAACA ACAAGGGCGA GATCGTGCAG AAGTACCGCA
                                              GGTA
150am13_00  AGATCATGCC GTGGGTTCCG ATCGAGGGCT GGTACCCCGG CAACTGCACC
150AM7_001  AGATCATGCC GTGGGTGCCG ATCGAAGGCT GGTATCCCGG CAACTGCACG
431am7_002  AGATCATGCC CTGGGTGCCG ATCGAAGGCT GGTATCCGGG CGATTGCACC
                                        TGAAG
150am13_00  TACGTCTCCG ACGGGCCGAA GGGCATGAAG GTTTCGCTGA TCATCTGCGA
150AM7_001  TACGTCTCCG AAGGCCCGAA GGGCATGAAG ATGTCGCTGA TCATCTGCGA
431am7_002  TATGTGTCGG AAGGCCCCAA GGGACTGAAG ATCAGCCTCA TCATCTGCGA
                                   TCTGGCG
150am13_00  TGACGGCAAC TATCCGGAAA TCTGGCGCGA CTGCGCCATG AAGGGCGCCG
150AM7_001  CGACGGCAAC TACCCGGAAA TCTGGCGTGA CTGCGCGATG AAGGGCGCCG
431am7_002  CGACGGCAAT TACCCCGAGA TCTGGCGCGA TTGCGCCATG CGCGGCGCCG
                             CCAG
150am13_00  AGCTGATCGT GCGCTGCCAG GGCTACATGT ATCCGGCCAA GGACCAGCAG
150AM7_001  AACTGATCAT CCGCTGCCAG GGCTACATGT ATCCCGCCAA GGATCAGCAG
431am7_002  AGCTGATCGT GCGTTGCCAG GGATACATGT ACCCGGCCAA GGACCAGCAG
```

*FIG. 7B*

```
                                GC
150am13_00   GTCATCATGG CGAAGGCGAT GGCGTGGGCG AATAATTGTT ACGTCGCGGT
150AM7_001   GTGCTGATGG CGAAAGCAAT GGCCTGGGCC AACAACGTTT ATGTCGCGGT
431am7_002   GTCATGGTGT CCAAGGCCAT GGCGTGGATG AACAACGTCT ACGTGGCGGT
                          GGGCTTCG
150am13_00   TTCCAATGCC GCGGGCTTCG ATGGCGTCTA TTCGTATTTC GGCCACTCGG
150AM7_001   CGCCAATGCC TCGGGCTTCG ACGGCGTCTA CTCGTATTTC GGCCATTCGG
431am7_002   GGCCAATGCC GCGGGCTTCG ACGGCGTGTA TTCCTACTTC GGCCATTCGG
                         TTCGA
150am13_00   CGATCATCGG CTTCGATGGC CGCACGCTCG GCGAATGCGG CGAGGAAGAA
150AM7_001   CGATCATCGG CTTCGACGGC CGTACCCTCG GCGAATGCGG CGAGGAGGAT
431am7_002   CCATCATCGG CTTCGACGGC CGCACGCTGG GCGAATGCGG TGAAGAAGAC
                      C AGTA
150am13_00   TACGGCATCC AGTATGCCCA GCTTTCGAAG ATGCTGATCC GCGACGCCCG
150AM7_001   TATGGCATCC AGTATGCCGC CATCTCCAAG TCGCTGATCC GCGACGCGCG
431am7_002   ATGGGCGTGC AGTACGCCGA GCTCTCCACC AGCCTGATCC GCGACGCGCG
                        CAATC
150am13_00   CCGCACCGGA CAATCGGAAA ACCATCTCTT CAAGCTGGTG CATCGTGGCT
150AM7_001   CCGCACCGGC CAATCGGAAA ACCATCTCTT CAAGCTGGTG CACCGTGGCT
431am7_002   CAAGAACATG CAGTCGCAGA ACCACTTGTT CAAGCTGGTG CACCGCGGCT
                        GATCAA
150am13_00   ACACCGGGTT GATCAACTCC GGCGAGGGCG ACCGCGGTCT CGCGGCCTGT
150AM7_001   ACACCGGCAT GATCAATTCC GGCGAGGGCG ACCGCGGTGT CGCGGCTTGC
431am7_002   ACACCGGCAA GATCAATTCC GGCGAAGAGG CCACCGGCGT CGCGGCATGC
```

*FIG. 7C*

```
                TTA
150am13_00   CCTTATGAGT TCTACAACAA ATGGATCGCC GATCCGGAAG GCACCCGCGA
150AM7_001   CCGTATGATT TCTATTCGAA ATGGATCGCC GATCCCGAGG GTACACGCGA
431am7_002   CCGTACAACT TCTACGCCAA CTGGATCAAC GATCCGGAGG GCACGCGCAA
              ATGGT
150am13_00   AATGGTCGAG TCCTTTACCC GGCCGACGGT GGGAACCGAT GAAGCGCCCA
150AM7_001   GATGGTGGAA TCCTTCACGC GTCCGACGGT GGGTGTGGAG GAATGCCCGA
431am7_002   GATGGTCGAA TCCTTCACCC GGTCCACCGT GGGCACGCCG GAGTGCCCCA
             TCGAG
150am13_00   TCGAAGGCAT CCCGAACAAG GTCGCGGTGC ACCGCTGA   aagct
150AM7_001   TCGAGGGCAT TCCGAACAAG GCCACCACGC ACCGCTGA   aagct
431am7_002   TGGACGGCAT CCCCAACGAG GACGCCAAGC ACCGCTAG   aagct
                                                         HindIII
```

*FIG. 7D*

FIG. 19A

```
                        1                                                  50
AF078102 Rhesus     (1) ATCGATTTAAACTGCCCGATTGAGGTTGTCGCTGAACACTTTGTGAGTC-
M67443 Towne        (1) ---------------------------GCCATGGCATCCGTACTGGGTCC

                        51                                                100
AF078102 Rhesus    (50) -TTTTCGAAGGTAGATATGACACTGCTTTTCCAGAAGTGCCGCTGAAGCCT
M67443 Towne       (24) CATTTCGGGGCACGTGCTGAAAGCCGTGTTTAGTCGCGGCGAC-ACGCCG

                       101                                               150
AF078102 Rhesus    (99) GGGGTACATATCTGAAGCAGCGAGATGAGCGTCCCGAGGACGTG-ATACG
M67443 Towne       (73) GTG--------CTGCCGCA-CGAGACGCGACTCCTGCAGACGGGTATCCA

                       151                                               200
AF078102 Rhesus   (148) C-TGCGACTACGGC-GTCTTCAGTTTGCGTAATCTCGTGTTCCAACGTTG
M67443 Towne      (114) CGTGCGCGTGAGCCAGCCCTCGCTGATCCTGGTGTCGCAGTACACGCCCG

                       201                                               250
AF078102 Rhesus   (196) TCT-GAC--TATGTTACAG-GGTGTTTATCTGCGACAATACGATCAACCG
M67443 Towne      (164) ACTCGACGCCATGCCACCGCGGCGACAATCAGCTGCAGGTGCAGCACACG

                       251                                               300
AF078102 Rhesus   (242) TG-TTTACGAGAATATATTAAAAAGAATTCTGGTACTATCATTCCGTTGC
M67443 Towne      (214) TACTTTACGGGCAGCGAGGTGGAGAACGTGTCGGTCAA------CGT-GC

                       301                                               350
AF078102 Rhesus   (291) GCAACCCCTGTAGCTGGTTTCTCGTCCTTCGCTCTGGTATAGATATTCCC
M67443 Towne      (257) ACAACCCCACGGGCCGGA------------GC----------ATCTGCCC
```

FIG. 19B

```
                        351                                                  400
AF078102 Rhesus   (341) CAGGTAGAAACCCGT-TCGTTCGACGAGTAT-CTTTGCTGCAAAGAGAAA
M67443 Towne      (285) CAGCCAAGAGCCCATGTCGATCTATGTGTACGCGCTGCCGCTCA-AGATG

                        401                                                  450
AF078102 Rhesus   (389) TTGGAAGCACTGGGAATATTGGGGGTGCAGTTGCGTGATGGCAGT-GATC
M67443 Towne      (334) CTGAACATCCCCAGCATCAACGTGCACCACTACCC-GTCGGCGGCCGAGC

                        451                                                  500
AF078102 Rhesus   (438) GCAAAAAAATCCAGGAGACTACGTGTGTGGTTCTGCTGGGAAGCTATGGA
M67443 Towne      (383) GCAAACACCGACACCTGCCCGTAGCTGACGCTGTGATTC-ACGCGTCGGG

                        501                                                  550
AF078102 Rhesus   (488) TTTGTGTACGTGTATGACTGG---GACAGTGACGG-ACTCTTTCAGATAG
M67443 Towne      (432) CAAGCAGATGTGGCAGGCGCGTCTCACGGTCTCGGGACTGGCCTGGACGC

                        551                                                  600
AF078102 Rhesus   (534) GT-ACCTCACTCAAAGAACTCGCGCACCACGGTTTACTG-ACATGTGAAT
M67443 Towne      (482) GTCAGCAGAACCAGTGGAAA-GAGCCCGACG-TCTACTACACGTCAGCGT

                        601                                                  650
AF078102 Rhesus   (582) CGGTATATCGCCATCCGCAAACGCCCTTCTCCACCACCGAGCCTCGTTTT
M67443 Towne      (530) TCGTGTTTC-----CCACCAAGGACGTGG--CACTGCGGCACGTGGTGTG

                        651                                                  700
AF078102 Rhesus   (632) CAAGTCGAGAAATTGTTGTGTCTCGATCCGACAGACGCACGTGGTCTAGC
M67443 Towne      (573) CGCG-CACGAGCTGGTT-TG-CTCCATGGAGAACACGCGCGCAACCAAGA
```

FIG. 19C

```
                        701                                                  750
AF078102 Rhesus   (682) TAAGACCGCAGAAGAGTTTCATGGCGTTAACGTAGTAGTGAAAACCC-CT
M67443 Towne      (620) T--GCAGGTGATAGGTGACCAGTACGTCAAGGTGTACCTGGAGTCCTTCT

                        751                                                  800
AF078102 Rhesus   (731) GGGCGATCGGAGGCCGATCCCTTGCTCCTTCTGG--GTACTGTGGAGAAG
M67443 Towne      (668) GCGAGGACGT-GCCCTCCGGCAAGCTCTTTATGCACGTCACGCTGGGCTC

                        801                                                  850
AF078102 Rhesus   (779) CTACGTCAAATGTATCCCTTTGCTAAAATGAGAGCTGATAACTTTAGTAA
M67443 Towne      (717) TGACGTGGAAGAGGACCTGACGATGACCCGCAACCCGCAACCCTTCATGC

                        851                                                  900
AF078102 Rhesus   (829) TCTC--ATAAAGTATATTAATCAACGCATGTGTTGCCGA------TGGTA
M67443 Towne      (767) GCCCCCACGAGCGCAACGGCTTTACGGTGTTGTGTCCCAAAAATATGATA

                        901                                                  950
AF078102 Rhesus   (871) --CGTACTTGGTGTTA-CTGGC-CGTTACGCTAATTTTGGAATTTTGCTG
M67443 Towne      (817) ATCAAACCGGGCAAGATCTCGCACATCATGCTGGATGTGGCTTTTACCTC

                        951                                                 1000
AF078102 Rhesus   (917) ACCTGTGGAATAATTCTGTTGGACGAGTGCGGCGTGTGTTATGTGC-TGA
M67443 Towne      (867) ACACGAGCATT--TTGGGCTGCT-GTGTCCCAAGAGCATCCCGGGCCTGA

                        1001                                                1050
AF078102 Rhesus   (966) GAATCGACGAAAGCGACGTGTTT--CGTCTAGCCGATAACATCCAAATGT
M67443 Towne      (914) GCATCTCAGGTAACCTATTGATGAACGGGCAGCAGAT--CTTCCTGGAGG
```

FIG. 19D

```
                        1051                                                1100
AF078102 Rhesus  (1014) TGTTCAGATGCGGCTTTCTTAAGCTCCGTGGCATTACGCGATTTGACCGC
M67443 Towne     (962)  TGC----AAGCGA--TACGCGAGA-CCGTGGAACTGCGTCAGT--AC---

                        1101                                                1150
AF078102 Rhesus  (1064) GGATTGCGTGGCGAGGCTCGTCTG----GAGAGTGAGT-GCTACTGCTAT
M67443 Towne     (1000) -GATCCCGTGGCTGCGCTCTTCTTTTTCGATATCGACTTGCTGCTGC-AG

                        1151                                                1200
AF078102 Rhesus  (1109) CACGGTGCCCGTAAGCAAGATCTCTCTTGGTGCTCTATGGTCAACACAGT
M67443 Towne     (1048) CGCGGGCCTCAGTACAGCGAACACCCCACCTTCACCA--GCCAGTATCGC

                        1201                                                1250
AF078102 Rhesus  (1159) TACCGCCGAGCAGCTCTGTGGTGCGT-ACGACTGGCTCACGCGCAGTAAT
M67443 Towne     (1096) ATCCA--GGGCAAGCTTGAGTACCGACACACCTGGG--ACCGGCACGACG

                        1251                                                1300
AF078102 Rhesus  (1208) CGCGCTCATGATAAAATACCTACCAGTTGTTGTTGGGGACGTAGTGATTT
M67443 Towne     (1142) AGGGTGCCGCCCAGGGCGACGACGACGTCTGGACCAGCGGATCGGACTCC

                        1301                                                1350
AF078102 Rhesus  (1258) GATGCCTACCGGAGTATTGCAAGAGAATCAGAATTGGTGCTTTCCGTGGA
M67443 Towne     (1192) GACGAGGAACTC-GTAACCACCGAGCGCAAGACGCCCCGCGTTACCGGCG

                        1351                                                1400
AF078102 Rhesus  (1308) GCAGTGTCACGGTTCTACAAGGGCC-CCAAAGCGGTGCGTGGCAA--GAA
M67443 Towne     (1241) GCGGCGCCATGG-----CGGGCGCCTCCACTTCCGCGGGCCGCAAACGCA
```

FIG. 19E

```
                        1401                                                1450
AF078102 Rhesus  (1355) AATGATGAGTTAACCGAGAAAACGTCTGATGGTACTGTGATGTTTCGTGT
M67443 Towne     (1286) AATCAGCA-TCCTCGGCGACGGCGTGCACGGCGGGCGTTATGACACGCGG

                        1451                                                1500
AF078102 Rhesus  (1405) A-GACAGAGGTTTTTCTCCCAGAACCGTAAAGTTCGAGGGTGAAAGCGAT
M67443 Towne     (1335) CCGCCTTAAGGCCGAGTCC----ACCGTCGCGCCCGAAGAGGACACCGAC

                        1501                                                1550
AF078102 Rhesus  (1454) GACTACACAGAAGAGGAGGAAGATGATGATAACCAGTCAGAAGAAACCCC
M67443 Towne     (1381) GAGGATTCCGACAACGA--AATCC----ACAATCCGGCCGTGTTCACCTG

                        1551                                                1600
AF078102 Rhesus  (1504) TCAGCATCAGCCTGTTGTCATTGTTTCACATGAAACAAACGGCAGTGTTG
M67443 Towne     (1425) GCCGCCCTGGCAGGCCGGCATCCTGGCCCGCAACCTGGTGCCCATGGTTG

                        1601                                                1650
AF078102 Rhesus  (1554) ATTCTTATGATGATGAGAGTGAGTCAT-CTCTG--TCCT-CAGATACCCA
M67443 Towne     (1475) CTACGGTTCAGGGTCAGAATCTGAAGTACCAGGAGTTCTTGTGGGACGCC

                        1651                                                1700
AF078102 Rhesus  (1600) TGATCCACCACCCCCAGACATTATGGCCATAATCCAAAAGGAATGGCA--
M67443 Towne     (1525) --AACGACATCTACCG--CATCTTCGCCGAATTGGAAGGCGTATGGCAGC

                        1701                                                1750
AF078102 Rhesus  (1648) ---------AAACGAAGAGCCGGTTACCAATGAAAGAGAATTGTTACTGC
M67443 Towne     (1571) CCGCTGCGCAACCCAAACGTCGCCGCCACCGGCAAGACGCCT-TGCCCGG
```

FIG. 19F

```
                        1751                                                                  1800
AF078102 Rhesus  (1689) GGCGTGCA---CGACGA-GCTAAACATATGAAAAAGTGGCATTGTTCCCT
   M67443 Towne  (1620) GCCATGCATCGCCTCGACGCCCAAAAAGCACCGAGGTTGAGCCACCCGCC

                        1801                                                                  1850
AF078102 Rhesus  (1735) GGAAAGGGTTAGCA------TTTATGACCCCTTGAATGCTAATATTCACT
   M67443 Towne  (1670) GCGCACGCTTAGGACGACTCTATAAAAACCCACGTCCACTCAGACACGCG

                        1851                                                                  1900
AF078102 Rhesus  (1779) GCTTTGATTAAACAATGCATTTGTATTCAATTATCTAATTCCGGT--GTA
   M67443 Towne  (1720) ACTTTTGGCCGCCA---CACCTGTCGCCGCTGCTATATTTGCGACAGTTG

                        1901                                                                  1950
AF078102 Rhesus  (1827) CCGTGTCATTTCTCCATGCAGTGGTGGGAAACACATTACATATTTAGACA
   M67443 Towne  (1767) CCGGAACCCTTCCCGA--CCTCCCACGAAGACCCGTT-CACCTTTGCGCA

                        1951                                                                  2000
AF078102 Rhesus  (1877) -CACGTATCACTTGTGAAAGCTGAGTCAACATCATGCAATTGTCGGACGA
   M67443 Towne  (1814) TCCCCTGACCCCCCCC----CTCATCCCGCCTTCGCGATGTCTCAGGCAT

                        2001                                                                  2050
AF078102 Rhesus  (1926) GGTCCGGGTCGTTCGTTCTGTGTTTCT-GTTACGAGTTTACATTTTATTA
   M67443 Towne  (1860) CGTCC---TCGCCCGGTGAGGGACCCTCGTCGGAAGCGGCCGCGATCAGC

                        2051                    2077
AF078102 Rhesus  (1975) TGGTTCAAAGTCTTCTATTTCTAA---
   M67443 Towne  (1907) GAGGCCGAAGCCGCC-AGCGGAAGCTT
```

FIG. 20A

```
                                          1                                                  50
AF081502 Marmota monax IFN-gamma     (1)  --------------------GGCCTAACTCTCTCTGAAACGATGAAATAC
   D30619 Felis catus IFN-gamma      (1)  CTACTGATTTCAACTTCTTTGGCCTAACTCTC--CGAAACGATGAATTAC
    X87308 Homo sapien IFN-gamma     (1)  --------------------------------------------------

                                          51                                                 100
AF081502 Marmota monax IFN-gamma    (31)  ACAAGTTATTTCTTGGCTTTTCAGCTCTGCATCATTTTGGGTTCTTCTAG
   D30619 Felis catus IFN-gamma     (49)  ACAAGTTTTATTTTCGCTTTCCAGCTTTGCATAATTTTGTGTTCTTCTGG
    X87308 Homo sapien IFN-gamma     (1)  --------------------------------------------------

                                         101                                                 150
AF081502 Marmota monax IFN-gamma    (81)  CTGTTACTCCCAGGACACAGTTAATAAAGAAATAGAAGATTTAAAAGGAT
   D30619 Felis catus IFN-gamma     (99)  TTATTACTGTCAGGCCATGTTTTTTAAAGAAATAGAAGAGCTAAAGGGAT
    X87308 Homo sapien IFN-gamma     (1)  -TGTTACTGCCAGGACCCATATGTAAAAGAAGCAGAAAACCTTAAGAAAT

                                         151                                                 200
AF081502 Marmota monax IFN-gamma   (131)  ATTTTAATGCAAGTAATTCAAATGTATCAGATGGCGGGTCTCTCTTCTTG
   D30619 Felis catus IFN-gamma    (149)  ATTTTAATGCAAGTAATCCAGATGTAGCAGATGGTGGGTCGCTTTTCGTA
    X87308 Homo sapien IFN-gamma    (50)  ATTTTAATGCAGGTCATTCAGATGTAGCGGATAATGGAACTCTTTTCTTA

                                         201                                                 250
AF081502 Marmota monax IFN-gamma   (181)  GATATTTTGGATAAATGGAAAGAGGAGAGTGACAAAAAAGTAATCCAGAG
   D30619 Felis catus IFN-gamma    (199)  GACATTTTGAAGAACTGGAAAGAGGAGAGTGATAAAACAATAATTCAAAG
    X87308 Homo sapien IFN-gamma   (100)  GGCATTTTGAAGAATTGGAAAGAGGAGAGTGACAGAAAAATAATGCAGAG

                                         251                                                 300
AF081502 Marmota monax IFN-gamma   (231)  CCAAATTGTCTCTTTCTACTTCAAACTCTTTGAACACTTAAAAGACAA--
   D30619 Felis catus IFN-gamma    (249)  CCAAATTGTCTCCTTCTACCTGAAAATGTTTGAAAACCTGAAAGATGATG
    X87308 Homo sapien IFN-gamma   (150)  CCAAATTGTCTCCTTTTACTTCAAACTTTTTAGAAACTTTAAAGATGA--
```

FIG. 20B

```
                                        301                                                  350
AF081502 Marmota monax IFN-gamma   (279) -CAAGATCATCCAAAGGAGCATGGACACCATCAAGGGGGATCTTTTTGCT
   D30619 Felis catus IFN-gamma    (299) ACCAGCGCATTCAAAGGAGCATGGACACCATCAAGGAAGACATGCTTGAT
    X87308 Homo sapien IFN-gamma   (198) -CCAGAGCATCCAAAAGAGTGTGGAGACCATCAAGGAAGACATGAATGTC

                                        351                                                  400
AF081502 Marmota monax IFN-gamma   (328) AAGTTCTTCAACAGCAGTACCAATAAGCTGCAGGACTTCCTAAAGGTGTC
   D30619 Felis catus IFN-gamma    (349) AAGTTGTTAAATAGCAGCTCCAGTAAACGGGATGACTTCCTCAAGCTGAT
    X87308 Homo sapien IFN-gamma   (247) AAGTTTTTCAATAGCAACAAAAAGAAACGAGATGACTTCGAAAAGCTGAC

                                        401                                                  450
AF081502 Marmota monax IFN-gamma   (378) TCAAGTTCAGGTAAATGACCTGAAGATCCAGCGTAAAGCAGTGAGTGAAC
   D30619 Felis catus IFN-gamma    (399) TCAAATCCCTGTGAATGATCTGCAGGTCCAGCGCAAAGCAATAAATGAAC
    X87308 Homo sapien IFN-gamma   (297) TAATTATTCGGTAACTGACTTGAATGTCCAACGCAAAGCAATACATGAAC

                                        451                                                  500
AF081502 Marmota monax IFN-gamma   (428) TCAAGAAAGTGATGAATGATCTGTTACCACACTCTACCCTAAGGAAGCGA
   D30619 Felis catus IFN-gamma    (449) TCTTCAAAGTGATGAATGATCTCTCACCAAGATCTAACCTCAGGAAGCGG
    X87308 Homo sapien IFN-gamma   (347) TCATCCAAGTGATGGCTGAACTGTCGCCAGCAGCTAAAACAGGGAAGCGG

                                        501                                                  550
AF081502 Marmota monax IFN-gamma   (478) AAAAGGAGTCAGTCTTCGATTCGGGGTCGGAGAGCATCCAAATAACAGTC
   D30619 Felis catus IFN-gamma    (499) AAAAGGAGCCAGAATCTGTTTCGAGGCCGTAGAGCATCGAAATAATGGTT
    X87308 Homo sapien IFN-gamma   (397) AAAAGGAGTCAGATGCTGTTTCGAGGTCGAAGAGCATCCCAG--------

                                        551              569
AF081502 Marmota monax IFN-gamma   (528) CTCATGCCTGC--------
   D30619 Felis catus IFN-gamma    (549) GTCCTGCCTGCAATATTTG
    X87308 Homo sapien IFN-gamma   (439) ------------------
```

SYNTHETIC LIGATION REASSEMBLY IN DIRECTED EVOLUTION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

The present application is a continuation-in-part of U.S. application Ser. No. 09/332,835, filed on Jun. 14, 1999, now [abandoned] *U.S. Pat. No. 6,537,776*, which is hereby incorporated by reference.

FIELD OF THE INVENTION

This invention relates to the field of protein engineering. Specifically, this invention relates to a directed evolution method for preparing a polynucleotide encoding a polypeptide. More specifically, this invention relates to a method of using mutagenesis to generate a novel polynucleotide encoding a novel polypeptide, which novel polypeptide is itself an improved biological molecule &/or contributes to the generation of another improved biological molecule. More specifically still, this invention relates to a method of performing both non-stochastic polynucleotide chimerization and non-stochastic site-directed point mutagenesis.

Thus, in one aspect, this invention relates to a method of generating a progeny set of chimeric polynucleotide(s) by means that are synthetic and non-stochastic, and where the design of the progeny polynucleotide(s) is derived by analysis of a parental set of polynucleotides &/or of the polypeptides correspondingly encoded by the parental polynucleotides. In another aspect this invention relates to a method of performing site-directed mutagenesis using means that are exhaustive, systematic, and non-stochastic.

Furthermore this invention relates to a step of selecting from among a generated set of progeny molecules a subset comprised of particularly desirable species, including by a process termed end-selection, which subset may then be screened further. This invention also relates to the step of screening a set of polynucleotides for the production of a polypeptide &/or of another expressed biological molecule having a useful property.

Novel biological molecules whose manufacture is taught by this invention include genes, gene pathways, and any molecules whose expression is affected thereby, including directly encoded polypetides &/or any molecules affected by such polypeptides. Said novel biological molecules include those that contain a carbohydrate, a lipid, a nucleic acid, &/or a protein component, and specific but non-limiting examples of these include antibiotics, antibodies, enzymes, and steroidal and non-steroidal hormones.

In a particular non-limiting aspect, the present invention relates to enzymes, particularly to thermostable enzymes, and to their generation by directed evolution. More particularly, the present invention relates to thermostable enzymes which are stable at high temperatures and which have improved activity at lower temperatures.

BACKGROUND OF THE INVENTION

General Overview of the Problem to Be Solved

Brief Summary: It is instantly appreciated that harvesting the full potential of nature's diversity can include both the step of discovery and the step of optimizing what is discovered. For example, the step of discovery allows one to mine biological molecules that have commercial utility. It is instantly appreciated that the ability to harvest the full richness of biodiversity, i.e. to mine biological molecules from a wide range of environmental conditions, is critical to the ability to discover novel molecules adapted to [funtion] *function* under a wide variety of conditions, including extremes of conditions, such as may be found in a commercial application.

However, it is also instantly appreciated that only [occassionally] *occasionally* are there criteria for selection &/or survival in nature that point in the exact direction of particular commercial needs. Instead, it is often the case that a naturally occurring molecule will require a certain amount of change—from fine tuning to sweeping modification—in order to fulfill a particular unmet commercial need. Thus, to meet certain commercial needs (e.g., a need for a molecule that is functional under a specific set of commercial processing conditions) it is sometimes advantageous to experimentally modify a naturally [expresed] *expressed* molecule to achieve properties beyond what natural evolution has provided &/or is likely to provide in the near future.

The approach, termed directed evolution, of experimentally modifying a biological molecule towards a desirable property, can be achieved by mutagenizing one or more parental molecular templates and by identifying any desirable molecules among the progeny molecules. Currently available technologies in directed evolution include methods for achieving stochastic (i.e. random) mutagenesis and methods for achieving non-stochastic (non-random) mutagenesis. However, critical shortfalls in both types of methods are identified in the instant disclosure.

In prelude, it is noteworthy that it may be argued philosophically by some that all mutagenesis—if considered from an objective point of view—is non-stochastic; and furthermore that the entire universe is undergoing a process that—if considered from an objective point of view—is non-stochastic. Whether this is true is outside of the scope of the instant consideration. Accordingly, as used herein, the terms "randomness", "uncertainty", and "unpredictability" have subjective meanings, and the knowledge, particularly the predictive knowledge, of the designer of an experimental process is a determinant of whether the process is stochastic or non-stochastic.

By way of illustration, stochastic or random mutagenesis is exemplified by a situation in which a progenitor molecular template is mutated (modified or changed) to yield a set of progeny molecules having mutation(s) that are not predetermined. Thus, in an in vitro stochastic mutagenesis reaction, for example, there is not a particular predetermined product whose production is intended; rather there is an uncertainty—hence randomness—regarding the exact nature of the mutations achieved, and thus also regarding the products generated. In contrast, non-stochastic or non-random mutagenesis is exemplified by a situation in which a progenitor molecular template is mutated (modified or changed) to yield a progeny molecule having one or more predetermined mutations. It is appreciated that the presence of background products in some quantity is a reality in many reactions where molecular processing occurs, and the presence of these background products does not detract from the non-stochastic nature of a mutagenesis process having a predetermined product.

Thus, as used herein, stochastic mutagenesis is manifested in processes such as error-prone PCR and stochastic shuffling, where the mutation(s) achieved are random or not predetermined. In contrast, as used herein, non-stochastic mutagenesis is manifested in the instantly disclosed processes such as gene site-saturation mutagenesis and synthetic ligation reassembly, where the exact chemical structure(s) of the intended product(s) are predetermined.

In brief, existing mutagenesis methods that are non-stochastic have been serviceable in generating from one to only a very small number of predetermined mutations per method application, and thus produce per method application from one to only a few progeny molecules that have predetermined molecular structures. Moreover, the types of mutations currently available by the application of these non-stochastic methods are also limited, and thus so are the types of progeny mutant molecules.

In contrast, existing methods for mutagenesis that are stochastic in nature have been serviceable for generating somewhat larger numbers of mutations per method application—though in a random fashion & usually with a large but unavoidable contingency of undesirable background products. Thus, these existing stochastic methods can produce per method application larger numbers of progeny molecules, but that have undetermined molecular structures. The types of mutations that can be achieved by application of these current stochastic methods are also limited, and thus so are the types of progeny mutant molecules.

It is instantly appreciated that there is a need for the development of non-stochastic mutagenesis methods that:

1) Can be used to generate large numbers of progeny molecules that have predetermined molecular structures;
2) Can be used to readily generate more types of mutations;
3) Can produce a correspondingly larger variety of progeny mutant molecules;
4) Produce decreased unwanted background products;
5) Can be used in a manner that is exhaustive of all possibilities; and
6) Can produce progeny molecules in a systematic & non-repetitive way.

The instant invention satisfies all of these needs.

Directed Evolution Supplements Natural Evolution: Natural evolution has been a springboard for directed or experimental evolution, serving both as a reservoir of methods to be mimicked and of molecular templates to be mutagenized. It is appreciated that, despite its intrinsic process-related limitations (in the types of favored &/or allowed mutagenesis processes) and in its speed, natural evolution has had the advantage of having been in process for millions of years and throughout a wide diversity of environments. Accordingly, natural evolution (molecular mutagenesis and selection in nature) has resulted in the generation of a wealth of biological compounds that have shown usefulness in certain commercial applications.

However, it is instantly appreciated that many unmet commercial needs are discordant with any evolutionary pressure &/or direction that can be found in nature. Moreover, it is often the case that when commercially useful mutations would otherwise be favored at the molecular level in nature, natural evolution often overrides the positive selection of such mutations, e.g. when there is a concurrent detriment to an organism as a whole (such as when a favorable mutation is accompanied by a detrimental mutation). Additionally, natural evolution is often slow, and favors fidelity in many types of replication. Additionally still, natural evolution often favors a path paved mainly by consecutive beneficial mutations while tending to avoid a plurality of successive negative mutations, even though such negative mutations may prove beneficial when combined, or may lead—through a circuitous route—to final state that is beneficial.

Moreover, natural evolution advances through specific steps (e.g. specific mutagenesis and selection processes), with avoidance of less favored steps. For example, many nucleic acids do not reach close enough proximity to each other in a operative environment to undergo chimerization or incorporation or other types of transfers from one species to another. Thus, e.g., when sexual intercourse between 2 particular species is avoided in nature, the chimerization of nucleic acids from these 2 species is likewise unlikely, with parasites common to the two species serving as an example of a very slow passageway for inter-molecular encounters and exchanges of DNA. For another example, the generation of a molecule causing self-toxicity or self-lethality or sexual sterility is avoided in nature. For yet another example, the propagation of a molecule having no particular immediate benefit to an organism is prone to vanish in subsequent generations of the organism. Furthermore, e.g., there is no selection pressure for improving the performance of molecule under conditions other than those to which it is exposed in its endogenous environment; e.g. a cytoplasmic molecule is not likely to acquire functional features extending beyond what is required of it in the cytoplasm. Furthermore still, the propagation of a biological molecule is susceptible to any global detrimental effects—whether caused by itself or not—on its ecosystem. These and other characteristics greatly limit the types of mutations that can be propagated in nature.

On the other hand, directed (or experimental) evolution—particularly as provided herein—can be performed much more rapidly and can be directed in a more streamlined manner at evolving a predetermined molecular property that is commercially desirable where nature does not provide one &/or is not likely to provide. Moreover, the directed evolution invention provided herein can provide more wide-ranging possibilities in the types of steps that can be used in mutagenesis and selection processes. Accordingly, using templates harvested from nature, the instant directed evolution invention provides more wide-ranging possibilities in the types of progeny molecules that can be generated and in the speed at which they can be generated than often nature itself might be expected to in the same length of time.

In a particular exemplification, the instantly disclosed directed evolution methods can be applied iteratively to produce a lineage of progeny molecules (e.g. comprising successive sets of progeny molecules) that would not likely be propagated (i.e., generated &/or selected for) in nature, but that could lead to the generation of a desirable downstream mutagenesis product that is not achievable by natural evolution.

Previous Directed Evolution Methods Are Suboptimal:

Mutagenesis has been attempted in the past on many occasions, but by methods that are inadequate for the purpose of this invention. For example, previously described non-stochastic methods have been serviceable in the generation of only very small sets of progeny molecules (comprised often of merely a solitary progeny molecule). By way of illustration, a chimeric gene has been made by joining 2 polynucleotide fragments using compatible sticky ends generated by restriction enzyme(s), where each fragment is derived from a separate progenitor (or parental) molecule. Another example might be the mutagenesis of a single codon position (i.e. to achieve a codon substitution, addition, or deletion) in a parental polynucleotide to generate a single progeny polynucleotide encoding for a single site-mutagenized polypeptide.

Previous non-stochastic approaches have only been serviceable in the generation of but one to a few mutations per method application. Thus, these previously described non-stochastic methods thus fail to address one of the central goals of this invention, namely the exhaustive and non-stochastic chimerization of nucleic acids. Accordingly previous non-stochastic methods leave untapped the vast majority of the possible point mutations, chimerizations, and combinations thereof, which may lead to the generation of highly desirable progeny molecules.

In contrast, stochastic methods have been used to achieve larger numbers of point mutations and/or chimerizations than non-stochastic methods; for this reason, stochastic methods have comprised the predominant approach for generating a set of progeny molecules that can be subjected to screening, and amongst which a desirable molecular species might hopefully be found. However, a major drawback of these approaches is that—because of their stochastic nature—there is a randomness to the exact components in each set of progeny molecules that is produced. Accordingly, the experimentalist typically has little or no idea what exact progeny molecular species are represented in a particular reaction vessel prior to their generation. Thus, when a stochastic procedure is repeated (e.g. in a continuation of a search for a desirable progeny molecule), the re-generation and re-screening of previously discarded undesirable molecular species becomes a labor-intensive obstruction to progress, causing a circuitous—if not circular—path to be taken. The drawbacks of such a highly suboptimal path can be addressed by subjecting a stochastically generated set of progeny molecules to a labor-incurring process, such as sequencing, in order to identify their molecular structures, but even this is an incomplete remedy.

Moreover, current stochastic approaches are highly unsuitable for comprehensively or exhaustively generating all the molecular species within a particular grouping of mutations, for attributing functionality to specific structural groups in a template molecule (e.g. a specific single amino acid position or a sequence comprised of two or more amino acids positions), and for categorizing and comparing specific grouping of mutations. Accordingly, current stochastic approaches do not inherently enable the systematic elimination of unwanted mutagenesis results, and are, in sum, burdened by too many inherently shortcomings to be optimal for directed evolution.

In a non-limiting aspect, the instant invention addresses these problems by providing non-stochastic means for comprehensively and exhaustively generating all possible point mutations in a parental template. In another non-limiting aspect, the instant invention further provides means for exhaustively generating all possible chimerizations within a group of chimerizations. Thus, the aforementioned problems are solved by the instant invention.

Specific shortfalls in the technological landscape addressed by this invention include:

1) Site-directed mutagenesis technologies, such as sloppy or low-fidelity PCR, are ineffective for systematically achieving at each position (site) along a polypeptide sequence the full (saturated) range of possible mutations (i.e. all possible amino acid substitutions).
2) There is no relatively easy systematic means for rapidly analyzing the large amount of information that can be contained in a molecular sequence and in the potentially colossal number or progeny molecules that could be conceivably obtained by the directed evolution of one or more molecular templates.
3) There is no relatively easy systematic means for providing comprehensive empirical information relating structure to function for molecular positions.
4) There is no easy systematic means for incorporating internal controls, such as positive controls, for key steps in certain mutagenesis (e.g. chimerization) procedures.
5) There is no easy systematic means to select for a specific group of progeny molecules, such as full-length chimeras, from among smaller partial sequences.

An exceedingly large number of possibilities exist for the purposeful and random combination of amino acids within a protein to produce useful hybrid proteins and their corresponding biological molecules encoding for these hybrid proteins, i.e., DNA, RNA. Accordingly, there is a need to produce and screen a wide variety of such hybrid proteins for a desirable utility, particularly widely varying random proteins.

The complexity of an active sequence of a biological macromolecule (e.g., polynucleotides, polypeptides, and molecules that are comprised of both polynucleotide and polypeptide sequences) has been called its information content ("IC"), which has been defined as the resistance of the active protein to amino acid sequence variation (calculated from the minimum number of invariable amino acids (bits) required to describe a family of related sequences with the same function). Proteins that are more sensitive to random mutagenesis have a high information content.

Molecular biology developments, such as molecular libraries, have allowed the identification of quite a large number of variable bases, and even provide ways to select functional sequences from random libraries. In such libraries, most residues can be varied (although typically not all at the same time) depending on compensating changes in the context. Thus, while a 100 amino acid protein can contain only 2,000 different mutations, $20^{100}$ sequence combinations are possible.

Information density is the IC per unit length of a sequence. Active sites of enzymes tend to have a high information density. By contrast, flexible linkers of information in enzymes have a low information density.

Current methods in widespread use for creating alternative proteins in a library format are error-prone polymerase chain reactions and cassette mutagenesis, in which the specific region to be optimized is replaced with a synthetically mutagenized oligonucleotide. In both cases, a substantial number of mutant sites are generated around certain sites in the original sequence.

Error-prone PCR uses low-fidelity polymerization conditions to introduce a low level of point mutations randomly over a long sequence. In a mixture of fragments of unknown sequence, error-prone PCR can be used to mutagenize the mixture. The published error-prone PCR protocols suffer from a low processivity of the polymerase. Therefore, the protocol is unable to result in the random mutagenesis of an average-sized gene. This inability limits the practical application of error-prone PCR. Some computer simulations have suggested that point mutagenesis alone may often be too gradual to allow the large-scale block changes that are required for continued and dramatic sequence evolution. Further, the published error-prone PCR protocols do not allow for amplification of DNA fragments greater than 0.5 to 1.0 kb, limiting their practical application. In addition, repeated cycles of error-prone PCR can lead to an accumulation of neutral mutations with undesired results, such as affecting a protein's immunogenicity but not its binding affinity.

In oligonucleotide-directed mutagenesis, a short sequence is replaced with a synthetically mutagenized oligonucleotide. This approach does not generate combinations of distant mutations and is thus not combinatorial. The limited library size relative to the vast sequence length means that many rounds of selection are unavoidable for protein optimization. Mutagenesis with synthetic oligonucleotides requires sequencing of individual clones after each selection round followed by grouping them into families, arbitrarily choosing a single family, and reducing it to a consensus motif. Such motif is re-synthesized and reinserted into a single gene followed by additional selection. This step process constitutes a statistical bottleneck, is labor intensive, and is not practical for many rounds of mutagenesis.

Error-prone PCR and oligonucleotide-directed mutagenesis are thus useful for single cycles of sequence fine tuning, but rapidly become too limiting when they are applied for multiple cycles.

Another limitation of error-prone PCR is that the rate of down-mutations grows with the information content of the sequence. As the information content, library size, and mutagenesis rate increase, the balance of down-mutations to up-mutations will statistically prevent the selection of further improvements (statistical ceiling).

In cassette mutagenesis, a sequence block of a single template is typically replaced by a (partially) randomized sequence. Therefore, the maximum information content that can be obtained is statistically limited by the number of random sequences (i.e., library size). This eliminates other sequence families which are not currently best, but which may have greater long term potential.

Also, mutagenesis with synthetic oligonucleotides requires sequencing of individual clones after each selection round. Thus, such an approach is tedious and impractical for many rounds of mutagenesis.

Thus, error-prone PCR and cassette mutagenesis are best suited, and have been widely used, for fine-tuning areas of comparatively low information content. One apparent exception is the selection of an RNA ligase ribozyme from a random library using many rounds of amplification by error-prone PCR and selection.

In nature, the evolution of most organisms occurs by natural selection and sexual reproduction. Sexual reproduction ensures mixing and combining of the genes in the offspring of the selected individuals. During meiosis, homologous chromosomes from the parents line up with one another and cross-over part way along their length, thus randomly swapping genetic material. Such swapping or shuffling of the DNA allows organisms to evolve more rapidly.

In recombination, because the inserted sequences were of proven utility in a homologous environment, the inserted sequences are likely to still have substantial information content once they are inserted into the new sequence.

Theoretically there are 2,000 different single mutants of a 100 amino acid protein. However, a protein of 100 amino acids has $20^{100}$ possible sequence combinations, a number which is too large to exhaustively explore by conventional methods. It would be advantageous to develop a system which would allow generation and screening of all of these possible combination mutations.

Some workers in the art have utilized an in vivo site specific recombination system to generate hybrids of combine light chain antibody genes with heavy chain antibody genes for expression in a phage system. However, their system relies on specific sites of recombination and is limited accordingly. Simultaneous mutagenesis of antibody CDR regions in single chain antibodies (scFv) by overlapping extension and PCR have been reported.

Others have described a method for generating a large population of multiple hybrids using random in vivo recombination. This method requires the recombination of two different libraries of plasmids, each library having a different selectable marker. The method is limited to a finite number of recombinations equal to the number of selectable markers existing, and produces a concomitant linear increase in the number of marker genes linked to the selected sequence(s).

In vivo recombination between two homologous, but truncated, insect-toxin genes on a plasmid has been reported as a method of producing a hybrid gene. The in vivo recombination of substantially mismatched DNA sequences in a host cell having defective mismatch repair enzymes, resulting in hybrid molecule formation has been reported.

SUMMARY OF THE INVENTION

This invention relates generally to the field of nucleic acid engineering and correspondingly encoded recombinant protein engineering. More particularly, the invention relates to the directed evolution of nucleic acids and screening of clones containing the evolved nucleic acids for resultant activity(ies) of interest, such nucleic acid activity(ies) &/or specified protein, particularly enzyme, activity(ies) of interest.

Mutagenized molecules provided by this invention may have chimeric molecules and molecules with point mutations, including biological molecules that contain a carbohydrate, a lipid, a nucleic acid, &/or a protein component, and specific but non-limiting examples of these include antibiotics, antibodies, enzymes, and steroidal and non-steroidal hormones.

This invention relates generally to a method of: 1) preparing a progeny generation of molecule(s) (including a molecule that is comprised of a polynucleotide sequence, a molecule that is comprised of a polypeptide sequence, and a molecule that is comprised in part of a polynucleotide sequence and in part of a polypeptide sequence), that is mutagenized to achieve at least one point mutation, addition, deletion, &/or chimerization, from one or more ancestral or parental generation template(s); 2) screening the progeny generation molecule(s)—preferably using a high throughput method—for at least one property of interest (such as an improvement in an enzyme activity or an increase in stability or a novel chemotherapeutic effect); 3) optionally obtaining &/or cataloguing structural &/or and functional information regarding the parental &/or progeny generation molecules; and 4) optionally repeating any of steps 1) to 3).

In a preferred embodiment, there is generated (e.g. from a parent polynucleotide template)—in what is termed "codon site-saturation mutagenesis"—a progeny generation of polynucleotides, each having at least one set of up to three contiguous point mutations (i.e. different bases comprising a new codon), such that every codon (or every family of degenerate codons encoding the same amino acid) is represented at each codon position. Corresponding to—and encoded by—this progeny generation of polynucleotides, there is also generated a set of progeny polypeptides, each having at least one single amino acid point mutation. In a preferred aspect, there is generated—in what is termed "amino acid site-saturation mutagenesis"—one such mutant polypeptide for each of the 19 naturally encoded polypeptide-forming alpha-amino acid substitutions at each and every amino acid position along the polypeptide. This yields—for each and every amino acid position along the parental polypeptide—a total of 20 distinct progeny polypeptides including the original amino acid, or potentially more than 21 distinct progeny polypeptides if additional amino acids are used either instead of or in addition to the 20 naturally encoded amino acids Thus, in another aspect, this approach is also serviceable for generating mutants containing—in addition to &/or in combination with the 20 naturally encoded polypeptide-forming alpha-amino acids—other rare &/or not naturally-encoded amino acids and amino acid derivatives. In yet another aspect, this approach is also serviceable for generating mutants by the use of—in addition to &/or in combination with natural or unaltered codon recognition systems of suitable hosts—altered, mutagenized, &/or designer codon recognition systems (such as in a host cell with one or more altered tRNA molecules).

In yet another aspect, this invention relates to recombination and more specifically to a method for preparing polynucleotides encoding a polypeptide by a method of in vivo re-assortment of polynucleotide sequences containing regions of partial homology, assembling the polynucleotides to form at least one polynucleotide and screening the polynucleotides for the production of polypeptide(s) having a useful property.

In yet another preferred embodiment, this invention is serviceable for analyzing and cataloguing—with respect to any molecular property (e.g. an enzymatic activity) or combination of properties allowed by current technology—the effects of any mutational change achieved (including particularly saturation mutagenesis). Thus, a comprehensive method is provided for determining the effect of changing each amino acid in a parental polypeptide into each of at least 19 possible substitutions. This allows each amino acid in a parental polypeptide to be characterized and catalogued according to its spectrum of potential effects on a measurable property of the polypeptide.

In another aspect, the method of the present invention utilizes the natural property of cells to recombine molecules and/or to mediate reductive processes that reduce the complexity of sequences and extent of repeated or consecutive sequences possessing regions of homology.

It is an object of the present invention to provide a method for generating hybrid polynucleotides encoding biologically active hybrid polypeptides with enhanced activities. In accomplishing these and other objects, there has been provided, in accordance with one aspect of the invention, a method for introducing polynucleotides into a suitable host cell and growing the host cell under conditions that produce a hybrid polynucleotide.

In another aspect of the invention, the invention provides a method for screening for biologically active hybrid polypeptides encoded by hybrid polynucleotides. The present method allows for the identification of biologically active hybrid polypeptides with enhanced biological activities.

According to another aspect of this invention is provided that an important advantage of the synthetic ligation reassembly methods provided herein is that the starting templates that can be aligned and subjected to ligation reassembly are not limited to full length genes. In fact when working with genomic sequences it is often the case that partial gene sequences are obtained, and these can be subjected to ligation reassembly according to this invention.

In an important aspect of this invention, it is appreciated herein that nucleic acid building blocks that are serviceable for this invention can be generated by synthetic means or alternatively by polymerase-based methods either in vivo or in vitro or alternatively by a combination of synthetic means and polymerase-based means. The likelihood of nucleotide incorporation errors is different for each method. Among such errors some may be undesirable at times. For example the presence of a single nucleotide mistake in the generation of up a nucleic acid building block can lead to the undesirable introduction of a stop codon. It is appreciated that several prescreening methods can be used to filter out to undesirable nucleotide incorporation errors. For example the finalized construct can be a fusion product that includes a reporter sequence, such as GFP or a 6×His tag (*SEQ ID NO: 23*), that is only generated in the absence of unwanted internal stop codons. It is also appreciated that the selection all of the method by which nucleic acid building blocks are generated can be based upon consideration of the error rates of each method considered.

Furthermore, it is provided that, according to this invention, nucleic acid building blocks may be single-stranded or double-stranded polynucleotides. Thus, ligation reassembly according to this invention may be performed using synthetic as well as non-synthetic nucleic acid building blocks up, or a combination thereof. Moreover both single-stranded and double-stranded polynucleotides may be used in ligation reassembly, either mutually exclusively or in combination.

In another aspect of this invention of, it is provided that blunt ended acid building blocks may be used without alteration of the blunt ends or alternatively may be subjected to treatment with an exonuclease, such as Exonuclease III, to create serviceable overhangs up for synthetic ligation couplings of. Such a treatment may be brief and controlled, e.g., by subjecting the working sample of to a temperature at which the Exonuclease III is operable, and then quickly chilling. In all aspects of ligation reassembly, treatment with a ligase such as T4 DNA Ligase is an optional step.

In specific embodiments, the invention provides a method of non-stochastically producing a library of chimeric nucleic acid molecules having an overall assembly order that is chosen by design, which method is comprised of (a) generating by design a plurality of specific synthetic nucleic acid building blocks having serviceable mutually compatible ligatable ends, and (b) assembling these nucleic acid building blocks, such that a designed overall assembly order is achieved; whereby a set of progenitor templates, such as genes (e.g. a family of esterase genes) or genes pathways (e.g. encoding antibiotics) can be shuffled to generate a sizable library of progeny polynucleotide molecules (e.g. $10^{100}$) and correspondingly encoded polypeptides, and whereby the expression screening of the progeny polynucleotide library provides a means to identify a desirable species that has a desirable property, such as a specific enzymatic activity serviceable for a commercial application.

Also included is a method of non-stochastically producing a library comprised of a defined number of groupings comprised of one or more groupings of chimeric nucleic acid molecules having an overall assembly order that is chosen by design, which method is comprised of (a) generating by design for each grouping a set of specific nucleic acid building blocks having serviceable mutually compatible ligatable ends, and (b) assembling these nucleic acid building blocks according to said groupings, such that a designed overall assembly order is achieved; whereby a set of progenitor templates, such as genes (e.g. a family of esterase genes) or genes pathways (e.g. encoding antibiotics) can be shuffled to generate a sizable library of progeny polynucleotide molecules (e.g. $10^{100}$) and correspondingly encoded polypeptides, and whereby the expression screening of the progeny polynucleotide library provides a means to identify a desirable species that has a desirable property, such as a specific enzymatic activity serviceable for a commercial application.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 shows the activity of the enzyme exonuclease III. This is an exemplary enzyme that can be used to shuffle, assemble, reassemble, recombine, and/or concatenate polynucleotide building blocks. The asterisk indicates that the enzyme acts from the 3' direction towards the 5' direction of the polynucleotide substrate.

FIG. 2 illustrates a method of generating a double-stranded nucleic acid building block with two overhangs using a polymerase-based amplification reaction (e.g., PCR). As illustrated, a first polymerase-based amplification reaction using a first set of primers, $F_2$ and $R_1$, is used to generate a blunt-ended product (labeled Reaction 1, Product 1), which is essentially identical to Product A. A second polymerase-based amplification reaction using a second set of primers, $F_1$ and $R_2$, is used to generate a blunt-ended product (labeled Reaction 2, Product 2), which is essentially identical to Product B. These two products are then mixed and allowed to melt and anneal, generating a potentially useful double-stranded nucleic acid building block with two overhangs. In the example of FIG. 1, the product with the 3' overhangs (Product C) is selected for by nuclease-based degradation of the other 3 products using a 3' acting exonuclease, such as exonuclease III. Alternate primers are shown in parenthesis to illustrate serviceable primers may overlap, and additionally that serviceable primers may be of different lengths, as shown.

FIG. 3 illustrates the point that the number of unique overhangs of each size (e.g. the total number of unique overhangs composed of 1 or 2 or 3, etc. nucleotides) exceeds the number of unique couplings that can result from the use of all the unique overhangs of that size. For example, there are 4 unique 3' overhangs composed of a single nucleotide, and 4 unique 5' overhangs composed of a single nucleotide. Yet the total number of unique couplings that can be made using all the 8 unique single-nucleotide 3' overhangs and single-nucleotide 5' overhangs is 4, as presented in Panel A. Panel B shows that the number of unique single-nucleotide 3' overhangs is greater than the number of unique couplings. Thus, only 2 intrinsically unique couplings exist using single-nucleotide 3' overhangs as shown, Panel C shows 4 unique-single nucleotide 5' overhangs are possible (i.e. A, C, G, & T). For each of these there is a complementary 5' overhang with which it can pair (i.e., T, G, C, & A, respectively), as shown. Panel D shows that the number of unique single-nucleotide 5' overhangs is greater than the number of unique couplings. Thus, only 2 intrinsically unique couplings exist using single-nucleotide 5' overhangs as shown.

In FIG. 4A, Panel A, for example, one could attempt to assemble the following nucleic acid product using the 5 nucleic acid building blocks as shown. FIG. 4A illustrates the fact that in order to assemble a total of "n" nucleic acid building blocks, "n−1" couplings are needed. Yet it is sometimes the case that the number of unique couplings available for use is fewer that the "n−1" value. In FIG. 4A, Panel B, degeneracy in the overall assembly order of the 5 nucleic acid building blocks would be present if the assembly process were carried out in one step. For example, building block #2 and building block #3 could both couple to building block #1 as shown. Under these, and other, circumstances a stringent non-stochastic overall assembly order can still be achieved by performing the assembly process in sequential steps.

For example, FIG. 4B illustrates a unique overall assembly order could be achieved by sequentially coupling the building blocks in 2 steps (rather than all at once) as shown. In this example, 2 sequential steps are used to achieve a designed overall assembly order for five nucleic acid building blocks. In this illustration the designed overall assembly order for the five nucleic acid building blocks is: 5'-(#1-#2-#3-#4-#5)-3', where #1 represents building block number 1, etc.

FIG. 5 further illustrates the point that the number of unique overhangs of each size (here, e.g. the total number of unique overhangs composed of 2 nucleotides) exceeds the number of unique couplings that can result from the use of all the unique overhangs of that size. For example, there are 16 unique 3' overhangs composed of two nucleotides, and another 16 unique 5' overhangs composed of two nucleotides, for a total of 32 as shown. Yet the total number of couplings that are unique and not self-binding that can be made using all the 32 unique double-nucleotide 3' overhangs and double-nucleotide 5' overhangs is 12. Some apparently unique couplings have "identical twins" (marked in the same shading), which are visually obvious in this illustration. Still other overhangs contain nucleotide sequences that can self-bind in a palindromic fashion, as shown and labeled in this figure; thus they do not contribute the high stringency to the overall assembly order.

FIG. 6 showcases the power of this invention in its ability to generate exhaustively and systematically all possible combinations of the nucleic acid building blocks designed in this example. Particularly large sets (or libraries) of progeny chimeric molecules can be generated. Because this method can be performed exhaustively and systematically, the method application can be repeated by choosing new demarcation points and with correspondingly newly designed nucleic acid building blocks, bypassing the burden of re-generating and re-screening previously examined and rejected molecular species. It is appreciated that, codon wobble can be used to advantage to increase the frequency of a demarcation point. In other words, a particular base can often be substituted into a nucleic acid building block without altering the amino acid encoded by progenitor codon (that is now altered codon) because of codon degeneracy. As illustrated, demarcation points are chosen upon alignment of 8 progenitor templates (*SEQ ID NOS 1-8: consensus sequence shown in SEQ ID NO: 9*). Nucleic acid building blocks including their overhangs (which are serviceable for the formation of ordered couplings) are then designed and synthesized. In this instance, 18 nucleic acid building blocks are generated based on the sequence of each of the 8 progenitor templates, for a total of 144 nucleic acid building blocks (or double-stranded oligos). Performing the ligation synthesis procedure will then produce a library of progeny molecules comprised of yield of $8^{18}$ (or over $1.8\times10^{16}$) chimeras.

FIG. 7 *A, B, C, and D*. Synthetic genes from oligos: According to one embodiment of this invention, double-stranded nucleic acid building blocks are designed by aligning a plurality of progenitor nucleic acid templates. Preferably these templates contain some homology and some heterology. The nucleic acids may encode related proteins, such as related enzymes, which relationship may be based on function or structure or both. FIG. 7 shows the alignment of three polynucleotide progenitor templates (*SEQ ID NOS 10-12, respectively, in order of appearance*) and the selection of demarcation points (boxed) shared by all the progenitor molecules. In this particular example, the nucleic acid building blocks derived from each of the progenitor templates were chosen to be approximately 30 to 50 nucleotides in length.

FIG. 8 shows the nucleic acid building blocks from the example in FIG. 7. The nucleic acid building blocks are shown here in generic cartoon form, with their compatible overhangs, including both 5' and 3' overhangs. There are 22 total nucleic acid building blocks derived from each of the 3 progenitor templates. Thus, the ligation synthesis procedure can produce a library of progeny molecules comprised of yield of $3^{22}$ (or over $3.1\times10^{10}$) chimeras.

FIG. 9 shows in generic cartoon form that an intron may be introduced into a chimeric progeny molecule by way of a nucleic acid building block. It is appreciated that introns often have consensus sequences at both termini in order to render them operational. It is also appreciated that, in addition to enabling gene splicing, introns may serve an additional purpose by providing sites of homology to other nucleic acids to enable homologous recombination. For this purpose, and potentially others, it may be sometimes desirable to generate a large nucleic acid building block for introducing an intron. If the size is overly large easily generated by direct chemical synthesis of two single stranded oligos, such a specialized nucleic acid building block may also be generated by direct chemical synthesis of more than two single stranded oligos or by using a polymerase-based amplification reaction as shown in FIG. 2.

FIG. 10 shows that coupling can occur in a manner that does not make use of every nucleotide in a participating overhang. The coupling is particularly likely to survive (e.g. in a transformed host) if the coupling reinforced by treatment with a ligase enzyme to form what may be referred to as a "gap ligation" or a "gapped ligation". It is appreciated that, as shown, this type of coupling can contribute to generation of unwanted background product(s), but it can also be used advantageously to increase the diversity of the progeny library generated by the designed ligation reassembly. The example in FIG. 10 shows ligation of one strand only; the gap in the second strand can be repaired in vivo.

FIG. 12 illustrates a preferred approach that may be taken to achieve this goal. It is appreciated that naturally-occurring microbial gene pathways are linked more often than naturally-occurring eukaryotic (e.g. plant) gene pathways, which are sometime only partially linked. In a particular embodiment, this invention provides that regulatory gene sequences (including promoters) can be introduced in the form of nucleic acid building blocks into progeny gene pathways generated by ligation reassembly processes. Thus, originally linked microbial gene pathways, as well as originally unlinked genes and gene pathways, can be thus converted to acquire operability in plants and other eukaryotes.

FIG. 13 illustrates that another goal of this invention, in addition to the generation of novel gene pathways, is the subjection of gene pathways—both naturally occurring and man-made—to mutagenesis and selection in order to achieve improved progeny molecules using the instantly disclosed methods of directed evolution (including saturation mutagenesis and synthetic ligation reassembly). In a particular embodiment, as provided by the instant invention, both microbial and plant pathways can be improved by directed evolution, and as shown, the directed evolution process can be performed both on genes prior to linking them into pathways, and on gene pathways themselves.

Dashes "------" indicate internal sequences not involved in couplings.) (2) Immobilization of 5' pre-annealed biotinylated fragment to conjugated beads. (3) Wash to remove free fragments. (4) Enzymatic ligation of consecutive pre-annealed fragments including washes between each addition to remove free fragments. (5) BsaI-mediated elution of reassembled gene (cuts inside of TOPO sequence). (6) Ligation to 5'- and 3' end PCR generated fragments (if necessary). (7) Cloning into appropriate vector.

Figure 18:
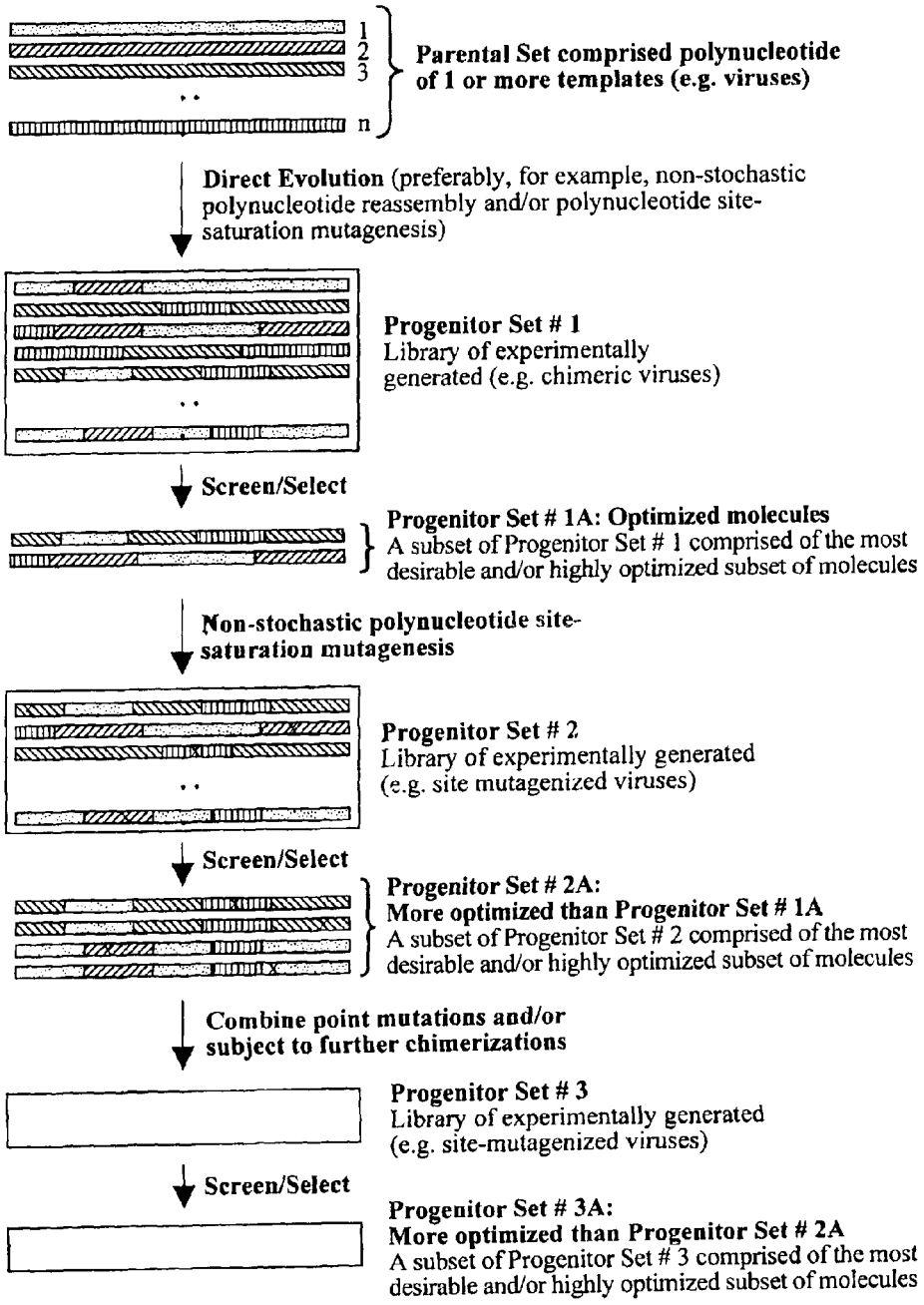

FIG. 18. Polynucleotide reassembly. Shown is an example of directed evolution. N different strains of a virus are used in this illustration, but the technique is applicable to any single nucleic acid as well as to any nucleic acid for which different strains, species, or gene families have homologous nucleic acids that have one or more nucleotide changes compared to other homologous nucleic acids. The different variant nucleic acids are experimentally generated, preferably non-stochastically, as described herein, and screened or selected to identify those variants that exhibit the desired property. The directed evolution method(s) and screening can be repeated one or more times to obtain further improvement. Panel B shows that successive rounds of directed evolution can produce progressively enhanced properties, and that the combination of individual beneficial mutations can lead to an enhanced improvement compared to the improvement achieved by an individual beneficial mutation. This figure illustrates the non-stochastic polynucleotide reassembly in combination with non-stochastic polynucleotide site-saturation mutagenesis.

FIGS. 19A-F. An alignment of two CMV-derived nucleotide sequences from human and primate species. Shown here is an alignment of two CMV-derived nucleotide sequences of human (*SEQ ID NO: 14*) and primate (*SEQ ID NO: 13*) strains. This alignment is serviceable for performing non-stochastic polynucleotide reassembly. Nucleotide sequences shared by two sequences are boxed to illustrate preferred but non-limiting examples of reassembly points.

FIGS. 20A-B. An alignment of the IFN-gamma nucleotide sequences from human, cat, rodent species. Shown here is an alignment of the IFN-gamma nucleotide sequences from human (*SEQ ID NO: 17*), cat (*SEQ ID NO: 16*), and rodent (*SEQ ID NO: 15*) species. This alignment is serviceable for performing non-stochastic polynucleotide reassembly. Nucleotide sequences shared by two or three sequences are boxed to illustrate preferred but non-limiting examples of reassembly points.

DEFINITIONS OF TERMS

In order to facilitate understanding of the examples provided herein, certain frequently occurring methods and/or terms will be described.

The term "agent" is used herein to denote a chemical compound, a mixture of chemical compounds, an array of spatially localized compounds (e.g., a VLSIPS peptide array, polynucleotide array, and/or combinatorial small molecule array), biological macromolecule, a bacteriophage peptide display library, a bacteriophage antibody (e.g., scFv) display library, a polysome peptide display library, or an extract made from biological materials such as bacteria, plants, fungi, or animal (particular mammalian) cells or tissues. Agents are evaluated for potential activity as anti-neoplastics, anti-inflammatories or apoptosis modulators by inclusion in screening assays described herein below. Agents are evaluated for potential activity as specific protein interaction inhibitors (i.e., an agent which selectively inhibits a binding interaction between two predetermined polypeptides but which does not substantially interfere with cell viability) by inclusion in screening assays described herein below.

An "ambiguous base requirement" in a restriction site refers to a nucleotide base requirement that is not specified to the fullest extent, i.e. that is not a specific base (such as, in a non-limiting exemplification, a specific base selected from A, C, G, and T), but rather may be any one of at least two or more bases. Commonly accepted abbreviations that are used in the art as well as herein to represent ambiguity in bases include the following: R=G or A; Y=C or T; M=A or C; K=G or T; S=G or C; W=A or T; H=A or C or T; B=G or T or C; V=G or C or A; D=G or A or T; N=A or C or G or T.

The term "amino acid" as used herein refers to any organic compound that contains an amino group (—$NH_2$) and a carboxyl group (—COOH); preferably either as free groups or alternatively after condensation as part of peptide bonds. The "twenty naturally encoded polypeptide-forming alpha-amino acids" are understood in the art and refer to: alanine (ala or A), arginine (arg or R), asparagine (asn or N), aspartic acid (asp or D), cysteine (cys or C), gluatamic acid (glu or E), glutamine (gln or Q), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (trp or W), tyrosine (tyr or Y), and valine (val or V).

The term "amplification" means that the number of copies of a polynucleotide is increased.

The term "antibody", as used herein, refers to intact immunoglobulin molecules, as well as fragments of immunoglobulin molecules, such as Fab, Fab', $(Fab')_2$, Fv, and SCA fragments, that are capable of binding to an epitope of an antigen. These antibody fragments, which retain some ability to selectively bind to an antigen (e.g., a polypeptide antigen) of the antibody from which they are derived, can be made using well known methods in the art (see, e.g., Harlow and Lane, supra), and are described further, as follows.

(1) An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) An $(Fab')_2$ fragment of an antibody can be obtained by treating a whole antibody molecule with the enzyme pepsin, without subsequent reduction. A $(Fab')_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) An single chain antibody ("SCA") is a genetically engineered single chain molecule containing the variable region of a light chain and the variable region of a heavy chain, linked by a suitable, flexible polypeptide linker.

The term "Applied Molecular Evolution" ("AME") means the application of an evolutionary design algorithm to a specific, useful goal. While many different library formats for AME have been reported for polynucleotides, peptides and proteins (phage, lacI and polysomes), none of these formats have provided for recombination by random cross-overs to deliberately create a combinatorial library.

A molecule that has a "chimeric property" is a molecule that is: 1) in part homologous and in part heterologous to a first reference molecule; while 2) at the same time being in part homologous and in part heterologous to a second reference molecule; without 3) precluding the possibility of being at the same time in part homologous and in part heterologous to still one or more additional reference molecules. In a non-limiting embodiment, a chimeric molecule may be prepared by assemblying a reassortment of partial molecular sequences. In a non-limiting aspect, a chimeric polynucleotide molecule may be prepared by synthesizing the chimeric polynucleotide using plurality of molecular templates, such that the resultant chimeric polynucleotide has properties of a plurality of templates.

The term "cognate" as used herein refers to a gene sequence that is evolutionarily and functionally related between species. For example, but not limitation, in the human genome the human CD4 gene is the cognate gene to the mouse 3d4 gene, since the sequences and structures of these two genes indicate that they are highly homologous and both genes encode a protein which functions in signaling T cell activation through MHC class II-restricted antigen recognition.

A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith (Smith and Waterman, Adv Appl Math, 1981; Smith and Waterman, J Teor Biol, 1981; Smith and Waterman, J Mol Biol, 1981; Smith et al, J Mol Evol, 1981), by the homology alignment algorithm of Needleman (Needleman and Wuncsch, 1970), by the search of similarity method of Pearson (Pearson and Lipman, 1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

As used herein, the term "complementarity-determining region" and "CDR" refer to the art-recognized term as exemplified by the Kabat and Chothia CDR definitions also generally known as supervariable regions or hypervariable loops (Chothia and Lesk, 1987; Clothia et al, 1989; Kabat et al, 1987; and Tramontano et al, 1990). Variable region domains typically comprise the amino-terminal approximately 105-115 amino acids of a naturally-occurring immunoglobulin chain (e.g., amino acids 1-110), although variable domains somewhat shorter or longer are also suitable for forming single-chain antibodies.

"Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference "TATAC" and is complementary to a reference sequence "GTATA."

The term "degrading effective" amount refers to the amount of enzyme which is required to process at least 50% of the substrate, as compared to substrate not contacted with the enzyme. Preferably, at least 80% of the substrate is degraded.

As used herein, the term "defined sequence framework" refers to a set of defined sequences that are selected on a non-random basis, generally on the basis of experimental data or structural data; for example, a defined sequence framework may comprise a set of amino acid sequences that are predicted to form a β-sheet structure or may comprise a leucine zipper heptad repeat motif, a zinc-finger domain, among other variations. A "defined sequence kemal" is a set of sequences which encompass a limited scope of variability. Whereas (1) a completely random 10-mer sequence of the 20 conventional amino acids can be any of $(20)^{10}$ sequences, and (2) a pseudorandom 10-mer sequence of the 20 conventional amino acids can be any of $(20)^{10}$ sequences but will exhibit a bias for certain residues at certain positions and/or overall, (3) a defined sequence kernal is a subset of sequences if each residue position was allowed to be any of the allowable 20 conventional amino acids (and/or allowable unconventional amino/imino acids). A defined sequence kernal generally comprises variant and invariant residue positions and/or comprises variant residue positions which can comprise a residue selected from a defined subset of amino acid residues), and the like, either segmentally or over the entire length of the individual selected library member sequence. Defined sequence kernels can refer to either amino acid sequences or polynucleotide sequences. Of illustration and not limitation, the sequences $(NNK)_{10}$ and $(NNM)_{10}$, wherein N represents A, T, G, or C; K represents G or T; and M represents A or C, are defined sequence kernels.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a gel to isolate the desired fragment.

"Directional ligation" refers to a ligation in which a 5' end and a 3' end of a polynuclotide are different enough to specify a preferred ligation orientation. For example, an otherwise untreated and undigested PCR product that has two blunt ends will typically be not have a preferred ligation orientation when ligated into a cloning vector digested to produce blunt ends in its multiple cloning site; thus, directional ligation will typically not be displayed under these circumstances. In contrast, directional ligation will typically displayed when a digested PCR product having a 5' EcoR I-treated end and a 3' BamH I-is ligated into a cloning vector that has a multiple cloning site digested with EcoR I and BamH I.

The term "DNA shuffling" is used herein to indicate recombination between substantially homologous but non-identical sequences, in some embodiments DNA shuffling may involve crossover via non-homologous recombination, such as via cer/lox and/or flp/frt systems and the like.

As used in this invention, the term "epitope" refers to an antigenic determinant on an antigen, such as a phytase polypeptide, to which the paratope of an antibody, such as an phytase-specific antibody, binds. Antigenic determinants usually consist of chemically active surface groupings of molecules, such as amino acids or sugar side chains, and can have specific three-dimensional structural characteristics, as well as specific charge characteristics. As used herein "epitope" refers to that portion of an antigen or other macromolecule capable of forming a binding interaction that interacts with the variable region binding body of an antibody. Typically, such binding interaction is manifested as an intermolecular contact with one or more amino acid residues of a CDR.

The terms "fragment", "derivative" and "analog" when referring to a reference polypeptide comprise a polypeptide which retains at least one biological function or activity that is at least essentially same as that of the reference polypeptide. Furthermore, the terms "fragment", "derivative" or "analog" are exemplified by a "pro-form" molecule, such as a low activity proprotein that can be modified by cleavage to produce a mature enzyme with significantly higher activity.

A method is provided herein for producing from a template polypeptide a set of progeny polypeptides in which a "full range of single amino acid substitutions" is represented at each amino acid position. As used herein, "full range of single amino acid substitutions" is in reference to the naturally encoded 20 naturally encoded polypeptide-forming alpha-amino acids, as described herein.

The term "gene" means the segment of DNA involved in producing a polypeptide chain; it includes regions preceding and following the coding region (leader and trailer) as well as intervening sequences (introns) between individual coding segments (exons).

"Genetic instability", as used herein, refers to the natural tendency of highly repetitive sequences to be lost through a process of reductive events generally involving sequence simplification through the loss of repeated sequences. Deletions tend to involve the loss of one copy of a repeat and everything between the repeats.

The term "heterologous" means that one single-stranded nucleic acid sequence is unable to hybridize to another single-stranded nucleic acid sequence or its complement. Thus areas of heterology means that areas of polynucleotides or polynucleotides have areas or regions within their sequence which are unable to hybridize to another nucleic acid or polynucleotide. Such regions or areas are for example areas of mutations.

The term "homologous" or "homeologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentrations as discussed later. Preferably the region of identity is greater than about 5 bp, more preferably the region of identity is greater than 10 bp.

An immunoglobulin light or heavy chain variable region consists of a "framework" region interrupted by three hypervariable regions, also called CDR's. The extent of the framework region and CDR's have been precisely defined; see "Sequences of Proteins of Immunological Interest" (Kabat et al, 1987). The sequences of the framework regions of different light or heavy chains are relatively conserved within a specie. As used herein, a "human framework region" is a framework region that is substantially identical (about 85 or more, usually 90-95 or more) to the framework region of a naturally occurring human immunoglobulin. the framework region of an antibody, that is the combined framework regions of the constituent light and heavy chains, serves to position and align the CDR's. The CDR's are primarily responsible for binding to an epitope of an antigen.

The benefits of this invention extend to "commercial applications" (or commercial processes), which term is used to include applications in commercial industry proper (or simply industry) as well as non-commercial commercial applications (e.g. biomedical research at a non-profit institution). Relevant applications include those in areas of diagnosis, medicine, agriculture, manufacturing, and academia.

The term "identical" or "identity" means that two nucleic acid sequences have the same sequence or a complementary sequence. Thus, "areas of identity" means that regions or areas of a polynucleotide or the overall polynucleotide are identical or complementary to areas of another polynucleotide or the polynucleotide.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

By "isolated nucleic acid" is meant a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

As used herein "ligand" refers to a molecule, such as a random peptide or variable segment sequence, that is recognized by a particular receptor. As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

"Ligation" refers to the process of forming phosphodiester bonds between two double stranded nucleic acid fragments (Sambrook et al, 1982, p. 146; Sambrook, 1989). Unless otherwise provided, ligation may be accomplished using known buffers and conditions with 10 units of T4 DNA ligase ("ligase") per 0.5 μg of approximately equimolar amounts of the DNA fragments to be ligated.

As used herein, "linker" or "spacer" refers to a molecule or group of molecules that connects two molecules, such as a DNA binding protein and a random peptide, and serves to place the two molecules in a preferred configuration, e.g., so that the random peptide can bind to a receptor with minimal steric hindrance from the DNA binding protein.

As used herein, a "molecular property to be evolved" includes reference to molecules comprised of a polynucleotide sequence, molecules comprised of a polypeptide sequence, and molecules comprised in part of a polynucleotide sequence and in part of a polypeptide sequence. Particularly relevant—but by no means limiting—examples of molecular properties to be evolved include enzymatic activities at specified conditions, such as related to temperature; salinity; pressure; pH; and concentration of glycerol, DMSO, detergent, &/or any other molecular species with which contact is made in a reaction environment. Additional particularly relevant—but by no means limiting—examples of molecular properties to be evolved include stabilities—e.g. the amount of a residual molecular property that is present after a specified exposure time to a specified environment, such as may be encountered during storage.

The term "mutations" includes changes in the sequence of a wild-type or parental nucleic acid sequence or changes in the sequence of a peptide. Such mutations may be point mutations such as transitions or transversions. The mutations may be deletions, insertions or duplications. A mutation can also be a "chimerization", which is exemplified in a progeny molecule that is generated to contain part or all of a sequence of one parental molecule as well as part or all of a sequence of at least one other parental molecule. This invention provides for both chimeric polynucleotides and chimeric polypeptides.

As used herein, the degenerate "N,N,G/T" nucleotide sequence represents 32 possible triplets, where "N" can be A, C, G or T.

The term "naturally-occurring" as used herein as applied to the object refers to the fact that an object can be found in nature. For example, a polypeptide or polynucleotide sequence that is present in an organism (including viruses) that can be isolated from a source in nature and which has not been intentionally modified by man in the laboratory is naturally occurring. Generally, the term naturally occurring refers to an object as present in a non-pathological (un-diseased) individual, such as would be typical for the species.

As used herein, a "nucleic acid molecule" is comprised of at least one base or one base pair, depending on whether it is single-stranded or double-stranded, respectively. Furthermore, a nucleic acid molecule may belong exclusively or chimerically to any group of nucleotide-containing molecules, as exemplified by, but not limited to, the following groups of nucleic acid molecules: RNA, DNA, genomic nucleic acids, non-genomic nucleic acids, naturally occurring and not naturally occurring nucleic acids, and synthetic nucleic acids. This includes, by way of non-limiting example, nucleic acids associated with any organelle, such as the mitochondria, ribosomal RNA, and nucleic acid molecules comprised chimerically of one or more components that are not naturally occurring along with naturally occurring components.

Additionally, a "nucleic acid molecule" may contain in part one or more non-nucleotide-based components as exemplified by, but not limited to, amino acids and sugars. Thus, by way of example, but not limitation, a ribozyme that is in part nucleotide-based and in part protein-based is considered a "nucleic acid molecule".

In addition, by way of example, but not limitation, a nucleic acid molecule that is labeled with a detectable moiety, such as a radioactive or alternatively a non-radioactive label, is likewise considered a "nucleic acid molecule".

The terms "nucleic acid sequence coding for" or a "DNA coding sequence of" or a "nucleotide sequence encoding" a particular enzyme—as well as other synonymous terms—refer to a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

The terms "nucleic acid encoding an enzyme (protein)" or "DNA encoding an enzyme (protein)" or "polynucleotide encoding an enzyme (protein)" and other synonymous terms encompasses a polynucleotide which includes only coding sequence for the enzyme as well as a polynucleotide which includes additional coding and/or non-coding sequence.

In one preferred embodiment, a "specific nucleic acid molecule species" is defined by its chemical structure, as exemplified by, but not limited to, its primary sequence. In another preferred embodiment, a specific "nucleic acid molecule species" is defined by a function of the nucleic acid species or by a function of a product derived from the nucleic acid species. Thus, by way of non-limiting example, a "specific nucleic acid molecule species" may be defined by one or more activities or properties attributable to it, including activities or properties attributable its expressed product.

The instant definition of "assembling a working nucleic acid sample into a nucleic acid library" includes the process of incorporating a nucleic acid sample into a vector-based collection, such as by ligation into a vector and transformation of a host. A description of relevant vectors, hosts, and other reagents as well as specific non-limiting examples thereof are provided hereinafter. The instant definition of "assembling a working nucleic acid sample into a nucleic acid library" also includes the process of incorporating a nucleic acid sample into a non-vector-based collection, such as by ligation to adaptors. Preferably the adaptors can anneal to PCR primers to facilitate amplification by PCR.

Accordingly, in a non-limiting embodiment, a "nucleic acid library" is comprised of a vector-based collection of one or more nucleic acid molecules. In another preferred embodiment a "nucleic acid library" is comprised of a non-vector-based collection of nucleic acid molecules. In yet another preferred embodiment a "nucleic acid library" is comprised of a combined collection of nucleic acid molecules that is in part vector-based and in part non-vector-based. Preferably, the collection of molecules comprising a library is searchable and separable according to individual nucleic acid molecule species.

The present invention provides a "nucleic acid construct" or alternatively a "nucleotide construct" or alternatively a "DNA construct". The term "construct" is used herein to describe a molecule, such as a polynucleotide (e.g., a phytase polynucleotide) may optionally be chemically bonded to one or more additional molecular moieties, such as a vector, or parts of a vector. In a specific—but by no means limiting—aspect, a nucleotide construct is exemplified by DNA expression constructs suitable for the transformation of a host cell.

An "oligonucleotide" (or synonymously an "oligo") refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated. To achieve polymerase-based amplification (such as with PCR), a "32-fold degenerate oligonucleotide that is comprised of, in series, at least a first homologous sequence, a degenerate N,N,G/T sequence, and a second homologous sequence" is mentioned. As used in this context, "homologous" is in reference to homology between the oligo and the parental polynucleotide that is subjected to the polymerase-based amplification.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

As used herein the term "parental polynucleotide set" is a set comprised of one or more distinct polynucleotide species. Usually this term is used in reference to a progeny polynucleotide set which is preferably obtained by mutagenization of the parental set, in which case the terms "parental", "starting" and "template" are used interchangeably.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50-200 mM NaCl or KCl, pH 6.5-8.5, 20-45° C. and 0.001-10 mM divalent cation (e.g., $Mg^{++}$, $Ca^{++}$); preferably about 150 mM NaCl or KCl, pH 7.2-7.6, 5 mM divalent cation, and often include 0.01-1.0 percent nonspecific protein (e.g., BSA). A non-ionic detergent (Tween, NP-40, Triton X-100) can often be present, usually at about 0.001 to 2%, typically 0.05-0.2% (v/v). Particular aqueous conditions may be selected by the practitioner according to conventional methods. For general guidance, the following buffered aqueous conditions may be applicable: 10-250 mM NaCl, 5-50 mM Tris HCl, pH 5-8, with optional addition of divalent cation(s) and/or metal chelators and/or non-ionic detergents and/or membrane fractions and/or antifoam agents and/or scintillants.

Standard convention (5' to 3') is used herein to describe the sequence of double standed polynucleotides.

The term "population" as used herein means a collection of components such as polynucleotides, portions or polynucleotides or proteins. A "mixed population: means a collection of components which belong to the same family of nucleic acids or proteins (i.e., are related) but which differ in their sequence (i.e., are not identical) and hence in their biological activity.

A molecule having a "pro-form" refers to a molecule that undergoes any combination of one or more covalent and noncovalent chemical modifications (e.g. glycosylation, proteolytic cleavage, dimerization or oligomerization, temperature-induced or pH-induced conformational change, association with a co-factor, etc.) en route to attain a more mature molecular form having a property difference (e.g. an increase in activity) in comparison with the reference proform molecule. When two or more chemical modification (e.g. two proteolytic cleavages, or a proteolytic cleavage and a deglycosylation) can be distinguished en route to the production of a mature molecule, the referemce precursor molecule may be termed a "pre-pro-form" molecule.

As used herein, the term "pseudorandom" refers to a set of sequences that have limited variability, such that, for example, the degree of residue variability at another position, but any pseudorandom position is allowed some degree of residue variation, however circumscribed.

"Quasi-repeated units", as used herein, refers to the repeats to be re-assorted and are by definition not identical. Indeed the method is proposed not only for practically identical encoding units produced by mutagenesis of the identical starting sequence, but also the reassortment of similar or related sequences which may diverge significantly in some regions. Nevertheless, if the sequences contain sufficient homologies to be reasserted by this approach, they can be referred to as "quasi-repeated" units.

As used herein "random peptide library" refers to a set of polynucleotide sequences that encodes a set of random peptides, and to the set of random peptides encoded by those polynucleotide sequences, as well as the fusion proteins contain those random peptides.

As used herein, "random peptide sequence" refers to an amino acid sequence composed of two or more amino acid monomers and constructed by a stochastic or random process. A random peptide can include framework or scaffolding motifs, which may comprise invariant sequences.

As used herein, "receptor" refers to a molecule that has an affinity for a given ligand. Receptors can be naturally occurring or synthetic molecules. Receptors can be employed in an unaltered state or as aggregates with other species. Receptors can be attached, covalently or non-covalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, complex carbohydrates and glycoproteins, enzymes, and hormone receptors.

"Recombinant" enzymes refer to enzymes produced by recombinant DNA techniques, i.e., produced from cells transformed by an exogenous DNA construct encoding the desired enzyme. "Synthetic" enzymes are those prepared by chemical synthesis.

The term "related polynucleotides" means that regions or areas of the polynucleotides are identical and regions or areas of the polynucleotides are heterologous.

"Reductive reassortment", as used herein, refers to the increase in molecular diversity that is accrued through deletion (and/or insertion) events that are mediated by repeated sequences.

The following terms are used to describe the sequence relationships between two or more polynucleotides: "reference sequence," "comparison window," "sequence identity," "percentage of sequence identity," and "substantial identity."

A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

"Repetitive Index (RI)", as used herein, is the average number of copies of the quasi-repeated units contained in the cloning vector.

The term "restriction site" refers to a recognition sequence that is necessary for the manifestation of the action of a restriction enzyme, and includes a site of catalytic cleavage. It is appreciated that a site of cleavage may or may not be contained within a portion of a restriction site that comprises a low ambiguity sequence (i.e. a sequence containing the principal determinant of the frequency of occurrence of the restriction site). Thus, in many cases, relevant restriction sites contain only a low ambiguity sequence with an internal cleavage site (e.g. G/AATTC in the EcoR I site) or an immediately adjacent cleavage site (e.g. /CCWGG in the EcoR II site). In other cases, relevant restriction enzymes [e.g. the Eco57 I site or CTGAAG(16/14) (*SEQ ID NO: 24*)] contain a low ambiguity sequence (e.g. the CTGAAG sequence in the Eco57 I site) with an external cleavage site (e.g. in the $N_{16}$ portion of the Eco57 I site). When an enzyme (e.g. a restriction enzyme) is said to "cleave" a polynucleotide, it is understood to mean that the restriction enzyme catalyzes or facilitates a cleavage of a polynucleotide.

In a non-limiting aspect, a "selectable polynucleotide" is comprised of a 5' terminal region (or end region), an intermediate region (i.e. an internal or central region), and a 3' terminal region (or end region). As used in this aspect, a 5' terminal region is a region that is located towards a 5' polynucleotide terminus (or a 5' polynucleotide end); thus it is either partially or entirely in a 5' half of a polynucleotide. Likewise, a 3' terminal region is a region that is located towards a 3' polynucleotide terminus (or a 3' polynucleotide end); thus it is either partially or entirely in a 3' half of a polynucleotide. As used in this non-limiting exemplification, there may be sequence overlap between any two regions or even among all three regions.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. This "substantial identity", as used herein, denotes a characteristic of a polynucleotide sequence, wherein the polynucleotide comprises a sequence having at least 80 percent sequence identity, preferably at least 85 percent identity, often 90 to 95 percent sequence identity, and most commonly at least 99 percent sequence identity as compared to a reference sequence of a comparison window of at least 25-50 nucleotides, wherein the percentage of sequence identity is calculated by comparing the reference sequence to the polynucleotide sequence which may include deletions or additions which total 20 percent or less of the reference sequence over the window of comparison.

As known in the art "similarity" between two enzymes is determined by comparing the amino acid sequence and its conserved amino acid substitutes of one enzyme to the sequence of a second enzyme. Similarity may be determined by procedures which are well-known in the art, for example, a BLAST program (Basic Local Alignment Search Tool at the National Center for Biological Information).

As used herein, the term "single-chain antibody" refers to a polypeptide comprising a $V_H$ domain and a $V_L$ domain in polypeptide linkage, generall linked via a spacer peptide (e.g., $[\text{Gly-Gly-Gly-Gly-Ser}]_x$ (*SEQ ID NO: 25*)), and which may comprise additional amino acid sequences at the amino- and/or carboxy-termini. For example, a single-chain antibody may comprise a tether segment for linking to the encoding polynucleotide. As an example, a scFv is a single-chain antibody. Single-chain antibodies are generally proteins consisting of one or more polypeptide segments of at least 10 contiguous amino substantially encoded by genes of the immunoglobulin superfamily (e.g., see Williams and Barclay, 1989, pp. 361-368, which is incorporated herein by reference), most frequently encoded by a rodent, non-human primate, avian, porcine bovine, ovine, goat, or human heavy chain or light chain gene sequence. A functional single-chain antibody generally contains a sufficient portion of an immunoglobulin superfamily gene product so as to retain the property of binding to a specific target molecule, typically a receptor or antigen (epitope).

The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a non-specific protein can be described as specifically binding to the antigen. (Similarly, a nucleic acid probe can be described as specifically binding to a nucleic acid target if it forms a specific duplex with the target by base pairing interactions (see above).)

"Specific hybridization" is defined herein as the formation of hybrids between a first polynucleotide and a second polynucleotide (e.g., a polynucleotide having a distinct but substantially identical sequence to the first polynucleotide), wherein substantially unrelated polynucleotide sequences do not form hybrids in the mixture.

The term "specific polynucleotide" means a polynucleotide having certain end points and having a certain nucleic acid sequence. Two polynucleotides wherein one polynucleotide has the identical sequence as a portion of the second polynucleotide but different ends comprises two different specific polynucleotides.

"Stringent hybridization conditions" means hybridization will occur only if there is at least 90% identity, preferably at least 95% identity and most preferably at least 97% identity between the sequences. See Sambrook et al, 1989, which is hereby incorporated by reference in its entirety.

Also included in the invention are polypeptides having sequences that are "substantially identical" to the sequence of a phytase polypeptide, such as one of SEQ ID 1. A "substantially identical" amino acid sequence is a sequence that differs from a reference sequence only by conservative amino acid substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine).

Additionally a "substantially identical" amino acid sequence is a sequence that differs from a reference sequence or by one or more non-conservative substitutions, deletions, or insertions, particularly when such a substitution occurs at a site that is not the active site the molecule, and provided that the polypeptide essentially retains its behavioural properties. For example, one or more amino acids can be deleted from a phytase polypeptide, resulting in modification of the structure of the polypeptide, without significantly altering its biological activity. For example, amino- or carboxyl-terminal amino acids that are not required for phytase biological activity can be removed. Such modifications can result in the development of smaller active phytase polypeptides.

The present invention provides a "substantially pure enzyme". The term "substantially pure enzyme" is used herein to describe a molecule, such as a polypeptide (e.g., a phytase polypeptide, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. The purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

As used herein, "substantially pure" means an object species is the predominant species present (i.e., on a molar basis it is more abundant than any other individual macromolecular species in the composition), and preferably substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

As used herein, the term "variable segment" refers to a portion of a nascent peptide which comprises a random, pseudorandom, or defined kernal sequence. A variable segment" refers to a portion of a nascent peptide which comprises a random pseudorandom, or defined kernal sequence. A variable segment can comprise both variant and invariant residue positions, and the degree of residue variation at a variant residue position may be limited: both options are selected at the discretion of the practitioner. Typically, variable segments are about 5 to 20 amino acid residues in length (e.g., 8 to 10), although variable segments may be longer and may comprise antibody portions or receptor proteins, such as an antibody fragment, a nucleic acid binding protein, a receptor protein, and the like.

The term "wild-type" means that the polynucleotide does not comprise any mutations. A "wild type" protein means that the protein will be active at a level of activity found in nature and will comprise the amino acid sequence found in nature.

The term "working", as in "working sample", for example, is simply a sample with which one is working. Likewise, a "working molecule", for example is a molecule with which one is working.

DETAILED DESCRIPTION OF THE INVENTION

The invention described herein is directed to the use of repeated cycles of reductive reassortment, recombination and selection which allow for the directed molecular evolution of highly complex linear sequences, such as DNA, RNA or proteins thorough recombination.

In vivo shuffling of molecules can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In a preferred embodiment, the invention relates to a method for producing a hybrid polynucleotide from at least a first polynucleotide and a second polynucleotide. The present invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

The invention provides a means for generating hybrid polynucleotides which may encode biologically active hybrid polypeptides. In one aspect, the original polynucleotides encode biologically active polypeptides. The method of the invention produces new hybrid polypeptides by utilizing cellular processes which integrate the sequence of the original polynucleotides such that the resulting hybrid polynucleotide encodes a polypeptide demonstrating activities derived from the original biologically active polypeptides. For example, the original polynucleotides may encode a particular enzyme from different microorganisms. An enzyme encoded by a first polynucleotide from one organism may, for example, function effectively under a particular environmental condition, e.g. high salinity. An enzyme encoded by a second polynucleotide from a different organism may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

Enzymes encoded by the original polynucleotides of the invention include, but are not limited to; oxidoreductases, transferases, hydrolases, lyases, isomerases and ligases. A hybrid polypeptide resulting from the method of the invention may exhibit specialized enzyme activity not displayed in the original enzymes. For example, following recombination and/or reductive reassortment of polynucleotides encoding hydrolase activities, the resulting hybrid polypeptide encoded by a hybrid polynucleotide can be screened for specialized hydrolase activities obtained from each of the original enzymes, i.e. the type of bond on which the hydrolase acts and the temperature at which the hydrolase functions. Thus, for example, the hydrolase may be screened to ascertain those chemical functionalities which distinguish the hybrid hydrolase from the original hydrolyases, such as: (a) amide (peptide bonds), i.e. proteases; (b) ester bonds, i.e. esterases and lipases; (c) acetals, i.e., glycosidases and, for example, the temperature, pH or salt concentration at which the hybrid polypeptide functions.

Sources of the original polynucleotides may be isolated from individual organisms ("isolates"), collections of organisms that have been grown in defined media ("enrichment cultures"), or, most preferably, uncultivated organisms ("environmental samples"). The use of a culture-independent approach to derive polynucleotides encoding novel bioactivities from environmental samples is most preferable since it allows one to access untapped resources of biodiversity.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

For example, gene libraries generated from one or more uncultivated microorganisms are screened for an activity of interest. Potential pathways encoding bioactive molecules of interest are first captured in prokaryotic cells in the form of gene expression libraries. Polynucleotides encoding activities of interest are isolated from such libraries and introduced into a host cell. The host cell is grown under conditions which promote recombination and/or reductive reassortment creating potentially active biomolecules with novel or enhanced activities.

The microorganisms from which the polynucleotide may be prepared include prokaryotic microorganisms, such as Eubacteria and Archaebacteria, and lower eukaryotic microorganisms such as fungi, some algae and protozoa. Polynucleotides may be isolated from environmental samples in which case the nucleic acid may be recovered without culturing of an organism or recovered from one or more cultured organisms. In one aspect, such microorganisms may be extremophiles, such as hyperthermophiles, psychrophiles, psychrotrophs, halophiles, barophiles and acidophiles. Polynucleotides encoding enzymes isolated from extremophilic microorganisms are particularly preferred. Such enzymes may function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. For example, several esterases and lipases cloned and expressed from extremophilic organisms show high activity throughout a wide range of temperatures and pHs.

Polynucleotides selected and isolated as hereinabove described are introduced into a suitable host cell. A suitable host cell is any cell which is capable of promoting recombination and/or reductive reassortment. The selected polynucleotides are preferably already in a vector which includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (Davis et al, 1986).

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma; adenoviruses; and plant cells. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described in "SV40-transformed simian cells support the replication of early SV40 mutants" (Gluzman, 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan. The clones which are identified as having the specified enzyme activity may then be sequenced to identify the polynucleotide sequence encoding an enzyme having the enhanced activity.

In another aspect, it is envisioned the method of the present invention can be used to generate novel polynucleotides encoding biochemical pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. Thus, a gene cluster is a group of adjacent genes that are either identical or related, usually as to their function. An example of a biochemical pathway encoded by gene clusters are polyketides. Polyketides are molecules which are an extremely rich source of bioactivities, including antibiotics (such as tetracyclines and erythromycin), anticancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of an enormous variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins.

The ability to select and combine desired components from a library of polyketides, or fragments thereof, and post-polyketide biosynthesis genes for generation of novel polyketides for study is appealing. The method of the present invention makes it possible to facilitate the production of novel polyketide synthases through intermolecular recombination.

Preferably, gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of E. coli. This f-factor of E. coli is a plasmid which affect high-frequency transfer of itself during conjugation and is ideal to achieve and stably propagate large DNA fragments, such as gene clusters from mixed microbial samples. Once ligated into an appropriate vector, two or more vectors containing different polyketide synthase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Therefore, in a preferred embodiment, the present invention relates to a method for producing a biologically active hybrid polypeptide and screening such a polypeptide for enhanced activity by:

1) introducing at least a first polynucleotide in operable linkage and a second polynucleotide in operable linkage, said at least first polynucleotide and second polynucleotide sharing at least one region of partial sequence homology, into a suitable host cell;
2) growing the host cell under conditions which promote sequence reorganization resulting in a hybrid polynucleotide in operable linkage;
3) expressing a hybrid polypeptide encoded by the hybrid polynucleotide;
4) screening the hybrid polypeptide under conditions which promote identification of enhanced biological activity; and
5) isolating the a polynucleotide encoding the hybrid polypeptide.

Methods for screening for various enzyme activities are known to those of skill in the art and discussed throughout the present specification. Such methods may be employed when isolating the polypeptides and polynucleotides of the present invention.

As representative examples of expression vectors which may be used there may be mentioned viral particles, baculovirus, phage, plasmids, phagemids, cosmids, fosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus and yeast). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSV-LSV40 (Pharmacia). However, any other plasmid or other vector may be used as long as they are replicable and viable in the host. Low copy number or high copy number vectors may be employed with the present invention.

A preferred type of vector for use in the present invention contains an f-factor origin replication. The f-factor (or fertility factor) in E. coli is a plasmid which effects high frequency transfer of itself during conjugation and less frequent transfer of the bacterial chromosome itself. A particularly preferred embodiment is to use cloning vectors, referred to as "fosmids" or bacterial artificial chromosome (BAC) vectors. These are derived from E. coli f-factor which is able to stably integrate large segments of genomic DNA. When integrated with DNA from a mixed uncultured environmental sample, this makes it possible to achieve large genomic fragments in the form of a stable "environmental DNA library."

Another preferred type of vector for use in the present invention is a cosmid vector. Cosmid vectors were originally designed to clone and propagate large segments of genomic DNA. Cloning into cosmid vectors is described in detail in "Molecular Cloning: A laboratory Manual" (Sambrook et al, 1989).

The DNA sequence in the expression vector is operatively linked to an appropriate expression control sequence(s) (promoter) to direct RNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium.

The cloning strategy permits expression via both vector driven and endogenous promoters; vector promotion may be important with expression of genes whose endogenous promoter will not function in E. coli.

The DNA isolated or derived from microorganisms can preferably be inserted into a vector or a plasmid prior to probing for selected DNA. Such vectors or plasmids are preferably those containing expression regulatory sequences, including promoters, enhancers and the like. Such polynucleotides can be part of a vector and/or a composition and still be isolated, in that such vector or composition is not part of its natural environment. Particularly preferred phage or plasmid and methods for introduction and packaging into them are described in detail in the protocol set forth herein.

The selection of the cloning vector depends upon the approach taken, for example, the vector can be any cloning vector with an adequate capacity to multiply repeated copies of a sequence, or multiple sequences that can be successfully transformed and selected in a host cell. One example of such a vector is described in "Polycos vectors: a system for packaging filamentous phage and phagemid vectors using lambda phage packaging extracts" (Alting-Mecs and Short, 1993). Propagation/maintenance can be by an antibiotic resistance carried by the cloning vector. After a period of growth, the naturally abbreviated molecules are recovered and identified by size fractionation on a gel or column, or amplified directly. The cloning vector utilized may contain a selectable gene that is disrupted by the insertion of the lengthy construct. As reductive reassortment progresses, the number of repeated units is reduced and the interrupted gene is again expressed and hence selection for the processed construct can be applied. The vector may be an expression/selection vector which will allow for the selection of an expressed product possessing desirable biologically properties. The insert may be positioned downstream of a functional promotor and the desirable property screened by appropriate means.

In vivo reassortment is focused on "inter-molecular" processes collectively referred to as "recombination" which in bacteria, is generally viewed as a "RecA-dependent" phenomenon. The present invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process.

Therefore, in another aspect of the present invention, novel polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassertment process recombines and/or reduces the complexity and extent of the repeated sequences, and results in the production of novel molecular species. Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. In the present invention, "quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units.

When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, it is preferable with the present method that the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following:

a) Primers that include a poly-A head and poly-T tail which when made single-stranded would provide orientation can be utilized. This is accomplished by having the first few bases of the primers made from RNA and hence easily removed RNAseH.

b) Primers that include unique restriction cleavage sites can be utilized. Multiple sites, a battery of unique sequences, and repeated synthesis and ligation steps would be required.

c) The inner few bases of the primer could be thiolated and an exonuclease used to produce properly tailed molecules.

The recovery of the re-assorted sequences relies on the identification of cloning vectors with a reduced RI. The re-assorted encoding sequences can then be recovered by amplification. The products are re-cloned and expressed. The recovery of cloning vectors with reduced RI can be effected by:

1) The use of vectors only stably maintained when the construct is reduced in complexity.

2) The physical recovery of shortened vectors by physical procedures. In this case, the cloning vector would be recovered using standard plasmid isolation procedures and size fractionated on either an agarose gel, or column with a low molecular weight cut off utilizing standard procedures.
3) The recovery of vectors containing interrupted genes which can be selected when insert size decreases.
4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, while the examples illustrated below demonstrate the reassortment of nearly identical original encoding sequences (quasi-repeats), this process is not limited to such nearly identical repeats.

The following example demonstrates the method of the invention. Encoding nucleic acid sequences (quasi-repeats) derived from three (3) unique species are depicted. Each sequence encodes a protein with a distinct set of properties. Each of the sequences differs by a single or a few base pairs at a unique position in the sequence which are designated "A", "B" and "C". The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI).

Once formed, the constructs may, or may not be size fractionated on an agarose gel according to published protocols, inserted into a cloning vector, and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intramolecular" mechanism, or mediated by recombination-like events through "inter-molecular" mechanisms is immaterial. The end result is a reassortment of the molecules into all possible combinations.

Optionally, the method comprises the additional step of screening the library members of the shuffled pool to identify individual shuffled library members having the ability to bind or otherwise interact (e.g., such as catalytic antibodies) with a predetermined macromolecule, such as for example a proteinaceous receptor, peptide oligosaccharide, viron, or other predetermined compound or structure.

The displayed polypeptides, antibodies, peptidomimetic antibodies, and variable region sequences that are identified from such libraries can be used for therapeutic, diagnostic, research and related purposes (e.g., catalysts, solutes for increasing osmolarity of an aqueous solution, and the like), and/or can be subjected to one or more additional cycles of shuffling and/or affinity selection. The method can be modified such that the step of selecting for a phenotypic characteristic can be other than of binding affinity for a predetermined molecule (e.g., for catalytic activity, stability oxidation resistance, drug resistance, or detectable phenotype conferred upon a host cell).

The present invention provides a method for generating libraries of displayed antibodies suitable for affinity interactions screening. The method comprises (1) obtaining first a plurality of selected library members comprising a displayed antibody and an associated polynucleotide encoding said displayed antibody, and obtaining said associated polynucleotide encoding for said displayed antibody and obtaining said associated polynucleotides or copies thereof, wherein said associated polynucleotides comprise a region of substantially identical variable region framework sequence, and (2) introducing said polynucleotides into a suitable host cell and growing the cells under conditions which promote recombination and reductive reassortment resulting in shuffled polynucleotides. CDR combinations comprised by the shuffled pool are not present in the first plurality of selected library members, said shuffled pool composing a library of displayed antibodies comprising CDR permutations and suitable for affinity interaction screening. Optionally, the shuffled pool is subjected to affinity screening to select shuffled library members which bind to a predetermined epitope (antigen) and thereby selecting a plurality of selected shuffled library members. Further, the plurality of selectively shuffled library members can be shuffled and screened iteratively, from 1 to about 1000 cycles or as desired until library members having a desired binding affinity are obtained.

In another aspect of the invention, it is envisioned that prior to or during recombination or reassortment, polynucleotides generated by the method of the present invention can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N3-Adenine, see Sun and Hurley, 1992); an N-acelylated or deacetylated 4'-fluro-4-aminobiphenyl adduct capable of inhibiting DNA synthesis (see, for example, van de Poll et al, 1992); or a N-acetylated or deacetylated 4-aminobiphenyl adduct capable of inhibiting DNA synthesis (see also, van de Poll et al, 1992, pp. 751-758); trivalent chromium, a trivalent chromium salt, a polycyclic aromatic hydrocarbon ("PAH") DNA adduct capable of inhibiting DNA replication, such as 7-bromomethyl-benz[a]anthracene ("BMA"), tris(2,3-dibromopropyl)phosphate ("Tris-BP"), 1,2-dibromo-3-chloropropane ("DBCP"), 2-bromoacrolein (2BA), benzo[a]pyrene-7,8-dihydrodiol-9-10-epoxide ("BPDE"), a platinum(II) halogen salt, N-hydroxy-2-amino-3-methylimidazo[4,5-f]-quinoline ("N-hydroxy-IQ"), and N-hydroxy-2-amino-1-methyl-6-phenylimidazo[4,5-f]-pyridine ("N-hydroxy-PhIP"). Especially preferred "means for slowing or halting PCR amplification consist of UV light (+)-CC-1065 and (+)-CC-1065-(N3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

In another aspect the present invention is directed to a method of producing recombinant proteins having biological activity by treating a sample comprising double-stranded template polynucleotides encoding a wild-type protein under conditions according to the present invention which provide for the production of hybrid or re-assorted polynucleotides.

The invention also provides the use of polynucleotide shuffling to shuffle a population of viral genes (e.g., capsid proteins, spike glycoproteins, polymerases, and proteases) or viral genomes (e.g., paramyxoviridae, orthomyxoviridae, herpesviruses, retroviruses, reoviruses and rhinoviruses). In an embodiment, the invention provides a method for shuffling sequences encoding all or portions of immunogenic viral proteins to generate novel combinations of epitopes as well as novel epitopes created by recombination; such shuffled viral proteins may comprise epitopes or combinations of epitopes as well as novel epitopes created by recombination; such shuffled viral proteins may comprise epitopes or combinations of epitopes which are likely to arise in the natural environment as a consequence of viral evolution; (e.g., such as recombination of influenza virus strains).

The invention also provides a method suitable for shuffling polynucleotide sequences for generating gene therapy vectors and replication-defective gene therapy constructs, such as may be used for human gene therapy, including but not limited to vaccination vectors for DNA-based vaccination, as well as anti-neoplastic gene therapy and other general therapy formats.

In the polypeptide notation used herein, the left-hand direction is the amino terminal direction and the right-hand direction is the carboxy-terminal direction, in accordance with standard usage and convention. Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the coding RNA transcript are referred to as "downstream sequences".

Methodology

Nucleic acid shuffling is a method for in vitro or in vivo homologous recombination of pools of shorter or smaller polynucleotides to produce a polynucleotide or polynucleotides. Mixtures of related nucleic acid sequences or polynucleotides are subjected to sexual PCR to provide random polynucleotides, and reassembled to yield a library or mixed population of recombinant hybrid nucleic acid molecules or polynucleotides.

In contrast to cassette mutagenesis, only shuffling and error-prone PCR allow one to mutate a pool of sequences blindly (without sequence information other than primers).

The advantage of the mutagenic shuffling of this invention over error-prone PCR alone for repeated selection can best be explained with an example from antibody engineering. Consider DNA shuffling as compared with error-prone PCR (not sexual PCR). The initial library of selected pooled sequences can consist of related sequences of diverse origin (i.e. antibodies from naive mRNA) or can be derived by any type of mutagenesis (including shuffling) of a single antibody gene. A collection of selected complementarity determining regions ("CDRs") is obtained after the first round of affinity selection. [In the diagram the thick] *The* CDRs confer onto the antibody molecule increased affinity for the antigen. Shuffling allows the free combinatorial association of all of the CDR1s with all of the CDR2s with all of the CDR3s, for example.

This method differs from error-prone PCR, in that it is an inverse chain reaction. In error-prone PCR, the number of polymerase start sites and the number of molecules grows exponentially. However, the sequence of the polymerase start sites and the sequence of the molecules remains essentially the same. In contrast, in nucleic acid reassembly or shuffling of random polynucleotides the number of start sites and the number (but not size) of the random polynucleotides decreases over time. For polynucleotides derived from whole plasmids the theoretical endpoint is a single, large concatemeric molecule.

Since cross-overs occur at regions of homology, recombination will primarily occur between members of the same sequence family. This discourages combinations of CDRs that are grossly incompatible (e.g., directed against different epitopes of the same antigen). It is contemplated that multiple families of sequences can be shuffled in the same reaction. Further, shuffling generally conserves the relative order, such that, for example, CDR1 will not be found in the position of CDR2.

Rare shufflants will contain a large number of the best (eg. highest affinity) CDRs and these rare shufflants may be selected based on their superior affinity.

CDRs from a pool of 100 different selected antibody sequences can be permutated in up to $100^6$ different ways. This large number of permutations cannot be represented in a single library of DNA sequences. Accordingly, it is contemplated that multiple cycles of DNA shuffling and selection may be required depending on the length of the sequence and the sequence diversity desired.

Error-prone PCR, in contrast, keeps all the selected CDRs in the same relative sequence, generating a much smaller mutant cloud.

The template polynucleotide which may be used in the methods of this invention may be DNA or RNA. It may be of various lengths depending on the size of the gene or shorter or smaller polynucleotide to be recombined or reassembled. Preferably, the template polynucleotide is from 50 by to 50 kb. It is contemplated that entire vectors containing the nucleic acid encoding the protein of interest can be used in the methods of this invention, and in fact have been successfully used.

The template polynucleotide may be obtained by amplification using the PCR reaction (U.S. Pat. No. 4,683,202 and U.S. Pat. No. 4,683,195) or other amplification or cloning methods. However, the removal of free primers from the PCR products before subjecting them to pooling of the PCR products and sexual PCR may provide more efficient results. Failure to adequately remove the primers from the original pool before sexual PCR can lead to a low frequency of cross-over clones.

The template polynucleotide often should be double-stranded. A double-stranded nucleic acid molecule is recommended to ensure that regions of the resulting single-stranded polynucleotides are complementary to each other and thus can hybridize to form a double-stranded molecule.

It is contemplated that single-stranded or double-stranded nucleic acid polynucleotides having regions of identity to the template polynucleotide and regions of heterology to the template polynucleotide may be added to the template polynucleotide, at this step. It is also contemplated that two different but related polynucleotide templates can be mixed at this step.

The double-stranded polynucleotide template and any added double- or single-stranded polynucleotides are subjected to sexual PCR which includes slowing or halting to provide a mixture of from about 5 bp to 5 kb or more. Preferably the size of the random polynucleotides is from about 10 bp to 1000 bp, more preferably the size of the polynucleotides is from about 20 bp to 500 bp.

Alternatively, it is also contemplated that double-stranded nucleic acid having multiple nicks may be used in the methods of this invention. A nick is a break in one strand of the double-stranded nucleic acid. The distance between such nicks is preferably 5 bp to 5 kb, more preferably between 10 bp to 1000 bp. This can provide areas of self-priming to produce shorter or smaller polynucleotides to be included with the polynucleotides resulting from random primers, for example.

The concentration of any one specific polynucleotide will not be greater than 1% by weight of the total polynucleotides, more preferably the concentration of any one specific nucleic acid sequence will not be greater than 0.1% by weight of the total nucleic acid.

The number of different specific polynucleotides in the mixture will be at least about 100, preferably at least about 500, and more preferably at least about 1000.

At this step single-stranded or double-stranded polynucleotides, either synthetic or natural, may be added to the random double-stranded shorter or smaller polynucleotides in order to increase the heterogeneity of the mixture of polynucleotides.

It is also contemplated that populations of double-stranded randomly broken polynucleotides may be mixed or combined at this step with the polynucleotides from the sexual PCR process and optionally subjected to one or more additional sexual PCR cycles.

Where insertion of mutations into the template polynucleotide is desired, single-stranded or double-stranded polynucleotides having a region of identity to the template polynucleotide and a region of heterology to the template polynucleotide may be added in a 20 fold excess by weight as compared to the total nucleic acid, more preferably the single-stranded polynucleotides may be added in a 10 fold excess by weight as compared to the total nucleic acid.

Where a mixture of different but related template polynucleotides is desired, populations of polynucleotides from each of the templates may be combined at a ratio of less than about 1:100, more preferably the ratio is less than about 1:40. For example, a backcross of the wild-type polynucleotide with a population of mutated polynucleotide may be desired to eliminate neutral mutations (e.g., mutations yielding an insubstantial alteration in the phenotypic property being selected for). In such an example, the ratio of randomly provided wild-type polynucleotides which may be added to the randomly provided sexual PCR cycle hybrid polynucleotides is approximately 1:1 to about 100:1, and more preferably from 1:1 to 40:1.

The mixed population of random polynucleotides are denatured to form single-stranded polynucleotides and then re-annealed. Only those single-stranded polynucleotides having regions of homology with other single-stranded polynucleotides will re-anneal.

The random polynucleotides may be denatured by heating. One skilled in the art could determine the conditions necessary to completely denature the double-stranded nucleic acid. Preferably the temperature is from 80° C. to 100° C., more preferably the temperature is from 90° C. to 96° C. other methods which may be used to denature the polynucleotides include pressure (36) and pH.

The polynucleotides may be re-annealed by cooling. Preferably the temperature is from 20° C. to 75° C., more preferably the temperature is from 40° C. to 65° C. If a high frequency of crossovers is needed based on an average of only 4 consecutive bases of homology, recombination can be forced by using a low annealing temperature, although the process becomes more difficult. The degree of renaturation which occurs will depend on the degree of homology between the population of single-stranded polynucleotides.

Renaturation can be accelerated by the addition of polyethylene glycol ("PEG") or salt. The salt concentration is preferably from 0 mM to 200 mM, more preferably the salt concentration is from 10 mM to 100 mm. The salt may be KCl or NaCl. The concentration of PEG is preferably from 0% to 20%, more preferably from 5% to 10%.

The annealed polynucleotides are next incubated in the presence of a nucleic acid polymerase and dNTP's (i.e. dATP, dCTP, DGTP and dTTP). The nucleic acid polymerase may be the Klenow fragment, the Taq polymerase or any other DNA polymerase known in the art.

The approach to be used for the assembly depends on the minimum degree of homology that should still yield cross-overs. If the areas of identity are large, Taq polymerase can be used with an annealing temperature of between 45-65° C. If the areas of identity are small, Klenow polymerase can be used with an annealing temperature of between 20-30° C. One skilled in the art could vary the temperature of annealing to increase the number of cross-overs achieved.

The polymerase may be added to the random polynucleotides prior to annealing, simultaneously with annealing or after annealing.

The cycle of denaturation, renaturation and incubation in the presence of polymerase is referred to herein as shuffling or reassembly of the nucleic acid. This cycle is repeated for a desired number of times. Preferably the cycle is repeated from 2 to 50 times, more preferably the sequence is repeated from 10 to 40 times.

The resulting nucleic acid is a larger double-stranded polynucleotide of from about 50 bp to about 100 kb, preferably the larger polynucleotide is from 500 bp to 50 kb.

This larger polynucleotide may contain a number of copies of a polynucleotide having the same size as the template polynucleotide in tandem. This concatemeric polynucleotide is then denatured into single copies of the template polynucleotide. The result will be a population of polynucleotides of approximately the same size as the template polynucleotide. The population will be a mixed population where single or double-stranded polynucleotides having an area of identity and an area of heterology have been added to the template polynucleotide prior to shuffling.

These polynucleotides are then cloned into the appropriate vector and the ligation mixture used to transform bacteria.

It is contemplated that the single polynucleotides may be obtained from the larger concatemeric polynucleotide by amplification of the single polynucleotide prior to cloning by a variety of methods including PCR (U.S. Pat. No. 4,683,195 and U.S. Pat. No. 4,683,202), rather than by digestion of the concatemer.

The vector used for cloning is not critical provided that it will accept a polynucleotide of the desired size. If expression of the particular polynucleotide is desired, the cloning vehicle should further comprise transcription and translation signals next to the site of insertion of the polynucleotide to allow expression of the polynucleotide in the host cell. Preferred vectors include the pUC series and the pBR series of plasmids.

The resulting bacterial population will include a number of recombinant polynucleotides having random mutations. This mixed population may be tested to identify the desired recombinant polynucleotides. The method of selection will depend on the polynucleotide desired.

For example, if a polynucleotide which encodes a protein with increased binding efficiency to a ligand is desired, the proteins expressed by each of the portions of the polynucleotides in the population or library may be tested for their ability to bind to the ligand by methods known in the art (i.e. panning, affinity chromatography). If a polynucleotide which encodes for a protein with increased drug resistance is desired, the proteins expressed by each of the polynucleotides in the population or library may be tested for their ability to confer drug resistance to the host organism. One skilled in the art, given knowledge of the desired protein, could readily test the population to identify polynucleotides which confer the desired properties onto the protein.

It is contemplated that one skilled in the art could use a phage display system in which fragments of the protein are expressed as fusion proteins on the phage surface (Pharmacia, Milwaukee Wis.). The recombinant DNA molecules are cloned into the phage DNA at a site which results in the transcription of a fusion protein a portion of which is encoded by the recombinant DNA molecule. The phage containing the recombinant nucleic acid molecule undergoes replication and transcription in the cell. The leader sequence of the fusion protein directs the transport of the fusion protein to the tip of the phage particle. Thus the fusion protein which is partially encoded by the recombinant DNA molecule is displayed on the phage particle for detection and selection by the methods described above.

It is further contemplated that a number of cycles of nucleic acid shuffling may be conducted with polynucleotides from a sub-population of the first population, which sub-population contains DNA encoding the desired recombinant protein. In this manner, proteins with even higher binding affinities or enzymatic activity could be achieved.

It is also contemplated that a number of cycles of nucleic acid shuffling may be conducted with a mixture of wild-type polynucleotides and a sub-population of nucleic acid from the first or subsequent rounds of nucleic acid shuffling in order to remove any silent mutations from the sub-population.

Any source of nucleic acid, in purified form can be utilized as the starting nucleic acid. Thus the process may employ DNA or RNA including messenger RNA, which DNA or RNA may be single or double stranded. In addition, a DNA-RNA hybrid which contains one strand of each may be utilized. The nucleic acid sequence may be of various lengths depending on the size of the nucleic acid sequence to be mutated. Preferably the specific nucleic acid sequence is from 50 to 50000 base pairs. It is contemplated that entire vectors containing the nucleic acid encoding the protein of interest may be used in the methods of this invention.

The nucleic acid may be obtained from any source, for example, from plasmids such a pBR322, from cloned DNA or RNA or from natural DNA or RNA from any source including bacteria, yeast, viruses and higher organisms such as plants or animals. DNA or RNA may be extracted from blood or tissue material. The template polynucleotide may be obtained by amplification using the polynucleotide chain reaction (PCR, see U.S. Pat. No. 4,683,202 and U.S. Pat. No. 4,683,195). Alternatively, the polynucleotide may be present in a vector present in a cell and sufficient nucleic acid may be obtained by culturing the cell and extracting the nucleic acid from the cell by methods known in the art.

Any specific nucleic acid sequence can be used to produce the population of hybrids by the present process. It is only necessary that a small population of hybrid sequences of the specific nucleic acid sequence exist or be created prior to the present process.

The initial small population of the specific nucleic acid sequences having mutations may be created by a number of different methods. Mutations may be created by error-prone PCR. Error-prone PCR uses low-fidelity polymerization conditions to introduce a low level of point mutations randomly over a long sequence. Alternatively, mutations can be introduced into the template polynucleotide by oligonucleotide-directed mutagenesis. In oligonucleotide-directed mutagenesis, a short sequence of the polynucleotide is removed from the polynucleotide using restriction enzyme digestion and is replaced with a synthetic polynucleotide in which various bases have been altered from the original sequence. The polynucleotide sequence can also be altered by chemical mutagenesis. Chemical mutagens include, for example, sodium bisulfite, nitrous acid, hydroxylamine, hydrazine or formic acid. other agents which are analogues of nucleotide precursors include nitrosoguanidine, 5-bromouracil, 2-aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X-rays or ultraviolet light. Generally, plasmid polynucleotides so mutagenized are introduced into E. coli and propagated as a pool or library of hybrid plasmids.

Alternatively the small mixed population of specific nucleic acids may be found in nature in that they may consist of different alleles of the same gene or the same gene from different related species (i.e., cognate genes). Alternatively, they may be related DNA sequences found within one species, for example, the immunoglobulin genes.

Once the mixed population of the specific nucleic acid sequences is generated, the polynucleotides can be used directly or inserted into an appropriate cloning vector, using techniques well-known [in,the] *in the* art.

The choice of vector depends on the size of the polynucleotide sequence and the host cell to be employed in the methods of this invention. The templates of this invention may be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids are preferred where the specific nucleic acid sequence to be mutated is larger because these vectors are able to stably propagate large polynucleotides.

If the mixed population of the specific nucleic acid sequence is cloned into a vector it can be clonally amplified by inserting each vector into a host cell and allowing the host cell to amplify the vector. This is referred to as clonal amplification because while the absolute number of nucleic acid sequences increases, the number of hybrids does not increase. Utility can be readily determined by screening expressed polypeptides.

The DNA shuffling method of this invention can be performed blindly on a pool of unknown sequences. By adding to the reassembly mixture oligonucleotides (with ends that are homologous to the sequences being reassembled) any sequence mixture can be incorporated at any specific position into another sequence mixture. Thus, it is contemplated that mixtures of synthetic oligonucleotides, PCR polynucleotides or even whole genes can be mixed into another [sequence. library] *sequence library* at defined positions. The insertion of one sequence (mixture) is independent from the insertion of a sequence in another part of the template. Thus, the degree of recombination, the homology required, and the diversity of the library can be independently and simultaneously varied along the length of the reassembled DNA.

This approach of mixing two genes may be useful for the humanization of antibodies from murine hybridomas. The approach of mixing two genes or inserting alternative sequences into genes may be useful for any therapeutically used protein, for example, interleukin I, antibodies, tPA and growth hormone. The approach may also be useful in any nucleic acid for example, promoters or introns or 31 untranslated region or 51 untranslated regions of genes to increase expression or alter specificity of expression of proteins. The approach may also be used to mutate ribozymes or aptamers.

Shuffling requires the presence of homologous regions separating regions of diversity. Scaffold-like protein structures may be particularly suitable for shuffling. The conserved scaffold determines the overall folding by self-association, while displaying relatively unrestricted loops that mediate the specific binding. Examples of such scaffolds are the immunoglobulin beta-barrel, and the four-helix bundle which are well-known in the art. This shuffling can be used to create scaffold-like proteins with various combinations of mutated sequences for binding.

Saturation Mutagenesis

In one aspect, this invention provides for the use of proprietary codon primers (containing a degenerate N,N,G/T sequence) to introduce point mutations into a polynucleotide, so as to generate a set of progeny polypeptides in which a full range of single amino acid substitutions is represented at each amino acid position. The oligos used are comprised contiguously of a first homologous sequence, a degenerate N,N,G/T sequence, and preferably but not necessarily a second homologous sequence. The downstream progeny translational products from the use of such oligos include all possible amino acid changes at each amino acid site along the polypeptide, because the degeneracy of the N,N,G/T sequence includes codons for all 20 amino acids.

In one aspect, one such degenerate oligo (comprised of one degenerate N,N,G/T cassette) is used for subjecting each original codon in a parental polynucleotide template to a full range of codon substitutions. In another aspect, at least two degenerate N,N,G/T cassettes are used—either in the same oligo or not, for subjecting at least two original codons in a parental polynucleotide template to a full range of codon substitutions. Thus, more than one N,N,G/T sequence can be contained in one oligo to introduce amino acid mutations at more than one site. This plurality of N,N,G/T sequences can be directly contiguous, or separated by one or more additional nucleotide sequence(s). In another aspect, oligos serviceable for introducing additions and deletions can be used either alone or in combination with the codons containing an N,N, G/T sequence, to introduce any combination or permutation of amino acid additions, deletions, and/or substitutions.

In a particular exemplification, it is possible to simultaneously mutagenize two or more contiguous amino acid Positions using an oligo that contains contiguous N,N,G/T triplets, i.e. a degenerate (N,N,G/T)N sequence.

In another aspect, the present invention provides for the use of degenerate cassettes having less degeneracy than the N,N, G/T sequence. For example, it may be desirable in some instances to use (e.g. in an oligo) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g. in an oligo) a degenerate N,N,N triplet sequence, or an N,N, G/C triplet sequence.

It is appreciated, however, that the use of a degenerate triplet (such as N,N,G/T or an N,N, G/C triplet sequence) as disclosed in the instant invention is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the instant invention provides a way to systematically and fairly easily generate 2000 distinct species (i.e. 20 possible amino acids per position×100 amino acid positions). It is appreciated that there is provided, through the use of an oligo containing a degenerate N,N,G/T or an N,N, G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can optionally be used in combination with degenerate primers disclosed. It is appreciated that in some situations, it is advantageous to use nondegenerate oligos to generate specific point mutations in a working polynucleotide. This provides a means to generate specific silent point mutations, point mutations leading to corresponding amino acid changes, and point mutations that cause the generation of stop codons and the corresponding expression of polypeptide fragments.

Thus, in a preferred embodiment of this invention, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g. cloned into a suitable E. Coli host using an expression vector) and subjected to expression screening. When an individual progeny polypeptide is identified by screening to display a favorable change in property (when compared to the parental polypeptide), it can be sequenced to identify the correspondingly favorable amino acid substitution contained therein.

It is appreciated that upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined —6 single point mutations (i.e. 2 at each of three positions) and no change at any position.

In yet another aspect, site-saturation mutagenesis can be used together with shuffling, chimerization, recombination and other mutagenizing processes, along with screening. This invention provides for the use of any mutagenizing process(es), including saturation mutagenesis, in an iterative manner. In one exemplification, the iterative use of any mutagenizing process(es) is used in combination with screening.

Thus, in a non-limiting exemplification, this invention provides for the use of saturation mutagenesis in combination with additional mutagenization processes, such as a process where two or more related polynucleotides are introduced into a suitable host cell such that a hybrid polynucleotide is generated by recombination and reductive reassortment.

In addition to performing mutagenesis along the entire sequence of a gene, the instant invention provides that mutagenesis can be use to replace each of any number of bases in a polynucleotide sequence, wherein the number of bases to be mutagenized is preferably every integer from 15 to 100,000. Thus, instead of mutagenizing every position along a molecule, one can subject every a discrete number of bases (preferably a subset totaling from 15 to 100,000) to mutagenesis. Preferably, a separate nucleotide is used for mutagenizing each position or group of positions along a polynucleotide sequence. A group of 3 positions to be mutagenized may be a codon. The mutations are preferably introduced using a mutagenic primer, containing a heterologous cassette, also referred to as a mutagenic cassette. Preferred cassettes can have from 1 to 500 bases. Each nucleotide position in such heterologous cassettes be N, A, C, G, T, A/C, NG, A/T, C/G, G/T, C/G/T, A/G/T, A/C/T, A/C/G, or E, where E is any base that is not A, C, G, or T (E can be referred to as a designer oligo). The tables below show exemplary tri-nucleotide cassettes (there are over 3000 possibilities in addition to N,N, G/T and N,N,N and N,N,A/C).

In a general sense, saturation mutagenesis is comprised of mutagenizing a complete set of mutagenic cassettes (wherein each cassette is preferably 1-500 bases in length) in defined polynucleotide sequence to be mutagenized (wherein the sequence to be mutagenized is preferably from 15 to 100,000 bases in length). Thusly, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Defined sequences to be mutagenized (see FIG. 20) include preferably a whole gene, pathway, cDNA, an entire open reading frame (ORF), and intire promoter, enhancer, repressor/transactivator, origin of replication, intron, operator, or any polynucleotide functional group. Generally, a preferred "defined sequences" for this purpose may be any polynucleotide that a 15 base-polynucleotide sequence, and polynucleotide sequences of lengths between 15 bases and 15,000 bases (this invention specifically names every integer in between). Considerations in choosing groupings of codons include types of amino acids encoded by a degenerate mutagenic cassette.

In a particularly preferred exemplification a grouping of mutations that can be introduced into a mutagenic cassette, this invention specifically provides for degenerate codon substitutions (using degenerate oligos) that code for 2, 3, 4, 5, 6, 7, 8, 9, 10, 11, 12, 13, 14, 15, 16, 17, 18, 19, and 20 amino acids at each position, and a library of polypeptides encoded thereby.

Chimerizations

In vitro Shuffling

The equivalents of some standard genetic matings may also be performed by shuffling in vitro. For example, a "molecular backcross" can be performed by repeatedly mixing the hybrid's nucleic acid with the wild-type nucleic acid while selecting for the mutations of interest. As in traditional breeding, this approach can be used to combine phenotypes from different sources into a background of choice. It is useful, for example, for the removal of neutral mutations that affect unselected characteristics (i.e. immunogenicity). Thus it can be useful to determine which mutations in a protein are involved in the enhanced biological activity and which are not, an advantage which cannot be achieved by error-prone mutagenesis or cassette mutagenesis methods.

Large, functional genes can be assembled correctly from a mixture of small random polynucleotides. This reaction may be of use for the reassembly of genes from the highly fragmented DNA of fossils. In addition random nucleic acid fragments from fossils may be combined with polynucleotides from similar genes from related species.

It is also contemplated that the method of this invention can be used for the in vitro amplification of a whole genome from a single cell as is needed for a variety of research and diagnostic applications. DNA amplification by PCR is in practice limited to a length of about 40 kb. Amplification of a whole genome such as that of E. coli (5,000 kb) by PCR would require about 250 primers yielding 125 forty kb polynucleotides. This approach is not practical due to the unavailability of sufficient sequence data. On the other hand, random production of polynucleotides of the genome with sexual PCR cycles, followed by gel purification of small polynucleotides will provide a multitude of possible primers. Use of this mix of random small polynucleotides as primers in a PCR reaction alone or with the whole genome as the template should result in an inverse chain reaction with the theoretical endpoint of a single concatamer containing many copies of the genome.

100 fold amplification in the copy number and an average polynucleotide size of greater than 50 kb may be obtained when only random polynucleotides are used. It is thought that the larger concatamer is generated by overlap of many smaller polynucleotides. The quality of specific PCR products obtained using synthetic primers will be indistinguishable from the product obtained from unamplified DNA. It is expected that this approach will be useful for the mapping of genomes.

The polynucleotide to be shuffled can be produced as random or non-random polynucleotides, at the discretion of the practitioner. Moreover, this invention provides a method of shuffling that is applicable to a wide range of polynucleotide sizes and types, including the step of generating polynucleotide monomers to be used as building blocks in the reassembly of a larger polynucleotide. For example, the building blocks can be fragments of genes or they can be comprised of entire genes or gene pathways, or any combination thereof.

Exonuclease-mediated Shuffling

In a particular embodiment, this invention provides for a method for shuffling, assembling, reassembling, recombining, &/or concatenating at least two polynucleotides to form a progeny polynucleotide (e.g. a chimeric progeny polynucleotide that can be expressed to produce a polypeptide or a gene pathway). In a particular embodiment, a double stranded polynucleotide end (e.g. two single stranded sequences hybridized to each other as hybridization partners) is treated with an exonuclease to liberate nucleotides from one of the two strands, leaving the remaining strand free of its original partner so that, if desired, the remaining strand may be used to achieve hybridization to another partner.

In a particular aspect, a double stranded polynucleotide end (that may be part of—or connected to—a polynucleotide or a nonpolynucleotide sequence) is subjected to a source of exonuclease activity. Serviceable sources of exonuclease activity may be an enzyme with 3' exonuclease activity, an enzyme with 5' exonuclease activity, an enzyme with both 3' exonuclease activity and 5' exonuclease activity, and any combination thereof. An exonuclease can be used to liberate nucleotides from one or both ends of a linear double stranded polynucleotide, and from one to all ends of a branched polynucleotide having more than two ends. The mechanism of action of this liberation is believed to be comprised of an enzymatically-catalyzed hydrolysis of terminal nucleotides, and can be allowed to proceed in a time-dependent fashion, allowing experimental control of the progression of the enzymatic process.

By contrast, a non-enzymatic step may be used to shuffle, assemble, reassemble, recombine, and/or concatenate polynucleotide building blocks that is comprised of subjecting a working sample to denaturing (or "melting") conditions (for example, by changing temperature, pH, and /or salinity conditions) so as to melt a working set of double stranded polynucleotides into single polynucleotide strands. For shuffling, it is desirable that the single polynucleotide strands participate to some extent in annealment with different hybridization partners (i.e. and not merely revert to exclusive reannealment between what were former partners before the denaturation step). The presence of the former hybridization partners in the reaction vessel, however, does not preclude, and may sometimes even favor, reannealment of a single stranded polynucleotide with its former partner, to recreate an original double stranded polynucleotide.

In contrast to this non-enzymatic shuffling step comprised of subjecting double stranded polynucleotide building blocks to denaturation, followed by annealment, the instant invention further provides an exonuclease-based approach requiring no denaturation—rather, the avoidance of denaturing conditions and the maintenance of double stranded polynucleotide substrates in annealed (i.e. non-denatured) state are necessary conditions for the action of exonucleases (e.g., exonuclease III and red alpha gene product). Additionally in contrast, the generation of single stranded polynucleotide sequences capable of hybridizing to other single stranded polynucleotide sequences is the result of covalent cleavage—and hence sequence destruction—in one of the hybridization partners. For example, an exonuclease III enzyme may be used to enzymatically liberate 3' terminal nucleotides in one hybridization strand (to achieve covalent hydrolysis in that polynucleotide strand); and this favors hybridization of the remaining single strand to a new partner (since its former partner was subjected to covalent cleavage).

By way of further illustration, a specific exonuclease, namely exonuclease III is provided herein as an example of a 3' exonuclease; however, other exonucleases may also be used, including enzymes with 5' exonuclease activity and enzymes with 3' exonuclease activity, and including enzymes not yet discovered and enzymes not yet developed. It is particularly appreciated that enzymes can be discovered, optimized (e.g. engineered by directed evolution), or both discovered and optimized specifically for the instantly disclosed approach that have more optimal rates &/or more highly specific activities &/or greater lack of unwanted activities. In fact it is expected that the instant invention may encourage the discovery &/or development of such designer enzymes. In sum, this invention may be practiced with a variety of currently available exonuclease enzymes, as well as enzymes not yet discovered and enzymes not yet developed.

Figure 1:
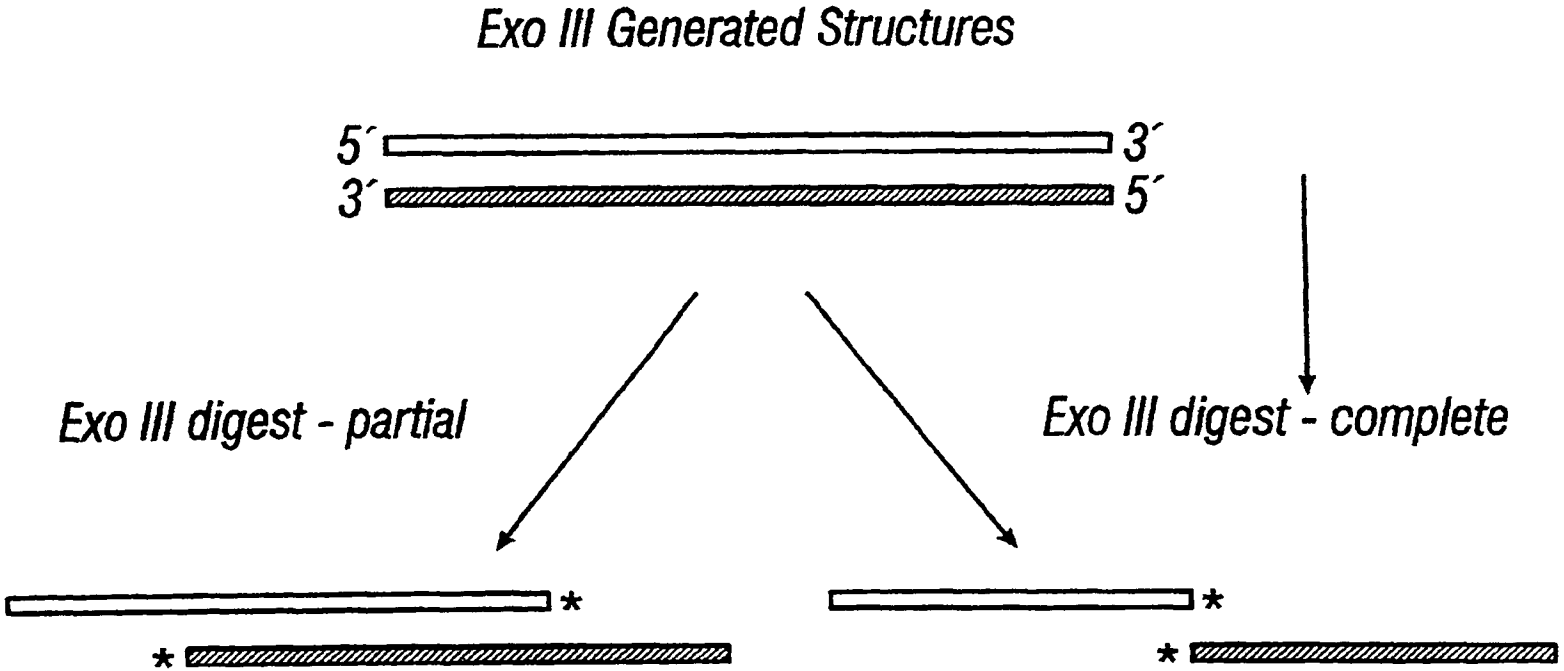
FIG. 1. Exonuclease Activity.

The exonuclease action of exonuclease III requires a working double stranded polynucleotide end that is either blunt or has a 5' overhang, and the exonuclease action is comprised of enzymatically liberating 3' terminal nucleotides, leaving a single stranded 5' end that becomes longer and longer as the exonuclease action proceeds (see FIG. 1). Any 5' overhangs produced by this approach may be used to hybridize to another single stranded polynucleotide sequence (which may also be a single stranded polynucleotide or a terminal overhang of a partially double stranded polynucleotide) that shares enough homology to allow hybridization. The ability of these exonuclease III-generated single stranded sequences (e.g. in 5' overhangs) to hybridize to other single stranded sequences allows two or more polynucleotides to be shuffled, assembled, reassembled, &/or concatenated.

Furthermore, it is appreciated that one can protect the end of a double stranded polynucleotide or render it susceptible to a desired enzymatic action of a serviceable exonuclease as necessary. For example, a double stranded polynucleotide end having a 3' overhang is not susceptible to the exonuclease action of exonuclease III. However, it may be rendered susceptible to the exonuclease action of exonuclease III by a variety of means; for example, it may be blunted by treatment with a polymerase, cleaved to provide a blunt end or a 5' overhang, joined (ligated or hybridized) to another double stranded polynucleotide to provide a blunt end or a 5' overhang, hybridized to a single stranded polynucleotide to provide a blunt end or a 5' overhang, or modified by any of a variety of means).

According to one aspect, an exonuclease may be allowed to act on one or on both ends of a linear double stranded polynucleotide and proceed to completion, to near completion, or to partial completion. When the exonuclease action is allowed to go to completion, the result will be that the length of each 5' overhang will be extended far towards the middle region of the polynucleotide in the direction of what might be considered a "rendezvous point" (which may be somewhere near the polynucleotide midpoint). Ultimately, this results in the production of single stranded polynucleotides (that can become dissociated) that are each about half the length of the original double stranded polynucleotide (see FIG. 1). Alternatively, an exonuclease-mediated reaction can be terminated before proceeding to completion.

Thus this exonuclease-mediated approach is serviceable for shuffling, assembling &/or reassembling, recombining, and concatenating polynucleotide building blocks, which polynucleotide building blocks can be up to ten bases long or tens of bases long or hundreds of bases long or thousands of bases long or tens of thousands of bases long or hundreds of thousands of bases long or millions of bases long or even longer.

This exonuclease-mediated approach is based on the action of double stranded DNA specific exodeoxyribonuclease activity of E. coli exonuclease III. Substrates for exonuclease III may be generated by subjecting a double stranded polynucleotide to fragmentation. Fragmentation may be achieved by mechanical means (e.g., shearing, sonication, etc.), by enzymatic means (e.g. using restriction enzymes), and by any combination thereof. Fragments of a larger polynucleotide may also be generated by polymerase-mediated synthesis.

Exonuclease III is a 28K monomeric enzyme, product of the xthA gene of E. Coli with four known activities: exodeoxyribonuclease (alternatively referred to as exonuclease herein), RNaseH, DNA-3'-phosphatase, and AP endonuclease. The exodeoxyribonuclease activity is specific for double stranded DNA. The mechanism of action is thought to involve enzymatic hydrolysis of DNA from a 3' end progressively towards a 5' direction, with formation of nucleoside 5'-phosphates and a residual single strand. The enzyme does not display efficient hydrolysis of single stranded DNA, single-stranded RNA, or double-stranded RNA; however it degrades RNA in an DNA-RNA hybrid releasing nucleoside 5'-phosphates. The enzyme also releases inorganic phosphate specifically from 3'phosphomonoester groups on DNA, but not from RNA or short oligonucleotides. Removal of these groups converts the terminus into a primer for DNA polymerase action.

Additional examples of enzymes with exonuclease activity include red-alpha and venom phosphodiesterases. Red alpha (redα) gene product (also referred to as lambda exonuclease) is of bacteriophage λ origin. The reds gene is transcribed from the leftward promoter and its product is involved (24 kD) in recombination. Red alpha gene product acts processively from 5'-phosphorylated termini to liberate mononucleotides from duplex DNA (Takahashi & Kobayashi, 1990). Venom phosphodiesterases (Laskowski, 1980) is capable of rapidly opening supercoiled DNA.

Synthetic Ligation Reassembly

In one aspect, the present invention provides a non-stochastic method termed synthetic ligation reassembly (SLR), that is somewhat related to stochastic shuffling, save that the nucleic acid building blocks are not shuffled or concatenated or chimerized randomly, but rather are assembled non-stochastically.

A particularly glaring difference is that the instant SLR method does not depend on the presence of a high level of homology between polynucleotides to be shuffled. In contrast, prior methods, particularly prior stochastic shuffling methods require that presence of a high level of homology, particularly at coupling sites, between polynucleotides to be shuffled. Accordingly these prior methods favor the regeneration of the original progenitor molecules, and are suboptimal for generating, large numbers of novel progeny chimeras, particularly full-length progenies. The instant invention, on the other hand, can be used to non-stochastically generate libraries (or sets) of progeny molecules comprised of over $10^{100}$ different chimeras. Conceivably, SLR can even be used to generate libraries comprised of over $10^{1000}$ different progeny chimeras with (no upper limit in sight).

Thus, in one aspect, the present invention provides a method, which method is non-stochastic, of producing a set of finalized chimeric nucleic acid molecules having an overall assembly order that is chosen by design, which method is comprised of the steps of generating by design a plurality of specific nucleic acid building blocks having serviceable mutually compatible ligatable ends, and assembling these nucleic acid building blocks, such that a designed overall assembly order is achieved.

Figure 4A:
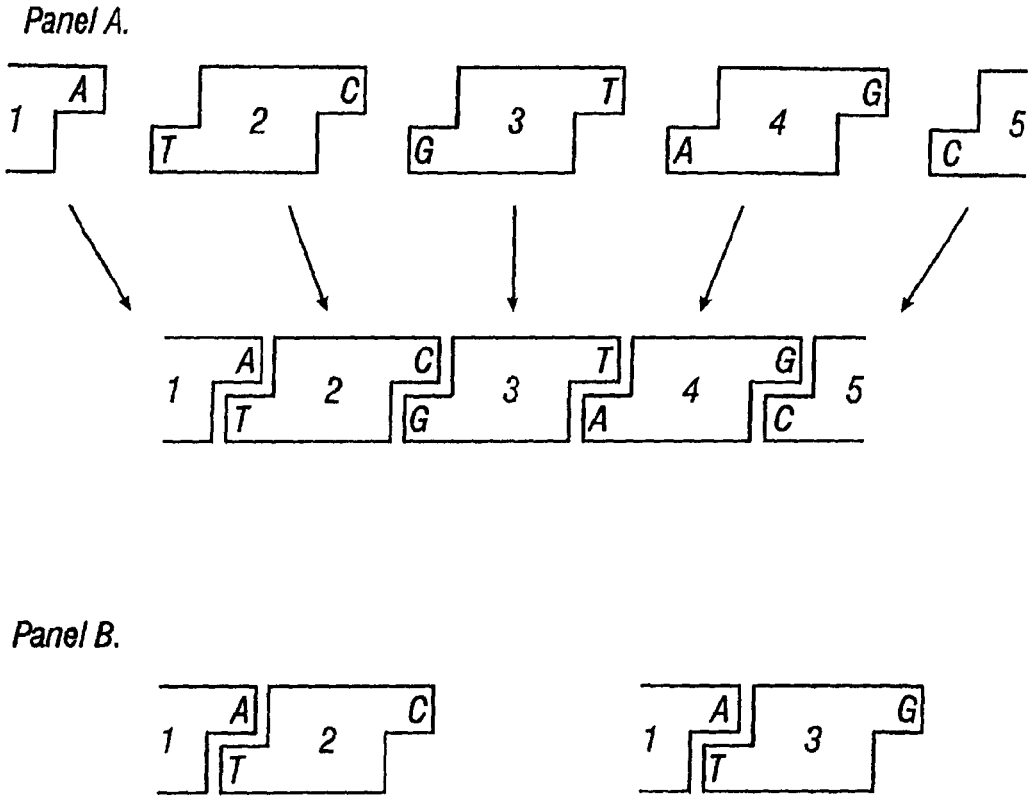
FIGS. 4A and 4B. Unique Overall Assembly Order Achieved by Sequentially Coupling the Building Blocks. Awareness of the degeneracy (between the number of unique overhangs and the number of unique couplings) is important in order to avoid the production of degeneracy in the overall assembly order of the finalized nucleic acid. However, a unique overall assembly order can also be achieved—despite the use of non-unique couplings—by using building blocks having distinct combinations of couplings, and/or by stepping the assembly of the building blocks in a deliberately chosen sequence.
Figure 4B:
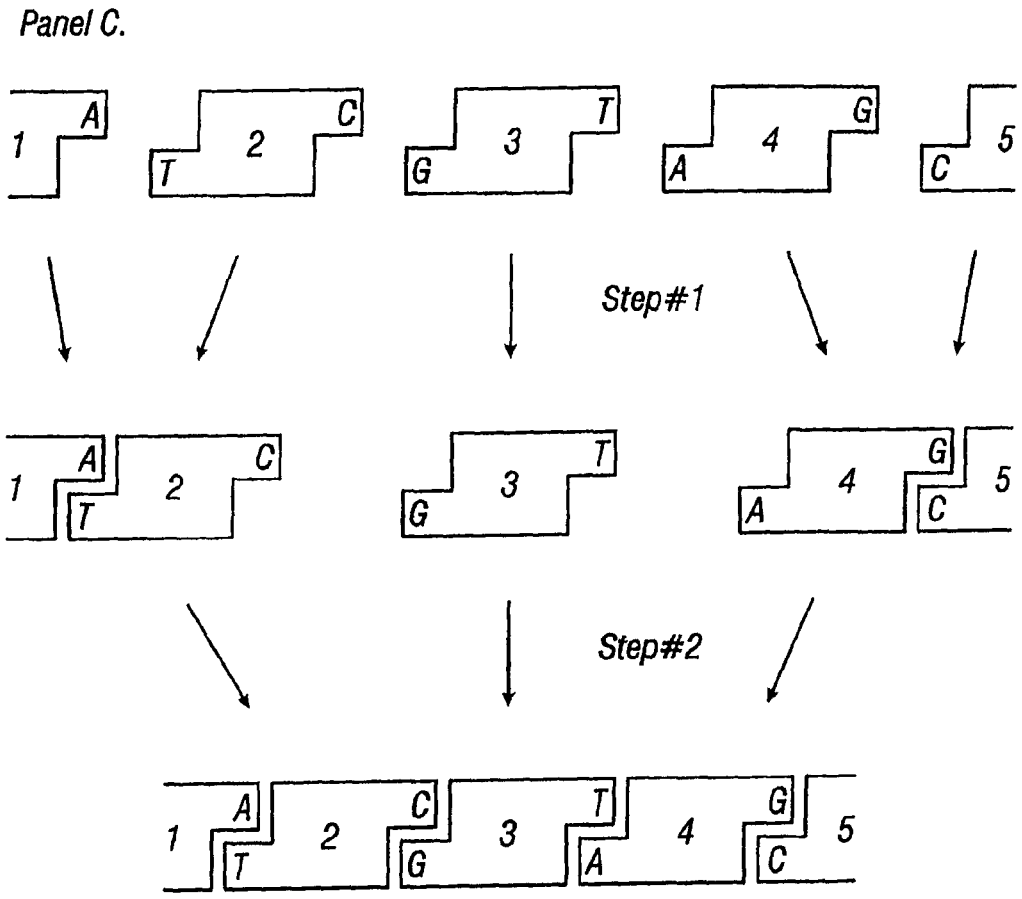
Figure 5:
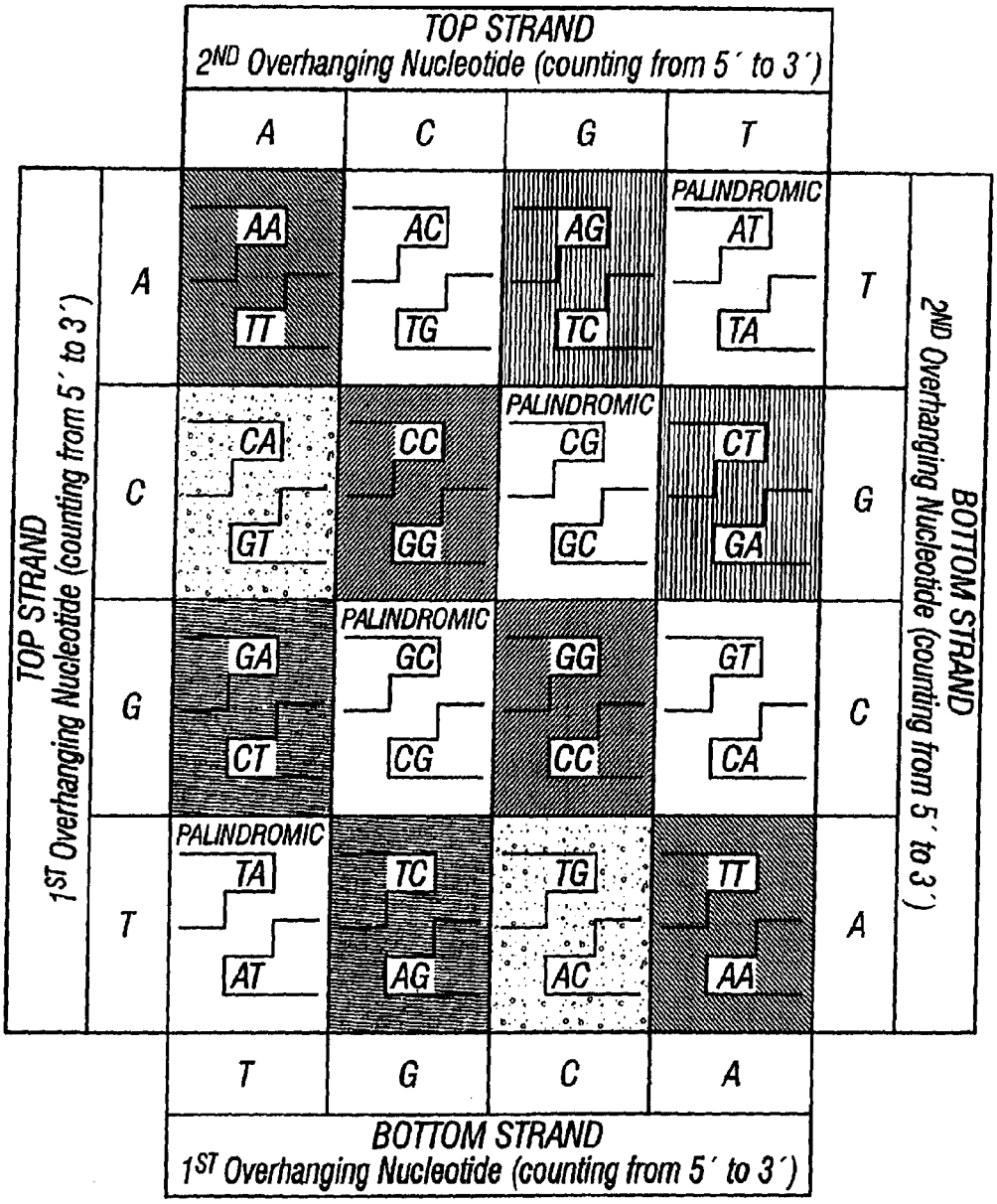
FIG. 5. Unique Couplings Available Using a Two-Nucleotide 3' Overhang.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). FIG. 4, Panel C illustrates an exemplary assembly process comprised of 2 sequential steps to achieve a designed (non-stochastic) overall assembly order for five nucleic acid building blocks. In a preferred embodiment of this invention, the annealed building pieces are treated with an enzyme, such as a ligase (e.g. T4 DNA ligase), achieve covalent bonding of the building pieces.

In a preferred embodiment, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized; i.e. chimerized or shuffled.

In one exemplification, this invention provides for the chimerization of a family of related genes and their encoded family of related products. In a particular exemplification, the encoded products are enzymes. As a representative list of families of enzymes which may be mutagenized in accordance with the aspects of the present invention, there may be mentioned, the following enzymes and their functions:

1 Lipase/Esterase
- a. Enantioselective hydrolysis of esters (lipids)/thioesters
  - 1) Resolution of racemic mixtures
  - 2) Synthesis of optically active acids or alcohols from meso-diesters
- b. Selective syntheses
  - 1) Regiospecific hydrolysis of carbohydrate esters
  - 2) Selective hydrolysis of cyclic secondary alcohols
- c. Synthesis of optically active esters, lactones, acids, alcohols
  - 1) Transesterification of activated/nonactivated esters
  - 2) Interesterification
  - 3) Optically active lactones from hydroxyesters
  - 4) Regio- and enantioselective ring opening of anhydrides
- d. Detergents
- e. Fat/Oil conversion
- f. Cheese ripening 2 Protease
- a. Ester/amide synthesis
- b. Peptide synthesis
- c. Resolution of racemic mixtures of amino acid esters
- d. Synthesis of non-natural amino acids
- e. Detergents/protein hydrolysis 3 Glycosidase/Glycosyl transferase
- a. Sugar/polymer synthesis
- b. Cleavage of glycosidic linkages to form mono, di-and oligosaccharides
- c. Synthesis of complex oligosaccharides
- d. Glycoside synthesis using UDP-galactosyl transferase
- e. Transglycosylation of disaccharides, glycosyl fluorides, aryl galactosides
- f. Glycosyl transfer in oligosaccharide synthesis
- g. Diastereoselective cleavage of β-glucosylsulfoxides
- h. Asymmetric glycosylations
- i. Food processing
- j. Paper processing 4 Phosphatase/Kinase
- a. Synthesis/hydrolysis of phosphate esters
  - 1) Regio-, enantioselective phosphorylation
  - 2) Introduction of phosphate esters
  - 3) Synthesize phospholipid precursors
  - 4) Controlled polynucleotide synthesis
- b. Activate biological molecule
- c. Selective phosphate bond formation without protecting groups 5 Mono/Dioxygenase
- a. Direct oxyfunctionalization of unactivated organic substrates
- b. Hydroxylation of alkane, aromatics, steroids
- c. Epoxidation of alkenes
- d. Enantioselective sulphoxidation
- e. Regio- and stereoselective Bayer-Villiger oxidations 6 Haloperoxidase
- a. Oxidative addition of halide ion to nucleophilic sites
- b. Addition of hypohalous acids to olefinic bonds
- c. Ring cleavage of cyclopropanes
- d. Activated aromatic substrates converted to ortho and para derivatives
- e. 1.3 diketones converted to 2-halo-derivatives
- f. Heteroatom oxidation of sulfur and nitrogen containing substrates
- g. Oxidation of enol acetates, alkynes and activated aromatic rings 7 Lignin peroxidase/Diarylpropane peroxidase
- a. Oxidative cleavage of C—C bonds
- b. Oxidation of benzylic alcohols to aldehydes
- c. Hydroxylation of benzylic carbons
- d. Phenol dimerization
- e. Hydroxylation of double bonds to form diols
- f. Cleavage of lignin aldehydes 8 Epoxide hydrolase
- a. Synthesis of enantiomerically pure bioactive compounds
- b. Regio- and enantioselective hydrolysis of epoxide
- c. Aromatic and olefinic epoxidation by monooxygenases to form epoxides
- d. Resolution of racemic epoxides
- e. Hydrolysis of steroid epoxides 9 Nitrile hydratase/nitrilase
- a. Hydrolysis of aliphatic nitriles to carboxamides
- b. Hydrolysis of aromatic, heterocyclic, unsaturated aliphatic nitriles to corresponding acids
- c. Hydrolysis of acrylonitrile
- d. Production of aromatic and carboxamides, carboxylic acids (nicotinamide, picolinamide, isonicotinamide)
- e. Regioselective hydrolysis of acrylic dinitrile
- f. α-amino acids from α-hydroxynitriles 10 Transaminase
- a. Transfer of amino groups into oxo-acids 11 Amidase/Acylase
- a. Hydrolysis of amides, amidines, and other C—N bonds
- b. Non-natural amino acid resolution and synthesis These exemplifications, while illustrating certain specific aspects of the invention, do not portray the limitations or circumscribe the scope of the disclosed invention.

Thus according to one aspect of this invention, the sequences of a plurality of progenitor nucleic acid templates are aligned in order to select one or more demarcation points, which demarcation points can be located at an area of homology, and are comprised of one or more nucleotides, and which demarcation points are shared by at least two of the progenitor templates. The demarcation points can be used to delineate the boundaries of nucleic acid building blocks to be generated. Thus, the demarcation points identified and selected in the progenitor molecules serve as potential chimerization points in the assembly of the progeny molecules.

Preferably a serviceable demarcation point is an area of homology (comprised of at least one homologous nucleotide base) shared by at least two progenitor templates. More preferably a serviceable demarcation point is an area of homology that is shared by at least half of the progenitor templates. More preferably still a serviceable demarcation point is an area of homology that is shared by at least two thirds of the progenitor templates. Even more preferably a serviceable demarcation points is an area of homology that is shared by at least three fourths of the progenitor templates. Even more preferably still a serviceable demarcation points is an area of homology that is shared by at almost all of the progenitor templates. Even more preferably still a serviceable demarcation point is an area of homology that is shared by all of the progenitor templates.

Figure 6A:
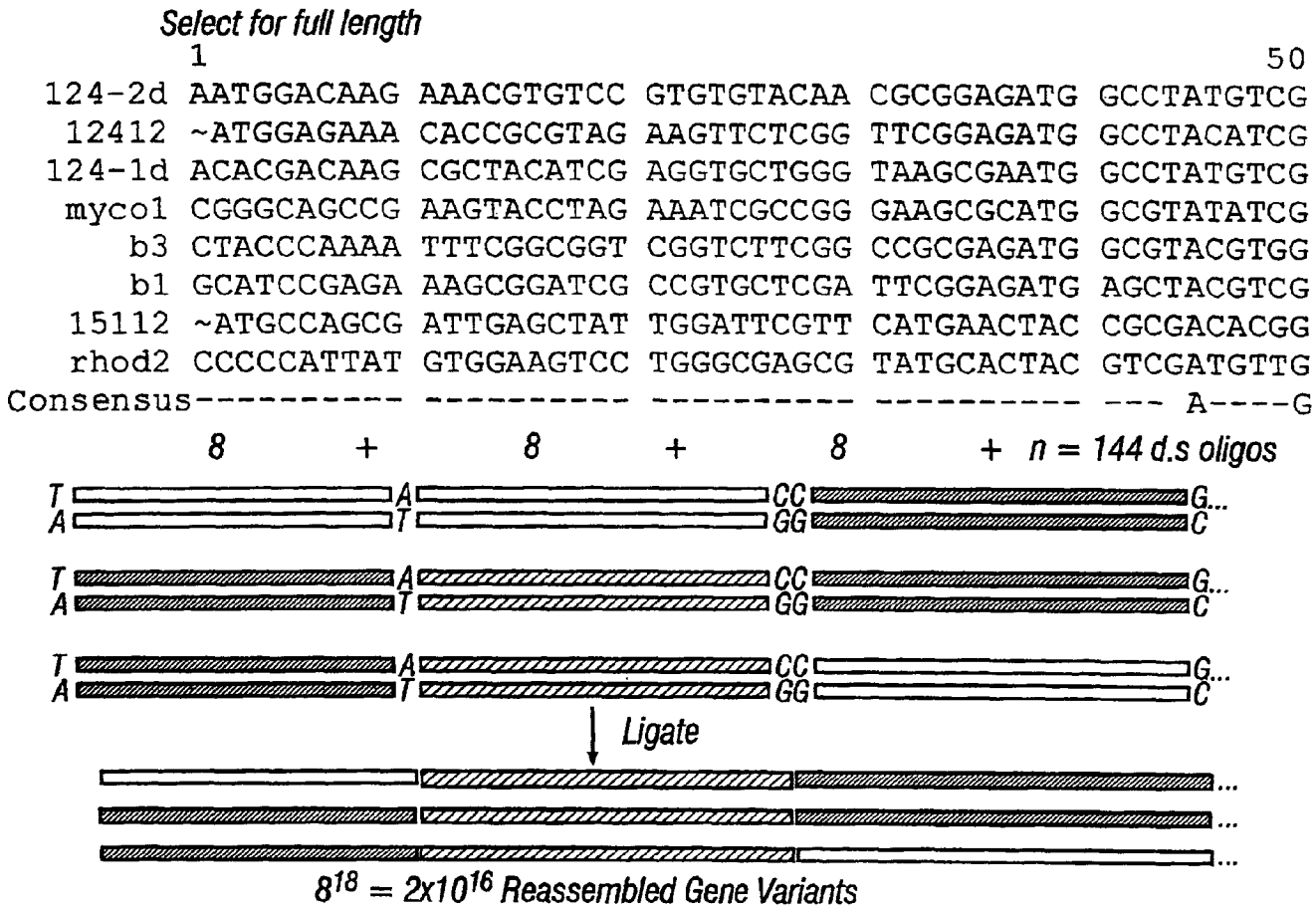
FIG. 6 *A, B, and C*. Generation of an Exhaustive Set of Chimeric Combinations by Synthetic Ligation Reassembly.
Figure 8:
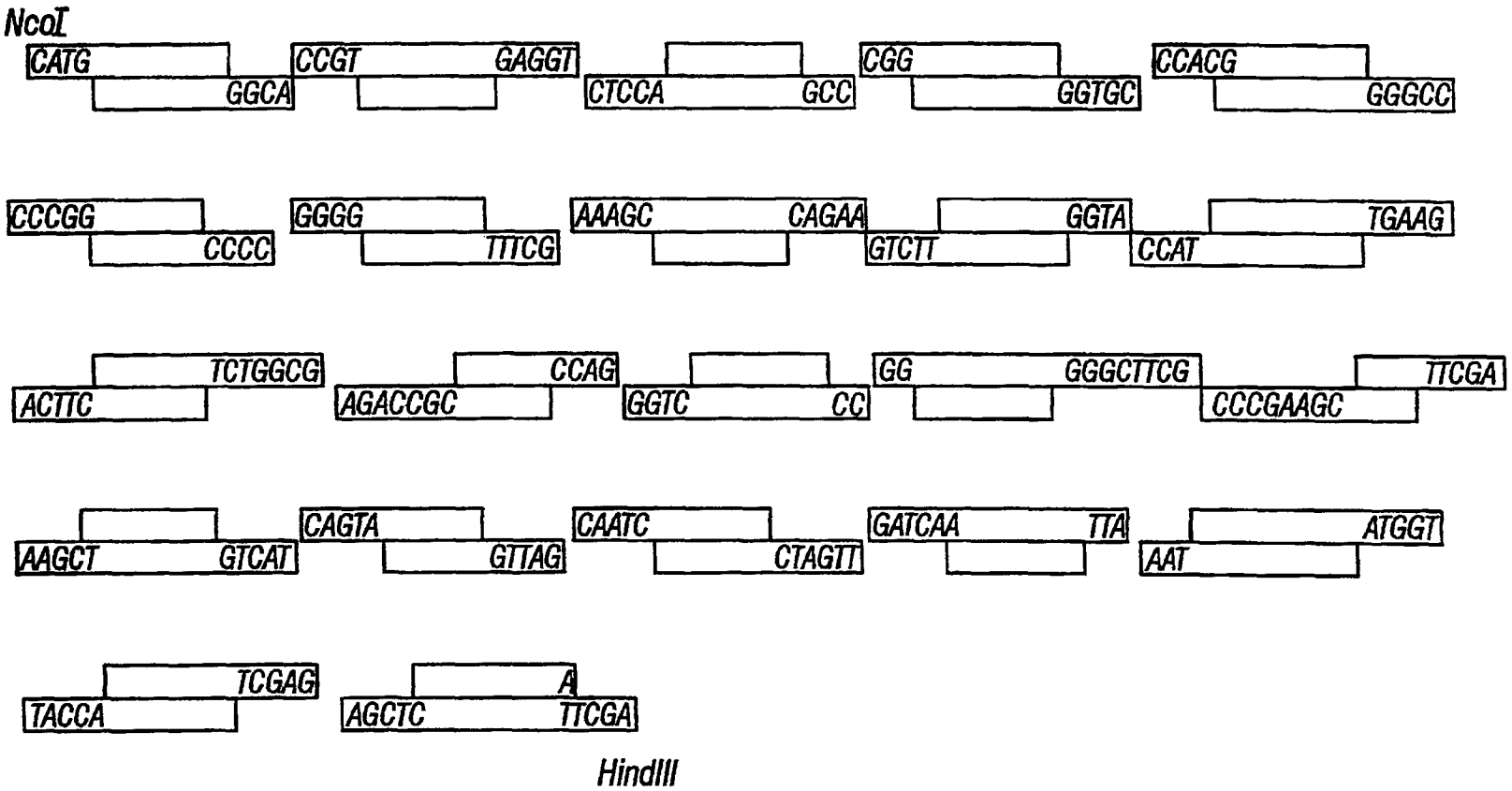
FIG. 8. Nucleic acid building blocks for synthetic ligation gene reassembly.
Figure 9:
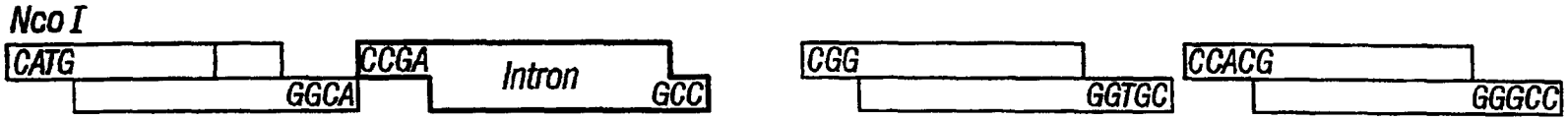
FIG. 9. Addition of Introns by Synthetic Ligation Reassembly.
Figure 10:
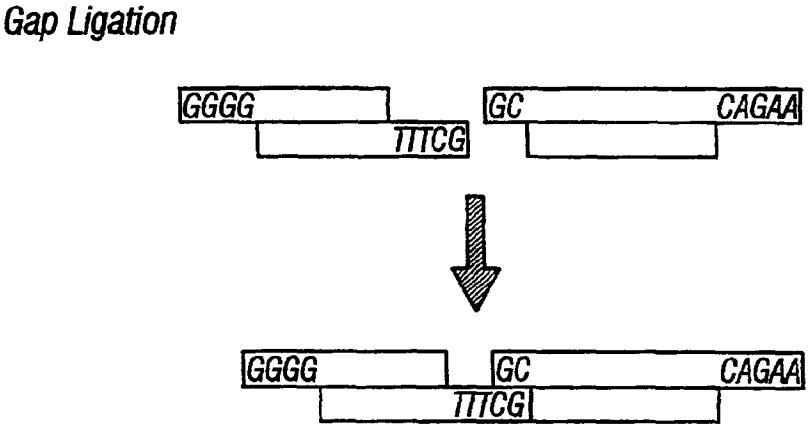
FIG. 10. Ligation Reassembly Using Fewer Than All The Nucleotides Of An Overhang.
Figure 11:
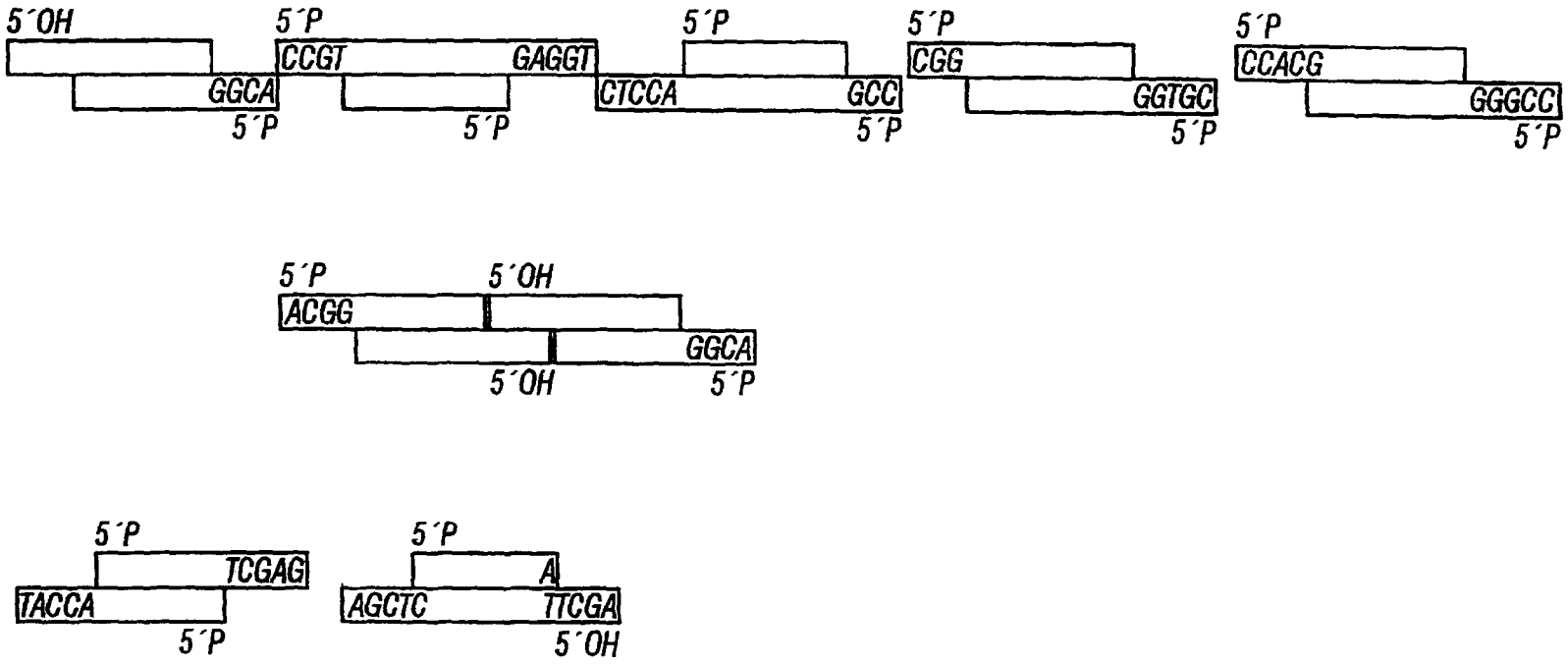
FIG. 11. Avoidance of unwanted self-ligation in palindromic couplings. As mentioned before and shown in FIG. 5, certain overhangs are able to undergo self-coupling to form a palindromic coupling. A coupling is strengthened substantially if it is reinforced by treatment with a ligase enzyme. Accordingly, it is appreciated that the lack of 5' phosphates on these overhangs, as shown, can be used advantageously to prevent this type of palindromic self-ligation. Accordingly, this invention provides that nucleic acid building blocks can be chemically made (or ordered) that lack a 5' phosphate group (or alternatively they can be removed-e.g. by treatment with a phosphatase enzyme such as a calf intestinal alkaline phosphatase (CIAP)—in order to prevent palindromic self-ligations in ligation reassembly processes. This figure shows that there is no self-ligation of end primers with palindromic overhangs.
Figure 12:
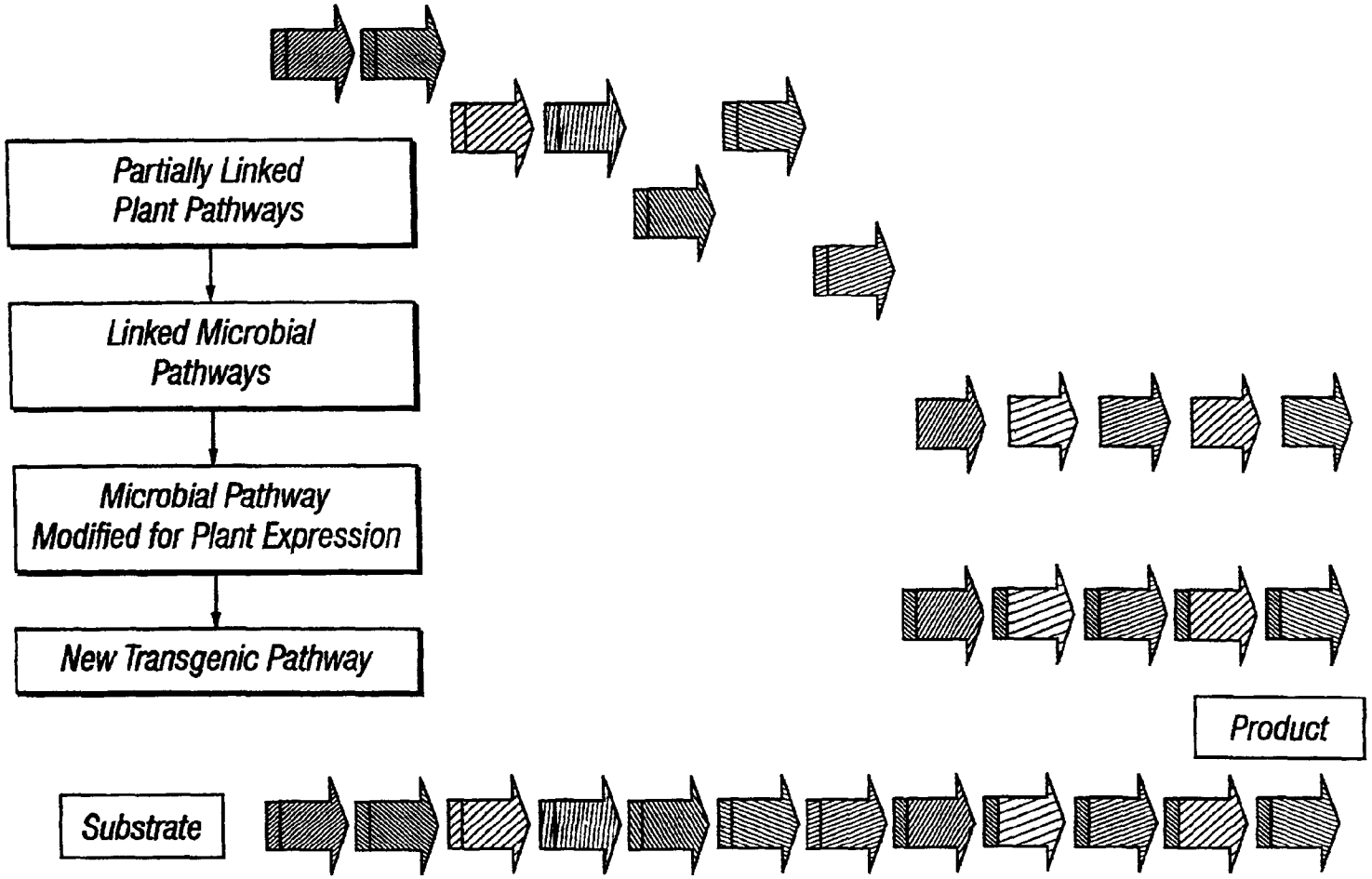
FIG. 12. Pathway Engineering. It is a goal of this invention to provide ways of making new gene pathways using ligation reassembly, optionally with other directed evolution methods such as saturation mutagenesis.
Figure 13:
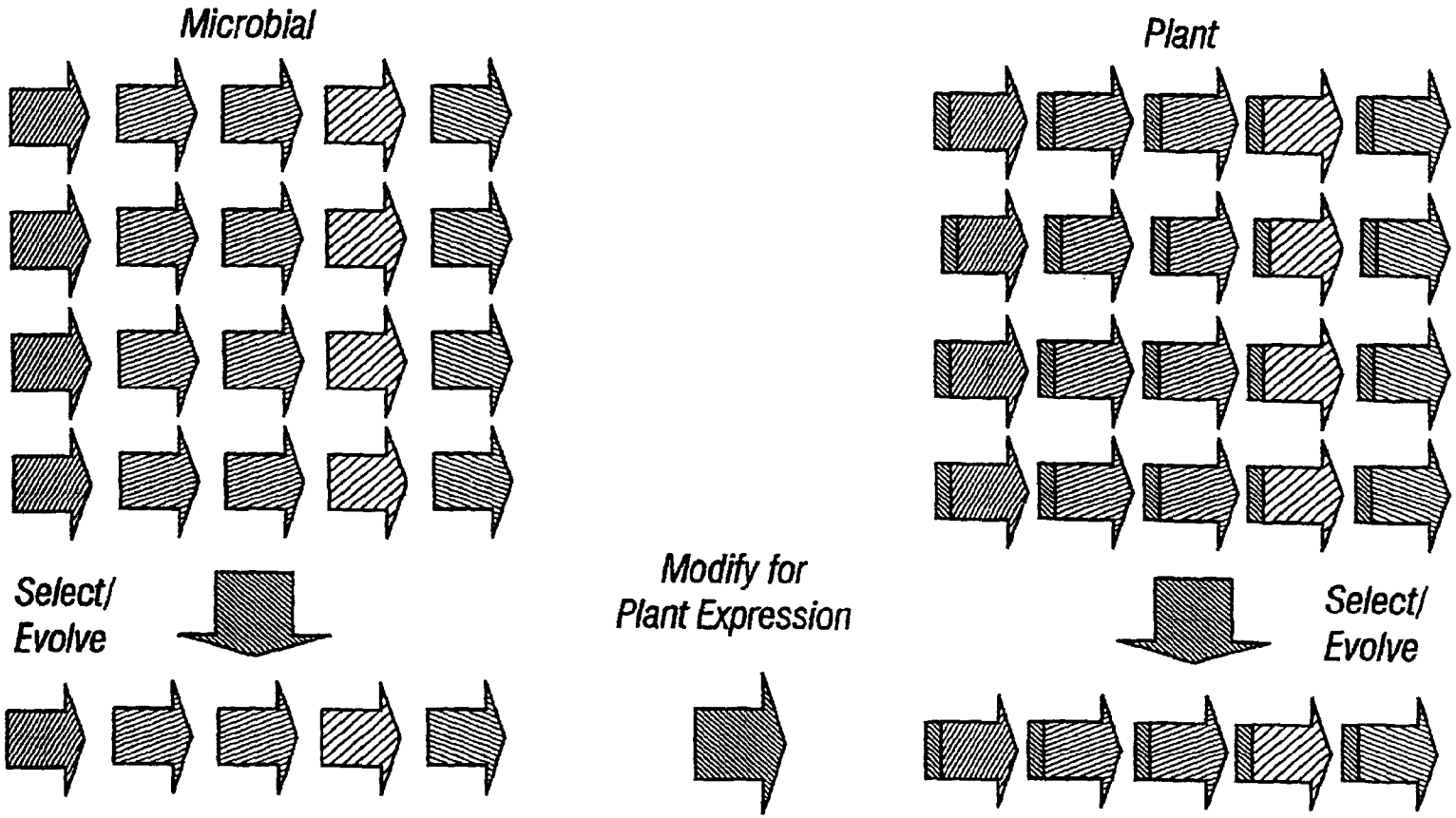
FIG. 13. Avoidance of unwanted self-ligation in palindromic couplings.
Figure 14:
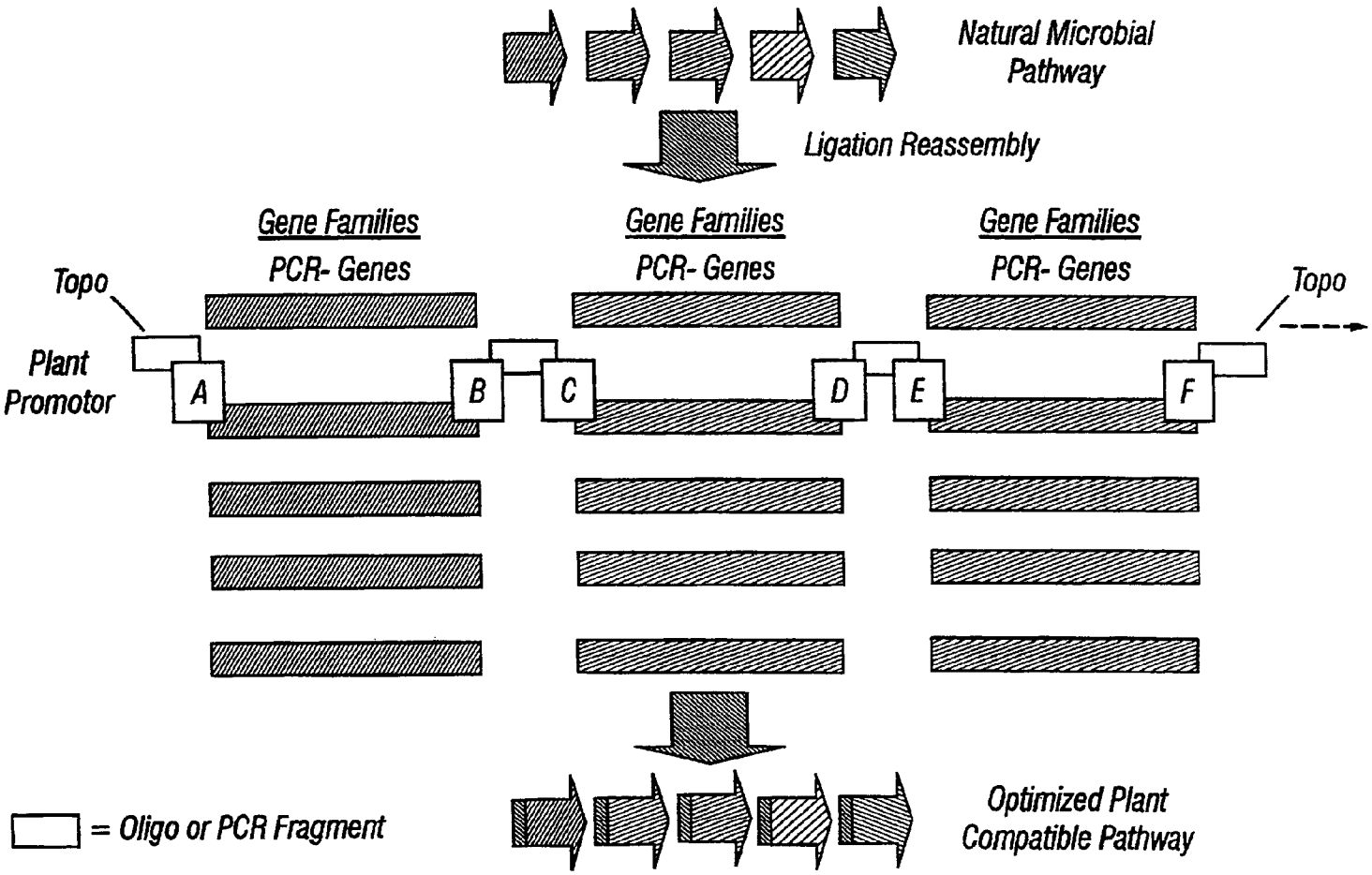
FIG. 14. Conversion of Microbial Pathways to Eukaryotic Pathways. In a particular embodiment, this invention provides that microbial pathways can be converted to pathways operable in plants and other eukaryotic species by the introduction of regulatory sequences that function in those species. Preferred regulatory sequences include promoters, operators, and activator binding sites. As shown, a preferred method of achieving the introduction of such serviceable regulatory sequences is in the form of nucleic acid building blocks, particularly through the use of couplings in ligation reassembly processes. These couplings in FIG. 14 are marked with the letters A, B, C, D and F.
Figure 15:
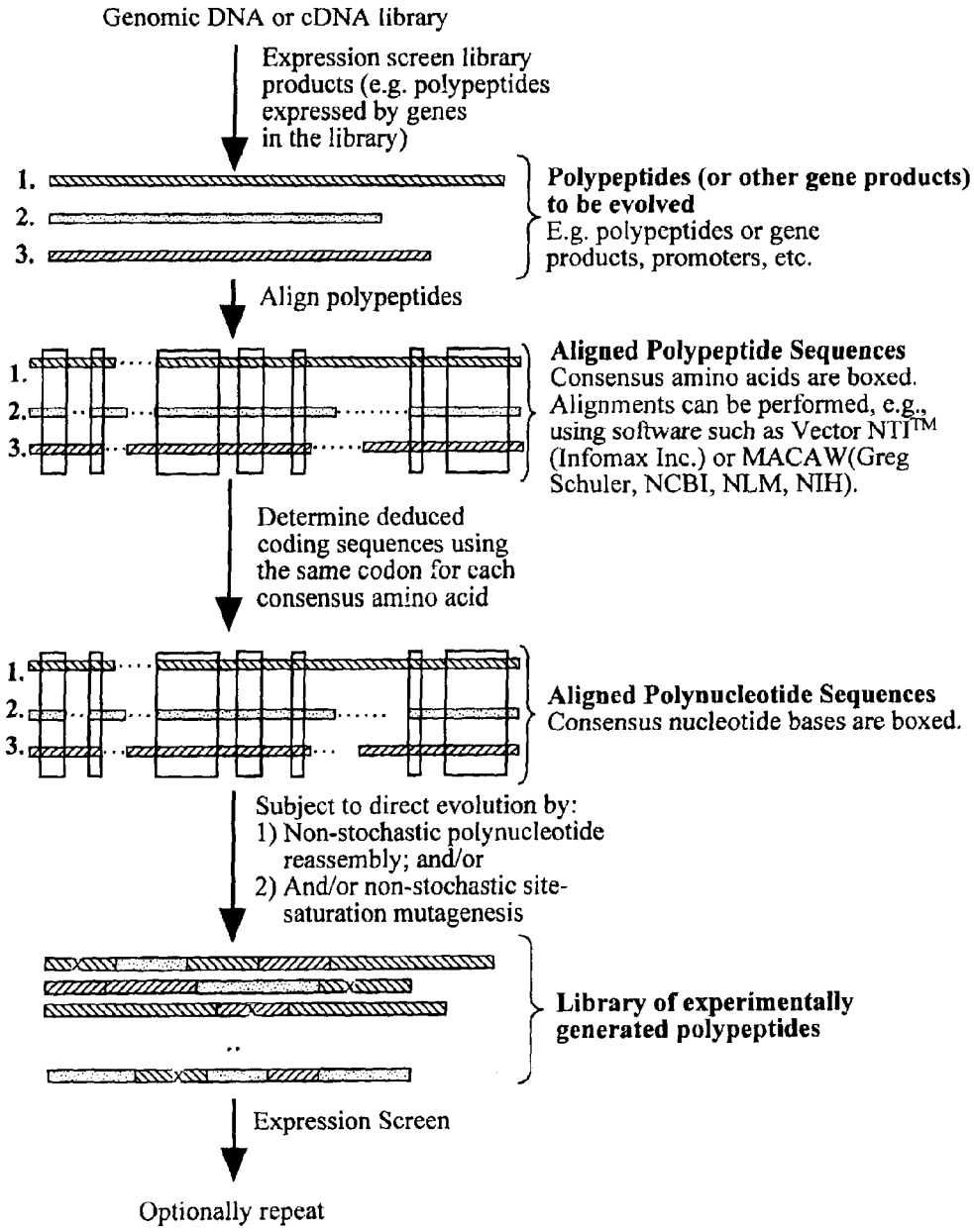
FIG. 15. Evolution of polypeptides by synthesizing (in vivo or in vitro) corresponding deduced polynucleotides and subjecting the deduced polynucleotides to directed evolution and expression screening subsequently expressed polypeptides. This invention provides that ligation reassembly and site saturation mutagenesis are each serviceable for introducing nucleotide substitutions as well as nucleotide deletions and nucleotide additions and combinations thereof. Furthermore synthetic ligation reassembly can be performed on a plurality of starting templates as well as on a single template to rearrange the order of the nucleotide cassettes in a non-stochastic predetermined manner. Additionally, when subjecting a plurality of starting templates to ligation reassembly, it is not necessary that the same number of nucleic acid building blocks be generated from each template (e.g. to participate to in each coupling). Thus for example if three templates are used, then a different number of nucleic acid building blocks may be generated corresponding to each template.
Figure 16:
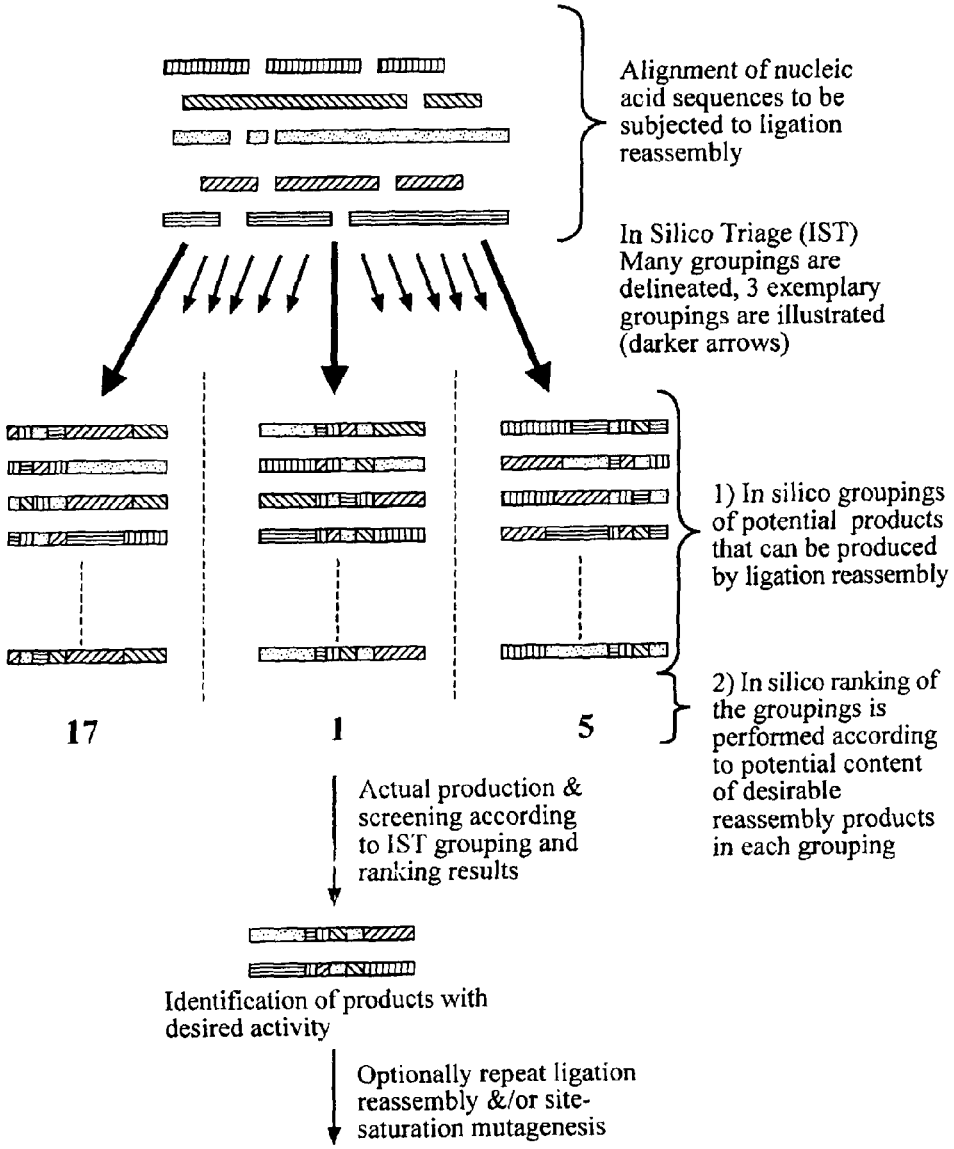
FIG. 16: In Silico Triage. This figure illustrates the grouping of potential products and the ranking of the groupings according to "structure-function" predictions, which steps are aspects of what is referred to herein as "triaging", and specifically "in silico triage" if performed using the aid of a computer.

The process of designing nucleic acid building blocks and of designing the mutually compatible ligatable ends of the nucleic acid building blocks to be assembled is illustrated in FIGS. 6 and 7. As shown, the alignment of a set of progenitor templates reveals several naturally occurring demarcation points, and the identification of demarcation points shared by these templates helps to non-stochastically determine the building blocks to be generated and used for the generation of the progeny chimeric molecules.

In a preferred embodiment, this invention provides that the ligation reassembly process is performed exhaustively in order to generate an exhaustive library. In other words, all possible ordered combinations of the nucleic acid building blocks are represented in the set of finalized chimeric nucleic acid molecules. At the same time, in a particularly preferred embodiment, the assembly order (i.e. the order of assembly of each building block in the 5' to 3' sequence of each finalized chimeric nucleic acid) in each combination is by design (or non-stochastic). Because of the non-stochastic nature of this invention, the possibility of unwanted side products is greatly reduced.

In another preferred embodiment, this invention provides that, the ligation reassembly process is performed systematically, for example in order to generate a systematically compartmentalized library, with compartments that can be screened systematically, e.g. one by one. In other words this invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant ligation reassembly invention, the progeny molecules generated preferably comprise a library of finalized chimeric nucleic acid molecules having an overall assembly order that is chosen by design. In a particularly preferred embodiment of this invention, such a generated library is comprised of preferably greater than $10^3$ different progeny molecular species, more preferably greater than $10^5$ different progeny molecular species, more preferably still greater than $10^{10}$ different progeny molecular species, more preferably still greater than $10^{15}$ different progeny molecular species, more preferably still greater than $10^{20}$ different progeny molecular species, more preferably still greater than $10^{30}$ different progeny molecular species, more preferably still greater than $10^{40}$ different progeny molecular species, more preferably still greater than $10^{50}$ different progeny molecular species, more preferably still greater than $10^{60}$ different progeny molecular species, more preferably still greater than $10^{70}$ different progeny molecular species, more preferably still greater than $10^{80}$ different progeny molecular species, more preferably still greater than $10^{100}$ different progeny molecular species, more preferably still greater than $10^{110}$ different progeny molecular species, more preferably still greater than $10^{120}$ different progeny molecular species, more preferably still greater than $10^{130}$ different progeny molecular species, more preferably still greater than $10^{140}$ different progeny molecular species, more preferably still greater than $10^{150}$ different progeny molecular species, more preferably still greater than $10^{175}$ different progeny molecular species, more preferably still greater than $10^{200}$ different progeny molecular species, more preferably still greater than $10^{300}$ different progeny molecular species, more preferably still greater than $10^{400}$ different progeny molecular species, more preferably still greater than $10^{500}$ different progeny molecular species, and even more preferably still greater than $10^{1000}$ different progeny molecular species.

In one aspect, a set of finalized chimeric nucleic acid molecules, produced as described is comprised of a polynucleotide encoding a polypeptide. According to one preferred embodiment, this polynucleotide is a gene, which may be a man-made gene. According to another preferred embodiment, this polynucleotide is a gene pathway, which may be a man-made gene pathway. This invention provides that one or more man-made genes generated by this invention may be incorporated into a man-made gene pathway, such as pathway operable in a eukaryotic organism (including a plant).

It is appreciated that the power of this invention is exceptional, as there is much freedom of choice and control regarding the selection of demarcation points, the size and number of the nucleic acid building blocks, and the size and design of the couplings. It is appreciated, furthermore, that the requirement for intermolecular homology is highly relaxed for the operability of this invention. In fact, demarcation points can even be chosen in areas of little or no intermolecular homology. For example, because of codon wobble, i.e. the degeneracy of codons, nucleotide substitutions can be introduced into nucleic acid building blocks without altering the amino acid originally encoded in the corresponding progenitor template. Alternatively, a codon can be altered such that the coding for an originally amino acid is altered. This invention provides that such substitutions can be introduced into the nucleic acid building block in order to increase the incidence of intermolecularly homologous demarcation points and thus to allow an increased number of couplings to be achieved among the building blocks, which in turn allows a greater number of progeny chimeric molecules to be generated.

In another exemplification, the synthetic nature of the step in which the building blocks are generated allows the design and introduction of nucleotides (e.g. one or more nucleotides, which may be, for example, codons or introns or regulatory sequences) that can later be optionally removed in an in vitro process (e.g. by [mutageneis] *mutagenesis*) or in an in vivo process (e.g. by utilizing the gene splicing ability of a host organism). It is appreciated that in many instances the introduction of these nucleotides may also be desirable for many other reasons in addition to the potential benefit of creating a serviceable demarcation point.

Thus, according to another embodiment, this invention provides that a nucleic acid building block can be used to introduce an intron. Thus, this invention provides that functional introns may be introduced into a man-made gene of this invention. This invention also provides that functional introns may be introduced into a man-made gene pathway of this invention. Accordingly, this invention provides for the generation of a chimeric polynucleotide that is a man-made gene containing one (or more) artificially introduced intron(s).

Accordingly, this invention also provides for the generation of a chimeric polynucleotide that is a man-made gene pathway containing one (or more) artificially introduced intron(s). Preferably, the artificially introduced intron(s) are functional in one or more host cells for gene splicing much in the way that naturally-occurring introns serve functionally in gene splicing. This invention provides a process of producing man-made intron-containing polynucleotides to be introduced into host organisms for recombination and/or splicing.

The ability to achieve chimerizations, using couplings as described herein, in areas of little or no homology among the progenitor molecules, is particularly useful, and in fact critical, for the assembly of novel gene pathways. This invention thus provides for the generation of novel man-made gene pathways using synthetic ligation reassembly. In a particular aspect, this is achieved by the introduction of regulatory sequences, such as promoters, that are operable in an intended host, to confer operability to a novel gene pathway when it is introduced into the intended host. In a particular exemplification, this invention provides for the generation of novel man-made gene pathways that is operable in a plurality of intended hosts (e.g. in a microbial organism as well as in a plant cell). This can be achieve, for example, by the introduction of a plurality of regulatory sequences, comprised of a regulatory sequence that is operable in a first intended host and a regulatory sequence that is operable in a second intended host. A similar process can be performed to achieve operability of a gene pathway in a third intended host species, etc. The number of intended host species can be each integer from 1 to 10 or alternatively over 10. Alternatively, for example, operability of a gene pathway in a plurality of intended hosts can be achieved by the introduction of a regulatory sequence having intrinsic operability in a plurality of intended hosts.

Thus, according to a particular embodiment, this invention provides that a nucleic acid building block can be used to introduce a regulatory sequence, particularly a regulatory sequence for gene expression. Preferred regulatory sequences include, but are not limited to, those that are man-made, and those found in archeal, bacterial, eukaryotic (including mitochondrial), viral, and prionic or prion-like organisms. Preferred regulatory sequences include but are not limited to, promoters, operators, and activator binding sites. Thus, this invention provides that functional regulatory sequences may be introduced into a man-made gene of this invention. This invention also provides that functional regulatory sequences may be introduced into a man-made gene pathway of this invention.

Accordingly, this invention provides for the generation of a chimeric polynucleotide that is a man-made gene containing one (or more) artificially introduced regulatory sequence(s). Accordingly, this invention also provides for the generation of a chimeric polynucleotide that is a man-made gene pathway containing one (or more) artificially introduced regulatory sequence(s). Preferably, an artificially introduced regulatory sequence(s) is operatively linked to one or more genes in the man-made polynucleotide, and are functional in one or more host cells.

Preferred bacterial promoters that are serviceable for this invention include lacI, lacZ, T3, T7, gpt, lambda $P_R$, $P_L$ and trp. Serviceable eukaryotic promoters include CMV immediate early, HSV thymidine kinase, early and late SV40, LTRs from retrovirus, and mouse metallothionein-I. Particular plant regulatory sequences include promoters active in directing transcription in plants, either constitutively or stage and/or tissue specific, depending on the use of the plant or parts thereof. These promoters include, but are not limited to promoters showing constitutive expression, such as the 35S promoter of Cauliflower Mosaic Virus (CaMV) (Guilley et al., 1982), those for leaf-specific expression, such as the promoter of the ribulose bisphosphate carboxylase small subunit gene (Coruzzi et al., 1984), those for root-specific expression, such as the promoter from the glutamin synthase gene (Tingey et al., 1987), those for seed-specific expression, such as the cruciferin A promoter from Brassica napus (Ryan et al., 1989), those for tuber-specific expression, such as the class-I patatin promoter from potato (Rocha-Sasa et al., 1989; Wenzler et al., 1989) or those for fruit-specific expression, such as the polygalacturonase (PG) promoter from tomato (Bird et al., 1988).

Other regulatory sequences that are preferred for this invention include terminator sequences and polyadenylation signals and any such sequence functioning as such in plants, the choice of which is within the level of the skilled artisan.

An example of such sequences is the 3' flanking region of the nopaline synthase (nos) gene of Agrobacterium tumefaciens (Bevan, 1984). The regulatory sequences may also include enhancer sequences, such as found in the 35S promoter of CaMV, and mRNA stabilizing sequences such as the leader sequence of Alfalfa Mosaic Cirus (A1MV) RNA4 (Brederode et al., 1980) or any other sequences functioning in a like manner.

A man-made genes produced using this invention can also serve as a substrate for recombination with another nucleic acid. Likewise, a man-made gene pathway produced using this invention can also serve as a substrate for recombination with another nucleic acid. In a preferred instance, the recombination is facilitated by, or occurs at, areas of homology between the man-made intron-containing gene and a nucleic acid with serves as a recombination partner. In a particularly preferred instance, the recombination partner may also be a nucleic acid generated by this invention, including a man-made gene or a man-made gene pathway. Recombination may be facilitated by or may occur at areas of homology that exist at the one (or more) artificially introduced intron(s) in the man-made gene.

The synthetic ligation reassembly method of this invention utilizes a plurality of nucleic acid building blocks, each of which preferably has two ligat able ends. The two ligatable ends on each nucleic acid building block may be two blunt ends (i.e. each having an overhang of zero nucleotides), or preferably one blunt end and one overhang, or more preferably still two overhangs.

A serviceable overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

According to one preferred embodiment, a nucleic acid building block is generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large depending on the choice of the experimenter. Preferred sizes for building block range from 1 base pair (not including any overhangs) to 100,000 base pairs (not including any overhangs). Other preferred size ranges are also provided, which have lower limits of from 1 bp to 10,000 bp (including every integer value in between), and upper limits of from 2 bp to 100, 000 bp (including every integer value in between).

It is appreciated that current methods of polymerase-based amplification can be used to generate double-stranded nucleic acids of up to thousands of base pairs, if not tens of thousands of base pairs, in length with high fidelity. Chemical synthesis (e.g. phosphoramidite-based) can be used to generate nucleic acids of up to hundreds of nucleotides in length with high fidelity; however, these can be assembled, e.g. using overhangs or sticky ends, to form double-stranded nucleic acids of up to thousands of base pairs, if not tens of thousands of base pairs, in length if so desired.

A combination of methods (e.g. phosphoramidite-based chemical synthesis and PCR) can also be used according to this invention. Thus, nucleic acid building block made by different methods can also be used in combination to generate a progeny molecule of this invention.

The use of chemical synthesis to generate nucleic acid building blocks is particularly preferred in this invention & is advantageous for other reasons as well, including procedural safety and ease. No cloning or harvesting or actual handling of any biological samples is required. The design of the nucleic acid building blocks can be accomplished on paper. Accordingly, this invention teaches an advance in procedural safety in recombinant technologies.

Figure 2:
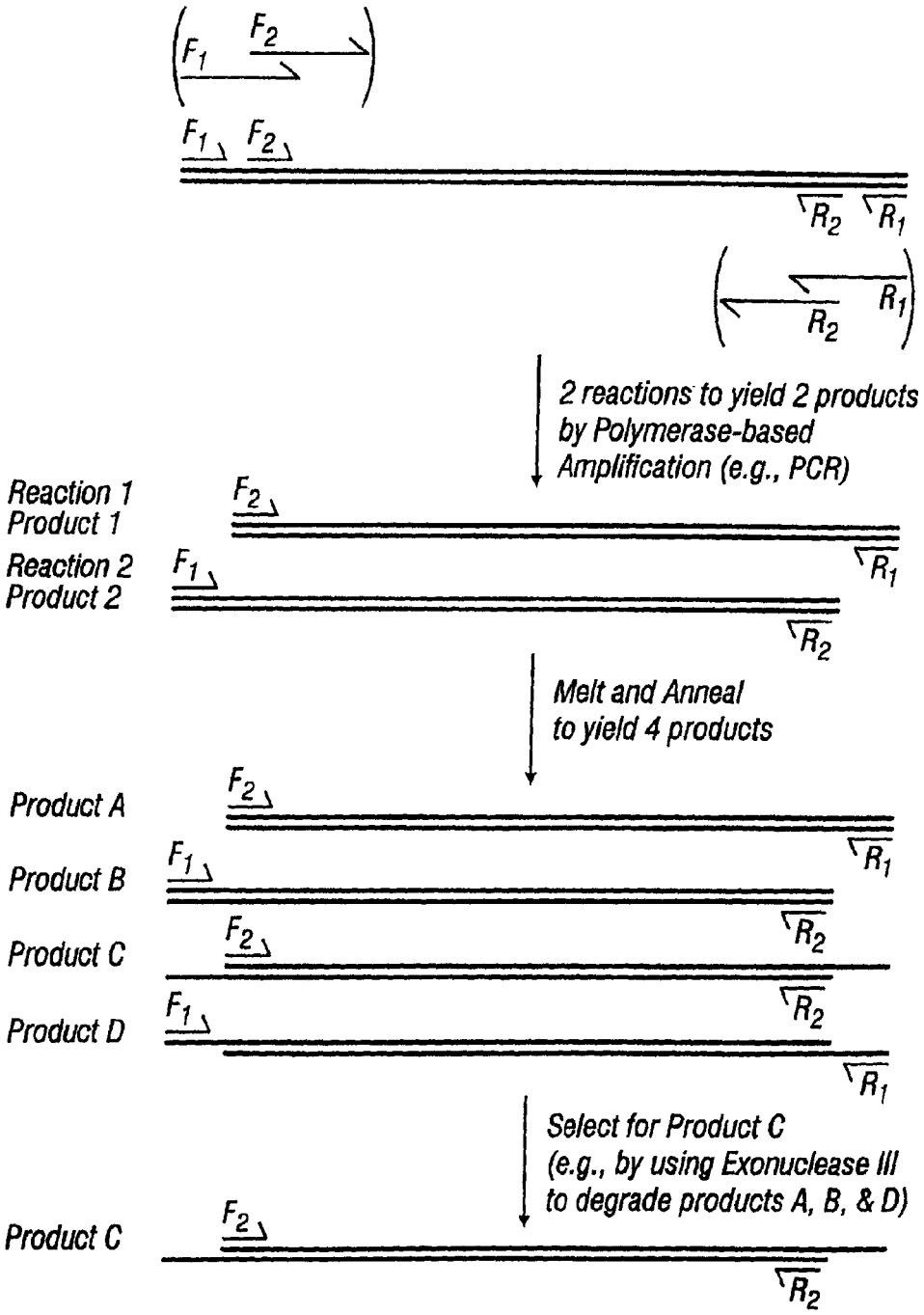
FIG. 2. Generation of A Nucleic Acid Building Block by Polymerase-Based Amplification.
Figure 3:
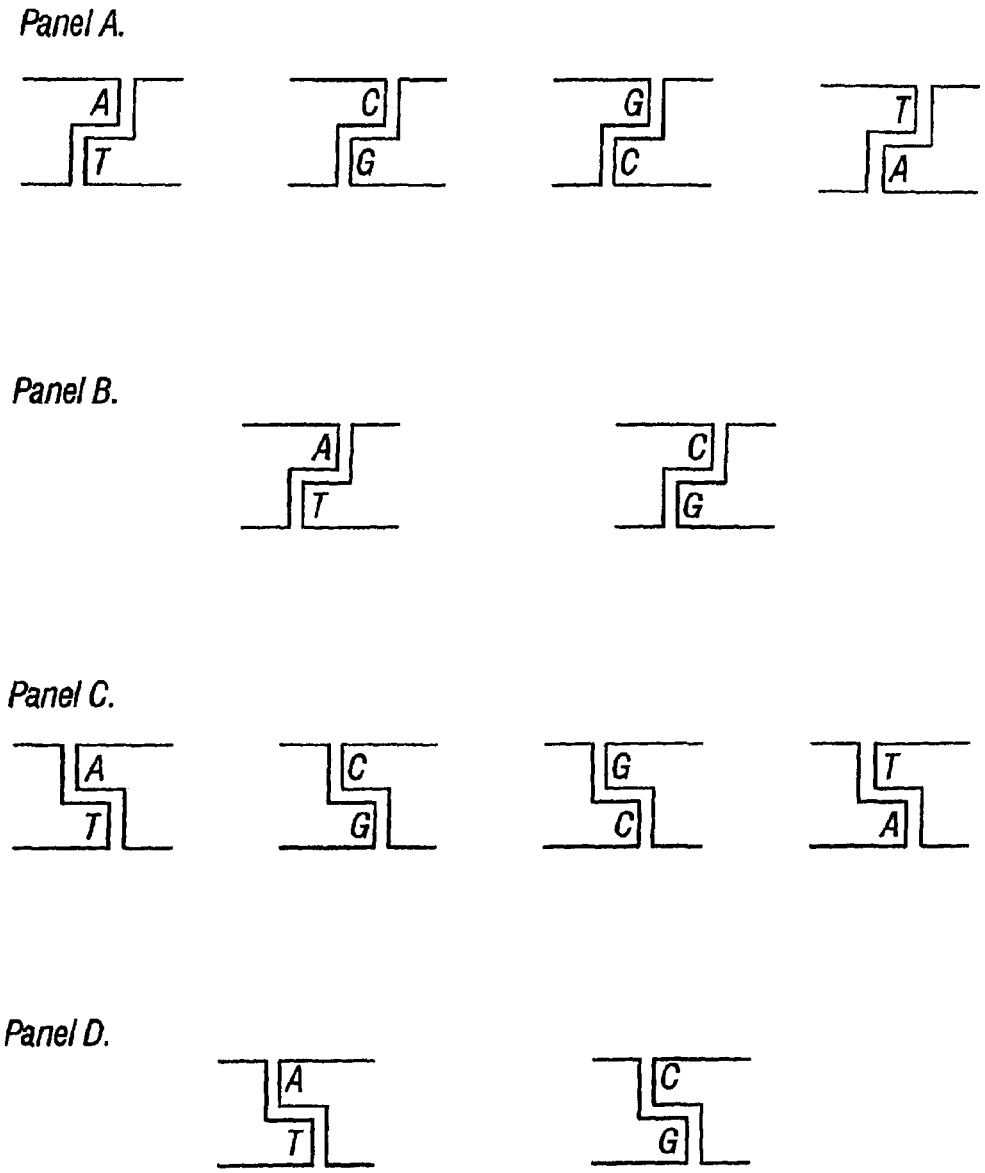
FIG. 3. Unique Overhangs And Unique Couplings.

Nonetheless, according to one preferred embodiment, a double-stranded nucleic acid building block according to this invention may also be generated by polymerase-based amplification of a polynucleotide template. In a non-limiting exemplification, as illustrated in FIG. 2, a first polymerase-based amplification reaction using a first set of primers, $F_2$ and $R_1$, is used to generate a blunt-ended product (labeled Reaction 1, Product 1), which is essentially identical to Product A. A second polymerase-based amplification reaction using a second set of primers, $F_1$ and $R_2$, is used to generate a blunt-ended product (labeled Reaction 2, Product 2), which is essentially identical to Product B. These two products are mixed and allowed to melt and anneal, generating potentially useful double-stranded nucleic acid building blocks with two overhangs. In the example of FIG. 2, the product with the 3' overhangs (Product C) is selected by nuclease-based degradation of the other 3 products using a 3' acting exonuclease, such as exonuclease III. It is appreciated that a 5' acting exonuclease (e.g. red alpha) may be also be used, for example to select Product D instead. It is also appreciated that other selection means can also be used, including hybridization-based means, and that these means can incorporate a further means, such as a magnetic bead-based means, to facilitate separation of the desired product.

Many other methods exist by which a double-stranded nucleic acid building block can be generated that is serviceable for this invention; and these are known in the art and can be readily performed by the skilled artisan.

According to particularly preferred embodiment, a double-stranded nucleic acid building block that is serviceable for this invention is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another embodiment, the two strands of a double-stranded nucleic acid building block are complementary at fewer than every nucleotide apart from any that form an overhang. Thus, according to this embodiment, a double-stranded nucleic acid building block can be used to introduce codon degeneracy. Preferably the codon degeneracy is introduced using the site-saturation mutagenesis described herein, using one or more N,N,G/T cassettes or alternatively using one or more N,N,N cassettes.

Contained within an exemplary experimental design for achieving an ordered assembly according to this invention are:

1) The design of specific nucleic acid building blocks.
2) The design of specific ligatable ends on each nucleic acid building block.
3) The design of a particular order of assembly of the nucleic acid building blocks.

An overhang may be a 3' overhang or a 5' overhang. An overhang may also have a terminal phosphate group or alternatively may be devoid of a terminal phosphate group (having, e.g., a hydroxyl group instead). An overhang may be comprised of any number of nucleotides. Preferably an overhang is comprised of 0 nucleotides (as in a blunt end) to 10,000 nucleotides. Thus, a wide range of overhang sizes may be serviceable. Accordingly, the lower limit may be each integer from 1-200 and the upper limit may be each integer from 2-10,000. According to a particular exemplification, an overhang may consist of anywhere from 1 nucleotide to 200 nucleotides (including every integer value in between).

The final chimeric nucleic acid molecule may be generated by sequentially assembling 2 or more building blocks at a time until all the designated building blocks have been assembled. A working sample may optionally be subjected to a process for size selection or purification or other selection or enrichment process between the performance of two assembly steps. Alternatively, the final chimeric nucleic acid molecule may be generated by assembling all the designated building blocks at once in one step.

The methods of these experiments allow reassembly to occur among nucleic acids having a little or no homology. Additionally fusion points or couplings can also occur in regions of low or no homology. The number of resulting molecules that can be generated in according to this experiment is very large.

Rather than to physically generate and screen this large number of potential products in random order, it is appreciated that, optionally with the aid of a computer, groupings of these potential products can be non-stochastically determined and furthermore ranked according to the predicted the likelihood that desirable products are contained in each grouping. Accordingly it is appreciated according to this experiment that computer modeling ("in silico") or mental calculations or considerations ("in cranio") may be useful to determine groupings all of potential reassembly products, where each such grouping is delineated by the potential products that can be generated using one set (or a finite set) of reagents and/or resulting from a one application (or a finite number of applications) of a method (or a finite as number of methods) disclosed herein. Additionally the groupings can be ranked against each other mentally or using computer modeling by predicting the number of potentially desirable or usable products in each grouping.

The grouping of potential products and the ranking of the groupings are different facets of what is referred to herein as "triaging", and specifically "in silico triage" if performed using the aid of a computer.

Examples of "structure-activity" considerations and serviceable computer software programs are abundant. The following examples are provided in a non-limiting fashion and are hereby incorporated by reference. Molecular Simulations Inc. of San Diego, Calif. is a subsidiary of Pharmacopeia, Inc. provides the following software programs that are useful for this invention: Gene Explorer™, ViewerPro™, SeqFold, Insight II, Biploymer, Homology, MODELER, Profiles-3D, Binding Site Analysis, and CFF.

In vivo Shuffling

In an embodiment of in vivo shuffling, the mixed population of the specific nucleic acid sequence is introduced into bacterial or eukaryotic cells under conditions such that at least two different nucleic acid sequences are present in each host cell. The polynucleotides can be introduced into the host cells by a variety of different methods. The host cells can be transformed with the smaller polynucleotides using methods known in the art, for example treatment with calcium chloride. If the polynucleotides are inserted into a phage genome, the host cell can be transfected with the recombinant phage genome having the specific nucleic acid sequences. Alternatively, the nucleic acid sequences can be introduced into the host cell using electroporation, transfection, lipofection, biolistics, conjugation, and the like.

In general, in this embodiment, the specific nucleic acids sequences will be present in vectors which are capable of stably replicating the sequence in the host cell. In addition, it is contemplated that the vectors will encode a marker gene such that host cells having the vector can be selected. This ensures that the mutated specific nucleic acid sequence can be recovered after introduction into the host cell. However, it is contemplated that the entire mixed population of the specific nucleic acid sequences need not be present on a vector sequence. Rather only a sufficient number of sequences need be cloned into vectors to ensure that after introduction of the polynucleotides into the host cells each host cell contains one vector having at least one specific nucleic acid sequence present therein. It is also contemplated that rather than having a subset of the population of the specific nucleic acids sequences cloned into vectors, this subset may be already stably integrated into the host cell.

It has been found that when two polynucleotides which have regions of identity are inserted into the host cells homologous recombination occurs between the two polynucleotides. Such recombination between the two mutated specific nucleic acid sequences will result in the production of double or triple hybrids in some situations.

It has also been found that the frequency of recombination is increased if some of the mutated specific nucleic acid sequences are present on linear nucleic acid molecules. Therefore, in a preferred embodiment, some of the specific nucleic acid sequences are present on linear polynucleotides.

After transformation, the host cell transformants are placed under selection to identify those host cell transformants which contain mutated specific nucleic acid sequences having the qualities desired. For example, if increased resistance to a particular drug is desired then the transformed host cells may be subjected to increased concentrations of the particular drug and those transformants producing mutated proteins able to confer increased drug resistance will be selected. If the enhanced ability of a particular protein to bind to a receptor is desired, then expression of the protein can be induced from the transformants and the resulting protein assayed in a ligand binding assay by methods known in the art to identify that subset of the mutated population which shows enhanced binding to the ligand. Alternatively, the protein can be expressed in another system to ensure proper processing.

Once a subset of the first recombined specific nucleic acid sequences (daughter sequences) having the desired characteristics are identified, they are then subject to a second round of recombination.

In the second cycle of recombination, the recombined specific nucleic acid sequences may be mixed with the original mutated specific nucleic acid sequences (parent sequences) and the cycle repeated as described above. In this way a set of second recombined specific nucleic acids sequences can be identified which have enhanced characteristics or encode for proteins having enhanced properties. This cycle can be repeated a number of times as desired.

It is also contemplated that in the second or subsequent recombination cycle, a backcross can be performed. A molecular backcross can be performed by mixing the desired specific nucleic acid sequences with a large number of the wild-type sequence, such that at least one wild-type nucleic acid sequence and a mutated nucleic acid sequence are present in the same host cell after transformation. Recombination with the wild-type specific nucleic acid sequence will eliminate those neutral mutations that may affect unselected characteristics such as immunogenicity but not the selected characteristics.

In another embodiment of this invention, it is contemplated that during the first round a subset of the specific nucleic acid sequences can be generated as smaller polynucleotides by slowing or halting their PCR amplification prior to introduction into the host cell. The size of the polynucleotides must be large enough to contain some regions of identity with the other sequences so as to homologously recombine with the other sequences. The size of the polynucleotides will range from 0.03 kb to 100 kb more preferably from 0.2 kb to 10 kb. It is also contemplated that in subsequent rounds, all of the specific nucleic acid sequences other than the sequences selected from the previous round may be utilized to generate PCR polynucleotides prior to introduction into the host cells.

The shorter polynucleotide sequences can be single-stranded or double-stranded. If the sequences were originally single-stranded and have become double-stranded they can be denatured with heat, chemicals or enzymes prior to insertion into the host cell. The reaction conditions suitable for separating the strands of nucleic acid are well known in the art.

The steps of this process can be repeated indefinitely, being limited only by the number of possible hybrids which can be achieved. After a certain number of cycles, all possible hybrids will have been achieved and further cycles are redundant.

In an embodiment the same mutated template nucleic acid is repeatedly recombined and the resulting recombinants selected for the desired characteristic.

Therefore, the initial pool or population of mutated template nucleic acid is cloned into a vector capable of replicating in a bacteria such as E. coli. The particular vector is not essential, so long as it is capable of autonomous replication in E. coli. In a preferred embodiment, the vector is designed to allow the expression and production of any protein encoded by the mutated specific nucleic acid linked to the vector. It is also preferred that the vector contain a gene encoding for a selectable marker.

The population of vectors containing the pool of mutated nucleic acid sequences is introduced into the E. coli host cells. The vector nucleic acid sequences may be introduced by transformation, transfection or infection in the case of phage. The concentration of vectors used to transform the bacteria is such that a number of vectors is introduced into each cell. Once present in the cell, the efficiency of homologous recombination is such that homologous recombination occurs between the various vectors. This results in the generation of hybrids (daughters) having a combination of mutations which differ from the original parent mutated sequences.

The host cells are then clonally replicated and selected for the marker gene present on the vector. Only those cells having a plasmid will grow under the selection.

The host cells which contain a vector are then tested for the presence of favorable mutations. Such testing may consist of placing the cells under selective pressure, for example, if the gene to be selected is an improved drug resistance gene. If the vector allows expression of the protein encoded by the mutated nucleic acid sequence, then such selection may include allowing expression of the protein so encoded, isolation of the protein and testing of the protein to determine whether, for example, it binds with increased efficiency to the ligand of interest.

Once a particular daughter mutated nucleic acid sequence has been identified which confers the desired characteristics, the nucleic acid is isolated either already linked to the vector or separated from the vector. This nucleic acid is then mixed with the first or parent population of nucleic acids and the cycle is repeated.

It has been shown that by this method nucleic acid sequences having enhanced desired properties can be selected.

In an alternate embodiment, the first generation of hybrids are retained in the cells and the parental mutated sequences are added again to the cells. Accordingly, the first cycle of Embodiment I is conducted as described above. However, after the daughter nucleic acid sequences are identified, the host cells containing these sequences are retained.

The parent mutated specific nucleic acid population, either as polynucleotides or cloned into the same vector is introduced into the host cells already containing the daughter nucleic acids. Recombination is allowed to occur in the cells and the next generation of recombinants, or granddaughters are selected by the methods described above.

This cycle can be repeated a number of times until the nucleic acid or peptide having the desired characteristics is obtained. It is contemplated that in subsequent cycles, the population of mutated sequences which are added to the preferred hybrids may come from the parental hybrids or any subsequent generation.

In an alternative embodiment, the invention provides a method of conducting a "molecular" backcross of the obtained recombinant specific nucleic acid in order to eliminate any neutral mutations. Neutral mutations are those mutations which do not confer onto the nucleic acid or peptide the desired properties. Such mutations may however confer on the nucleic acid or peptide undesirable characteristics. Accordingly, it is desirable to eliminate such neutral mutations. The method of this invention provide a means of doing so.

In this embodiment, after the hybrid nucleic acid, having the desired characteristics, is obtained by the methods of the embodiments, the nucleic acid, the vector having the nucleic acid or the host cell containing the vector and nucleic acid is isolated.

The nucleic acid or vector is then introduced into the host cell with a large excess of the wild-type nucleic acid. The nucleic acid of the hybrid and the nucleic acid of the wild-type sequence are allowed to recombine. The resulting recombinants are placed under the same selection as the hybrid nucleic acid. Only those recombinants which retained the desired characteristics will be selected. Any silent mutations which do not provide the desired characteristics will be lost through recombination with the wild-type DNA. This cycle can be repeated a number of times until all of the silent mutations are eliminated.

Thus the methods of this invention can be used in a molecular backcross to eliminate unnecessary or silent mutations.

Utility

The in vivo recombination method of this invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to mutate ribozymes or aptamers.

Scaffold-like regions separating regions of diversity in proteins may be particularly suitable for the methods of this invention. The conserved scaffold determines the overall folding by self-association, while displaying relatively unrestricted loops that mediate the specific binding. Examples of such scaffolds are the immunoglobulin beta barrel, and the four-helix bundle. The methods of this invention can be used to create scaffold-like proteins with various combinations of mutated sequences for binding.

The equivalents of some standard genetic matings may also be performed by the methods of this invention. For example, a "molecular" backcross can be performed by repeated mixing of the hybrid's nucleic acid with the wild-type nucleic acid while selecting for the mutations of interest. As in traditional breeding, this approach can be used to combine phenotypes from different sources into a background of choice. It is useful, for example, for the removal of neutral mutations that affect unselected characteristics (i.e. immunogenicity). Thus it can be useful to determine which mutations in a protein are involved in the enhanced biological activity and which are not.

Peptide Display Methods

The present method can be used to shuffle, by in vitro and/or in vivo recombination by any of the disclosed methods, and in any combination, polynucleotide sequences selected by peptide display methods, wherein an associated polynucleotide encodes a displayed peptide which is screened for a phenotype (e.g., for affinity for a predetermined receptor (ligand).

An increasingly important aspect of bio-pharmaceutical drug development and molecular biology is the identification of peptide structures, including the primary amino acid sequences, of peptides or peptidomimetics that interact with biological macromolecules. one method of identifying peptides that possess a desired structure or functional property, such as binding to a predetermined biological macromolecule (e.g., a receptor), involves the screening of a large library or peptides for individual library members which possess the desired structure or functional property conferred by the amino acid sequence of the peptide.

In addition to direct chemical synthesis methods for generating peptide libraries, several recombinant DNA methods also have been reported. One type involves the display of a peptide sequence, antibody, or other protein on the surface of a bacteriophage particle or cell. Generally, in these methods each bacteriophage particle or cell serves as an individual library member displaying a single species of displayed peptide in addition to the natural bacteriophage or cell protein sequences. Each bacteriophage or cell contains the nucleotide sequence information encoding the particular displayed peptide sequence; thus, the displayed peptide sequence can be ascertained by nucleotide sequence determination of an isolated library member.

A well-known peptide display method involves the presentation of a peptide sequence on the surface of a filamentous bacteriophage, typically as a fusion with a bacteriophage coat protein. The bacteriophage library can be incubated with an immobilized, predetermined macromolecule or small molecule (e.g., a receptor) so that bacteriophage particles which present a peptide sequence that binds to the immobilized macromolecule can be differentially partitioned from those that do not present peptide sequences that bind to the predetermined macromolecule. The bacteriophage particles (i.e., library members) which are bound to the immobilized macromolecule are then recovered and replicated to amplify the selected bacteriophage sub-population for a subsequent round of affinity enrichment and phage replication. After several rounds of affinity enrichment and phage replication, the bacteriophage library members that are thus selected are isolated and the nucleotide sequence encoding the displayed peptide sequence is determined, thereby identifying the sequence(s) of peptides that bind to the predetermined macromolecule (e.g., receptor). Such methods are further described in PCT patent publications WO 91/17271, WO 91/18980, WO 91/19818 and WO 93108278.

The latter PCT publication describes a recombinant DNA method for the display of peptide ligands that involves the production of a library of fusion proteins with each fusion protein composed of a first polypeptide portion, typically comprising a variable sequence, that is available for potential binding to a predetermined macromolecule, and a second polypeptide portion that binds to DNA, such as the DNA vector encoding the individual fusion protein. When transformed host cells are cultured under conditions that allow for expression of the fusion protein, the fusion protein binds to the DNA vector encoding it. Upon lysis of the host cell, the fusion protein/vector DNA complexes can be screened against a predetermined macromolecule in much the same way as bacteriophage particles are screened in the phage-based display system, with the replication and sequencing of the DNA vectors in the selected fusion protein/vector DNA complexes serving as the basis for identification of the selected library peptide sequence(s).

Other systems for generating libraries of peptides and like polymers have aspects of both the recombinant and in vitro chemical synthesis methods. In these hybrid methods, cell-free enzymatic machinery is employed to accomplish the in vitro synthesis of the library members (i.e., peptides or polynucleotides). In one type of method, RNA molecules with the ability to bind a predetermined protein or a predetermined dye molecule were selected by alternate rounds of selection and PCR amplification (Therk and Gold, 1990; Ellington and Szostak, 1990). A similar technique was used to identify DNA sequences which bind a predetermined human transcription factor (Thiesen and Bach, 1990; Beaudry and Joyce, 1992; PCT patent publications WO 92/05258 and WO 92/14843). In a similar fashion, the technique of in vitro translation has been used to synthesize proteins of interest and has been proposed as a method for generating large libraries of peptides. These methods which rely upon in vitro translation, generally comprising stabilized polysome complexes, are described further in PCT patent publications WO 88/08453, WO 90/05785, WO 90/07003, WO 91/02076, WO 91/05058, and WO 92/02536. Applicants have described methods in which library members comprise a fusion protein having a first polypeptide portion with DNA binding activity and a second polypeptide portion having the library member unique peptide sequence; such methods are suitable for use in cell-free in vitro selection formats, among others.

The displayed peptide sequences can be of varying lengths, typically from 3-5000 amino acids long or longer, frequently from 5-100 amino acids long, and often from about 8-15 amino acids long. A library can comprise library members having varying lengths of displayed peptide sequence, or may comprise library members having a fixed length of displayed peptide sequence. Portions or all of the displayed peptide sequence(s) can be random, pseudorandom, defined set kernal, fixed, or the like. The present display methods include methods for in vitro and in vivo display of single-chain antibodies, such as nascent scFv on polysomes or scfv displayed on phage, which enable large-scale screening of scfv libraries having broad diversity of variable region sequences and binding specificities.

The present invention also provides random, pseudorandom, and defined sequence framework peptide libraries and methods for generating and screening those libraries to identify useful compounds (e.g., peptides, including single-chain antibodies) that bind to receptor molecules or epitopes of interest or gene products that modify peptides or RNA in a desired fashion. The random, pseudorandom, and defined sequence framework peptides are produced from libraries of peptide library members that comprise displayed peptides or displayed single-chain antibodies attached to a polynucleotide template from which the displayed peptide was synthesized. The mode of attachment may vary according to the specific embodiment of the invention selected, and can include encapsulation in a phage particle or incorporation in a cell.

A method of affinity enrichment allows a very large library of peptides and single-chain antibodies to be screened and the polynucleotide sequence encoding the desired peptide(s) or single-chain antibodies to be selected. The polynucleotide can then be isolated and shuffled to recombine combinatorially the amino acid sequence of the selected peptide(s) (or predetermined portions thereof) or single-chain antibodies (or just VHI, VLI or CDR portions thereof). Using these methods, one can identify a peptide or single-chain antibody as having a desired binding affinity for a molecule and can exploit the process of shuffling to converge rapidly to a desired high-affinity peptide or scfv. The peptide or antibody can then be synthesized in bulk by conventional means for any suitable use (e.g., as a therapeutic or diagnostic agent).

A significant advantage of the present invention is that no prior information regarding an expected ligand structure is required to isolate peptide ligands or antibodies of interest. The peptide identified can have biological activity, which is meant to include at least specific binding affinity for a selected receptor molecule and, in some instances, will further include the ability to block the binding of other compounds, to stimulate or inhibit metabolic pathways, to act as a signal or messenger, to stimulate or inhibit cellular activity, and the like.

The present invention also provides a method for shuffling a pool of polynucleotide sequences selected by affinity screening a library of polysomes displaying nascent peptides (including single-chain antibodies) for library members which bind to a predetermined receptor (e.g., a mammalian proteinaceous receptor such as, for example, a peptidergic hormone receptor, a cell surface receptor, an intracellular protein which binds to other protein(s) to form intracellular protein complexes such as hetero-dimers and the like) or epitope (e.g., an immobilized protein, glycoprotein, oligosaccharide, and the like).

Polynucleotide sequences selected in a first selection round (typically by affinity selection for binding to a receptor (e.g., a ligand)) by any of these methods are pooled and the pool(s) is/are shuffled by in vitro and/or in vivo recombination to produce a shuffled pool comprising a population of recombined selected polynucleotide sequences. The recombined selected polynucleotide sequences are subjected to at least one subsequent selection round. The polynucleotide sequences selected in the subsequent selection round(s) can be used directly, sequenced, and/or subjected to one or more additional rounds of shuffling and subsequent selection. Selected sequences can also be back-crossed with polynucleotide sequences encoding neutral sequences (i.e., having insubstantial functional effect on binding), such as for example by back-crossing with a wild-type or naturally-occurring sequence substantially identical to a selected sequence to produce native-like functional peptides, which may be less immunogenic. Generally, during back-crossing subsequent selection is applied to retain the property of binding to the predetermined receptor (ligand).

Prior to or concomitant with the shuffling of selected sequences, the sequences can be mutagenized. In one embodiment, selected library members are cloned in a prokaryotic vector (e.g., plasmid, phagemid, or bacteriophage) wherein a collection of individual colonies (or plaques) representing discrete library members are produced. Individual selected library members can then be manipulated (e.g., by site-directed mutagenesis, cassette mutagenesis, chemical mutagenesis, PCR mutagenesis, and the like) to generate a collection of library members representing a kernal of sequence diversity based on the sequence of the selected library member. The sequence of an individual selected library member or pool can be manipulated to incorporate random mutation, pseudorandom mutation, defined kernal mutation (i.e., comprising variant and invariant residue positions and/or comprising variant residue positions which can comprise a residue selected from a defined subset of amino acid residues), codon-based mutation, and the like, either segmentally or over the entire length of the individual selected library member sequence. The mutagenized selected library members are then shuffled by in vitro and/or in vivo recombinatorial shuffling as disclosed herein.

The invention also provides peptide libraries comprising a plurality of individual library members of the invention, wherein (1) each individual library member of said plurality comprises a sequence produced by shuffling of a pool of selected sequences, and (2) each individual library member comprises a variable peptide segment sequence or single-chain antibody segment sequence which is distinct from the variable peptide segment sequences or single-chain antibody sequences of other individual library members in said plurality (although some library members may be present in more than one copy per library due to uneven amplification, stochastic probability, or the like).

The invention also provides a product-by-process, wherein selected polynucleotide sequences having (or encoding a peptide having) a predetermined binding specificity are formed by the process of: (1) screening a displayed peptide or displayed single-chain antibody library against a predetermined receptor (e.g., ligand) or epitope (e.g., antigen macromolecule) and identifying and/or enriching library members which bind to the predetermined receptor or epitope to produce a pool of selected library members, (2) shuffling by recombination the selected library members (or amplified or cloned copies thereof) which binds the predetermined epitope and has been thereby isolated and/or enriched from the library to generate a shuffled library, and (3) screening the shuffled library against the predetermined receptor (e.g., ligand) or epitope (e.g., antigen macromolecule) and identifying and/or enriching shuffled library members which bind to the predetermined receptor or epitope to produce a pool of selected shuffled library members.

Antibody Display and Screening Methods

The present method can be used to shuffle, by in vitro and/or in vivo recombination by any of the disclosed methods, and in any combination, polynucleotide sequences selected by antibody display methods, wherein an associated polynucleotide encodes a displayed antibody which is screened for a phenotype (e.g., for affinity for binding a predetermined antigen (ligand).

Various molecular genetic approaches have been devised to capture the vast immunological repertoire represented by the extremely large number of distinct variable regions which can be present in immunoglobulin chains. The naturally-occurring germ line immunoglobulin heavy chain locus is composed of separate tandem arrays of variable segment genes located upstream of a tandem array of diversity segment genes, which are themselves located upstream of a tandem array of joining (i) region genes, which are located upstream of the constant region genes. During B lymphocyte development, V-D-J rearrangement occurs wherein a heavy chain variable region gene (VH) is formed by rearrangement to form a fused D segment followed by rearrangement with a V segment to form a V-D-J joined product gene which, if productively rearranged, encodes a functional variable region (VH) of a heavy chain. Similarly, light chain loci rearrange one of several V segments with one of several J segments to form a gene encoding the variable region (VL) of a light chain.

The vast repertoire of variable regions possible in immunoglobulins derives in part from the numerous combinatorial possibilities of joining V and [i] *J* segments (and, in the case of heavy chain loci, D segments) during rearrangement in B cell development. Additional sequence diversity in the heavy chain variable regions arises from non-uniform rearrangements of the D segments during V-D-J joining and from N region addition. Further, antigen-selection of specific B cell clones selects for higher affinity variants having non-[germnline] *germline* mutations in one or both of the heavy and light chain variable regions; a phenomenon referred to as "affinity maturation" or "affinity sharpening". Typically, these "affinity sharpening" mutations cluster in specific areas of the variable region, most commonly in the complementarity-determining regions (CDRs).

In order to overcome many of the limitations in producing and identifying high-affinity immunoglobulins through antigen-stimulated B cell development (i.e., immunization), various prokaryotic expression systems have been developed that can be manipulated to produce combinatorial antibody libraries which may be screened for high-affinity antibodies to specific antigens. Recent advances in the expression of antibodies in Escherichia coli and bacteriophage systems (see "alternative peptide display methods", infra) have raised the possibility that virtually any specificity can be obtained by either cloning antibody genes from characterized hybridomas or by de novo selection using antibody gene libraries (e.g., from Ig cDNA).

Combinatorial libraries of antibodies have been generated in bacteriophage lambda expression systems which may be screened as bacteriophage plaques or as colonies of lysogens (Huse et al, 1989); Caton and Koprowski, 1990; Mullinax et al, 1990; Persson et al, 1991). Various embodiments of bacteriophage antibody display libraries and lambda phage expression libraries have been described (Kang et al, 1991; Clackson et al, 1991; McCafferty et al, 1990; Burton et al, 1991; Hoogenboom et al, 1991; Chang et al, 1991; Breitling et al, 1991; Marks et al, 1991, p. 581; Barbas et al, 1992; Hawkins and Winter, 1992; Marks et al, 1992, p. 779; Marks et al, 1992, p. 16007; and Lowman et al, 1991; Lerner et al, 1992; all incorporated herein by reference). Typically, a bacteriophage antibody display library is screened with a receptor (e.g., polypeptide, carbohydrate, glycoprotein, nucleic acid) that is immobilized (e.g., by covalent linkage to a chromatography resin to enrich for reactive phage by affinity chromatography) and/or labeled (e.g., to screen plaque or colony lifts).

One particularly advantageous approach has been the use of so-called single-chain fragment variable (scfv) libraries (Marks et al, 1992, p. 779; Winter and Milstein, 1991; Clackson et al, 1991; Marks et al, 1991, p. 581; Chaudhary et al, 1990; Chiiswell et al, 1992; McCafferty et al, 1990; and Huston et al, 1988). Various embodiments of scfv libraries displayed on bacteriophage coat proteins have been described.

Beginning in 1988, single-chain analogues of Fv fragments and their fusion proteins have been reliably generated by antibody engineering methods. The first step generally involves obtaining the genes encoding VH and VL domains with desired binding properties; these V genes may be isolated from a specific hybridoma cell line, selected from a combinatorial V-gene library, or made by V gene synthesis. The single-chain Fv is formed by connecting the component V genes with an oligonucleotide that encodes an appropriately designed linker peptide, such as (Gly-Gly-Gly-Gly-Ser)3 (*SEQ ID NO: 26*) or equivalent linker peptide(s). The linker bridges the C-terminus of the first V region and N-terminus of the second, ordered as either VH-linker-VL or VL-linker-VH' In principle, the scfv binding site can faithfully replicate both the affinity and specificity of its parent antibody combining site.

Thus, scfv fragments are comprised of VH and VL domains linked into a single polypeptide chain by a flexible linker peptide. After the scfv genes are assembled, they are cloned into a phagemid and expressed at the tip of the M13 phage (or similar filamentous bacteriophage) as fusion proteins with the bacteriophage PIII (gene 3) coat protein. Enriching for phage expressing an antibody of interest is accomplished by panning the recombinant phage displaying a population scfv for binding to a predetermined epitope (e.g., target antigen, receptor).

The linked polynucleotide of a library member provides the basis for replication of the library member after a screening or selection procedure, and also provides the basis for the determination, by nucleotide sequencing, of the identity of the displayed peptide sequence or VH and VL amino acid sequence. The displayed peptide (s) or single-chain antibody (e.g., scfv) and/or its VH and VL domains or their CDRs can be cloned and expressed in a suitable expression system. Often polynucleotides encoding the isolated VH and VL domains will be ligated to polynucleotides encoding constant regions (CH and CL) to form polynucleotides encoding complete antibodies (e.g., chimeric or fully-human), antibody fragments, and the like. Often polynucleotides encoding the isolated CDRs will be grafted into polynucleotides encoding a suitable variable region framework (and optionally constant regions) to form polynucleotides encoding complete antibodies (e.g., humanized or fully-human), antibody fragments, and the like. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like.

Various methods have been reported for increasing the combinatorial diversity of a scfv library to broaden the repertoire of binding species (idiotype spectrum) The use of PCR has permitted the variable regions to be rapidly cloned either from a specific hybridoma source or as a gene library from non-immunized cells, affording combinatorial diversity in the assortment of VH and VL cassettes which can be combined. Furthermore, the VH and VL cassettes can themselves be diversified, such as by random, pseudorandom, or directed mutagenesis. Typically, VH and VL cassettes are diversified in. or near the complementarity-determining regions (CDRS), often the third CDR, CDR3. Enzymatic inverse PCR mutagenesis has been shown to be a simple and reliable method for constructing relatively large libraries of scfv site-directed hybrids (Stemmer et al, 1993), as has error-prone PCR and chemical mutagenesis (Deng et al, 1994). Riechmann (Riechmann et al, 1993) showed semirational design of an antibody scfv fragment using site-directed randomization by degenerate oligonucleotide PCR and subsequent phage display of the resultant scfv hybrids. Barbas (Barbas et al, 1992) attempted to circumvent the problem of limited repertoire sizes resulting from using biased variable region sequences by randomizing the sequence in a synthetic CDR region of a human tetanus toxoid-binding Fab.

CDR randomization has the potential to create approximately $1\times10^{20}$ CDRs for the heavy chain CDR3 alone, and a roughly similar number of variants of the heavy chain CDR1 and CDR2, and light chain CDR1-3 variants. Taken individually or together, the combination possibilities of CDR randomization of heavy and/or light chains requires generating a prohibitive number of bacteriophage clones to produce a clone library representing all possible combinations, the vast majority of which will be non-binding. Generation of such large numbers of primary transformants is not feasible with current transformation technology and bacteriophage display systems. For example, Barbas (Barbas et al, 1992) only generated $5\times10^{7}$ transformants, which represents only a tiny fraction of the potential diversity of a library of thoroughly randomized CDRS.

Despite these substantial limitations, bacteriophage display of scfv have already yielded a variety of useful antibodies and antibody fusion proteins. A bispecific single chain antibody has been shown to mediate efficient tumor cell lysis (Gruber et al, 1994). Intracellular expression of an anti-Rev scfv has been shown to inhibit HIV-1 virus replication in vitro (Duan et al, 1994), and intracellular expression of an anti-p21rar, scfv has been shown to inhibit meiotic maturation of Xenopus oocytes (Biocca et al, 1993). Recombinant scfv which can be used to diagnose HIV infection have also been reported, demonstrating the diagnostic utility of scfv (Lilley et al, 1994). Fusion proteins wherein an scFv is linked to a second polypeptide, such as a toxin or fibrinolytic activator protein, have also been reported (Holvost et al, 1992; Nicholls et al, 1993).

If it were possible to generate scfv libraries having broader antibody diversity and overcoming many of the limitations of conventional CDR mutagenesis and randomization methods which can cover only a very tiny fraction of the potential sequence combinations, the number and quality of scfv antibodies suitable for therapeutic and diagnostic use could be vastly improved. To address this, the in vitro and in vivo shuffling methods of the invention are used to recombine CDRs which have been obtained (typically via PCR amplification or cloning) from nucleic acids obtained from selected displayed antibodies. Such displayed antibodies can be displayed on cells, on bacteriophage particles, on polysomes, or any suitable antibody display system wherein the antibody is associated with its encoding nucleic acid(s). In a variation, the CDRs are initially obtained from mRNA (or cDNA) from antibody-producing cells (e.g., plasma cells/splenocytes from an immunized wild-type mouse, a human, or a transgenic mouse capable of making a human antibody as in WO 92/03918, WO 93/12227, and WO 94/25585), including hybridomas derived therefrom.

Polynucleotide sequences selected in a first selection round (typically by affinity selection for displayed antibody binding to an antigen (e.g., a ligand) by any of these methods are pooled and the pool(s) is/are shuffled by in vitro and/or in vivo recombination, especially shuffling of CDRs (typically shuffling heavy chain CDRs with other heavy chain CDRs and light chain CDRs with other light chain CDRs) to produce a shuffled pool comprising a population of recombined selected polynucleotide sequences. The recombined selected polynucleotide sequences are expressed in a selection format as a displayed antibody and subjected to at least one subsequent selection round. The polynucleotide sequences selected in the subsequent selection round(s) can be used directly, sequenced, and/or subjected to one or more additional rounds of shuffling and subsequent selection until an antibody of the desired binding affinity is obtained. Selected sequences can also be back-crossed with polynucleotide sequences encoding neutral antibody framework sequences (i.e., having insubstantial functional effect on antigen binding), such as for example by back-crossing with a human variable region framework to produce human-like sequence antibodies. Generally, during back-crossing subsequent selection is applied to retain the property of binding to the predetermined antigen.

Alternatively, or in combination with the noted variations, the valency of the target epitope may be varied to control the average binding affinity of selected scfv library members. The target epitope can be bound to a surface or substrate at varying densities, such as by including a competitor epitope, by dilution, or by other method known to those in the art. A high density (valency) of predetermined epitope can be used to enrich for scfv library members which have relatively low affinity, whereas a low density (valency) can preferentially enrich for higher affinity scfv library members.

For generating diverse variable segments, a collection of synthetic oligonucleotides encoding random, pseudorandom, or a defined sequence kernal set of peptide sequences can be inserted by ligation into a predetermined site (e.g., a CDR). Similarly, the sequence diversity of one or more CDRs of the single-chain antibody cassette(s) can be expanded by mutating the CDR(s) with site-directed mutagenesis, CDR-replacement, and the like. The resultant DNA molecules can be propagated in a host for cloning and amplification prior to shuffling, or can be used directly (i.e., may avoid loss of diversity which may occur upon propagation in a host cell) and the selected library members subsequently shuffled.

Displayed peptide/polynucleotide complexes (library members) which encode a variable segment peptide sequence of interest or a single-chain antibody of interest are selected from the library by an affinity enrichment technique. This is accomplished by means of a immobilized macromolecule or epitope specific for the peptide sequence of interest, such as a receptor, other macromolecule, or other epitope species. Repeating the affinity selection procedure provides an enrichment of library members encoding the desired sequences, which may then be isolated for pooling and shuffling, for sequencing, and/or for further propagation and affinity enrichment.

The library members without the desired specificity are removed by washing. The degree and stringency of washing required will be determined for each peptide sequence or single-chain antibody of interest and the immobilized predetermined macromolecule or epitope. A certain degree of control can be exerted over the binding characteristics of the nascent peptide/DNA complexes recovered by adjusting the conditions of the binding incubation and the subsequent washing. The temperature, pH, ionic strength, divalent cations concentration, and the volume and duration of the washing will select for nascent peptide/DNA complexes within particular ranges of affinity for the immobilized macromolecule. Selection based on slow dissociation rate, which is usually predictive of high affinity, is often the most practical route. This may be done either by continued incubation in the presence of a saturating amount of free predetermined macromolecule, or by increasing the volume, number, and length of the washes. In each case, the rebinding of dissociated nascent peptide/DNA or peptide/RNA complex is prevented, and with increasing time, nascent peptide/DNA or peptide/RNA complexes of higher and higher affinity are recovered.

Additional modifications of the binding and washing procedures may be applied to find peptides with special characteristics. The affinities of some peptides are dependent on ionic strength or cation concentration. This is a useful characteristic for peptides that will be used in affinity purification of various proteins when gentle conditions for removing the protein from the peptides are required.

One variation involves the use of multiple binding targets (multiple epitope species, multiple receptor species), such that a scfv library can be simultaneously screened for a multiplicity of scfv which have different binding specificities. Given that the size of a scfv library often limits the diversity of potential scfv sequences, it is typically desirable to us scfv libraries of as large a size as possible. The time and economic considerations of generating a number of very large polysome scFv-display libraries can become prohibitive. To avoid this substantial problem, multiple predetermined epitope species (receptor species) can be concomitantly screened in a single library, or sequential screening against a number of epitope species can be used. In one variation, multiple target epitope species, each encoded on a separate bead (or subset of beads), can be mixed and incubated with a polysome-display scfv library under suitable binding conditions. The collection of beads, comprising multiple epitope species, can then be used to isolate, by affinity selection, scfv library members. Generally, subsequent affinity screening rounds can include the same mixture of beads, subsets thereof, or beads containing only one or two individual epitope species. This approach affords efficient screening, and is compatible with laboratory automation, batch processing, and high throughput screening methods.

A variety of techniques can be used in the present invention to diversify a peptide library or single-chain antibody library, or to diversify, prior to or concomitant with shuffling, around variable segment peptides found in early rounds of panning to have sufficient binding activity to the predetermined macromolecule or epitope. In one approach, the positive selected peptide/polynucleotide complexes (those identified in an early round of affinity enrichment) are sequenced to determine the identity of the active peptides. Oligonucleotides are then synthesized based on these active peptide sequences, employing a low level of all bases incorporated at each step to produce slight variations of the primary oligonucleotide sequences. This mixture of (slightly) degenerate oligonucleotides is then cloned into the variable segment sequences at the appropriate locations. This method produces systematic, controlled variations of the starting peptide sequences, which can then be shuffled. It requires, however, that individual positive nascent peptide/polynucleotide complexes be sequenced before mutagenesis, and thus is useful for expanding the diversity of small numbers of recovered complexes and selecting variants having higher binding affinity and/or higher binding specificity. In a variation, mutagenic PCR amplification of positive selected peptide/polynucleotide complexes (especially of the variable region sequences, the amplification products of which are shuffled in vitro and/or in vivo and one or more additional rounds of screening is done prior to sequencing. The same general approach can be employed with single-chain antibodies in order to expand the diversity and enhance the binding affinity/specificity, typically by diversifying CDRs or adjacent framework regions prior to or concomitant with shuffling. If desired, shuffling reactions can be spiked with mutagenic oligonucleotides capable of in vitro recombination with the selected library members can be included. Thus, mixtures of synthetic oligonucleotides and PCR produced polynucleotides (synthesized by error-prone or high-fidelity methods) can be added to the in vitro shuffling mix and be incorporated into resulting shuffled library members (shufflants).

The present invention of shuffling enables the generation of a vast library of CDR-variant single-chain antibodies. One way to generate such antibodies is to insert synthetic CDRs into the single-chain antibody and/or CDR randomization prior to or concomitant with shuffling. The sequences of the synthetic CDR cassettes are selected by referring to known sequence data of human CDR and are selected in the discretion of the practitioner according to the following guidelines: synthetic CDRs will have at least 40 percent positional sequence identity to known CDR sequences, and preferably will have at least 50 to 70 percent positional sequence identity to known CDR sequences. For example, a collection of synthetic CDR sequences can be generated by synthesizing a collection of oligonucleotide sequences on the basis of naturally-occurring human CDR sequences listed in Kabat (Kabat et al, 1991); the pool(s) of synthetic CDR sequences are calculated to encode CDR peptide sequences having at least 40 percent sequence identity to at least one known naturally-occurring human CDR sequence. Alternatively, a collection of naturally-occurring CDR sequences may be compared to generate consensus sequences so that amino acids used at a residue position frequently (i.e., in at least 5 percent of known CDR sequences) are incorporated into the synthetic CDRs at the corresponding position(s). Typically, several (e.g., 3 to about 50) known CDR sequences are compared and observed natural sequence variations between the known CDRs are tabulated, and a collection of oligonucleotides encoding CDR peptide sequences encompassing all or most permutations of the observed natural sequence variations is synthesized. For example but not for limitation, if a collection of human VH CDR sequences have carboxy-terminal amino acids which are either Tyr, Val, Phe, or Asp, then the pool(s) of synthetic CDR oligonucleotide sequences are designed to allow the carboxy-terminal CDR residue to be any of these amino acids. In some embodiments, residues other than those which naturally-occur at a residue position in the collection of CDR sequences are incorporated: conservative amino acid substitutions are frequently incorporated and up to 5 residue positions may be varied to incorporate non-conservative amino acid substitutions as compared to known naturally-occurring CDR sequences. Such CDR sequences can be used in primary library members (prior to first round screening) and/or can be used to spike in vitro shuffling reactions of selected library member sequences. Construction of such pools of defined and/or degenerate sequences will be readily accomplished by those of ordinary skill in the art.

The collection of synthetic CDR sequences comprises at least one member that is not known to be a naturally-occurring CDR sequence. It is within the discretion of the practitioner to include or not include a portion of random or pseudorandom sequence corresponding to N region addition in the heavy chain CDR; the N region sequence ranges from 1 nucleotide to about 4 nucleotides occurring at V-D and D-J junctions. A collection of synthetic heavy chain CDR sequences comprises at least about 100 unique CDR sequences, typically at least about 1,000 unique CDR sequences, preferably at least about 10,000 unique CDR sequences, frequently more than 50,000 unique CDR sequences; however, usually not more than about 1×106 unique CDR sequences are included in the collection, although occasionally 1×107 to 1×108 unique CDR sequences are present, especially if conservative amino acid substitutions are permitted at positions where the conservative amino acid substituent is not present or is rare (i.e., less than 0.1 percent) in that position in naturally-occurring human CDRS. In general, the number of unique CDR sequences included in a library should not exceed the expected number of primary transformants in the library by more than a factor of 10. Such single-chain antibodies generally bind of about at least 1×10 m-, preferably with an affinity of about at least $5\times10^{7}$ M−1, more preferably with an affinity of at least $1\times10^{8}$ M−1 to $1\times10^{9}$ M−1 or more, sometimes up to $1\times10^{10}$ M−1 or more. Frequently, the predetermined antigen is a human protein, such as for example a human cell surface antigen (e. g., CD4, CD8, IL-2 receptor, EGF receptor, PDGF receptor), other human biological macromolecule (e.g., thrombomodulin, protein C, carbohydrate antigen, sialyl Lewis antigen, Lselectin), or nonhuman disease associated macromolecule (e.g., bacterial LPS, virion capsid protein or envelope glycoprotein) and the like.

High affinity single-chain antibodies of the desired specificity can be engineered and expressed in a variety of as systems. For example, scfv have been produced in plants (Firek et al, 1993) and can be readily made in prokaryotic systems (Owens and Young, 1994; Johnson and Bird, 1991). Furthermore, the single-chain antibodies can be used as a basis for constructing whole antibodies or various fragments thereof (Kettleborough et al, 1994). The variable region encoding sequence may be isolated (e.g., by PCR amplification or subcloning) and spliced to a sequence encoding a desired human constant region to encode a human sequence antibody more suitable for human therapeutic uses where immunogenicity is preferably minimized. The polynucleotide(s) having the resultant fully human encoding sequence(s) can be expressed in a host cell (e.g., from an expression vector in a mammalian cell) and purified for pharmaceutical formulation.

The DNA expression constructs will typically include an expression control DNA sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the mutant' "engineered" antibodies.

As stated previously, the DNA sequences will be expressed in hosts after the sequences have been operably linked to an expression control sequence (i.e., positioned to ensure the transcription and translation of the structural gene). These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

In addition to eukaryotic microorganisms such as yeast, mammalian tissue cell culture may also be used to produce the polypeptides of the present invention (see Winnacker, 1987), which is incorporated herein by reference). Eukaryotic cells are actually preferred, because a number of suitable host cell lines capable of secreting intact immunoglobulins have been developed in the art, and include the CHO cell lines, various COS cell lines, HeLa cells, and myeloma cell lines, but preferably transformed Bcells or hybridomas. Expression vectors for these cells can include expression control sequences, such as an origin of replication, a promoter, an enhancer (Queen et al, 1986), and necessary processing information sites, such as ribosome binding sites, RNA splice sites, polyadenylation sites, and transcriptional terminator sequences. Preferred expression control sequences are promoters derived from immunoglobulin genes, cytomegalovirus, SV40, Adenovirus, Bovine Papilloma Virus, and the like.

Eukaryotic DNA transcription can be increased by inserting an enhancer sequence into the vector. Enhancers are cis-acting sequences of between 10 to 300 bp that increase transcription by a promoter. Enhancers can effectively increase transcription when either 51 or 31 to the transcription unit. They are also effective if located within an intron or within the coding sequence itself. Typically, viral enhancers are used, including SV40 enhancers, cytomegalovirus enhancers, polyoma enhancers, and adenovirus enhancers. Enhancer sequences from mammalian systems are also commonly used, such as the mouse immunoglobulin heavy chain enhancer.

Mammalian expression vector systems will also typically include a selectable marker gene. Examples of suitable markers include, the dihydrofolate reductase gene (DHFR), the thymidine kinase gene (TK), or prokaryotic genes conferring drug resistance. The first two marker genes prefer the use of mutant cell lines that lack the ability to grow without the addition of thymidine to the growth medium. Transformed cells can then be identified by their ability to grow on non-supplemented media. Examples of prokaryotic drug resistance genes useful as markers include genes conferring resistance to G418, mycophenolic acid and hygromycin.

The vectors containing the DNA segments of interest can be transferred into the host cell by well-known methods, depending on the type of cellular host. For example, calcium chloride transfection is commonly utilized for prokaryotic cells, whereas calcium phosphate treatment. lipofection, or electroporation may be used for other cellular hosts. Other methods used to transform mammalian cells include the use of Polybrene, protoplast fusion, liposomes, electroporation, and micro-injection (see, generally, Sambrook et al, 1982 and 1989).

Once expressed, the antibodies, individual mutated immunoglobulin chains, mutated antibody fragments, and other immunoglobulin polypeptides of the invention can be purified according to standard procedures of the art, including ammonium sulfate precipitation, fraction column chromatography, gel electrophoresis and the like (see. generally, Scopes, 1982). Once purified, partially or to homogeneity as desired, the polypeptides may then be used therapeutically or in developing and performing assay procedures, immunofluorescent stainings, and the like (see, generally, Lefkovits and Pernis, 1979 and 1981; Lefkovits, 1997).

The antibodies generated by the method of the present invention can be used for diagnosis and therapy. By way of illustration and not limitation, they can be used to treat cancer, autoimmune diseases, or viral infections. For treatment of cancer, the antibodies will typically bind to an antigen expressed preferentially on cancer cells, such as erbB-2, CEA, CD33, and many other antigens and binding members well known to those skilled in the art.

End-Selection

This invention provides a method for selecting a subset of polynucleotides from a starting set of polynucleotides, which method is based on the ability to discriminate one or more selectable features (or selection markers) present anywhere in a working polynucleotide, so as to allow one to perform selection for (positive selection) &/or against (negative selection) each selectable polynucleotide. In a preferred aspect, a method is provided termed end-selection, which method is based on the use of a selection marker located in part or entirely in a terminal region of a selectable polynucleotide, and such a selection marker may be termed an "end-selection marker".

End-selection may be based on detection of naturally occurring sequences or on detection of sequences introduced experimentally (including by any mutagenesis procedure mentioned herein and not mentioned herein) or on both, even within the same polynucleotide. An end-selection marker can be a structural selection marker or a functional selection marker or both a structural and a functional selection marker. An end-selection marker may be comprised of a polynucleotide sequence or of a polypeptide sequence or of any chemical structure or of any biological or biochemical tag, including markers that can be selected using methods based on the detection of radioactivity, of enzymatic activity, of fluorescence, of any optical feature, of a magnetic property (e.g. using magnetic beads), of immunoreactivity, and of hybridization.

End-selection may be applied in combination with any method serviceable for performing mutagenesis. Such mutagenesis methods include, but are not limited to, methods described herein (supra and infra). Such methods include, by way of non-limiting exemplification, any method that may be referred herein or by others in the art by any of the following terms: "saturation mutagenesis", "shuffling", "recombination", "re-assembly", "error-prone PCR", "assembly PCR", "sexual PCR", "crossover PCR"; "oligonucleotide primer-directed mutagenesis", "recursive (&/or exponential) ensemble mutagenesis (see Arkin and Youvan, 1992)", "cassette mutagenesis", "in vivo mutagenesis", and "in vitro mutagenesis". Moreover, end-selection may be performed on molecules produced by any mutagenesis &/or amplification method (see, e.g., Arnold, 1993; Caldwell and Joyce, 1992; Stemmer, 1994; following which method it is desirable to select for (including to screen for the presence of) desirable progeny molecules.

In addition, end-selection may be applied to a polynucleotide apart from any mutagenesis method. In a preferred embodiment, end-selection, as provided herein, can be used in order to facilitate a cloning step, such as a step of ligation to another polynucleotide (including ligation to a vector). This invention thus provides for end-selection as a serviceable means to facilitate library construction, selection &/or enrichment for desirable polynucleotides, and cloning in general.

In a particularly preferred embodiment, end-selection can be based on (positive) selection for a polynucleotide; alternatively end-selection can be based on (negative) selection against a polynucleotide; and alternatively still, end-selection can be based on both (positive) selection for, and on (negative) selection against, a polynucleotide. End-selection, along with other methods of selection &/or screening, can be performed in an iterative fashion, with any combination of like or unlike selection &/or screening methods and serviceable mutagenesis methods, all of which can be performed in an iterative fashion and in any order, combination, and permutation.

It is also appreciated that, according to one embodiment of this invention, end-selection may also be used to select a polynucleotide is at least in part: circular (e.g. a plasmid or any other circular vector or any other polynucleotide that is partly circular), &/or branched, &/or modified or substituted with any chemical group or moiety. In accord with this embodiment, a polynucleotide may be a circular molecule comprised of an intermediate or central region, which region is flanked on a 5' side by a 5' flanking region (which, for the purpose of end-selection, serves in like manner to a 5' terminal region of a non-circular polynucleotide) and on a 3' side by a 3' terminal region (which, for the purpose of end-selection, serves in like manner to a 3' terminal region of a non-circular polynucleotide). As used in this non-limiting exemplification, there may be sequence overlap between any two regions or even among all three regions.

In one non-limiting aspect of this invention, end-selection of a linear polynucleotide is performed using a general approach based on the presence of at least one end-selection marker located at or near a polynucleotide end or terminus (that can be either a 5' end or a 3' end). In one particular non-limiting exemplification, end-selection is based on selection for a specific sequence at or near a terminus such as, but not limited to, a sequence recognized by an enzyme that recognizes a polynucleotide sequence. An enzyme that recognizes and catalyzes a chemical modification of a polynucleotide is referred to herein as a polynucleotide-acting enzyme. In a preferred embodiment, serviceable polynucleotide-acting enzymes are exemplified non-exclusively by enzymes with polynucleotide-cleaving activity, enzymes with polynucleotide-methylating activity, enzymes with polynucleotide-ligating activity, and enzymes with a plurality of distinguishable enzymatic activities (including non-exclusively, e.g., both polynucleotide-cleaving activity and polynucleotide-ligating activity).

Relevant polynucleotide-acting enzymes thus also include any commercially available or non-commercially available polynucleotide endonucleases and their companion methylases including those catalogued at the website http://www.neb.com/rebase, and those mentioned in the following cited reference (Roberts and Macelis, 1996). Preferred polynucleotide endonucleases include—but are not limited to—type II restriction enzymes (including type IIS), and include enzymes that cleave both strands of a double stranded polynucleotide (e.g. Not I, which cleaves both strands at 5' . . . GC/GGCCGC . . . 3') and enzymes that cleave only one strand of a double stranded polynucleotide, i.e. enzymes that have polynucleotide-nicking activity, (e.g. N. BstNB I, which cleaves only one strand at 5' . . . GAGTCNNNN/N . . . 3' (*SEQ ID NO: 27*)). Relevant polynucleotide-acting enzymes also include type III restriction enzymes.

It is appreciated that relevant polynucleotide-acting enzymes also include any enzymes that may be developed in the future, though currently unavailable, that are serviceable for generating a ligation compatible end, preferably a sticky end, in a polynucleotide.

In one preferred exemplification, a serviceable selection marker is a restriction site in a polynucleotide that allows a corresponding type II (or type IIS) restriction enzyme to cleave an end of the polynucleotide so as to provide a ligatable end (including a blunt end or alternatively a sticky end with at least a one base overhang) that is serviceable for a desirable ligation reaction without cleaving the polynucleotide internally in a manner that destroys a desired internal sequence in the polynucleotide. Thus it is provided that, among relevant restriction sites, those sites that do not occur internally (i.e. that do not occur apart from the termini) in a specific working polynucleotide are preferred when the use of a corresponding restriction enzyme(s) is not intended to cut the working polynucleotide internally. This allows one to perform restriction digestion reactions to completion or to near completion without incurring unwanted internal cleavage in a working polynucleotide.

According to a preferred aspect, it is thus preferable to use restriction sites that are not contained, or alternatively that are not expected to be contained, or alternatively that unlikely to be contained (e.g. when sequence information regarding a working polynucleotide is incomplete) internally in a polynucleotide to be subjected to end-selection. In accordance with this aspect, it is appreciated that restriction sites that occur relatively infrequently are usually preferred over those that occur more frequently. On the other hand it is also appreciated that there are occasions where internal cleavage of a polypeptide is desired, e.g. to achieve recombination or other mutagenic procedures along with end-selection.

In accord with this invention, it is also appreciated that methods (e.g. mutagenesis methods) can be used to remove unwanted internal restriction sites. It is also appreciated that a partial digestion reaction (i.e. a digestion reaction that proceeds to partial completion) can be used to achieve digestion at a recognition site in a terminal region while sparing a susceptible restriction site that occurs internally in a polynucleotide and that is recognized by the same enzyme. In one aspect, partial digest are useful because it is appreciated that certain enzymes show preferential cleavage of the same recognition sequence depending on the location and environment in which the recognition sequence occurs. For example, it is appreciated that, while lambda DNA has 5 EcoR I sites, cleavage of the site nearest to the right terminus has been reported to occur 10 times faster than the sites in the middle of the molecule. Also, for example, it has been reported that, while Sac II has four sites on lambda DNA, the three clustered centrally in lambda are cleaved 50 times faster than the remaining site near the terminus (at nucleotide 40,386). Summarily, site preferences have been reported for various enzymes by many investigators (e.g., Thomas and Davis, 1975; Forsblum et al, 1976; Nath and Azzolina, 1981; Brown and Smith, 1977; Gingeras and Brooks, 1983; Krüger et al, 1988; Conrad and Topal, 1989; Oller et al, 1991; Topal, 1991; and Pein, 1991; to name but a few). It is appreciated that any empirical observations as well as any mechanistic understandings of site preferences by any serviceable polynucleotide-acting enzymes, whether currently available or to be procured in the future, may be serviceable in end-selection according to this invention.

It is also appreciated that protection methods can be used to selectively protect specified restriction sites (e.g. internal sites) against unwanted digestion by enzymes that would otherwise cut a working polypeptide in response to the presence of those sites; and that such protection methods include modifications such as methylations and base substitutions (e.g. U instead of T) that inhibit an unwanted enzyme activity. It is appreciated that there are limited numbers of available restriction enzymes that are rare enough (e.g. having very long recognition sequences) to create large (e.g. megabase-long) restriction fragments, and that protection approaches (e.g. by methylation) are serviceable for increasing the rarity of enzyme cleavage sites. The use of M.Fnu II (mCGCG) to increase the apparent rarity of Not I approximately twofold is but one example among many (Qiang et al, 1990; Nelson et al, 1984; Maxam and Gilbert, 1980; Raleigh and Wilson, 1986).

According to a preferred aspect of this invention, it is provided that, in general, the use of rare restriction sites is preferred. It is appreciated that, in general, the frequency of occurrence of a restriction site is determined by the number of nucleotides contained therein, as well as by the ambiguity of the base requirements contained therein. Thus, in a non-limiting exemplification, it is appreciated that, in general, a restriction site composed of, for example, 8 specific nucleotides (e.g. the Not I site or GC/GGCCGC, with an estimated relative occurrence of 1 in $4^8$, i.e. 1 in 65,536, random 8-mers) is relatively more infrequent than one composed of, for example, 6 nucleotides (e.g. the Sma I site or CCC/GGG, having an estimated relative occurrence of 1 in $4^6$, i.e. 1 in 4,096, random 6-mers), which in turn is relatively more infrequent than one composed of, for example, 4 nucleotides (e.g. the Msp I site or C/CGG, having an estimated relative occurrence of 1 in $4^4$, i.e. 1 in 256, random 4-mers). Moreover, in another non-limiting exemplification, it is appreciated that, in general, a restriction site having no ambiguous (but only specific) base requirements (e.g. the Fin I site or GTCCC, having an estimated relative occurrence of 1 in $4^5$, i.e. 1 in 1024, random 5-mers) is relatively more infrequent than one having an ambiguous W (where W=A or T) base requirement (e.g. the Ava II site or G/GWCC, having an estimated relative occurrence of 1 in 4×4×2×4×4—i.e. 1 in 512—random 5-mers), which in turn is relatively more infrequent than one having an ambiguous N (where N=A or C or G or T) base requirement (e.g. the Asu I site or G/GNCC, having an estimated relative occurrence of 1 in 4×4×1×4×4, i.e. I in 256—random 5-mers). These relative occurrences are considered general estimates for actual polynucleotides, because it is appreciated that specific nucleotide bases (not to mention specific nucleotide sequences) occur with dissimilar frequencies in specific polynucleotides, in specific species of organisms, and in specific groupings of organisms. For example, it is appreciated that the % G+C contents of different species of organisms are often very different and wide ranging.

The use of relatively more infrequent restriction sites as a selection marker include—in a non-limiting fashion—preferably those sites composed at least a 4 nucleotide sequence, more preferably those composed at least a 5 nucleotide sequence, more preferably still those composed at least a 6 nucleotide sequence (e.g. the BamH I site or G/GATCC, the Bgl II site or A/GATCT, the Pst I site or CTGCA/G, and the Xba I site or T/CTAGA), more preferably still those composed at least a 7 nucleotide sequence, more preferably still those composed of an 8 nucleotide sequence nucleotide sequence (e.g. the Asc I site or GG/CGCGCC, the Not I site or GC/GGCCGC, the Pac-I site or TTAAT/TAA, the Pme I site or GTTT/AAAC, the Srf I site or GCCC/GGGC, the Sse838 I site or CCTGCA/GG, and the Swa I site or ATTT/AAAT), more preferably still those composed of a 9 nucleotide sequence, and even more preferably still those composed of at least a 10 nucleotide sequence (e.g. the BspG I site or CG/CGCTGGAC (*SEQ ID NO: 28*)). It is further appreciated that some restriction sites (e.g. for class IIS enzymes) are comprised of a portion of relatively high specificity (i.e. a portion containing a principal determinant of the frequency of occurrence of the restriction site) and a portion of relatively low specificity; and that a site of cleavage may or may not be contained within a portion of relatively low specificity. For example, in the Eco57 I site or CTGAAG(16/14) (*SEQ ID NO: 24*), there is a portion of relatively high specificity (i.e. the CTGAAG portion) and a portion of relatively low specificity (i.e. the N16 sequence) that contains a site of cleavage.

In another preferred embodiment of this invention, a serviceable end-selection marker is a terminal sequence that is recognized by a polynucleotide-acting enzyme that recognizes a specific polynucleotide sequence. In a preferred aspect of this invention, serviceable polynucleotide-acting enzymes also include other enzymes in addition to classic type II restriction enzymes. According to this preferred aspect of this invention, serviceable polynucleotide-acting enzymes also include gyrases, helicases, recombinases, relaxases, and any enzymes related thereto.

Among preferred examples are topoisomerases (which have been categorized by some as a subset of the gyrases) and any other enzymes that have polynucleotide-cleaving activity (including preferably polynucleotide-nicking activity) &/or polynucleotide-ligating activity. Among preferred topoisomerase enzymes are topoisomerase I enzymes, which is available from many commercial sources (Epicentre Technologies, Madison, Wis.; Invitrogen, Carlsbad, Calif.; Life Technologies, [Gathesburg] *Gaithersburg*, Md.) and conceivably even more private sources. It is appreciated that similar enzymes may be developed in the future that are serviceable for end-selection as provided herein. A particularly preferred topoisomerase I enzyme is a topoisomerase I enzyme of vaccinia virus origin, that has a specific recognition sequence (e.g. 5' . . . AAGGG . . . 3') and has both polynucleotide-nicking activity and polynucleotide-ligating activity. Due to the specific nicking-activity of this enzyme (cleavage of one strand), internal recognition sites are not prone to polynucleotide destruction resulting from the nicking activity (but rather remain annealed) at a temperature that causes denaturation of a terminal site that has been nicked. Thus for use in end-selection, it is preferable that a nicking site for topoisomerase-based end-selection be no more than 100 nucleotides from a terminus, more preferably no more than 50 nucleotides from a terminus, more preferably still no more than 25 [nucloetides] *nucleotides* from a terminus, even more preferably still no more than 20 nucleotides from a terminus, even more preferably still no more than 15 nucleotides from a terminus, even more preferably still no more than 10 nucleotides from a terminus, even more preferably still no more than 8 nucleotides from a terminus, even more preferably still no more than 6 nucleotides from a terminus, and even more preferably still no more than 4 nucleotides from a terminus.

In a particularly preferred exemplification that is non-limiting yet clearly illustrative, it is appreciated that when a nicking site for topoisomerase-based end-selection is 4 nucleotides from a terminus, nicking produces a single stranded oligo of 4 bases (in a terminal region) that can be denatured from its complementary strand in an end-selectable polynucleotide; this provides a sticky end (comprised of 4 bases) in a polynucleotide that is serviceable for an ensuing ligation reaction. To accomplish ligation to a cloning vector (preferably an expression vector), compatible sticky ends can be generated in a cloning vector by any means including by restriction enzyme-based means. The terminal nucleotides (comprised of 4 terminal bases in this specific example) in an end-selectable polynucleotide terminus are thus wisely chosen to provide compatibility with a sticky end generated in a cloning vector to which the polynucleotide is to be ligated.

On the other hand, internal nicking of an end-selectable polynucleotide, e.g. 500 bases from a terminus, produces a single stranded oligo of 500 bases that is not easily denatured from its complementary strand, but rather is serviceable for repair (e.g. by the same topoisomerase enzyme that produced the nick).

This invention thus provides a method—e.g. that is vaccinia topoisomerase-based &/or type II (or IIS) restriction endonuclease-based &/or type III restriction endonuclease-based &/or nicking enzyme-based (e.g. using N. BstNB I)—for producing a sticky end in a working polynucleotide, which end is ligation compatible, and which end can be comprised of at least a 1 base overhang. Preferably such a sticky end is comprised of at least a 2-base overhang, more preferably such a sticky end is comprised of at least a 3-base overhang, more preferably still such a sticky end is comprised of at least a 4-base overhang, even more preferably still such a sticky end is comprised of at least a 5-base overhang, even more preferably still such a sticky end is comprised of at least a 6-base overhang. Such a sticky end may also be comprised of at least a 7-base overhang, or at least an 8-base overhang, or at least a 9-base overhang, or at least a 10-base overhang, or at least 15-base overhang, or at least a 20-base overhang, or at least a 25-base overhang, or at least a 30-base overhang. These overhangs can be comprised of any bases, including A, C, G, or T.

It is appreciated that sticky end overhangs introduced using topoisomerase or a nicking enzyme (e.g. using N. BstNB I) can be designed to be unique in a ligation environment, so as to prevent unwanted fragment reassemblies, such as self-dimerizations and other unwanted concatamerizations.

According to one aspect of this invention, a plurality of sequences (which may but do not necessarily overlap) can be introduced into a terminal region of an end-selectable polynucleotide by the use of an oligo in a polymerase-based reaction. In a relevant, but by no means limiting example, such an oligo can be used to provide a preferred 5' terminal region that is serviceable for topoisomerase I-based end-selection, which oligo is comprised of: a 1-10 base sequence that is convertible into a sticky end (preferably by a vaccinia topoisomerase 1), a ribosome binding site (i.e. and "RBS", that is preferably serviceable for expression cloning), and optional linker sequence followed by an ATG start site and a template-specific sequence of 0-100 bases (to facilitate annealment to the template in a polymerase-based reaction). Thus, according to this example, a serviceable oligo (which may be termed a forward primer) can have the sequence: 5'[terminal sequence=$(N)_{1-10}$][topoisomerase I site & RBS=AAGGGAGGAG][linker=$(N)_{1-110}$][start codon and template-specific sequence=ATG$(N)_{0-100}$]3' (*SEQ ID NO: 29*).

Analogously, in a relevant, but by no means limiting example, an oligo can be used to provide a preferred 3' terminal region that is serviceable for topoisomerase I-based end-selection, which oligo is comprised of: a 1-10 base sequence that is convertible into a sticky end (preferably by a vaccinia topoisomerase I), and optional linker sequence followed by a template-specific sequence of 0-100 bases (to facilitate annealment to the template in a polymerase-based reaction). Thus, according to this example, a serviceable oligo (which may be termed a reverse primer) can have the sequence: 5'[terminal sequence=$(N)_{1-10}$][topoisomerase I site=AAGGG][linker=$(N)_{1-100}$][template-specific sequence=$(N)_{1-100}$]3' (*SEQ ID NO: 30*).

It is appreciated that, end-selection can be used to distinguish and separate parental template molecules (e.g. to be subjected to mutagenesis) from progeny molecules (e.g. generated by mutagenesis). For example, a first set of primers, lacking in a topoisomerase I recognition site, can be used to modify the terminal regions of the parental molecules (e.g. in polymerase-based amplification). A different second set of primers (e.g. having a topoisomerase I recognition site) can then be used to generate mutated progeny molecules (e.g. using any polynucleotide chimerization method, such as interrupted synthesis, template-switching polymerase-based amplification, or interrupted synthesis; or using saturation mutagenesis; or using any other method for introducing a topoisomerase I recognition site into a mutagenized progeny molecule as disclosed herein) from the amplified template molecules. The use of topoisomerase I-based end-selection can then facilitate, not only discernment, but selective topoisomerase I-based ligation of the desired progeny molecules.

Annealment of a second set of primers to thusly amplified parental molecules can be facilitated by including sequences in a first set of primers (i.e. primers used for amplifying a set parental molecules) that are similar to a toposiomerase I recognition site, yet different enough to prevent functional toposiomerase I enzyme recognition. For example, sequences that diverge from the AAGGG site by anywhere from 1 base to all 5 bases can be incorporated into a first set of primers (to be used for amplifying the parental templates prior to subjection to mutagenesis). In a specific, but non-limiting aspect, it is thus provided that a parental molecule can be amplified using the following exemplary—but by no means limiting—set of forward and reverse primers:

Forward Primer: 5' CTAGAAGAGAGGAGAAAACCATG$(N)_{10-100}$ 3' (*SEQ ID NO: 31*), and Reverse Primer: 5' GATCAAAGGCGCGCCTGCAGG $(N)_{10-100}$ 3' (*SEQ ID NO: 32*).

According to this specific example of a first set of primers, $(N)_{10-100}$ represents preferably a 10 to 100 nucleotide-long template-specific sequence, more preferably a 10 to 50 nucleotide-long template-specific sequence, more preferably still a 10 to 30 nucleotide-long template-specific sequence, and even more preferably still a 15 to 25 nucleotide-long template-specific sequence.

According to a specific, but non-limiting aspect, it is thus provided that, after this amplification (using a disclosed first set of primers lacking in a true topoisomerase I recognition site), amplified parental molecules can then be subjected to mutagenesis using one or more sets of forward and reverse primers that do have a true topoisomerase I recognition site. In a specific, but non-limiting aspect, it is thus provided that a parental molecule can be used as templates for the generation of a mutagenized progeny molecule using the following exemplary—but by no means limiting—second set of forward and reverse primers:

Forward Primer: 5' CTAGAAGGGAGGAGAAAACCATG 3' (*SEQ ID NO: 33*);

Reverse Primer: 5' GATCAAAGGCGCGCCTGCAGG 3' (*SEQ ID NO: 34*) (contains Asc I recognition sequence).

It is appreciated that any number of different primers sets not specifically mentioned can be used as first, second, or subsequent sets of primers for end-selection consistent with this invention. Notice that type II restriction enzyme sites can be incorporated (e.g. an Asc I site in the above example). It is provided that, in addition to the other sequences mentioned, the experimentalist can incorporate one or more N,N,G/T triplets into a serviceable primer in order to subject a working polynucleotide to saturation mutagenesis. Summarily, use of a second and/or subsequent set of primers can achieve dual goals of introducing a topoisomerase I site and of generating mutations in a progeny polynucleotide.

Thus, according to one use provided, a serviceable end-selection marker is an enzyme recognition site that allows an enzyme to cleave (including nick) a polynucleotide at a specified site, to produce a ligation-compatible end upon denaturation of a generated single stranded oligo. Ligation of the produced polynucleotide end can then be accomplished by the same enzyme (e.g. in the case of vaccinia virus topoisomerase I), or alternatively with the use of a different enzyme. According to one aspect of this invention, any serviceable end-selection markers, whether like (e.g. two vaccinia virus topoisomerase I recognition sites) or unlike (e.g. a class II restriction enzyme recognition site and a vaccinia virus topoisomerase I recognition site) can be used in combination to select a polynucleotide. Each selectable polynucleotide can thus have one or more end-selection markers, and they can be like or unlike end-selection markers. In a particular aspect, a plurality of end-selection markers can be located on one end of a polynucleotide and can have overlapping sequences with each other.

It is important to emphasize that any number of enzymes, whether currently in existence or to be developed, can be serviceable in end-selection according to this invention. For example, in a particular aspect of this invention, a nicking enzyme (e.g. N. BstNB I, which cleaves only one strand at 5' . . . GAGTCNNNN/N . . . 3' (*SEQ ID NO: 27*)) can be used in conjunction with a source of polynucleotide-ligating activity in order to achieve end-selection. According to this embodiment, a recognition site for N. BstNB I—instead of a recognition site for topoisomerase I—should be incorporated into an end-selectable polynucleotide (whether end-selection is used for selection of a mutagenized progeny molecule or whether end-selection is used apart from any mutagenesis procedure).

It is appreciated that the instantly disclosed end-selection approach using topoisomerase-based nicking and ligation has several advantages over previously available selection methods. In sum, this approach allows one to achieve direction cloning (including expression cloning). Specifically, this approach can be used for the achievement of: direct ligation (i.e. without subjection to a classic restriction-purification-ligation reaction, that is susceptible to a multitude of potential problems from an initial restriction reaction to a ligation reaction dependent on the use of T4 DNA ligase); separation of progeny molecules from original template molecules (e.g. original template molecules lack topoisomerase I sites that not introduced until after mutagenesis), obviation of the need for size separation steps (e.g. by gel chromatography or by other electrophoretic means or by the use of size-exclusion membranes), preservation of internal sequences (even when topoisomerase I sites are present), obviation of concerns about unsuccessful ligation reactions (e.g. dependent on the use of T4 DNA ligase, particularly in the presence of unwanted residual restriction enzyme activity), and facilitated expression cloning (including obviation of frame shift concerns). Concerns about unwanted restriction enzyme-based cleavages—especially at internal restriction sites (or even at often unpredictable sites of unwanted star activity) in a working polynucleotide—that are potential sites of destruction of a working polynucleotide can also be obviated by the instantly disclosed end-selection approach using topoisomerase-based nicking and ligation.

Two-Hybrid Based Screening Assays

Shuffling can also be used to recombinatorially diversify a pool of selected library members obtained by screening a two-hybrid screening system to identify library members which bind a predetermined polypeptide sequence. The selected library members are pooled and shuffled by in vitro and/or in vivo recombination. The shuffled pool can then be screened in a yeast two hybrid system to select library members which bind said predetermined polypeptide sequence (e.g., and SH2 domain) or which bind an alternate predetermined polypeptide sequence (e.g., an SH2 domain from another protein species).

An approach to identifying polypeptide sequences which bind to a predetermined polypeptide sequence has been to use a so-called "two-hybrid" system wherein the predetermined polypeptide sequence is present in a fusion protein (Chien et al, 1991). This approach identifies protein-protein interactions in vivo through reconstitution of a transcriptional activator (Fields and Song, 1989), the yeast Gal4 transcription protein. Typically, the method is based on the properties of the yeast Gal4 protein, which consists of separable domains responsible for DNA-binding and transcriptional activation. Polynucleotides encoding two hybrid proteins, one consisting of the yeast Gal4 DNA-binding domain fused to a polypeptide sequence of a known protein and the other consisting of the Gal4 activation domain fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacz, HIS3) which is operably linked to a Gal4 binding site. Typically, the two-hybrid method is used to identify novel polypeptide sequences which interact with a known protein (Silver and Hunt, 1993; Durfee et al, 1993; Yang et al, 1992; Luban et al, 1993; Hardy et al, 1992; Bartel et al, 1993; and Vojtek et al, 1993). However, variations of the two-hybrid method have been used to identify mutations of a known protein that affect its binding to a second known protein (Li and Fields, 1993; Lalo et al, 1993; Jackson et al, 1993; and Madura et al, 1993). Two-hybrid systems have also been used to identify interacting structural domains of two known proteins (Bardwell et al, 1993; Chakrabarty et al, 1992; Staudinger et al, 1993; and Milne and Weaver 1993) or domains responsible for oligomerization of a single protein (Iwabuchi et al, 1993; Bogerd et al, 1993). Variations of two-hybrid systems have been used to study the in vivo activity of a proteolytic enzyme (Dasmahapatra et al, 1992). Alternatively, an E. coli/BCCP interactive screening system (Germino et al, 1993; Guarente, 1993) can be used to identify interacting protein sequences (i.e., protein sequences which heterodimerize or form higher order heteromultimers). Sequences selected by a two-hybrid system can be pooled and shuffled and introduced into a two-hybrid system for one or more subsequent rounds of screening to identify polypeptide sequences which bind to the hybrid containing the predetermined binding sequence. The sequences thus identified can be compared to identify consensus sequence(s) and consensus sequence kernals.

In general, standard techniques of recombination DNA technology are described in various publications (e.g. Sambrook et al, 1989; Ausubel et al, 1987; and Berger and Kimmel, 1987) each of which is incorporated herein in its entirety by reference. Polynucleotide modifying enzymes were used according to the manufacturer's recommendations. Oligonucleotides were synthesized on an Applied Biosystems Inc. Model 394 DNA synthesizer using ABI chemicals. If desired, PCR amplimers for amplifying a predetermined DNA sequence may be selected at the discretion of the practitioner.

One microgram samples of template DNA are obtained and treated with U.V. light to cause the formation of dimers, including TT dimers, particularly purine dimers. U.V. exposure is limited so that only a few photoproducts are generated per gene on the template DNA sample. Multiple samples are treated with U.V. light for varying periods of time to obtain template DNA samples with varying numbers of dimers from U.V. exposure.

A random priming kit which utilizes a non-proofreading [polymease] *polymerase* (for example, Prime-It II Random Primer Labeling kit by Stratagene Cloning Systems) is utilized to generate different size polynucleotides by priming at random sites on templates which are prepared by U.V. light (as described above) and extending along the templates. The priming protocols such as described in the Prime-It II Random Primer Labeling kit may be utilized to extend the primers. The dimers formed by U.V. exposure serve as a roadblock for the extension by the non-proofreading polymerase. Thus, a pool of random size polynucleotides is present after extension with the random primers is finished.

The present invention is further directed to a method for generating a selected mutant polynucleotide sequence (or a population of selected polynucleotide sequences) typically in the form of amplified and/or cloned polynucleotides, whereby the selected polynucleotide sequences(s) possess at least one desired phenotypic characteristic (e.g., encodes a polypeptide, promotes transcription of linked polynucleotides, binds a protein, and the like) which can be selected for. One method for identifying hybrid polypeptides that possess a desired structure or functional property, such as binding to a predetermined biological macromolecule (e.g., a receptor), involves the screening of a large library of polypeptides for individual library members which possess the desired structure or functional property conferred by the amino acid sequence of the polypeptide.

In one embodiment, the present invention provides a method for generating libraries of displayed polypeptides or displayed antibodies suitable for affinity interaction screening or phenotypic screening. The method comprises (1) obtaining a first plurality of selected library members comprising a displayed polypeptide or displayed antibody and an associated polynucleotide encoding said displayed polypeptide or displayed antibody, and obtaining said associated polynucleotides or copies thereof wherein said associated polynucleotides comprise a region of substantially identical sequences, optimally introducing mutations into said polynucleotides or copies, (2) pooling the polynucleotides or copies, (3) producing smaller or shorter polynucleotides by interrupting a random or particularized priming and synthesis process or an amplification process, and (4) performing amplification, preferably PCR amplification, and optionally mutagenesis to homologously recombine the newly synthesized polynucleotides.

It is a particularly preferred object of the invention to provide a process for producing hybrid polynucleotides which express a useful hybrid polypeptide by a series of steps comprising:

(a) producing polynucleotides by interrupting a polynucleotide amplification or synthesis process with a means for blocking or interrupting the amplification or synthesis process and thus providing a plurality of smaller or shorter polynucleotides due to the replication of the polynucleotide being in various stages of completion;

(b) adding to the resultant population of single- or double-stranded polynucleotides one or more single- or double-stranded oligonucleotides, wherein said added oligonucleotides comprise an area of identity in an area of heterology to one or more of the single- or double-stranded polynucleotides of the population;

(c) denaturing the resulting single- or double-stranded [olgonucleotides] *oligonucleotides* to produce a mixture of single-stranded polynucleotides, optionally separating the shorter or smaller polynucleotides into pools of polynucleotides having various lengths and further optionally subjecting said polynucleotides to a PCR procedure to amplify one or more oligonucleotides comprised by at least one of said polynucleotide pools;

(d) incubating a plurality of said polynucleotides or at least one pool of said polynucleotides with a polymerase under conditions which result in annealing of said single-stranded polynucleotides at regions of identity between the single-stranded polynucleotides and thus forming of a mutagenized double-stranded polynucleotide chain;

(e) optionally repeating steps (c) and (d);

(f) expressing at least one hybrid polypeptide from said polynucleotide chain, or chains; and (g) screening said at least one hybrid polypeptide for a useful activity.

In a preferred aspect of the invention, the means for blocking or interrupting the amplification or synthesis process is by utilization of U.V. light, DNA adducts, DNA binding proteins.

In one embodiment of the invention, the DNA adducts, or polynucleotides comprising the DNA adducts, are removed from the polynucleotides or polynucleotide pool, such as by a process including heating the solution comprising the DNA fragments prior to further processing.

Having thus disclosed exemplary embodiments of the present invention, it should be noted by those skilled in the art that the disclosures are exemplary only and that various other alternatives, adaptations and modifications may be made within the scope of the present invention. Accordingly, the present invention is not limited to the specific embodiments as illustrated herein.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLE 1

Generation of Random Size Polynucleotides Using U.V. Induced Photoproducts

One microgram samples of template DNA are obtained and treated with U.V. light to cause the formation of dimers, including TT dimers, particularly purine dimers. U.V. exposure is limited so that only a few photoproducts are generated per gene on the template DNA sample. Multiple samples are treated with U.V. light for varying periods of time to obtain template DNA samples with varying numbers of dimers from U.V. exposure.

A random priming kit which utilizes a non-proofreading polymerase (for example, Prime-It II Random Primer Labeling kit by Stratagene Cloning Systems) is utilized to generate different size polynucleotides by priming at random sites on templates which are prepared by U.V. light (as described above) and extending along the templates. The priming protocols such as described in the Prime-It II Random Primer Labeling kit may be utilized to extend the primers. The dimers formed by U.V. exposure serve as a roadblock for the extension by the non-proofreading polymerase. Thus, a pool of random size polynucleotides is present after extension with the random primers is finished.

EXAMPLE 2

Isolation of Random Size Polynucleotides

Polynucleotides of interest which are generated according to Example 1 are gel isolated on a 1.5% agarose gel. Polynucleotides in the 100-300 bp range are cut out of the gel and 3 volumes of 6 M NaI is added to the gel slice. The mixture is incubated at 50° C. for 10 minutes and 10 μl of glass milk (Bio 101) is added. The mixture is spun for 1 minute and the supernatant is decanted. The pellet is washed with 500 μl of Column Wash (Column Wash is 50% ethanol, 10 mM Tris-HCl pH 7.5, 100 mM NaCl and 2.5 mM EDTA) and spin for 1 minute, after which the supernatant is decanted. The washing, spinning and decanting steps are then repeated. The glass milk pellet is resuspended in 20 μl of $H_2O$ and spun for 1 minute. DNA remains in the aqueous phase.

EXAMPLE 3

Shuffling of Isolated Random Size 100-300 bp Polynucleotides

The 100-300 by polynucleotides obtained in Example 2 are recombined in an annealing mixture (0.2 mM each dNTP, 2.2 mM $MgCl_2$, 50 mM KCl, 10 mM Tris-HCl ph 8.8, 0.1% Triton X-100, 0.3μ; Taq DNA polymerase, 50 μl total volume) without adding primers. A Robocycler by Stratagene was used for the annealing step with the following program: 95° C. for 30 seconds, 25-50 cycles of [95° C. for 30 seconds, 50-60° C. (preferably 58° C.) for 30 seconds, and 72° C. for 30 seconds] and 5 minutes at 72° C. Thus, the 100-300 bp polynucleotides combine to yield double-stranded polynucleotides having a longer sequence. After separating out the reassembled double-stranded polynucleotides and denaturing them to form single stranded polynucleotides, the cycling is optionally again repeated with some samples utilizing the single strands as template and primer DNA and other samples utilizing random primers in addition to the single strands.

EXAMPLE 4

Screening of Polypeptides from Shuffled Polynucleotides

The polynucleotides of Example 3 are separated and polypeptides are expressed therefrom. The original template DNA is utilized as a comparative control by obtaining comparative polypeptides therefrom. The polypeptides obtained from the shuffled polynucleotides of Example 3 are screened for the activity of the polypeptides obtained from the original template and compared with the activity levels of the control. The shuffled polynucleotides coding for interesting polypeptides discovered during screening are compared further for secondary desirable traits. Some shuffled polynucleotides corresponding to less interesting screened polypeptides are subjected to reshuffling.

EXAMPLE 5

Directed Evolution an Enzyme by Saturation Mutagenesis

Site-Saturation Mutagenesis: To accomplish site-saturation mutagenesis every residue (316) of a dehalogenase enzyme was converted into all 20 amino acids by site directed mutagenesis using 32-fold degenerate oligonucleotide primers, as follows:

1. A culture of the dehalogenase expression construct was grown and a preparation of the plasmid was made
2. Primers were made to randomize each codon—they have the common structure $X_{20}NN(G/T)X_{20}$
3. A reaction mix of 25 ul was prepared containing ~50 ng of plasmid template, 125 ng of each primer, 1×native Pfu buffer, 200 uM each dNTP and 2.5 U native Pfu DNA polymerase
4. The reaction was cycled in a Robo96 Gradient Cycler as follows:
   Initial denaturation at 95° C. for 1 min
   20 cycles of 95° C. for 45 sec, 53° C. for 1 min and 72° C. for 11 min
   Final elongation step of 72° C. for 10 min 5. The reaction mix was digested with 10 U of DpnI at 37° C. for 1 hour to digest the methylated template DNA
6. Two ul of the reaction mix were used to transform 50 ul of XL1-Blue MRF' cells and the entire transformation mix was plated on a large LB-Amp-Met plate yielding 200-1000 colonies
7. Individual colonies were toothpicked into the wells of 96-well microtiter plates containing LB-Amp-IPTG and grown overnight
8. The clones on these plates were assayed the following day Approximately 200 clones of mutants for each position were grown in liquid media (384 well microtiter plates) and screened as follows:

1. Overnight cultures in 384-well plates were centrifuged and the media removed. To each well was added 0.06 mL 1 mM Tris/$SO_4^{2-}$ pH 7.8.
2. Made 2 assay plates from each parent growth plate consisting of 0.02 mL cell suspension.
3. One assay plate was placed at room temperature and the other at elevated temperature (initial screen used 55° C.) for a period of time (initially 30 minutes).
4. After the prescribed time 0.08 mL room temperature substrate (TCP saturated 1 mM Tris/$SO_4^{2-}$ pH 7.8 with 1.5 mM $NaN_3$ and 0.1 mM bromothymol blue) was added to each well.
5. Measurements at 620 nm were taken at various time points to generate a progress curve for each well.
6. Data were analyzed and the kinetics of the cells heated to those not heated were compared. Each plate contained 1-2 columns (24 wells) of unmutated 20F12 controls.
7. Wells that appeared to have improved stability were regrown and tested under the same conditions.

Following this procedure nine single site mutations appeared to confer increased thermal stability on the enzyme. Sequence analysis was performed to determine of the exact amino acid changes at each position that were specifically responsible for the improvement. In sum, the improvement was conferred at 7 sites by one amino acid change alone, at an eighth site by each of two amino acid changes, and at a ninth site by each of three amino acid changes. Several mutants were then made each having a plurality of these nine beneficial site mutations in combination; of these two mutants proved superior to all the other mutants, including those with single point mutations.

EXAMPLE 6

Direct Expression Cloning Using End-selection

An esterase gene was amplified using 5' phosphorylated primers in a standard PCR reaction (10 ng template; PCR conditions: 3' 94 C; [1' 94 C; 1' 50 C; 1'30" 68 C]×30; 10' 68 C.

Forward Primer=9511TopF (CTAGAAGGGAGGAGAATTACATGAAGCG-GCTTTTAGCCC) (*SEQ ID NO: 35*)

Reverse Primer=9511TopR (AGCTAAGGGTCAAGGCCG-CACCCGAGG) (*SEQ ID NO: 36*)

The resulting PCR product (ca. 1000 bp) was gel purified and quantified.

A vector for expression cloning, pASK3 (Institut fuer Bioanalytik, Goettingen, Germany), was cut with Xba I and Bgl II and dephosphorylated with CIP.

0.5 pmoles Vaccina Topoisomerase I (Invitrogen, Carlsbad, Calif.) was added to 60 ng (ca. 0.1 pmole) purified PCR product for 5' 37 C in buffer NEB I (New England Biolabs, Beverly, Mass.) in 5 μl total volume.

The topogated PCR product was cloned into the vector pASK3 (5 μl, ca. 200 ng in NEB I) for 5' at room temperature.

This mixture was dialyzed against $H_2O$ for 30'.

2 μl were used for electroporation of DH10B cells (Gibco BRL, Gaithersburg, Md.).

Efficiency: Based on the actual clone numbers this method can produce $2\times10^6$ clones per μg vector. All tested recombinants showed esterase activity after induction with anhydrotetracycline.

EXAMPLE 7

Dehalogenase Thermal Stability

This invention provides that a desirable property to be generated by directed evolution is exemplified in a limiting fashion by an improved residual activity (e.g. an enzymatic activity, an immunoreactivity, an antibiotic [acivity] *activity*, etc.) of a molecule upon subjection to altered environment, including what may be considered a harsh [enviroment] *environment*, for a specified time. Such a harsh environment may comprise any combination of the following (iteratively or not, and in any order or permutation): an elevated temperature (including a temperature that may cause denaturation of a working enzyme), a decreased temperature, an elevated salinity, a decreased salinity, an elevated pH, a decreased pH, an elevated pressure, a [decreassed] *decreased* pressure, and an change in exposure to a radiation source (including uv radiation, visible light, as well as the entire electromagnetic spectrum).

The following example shows an application of directed evolution to evolve the ability of an enzyme to regain &/or retain activity upon exposure to an elevated temperature. Every residue (316) of a dehalogenase enzyme was converted into all 20 amino acids by site directed mutagenesis using 32-fold degenerate oligonucleotide primers. These mutations were introduced into the already rate-improved variant Dhla 20F 12. Approximately 200 clones of each position were grown in liquid media (384 well microtiter plates) to be screened. The screening procedure was as follows:

1. Overnight cultures in 384-well plates were centrifuged and the media removed. To each well was added 0.06 mL 1 mM Tris/$SO_4^{2-}$ pH 7.8.
2. The robot made 2 assay plates from each parent growth plate consisting of 0.02 mL cell suspension.
3. One assay plate was placed at room temperature and the other at elevated temperature (initial screen used 55° C.) for a period of time (initially 30 minutes).
4. After the prescribed time 0.08 mL room temperature substrate (TCP saturated 1 mM Tris/$SO_4^{2-}$ pH 7.8 with 1.5 mM $NaN_3$ and 0.1 mM bromothymol blue) was added to each well. TCP=trichloropropane.
5. Measurements at 620 nm were taken at various time points to generate a progress curve for each well.
6. Data were analyzed and the kinetics of the cells heated to those not heated were compared. Each plate contained 1-2 columns (24 wells) of un-mutated 20F12 controls.
7. Wells that appeared to have improved stability were regrown and tested under the same conditions.

Following this procedure nine single site mutations appeared to confer increased thermal stability on Dhla-20F12. Sequence analysis showed that the following changes were beneficial:

D89G
F91S
T159L
G189Q, G189V

1220L
N238T
W251Y
P302A, P302L, P302S, P302K
P302R/S306R

Only two sites (189 and 302) had more than one substitution. The first 5 on the list were combined (using G189Q) into a single gene (this mutant is referred to as "Dhla5"). All changes but S306R were incorporated into another variant referred to as Dhla8.

Thermal stability was assessed by incubating the enzyme at the elevated temperature (55° C. and 80° C.) for some period of time and activity assay at 30° C. Initial rates were plotted vs. time at the higher temperature. The enzyme was in 50 mM Tris/$SO_4$ pH 7.8 for both the incubation and the assay. Product ($Cl^-$) was detected by a standard method using $Fe(NO_3)_3$ and HgSCN. Dhla 20F12 was used as the defacto wild type. The apparent half-life ($T_{1/2}$) was calculated by fitting the data to an exponential decay function.

Figure 17:
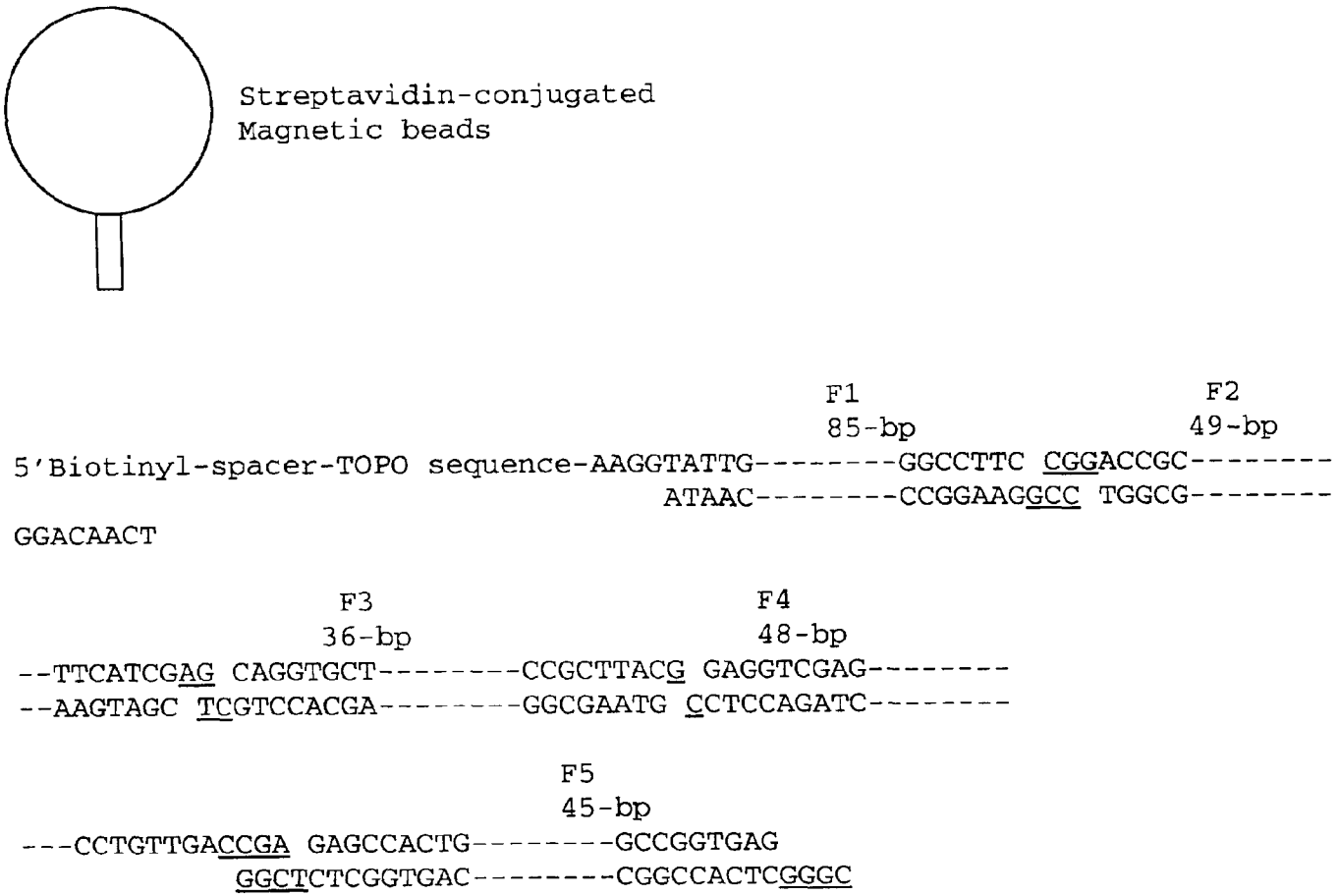
FIG. 17: Solid Phase Ligation Reassembly. The outline of the procedure used is the following: (1) Annealing of complementary oligos. *Oligonucleotides of 10 or more nucleotide bases are shown in SEQ ID NOS 18-22, respectively in order of appearance.* (Couplings are shown underlined and in bold.

According to another aspect of this invention, ligation reassembly can be performed using a solid support. The following example 8 (corresponding to FIG. 17) is illustrative but non-limiting.

EXAMPLE 8

Solid Phase Gene Family Reassembly Protocol

The objective can be, e.g., to reassemble/shuffle molecules of DNA to generate gene libraries of specific genes, libraries of gene families, and libraries of unrelated genes. The synthesis of the full-length molecules is carried out on a solid support. As solid support we use paramagnetic beads coated with Streptavidin. The principle is based on the strong interaction between Biotin and Streptavidin and the ability to stepwise or [simulataneously] *simultaneously* ligate DNA fragments generated from the annealing of nucleic acid building blocks (such as ssDNA building blocks). The use of a solid support facilitates the reassembly of nucleic acid building blocks in a sequential manner and thus allows one to use not only unique couplings, but also redundant or repeated couplings throughout the length of a nucleic acid molecule that is to be generated by ligation reassembly.

A "capture oligonucleotide" is biotinylated at the 5' end for binding to the beads. The "capture oligo" is annealed to a complementary sequence (no biotinylated). The double stranded capture fragment contains two restriction sites at the 5'-end which allows release of the assembled molecules from the solid support.

Ligation reassembly is performed by step-wise ligation of annealed oligonucleotides of 20-100 bases. The first fragment of the assembly contains a 5'-end compatible with the 3'-end of the capture biotinylated fragment. Consecutive ligation of double stranded fragments containing complementary ends allows the generation of full-length molecules. Half way synthesis (midpoint) molecules are released from the solid support. A final ligation step between molecules generated from both ends results in the generation a full-length reassembled DNA.

Materials and Methods:

Streptavidin coated magnetic beads M280 (Dynal corp.)
Magnetic stand or magnetic particle concentrator (MPC stand)
Biotinylated capture oligos containing a 7 or 15 atom-spacer and two restriction sites not internally found in the sequences being reassembled. Ensure that the biotinylated capture oligo does not contain free biotin.
Design capture oligos to allow reassembly from both ends of the sequences being reassembled.
Design internal oligos according to the sequence (s) being reassembled
STE buffer
Washing/Binding buffer (1M NaCl, 10 mM Tris-HCl pH 7.5, 1 mM EDTA) PBS, pH 7.4 buffer containing 0.1% BSA.
Annealing/ligation buffer
Spin columns for DNA purification 1) Anneal equimolar amounts of complementary oligos by heating at 90° C. and slowly cooling down to room temperature in STE buffer. Dilute annealed oligos to 5 pmole/ul.
2) Aliquot 300-ug of 10 mg/ml bead suspension in a 500 ul Eppendorf tube.
3) Wash the beads with 300-ul of PBS buffer using a magnetic stand. Repeat 3 times.
4) Wash the beads with 300-ul of 1×Washing/Binding buffer using a magnetic stand. Repeat once.
5) Immobilize the pre-annealed biotinylated capture fragments to the beads (55 pmole of 500-bp dsDNA binds to 1 mg of beads). The binding capacity of the beads is fragment length dependent. Mix beads and capture fragment in binding buffer. Incubate at room temperature for 12 h in a 360 degree rotator
6) Wash the beads with 300-ul of 60° C. pre-heated 1×Washing/binding buffer using. Repeat 3 times.
7) Wash the beads with 300-ul of freshly thawed 1×ligation buffer.
8) For a reassembly of "n" (5' to 3' and 3' to 5')fragments:

| | | |
|---|---|---|
| Mix: | Fragment #1 (or "n") (5 pmole) | 10 ul |
| | 5 × ligase buffer | 60 ul |
| | 1 U/ul T4 Ligase | 15 ul |
| | $dH_2O$ | 215 ul |
| | | 300 ul |

9) Incubate with rotation at RT for 30 min.
10) Wash the beads with 300-ul of 60° C. pre-heated 1×Washing/Binding buffer. Repeat 3 times.
11) Wash the beads with 300-ul of freshly thawed 1×ligation buffer.

| | | |
|---|---|---|
| Add: | Fragment #2 (n − 1)(5 pmole) | 10 ul |
| | 5 × ligase buffer | 60 ul |
| | 1 U/ul T4 Ligase | 15 ul |
| | $dH_2O$ | 215 ul |
| | | 300 ul |

13) Incubate with rotation at RT for 30 min.
14) Wash the beads with 300-ul of 60° C. pre-heated 1×Washing/binding buffer. Repeat 3 times.
15) Wash the beads with 300-ul of freshly thawed 1×ligation buffer.
16) Repeat the procedure until n/2 fragments have been added from each end of the synthesis
17) Elute the partially assembled products from the solid support by cutting with the corresponding restriction enzyme

| | |
|---|---|
| Beads with immobilized reassembled gene | x ul |
| 10 × enzyme buffer | 30 ul |

-continued

| | |
|---|---|
| 1 U/ul restriction enzyme | 5 ul |
| $dH_2O$ | to 300 ul |

18) Replace restriction buffer of eluted DNA for ligation buffer using a spin column. Elute from spin column with $H_2O$ 19) Ligate both partially assembled products to generate reassembled full-length molecules

| | |
|---|---|
| partial synthesis product (5' to 3') | 60 ul |
| partial synthesis product (3' to 5') | 60 ul |
| 5 × ligase buffer | 20 ul |
| 1 U/ul T4 ligase | 10 ul |
| $dH_2O$ | 50 ul |
| | 200 ul |

20) Clone full-length genes in corresponding vector.

21) Sequence a few clones and screen for different kinetic parameters of the expressed enzymes.

LITERATURE CITED

Unless otherwise indicated, all references cited herein (supra and infra) are incorporated by reference in their entirety.

Barret A J, et al., eds.: Enzyme Nomenclature: Recommendations of the Nomenclature Committee of the International Union of Biochemistry and Molecular Biology. San Diego: Academic Press, Inc., 1992.

Boyce C O L, ed.: Novo's Handbook of Practical Biotechnology. 2nd ed. Bagsvaerd, Denmark, 1986.

Drauz K, Waldman H, eds.: Enzyme Catalysis in Organic Synthesis: A Comprehensive Handbook. Vol. 1. New York: VCH Publishers, 1995.

Drauz K, Waldman H, eds.: Enzyme Catalysis in Organic Synthesis: A Comprehensive Handbook. Vol. 2. New York: VCH Publishers, 1995.

Foster G D, Taylor S C, eds.: Plant Virology Protocols: From Virus Isolation to Transgenic Resistance. Methods in Molecular Biology, Vol. 81. New Jersey: Humana Press Inc., 1998.

Franks F, ed.: Protein Biotechnology: Isolation, Characterization, and Stabilization. New Jersey: Humana Press Inc., 1993.

Godfrey T, West S, eds.: Industrial Enzymology. 2nd ed. London: Macmillan Press Ltd, 1996.

Gottschalk G: Bacterial Metabolism. 2nd ed. New York: Springer-Verlag Inc., 1986.

Gresshoff P M, ed.: Technology Transfer of Plant Biotechnology. Current Topics in Plant Molecular Biology. Boca Raton: CRC Press, 1997.

Griffin H G, Griffin A M, eds.: PCR Technology: Currrent Innovations. Boca Raton: CRC Press, Inc., 1994.

Hansen G, Chilton M D: Lessons in gene transfer to plants by a gifted microbe. Curr Top Microbiol Immunol 240:21-57, 1999.

Hartmann H T, et al.: Plant Propagation: Principles and Practices. 6th ed. New Jersey: Prentice Hall, Inc., 1997.

Perun T J, Propst C L, eds.: Computer-Aided Drug Design: Methods and Applications. New York: Marcel Dekker, Inc., 1989.

Owen M R L, Pen J: Transgenic Plants: A Production System for Industrial and Pharmaceutical Proteins. Chichester: John Wiley & Sons, 1996.

Segel I H: Enzyme Kinetics: Behavior and Analysis of Rapid Equilibrium and Steady-State Enzyme Systems. New York: John Wiley & Sons, Inc., 1993.

White J S, White D C: Source Book of Enzymes. Boca Raton: CRC Press, 1997.

Wong C H, Whitesides G M: Enzymes in Synthetic Organic Chemistry. Vol. 12. New York: Elsevier Science Publications, 1995.

WO 97/35966; Filed Mar. 20, 1997, Published Oct. 2, 1997. Minshull J, Stemmer W P: Mehtods and Compositions for Cellular and Metabolic Engineering.

WO 98/31837; Filed Jan. 16, 1998, Published Jul. 23, 1998. Delcardayre S B, Tobin M B, Stemmer W P, Minshull, J: Evolution of Whole Cells and Organisms by Recursive Sequence Recombination.

WO 98/37223; Filed Feb. 18 1998, Published Aug. 27, 1998. Pang S Z, Gonsalves D, Jan F J: DNA Construct to Confer Multiple Traits on Plants.

Alting-Mecs M A and Short J M: Polycos vectors: a system for packaging filamentous phage and phagemid vectors using lambda phage packaging extracts. Gene 137:1, 93-100, 1993.

Arkin A P and Youvan D C: An algorithm for protein engineering: simulations of recursive ensemble mutagenesis. Proc Natl Acad Sci USA 89(16):7811-7815, (Aug. 15) 1992.

Arnold F H: Protein engineering for unusual environments. Current Opinion in Biotechnology 4(4):450-455, 1993.

Ausubel F M, et al Editors. Current Protocols in Molecular Biology, Vols. 1 and 2 and supplements. (a.k.a. "The Red Book") Greene Publishing Assoc., Brooklyn, N.Y., ©1987.

Ausubel F M, et al Editors. Current Protocols in Molecular Biology, Vols. 1 and 2 and supplements. (a.k.a. "The Red Book") Greene Publishing Assoc., Brooklyn, N.Y. ©1989.

Ausubel F M, et al Editors. Short Protocols in Molecular Biology: A Compendium of Methods from Current Protocols in Molecular Biology. Greene Publishing Assoc., Brooklyn, N.Y., ©1989.

Ausubel F M, et al Editors. Short Protocols in Molecular Biology: A Compendium of Methods from Current Protocols in Molecular Biology, 2nd Edition. Greene Publishing Assoc., Brooklyn, N.Y., ©1992.

Barbas C F 3d, Bain J D, Hoekstra D M, Lemer R A: Semisynthetic combinatorial antibody libraries: a chemical solution to the diversity problem. Proc Natl Acad Sci USA 89(10):4457-4461, 1992.

Bardwell A J, Bardwell L, Johnson D K, Friedberg E C: Yeast DNA recombination and repair proteins Rad1 and Rad10 constitute a complex in vivo mediated by localized ydrophobic domains. Mol Microbiol 8(6):1177-1188, 1993.

Bartel P, Chien C T, Stemglanz R, Fields S: Elimination of false positives that arise in using the two-hybrid system. Biotechniques 14(6):920-924, 1993.

Beaudry A A and Joyce G F: Directed evolution of an RNA enzyme. Science 257(5070):635-641, 1992.

Berger and Kimmel, Methods in Enzymology, Volume 152, Guide to Molecular Cloning Techniques. Academic Press, Inc., San Diego, Calif., ©1987. (Cumulative Subject Index: Volumes 135-139, 141-167, 1990, 272 pp.)

Bevan M: Binary Agrobacterium vectors for plant transformation. Nucleic Acids Research 12(22):8711-21, 1984.

Biocca S, Pierandrei-Amaldi P, Cattaneo A: Intracellular expression ofanti-p21ras single chain Fv fragments inhibits meiotic maturation of xenopus oocytes. Biochem Biophys Res Commun 197(2):422-427, 1993.

Bird et al. Plant Mol Biol 11:651, 1988.

Bogerd H P, Fridell R A, Blair W S, Cullen B R: Genetic evidence that the Tat proteins of human immunodeficiency virus types 1 and 2 can multimerize in the eukaryotic cell nucleus. J Virol 67(8):5030-5034, 1993.

Brederode F T, Koper-Zawrthoff E C, Bol J F: Complete nucleotide sequence of alfalfa mosaic virus RNA 4. Nucleic Acids Research 8(10):2213-23, 1980.

Breitling F, Dubel S, Seehaus T, Klewinghaus I, Little M: A surface expression vector for antibody screening. Gene 104(2): 147-153, 1991.

Brown N L, Smith M: Cleavage specificity of the restriction endonuclease isolated from Haemophilus gallinarum (Hga I). Proc Natl Acad Sci USA 74(8):3213-6, (August) 1977.

Burton D R, Barbas C F 3d, Persson M A, Koenig S, Chanock R M, Lerner R A: A large array of human monoclonal antibodies to type 1 human immunodeficiency virus from combinatorial libraries of asymptomatic seropositive individuals. Proc Natl Acad Sci USA 88(22):10134-7, (Nov. 15) 1991.

Caldwell R C and Joyce G F: Randomization of genes by PCR mutagenesis. PCR Methods Appl 2(10):28-33, 1992.

Caton A J and Koprowski H: Influenze virus hemagglutinin-specific antibodies isolatedf froma combinatorial expression library are closely related to the immune response of the donor. Proc NatlAcad Sci USA 87(16):6450-6454, 1990.

Chakraborty T, Martin J F, Olson E N: Analysis of the oligomerization of myogenin and E2A products in vivo using a two-hybrid assay system. J Biol Chem 267(25): 17498-501, 1992.

Chang C N, Landolfi N F, Queen C: Expression of antibody Fab domains on bacteriophage surfaces. Potential use for antibody selection. J Immunol 147(10):3610-4, (Nov. 15) 1991.

Chaudhary V K, Batra J K, Gallo M G, Willingham M C, FitzGerald D J, Pastan I: A rapid method of cloning functional variable-region antibody genes in Escherichia coli as single-chain immunotoxins. Proc Natl Acad Sci USA 87(3):1066-1070, 1990.

Chien C T, Bartel P L, Stemglanz R, Fields S: The two-hybrid system: a method to identify and clone genes for proteins that interact with a protein of interest. Proc Natl A cad Sci USA 88(21):9578-9582, 1991.

Chiswell D J, McCafferty J: Phage antibodies: will new 'coli-clonal' antibodies replace monoclonal antibodies? Trends Biotechnol 10(3):80-84, 1992.

Chothia C and Lesk A M: Canonical structures for the hypervariable regions of immunoglobulins. J Mol Biol 196)4): 901-917, 1987.

Chothia C, Lesk A M, Tramontano A, Levitt M, Smith-Gill S J, Air G, Sheriff S, Padlan E A, Davies D, Tulip W R, et al: Conformations of immunoglobulin hypervariable regions. Nature 342(6252):877-883, 1989.

Clackson T, Hoogenboom H R, Griffiths A D, Winter G: Making antibody fragments using phage display libraries. Nature 352(6336):624-628, 1991.

Conrad M, Topal M D: DNA and spermidine provide a switch mechanism to regulate the activity of restriction enzyme Nae I. Proc Natl Acad Sci USA 86(24):9707- 11, (December) 1989.

Coruzzi G, Broglie R. Edwards C, Chua N H: Tissue-specific and light-regulated expression of a pea nuclear gene encoding the small subunit of ribulose- 1,5-bisphosphate carboxylase. EMBO J 3(8): 1671-9, 1984.

Dasmahapatra B, DiDomenico B, Dwyer S, Ma J, Sadowski I, Schwartz J: A genetic system for studying the activity of a proteolytic enzyme. Proc Natl Acad Sci USA 89(9): 4159-4162, 1992.

Davis L G, Dibner M D, Battey J F. Basic Methods in Molecular Biology. Elsevier, New York, N.Y., ©1986.

Delegrave S and Youvan D C. Biotechnology Research 11:1548-1552,1993.

DeLong E F, Wu K Y, Prezelin B B, Jovine R V: High abundance of Archaea in Antarctic marine picoplankton. Nature 371(6499):695-697, 1994.

Deng S J, MacKenzie C R, Sadowska J, Michniewicz J, Young N M, Bundle Dr, Narang S A: Selection of antibody single-chain variable fragments with improved carbohydrate binding by phage display. J Biol Chem 269(13):9533-9538, 1994.

Duan L, Bagasra O, Laughlin M A, Oakes J W, Pomerantz R J: Potent inhibition of human immunodeficiency virus type 1 replication by an intracellular anti-Rev single-chain antibody. Proc NatlAcadSci USA 91(11):5075-5079, 1994.

Durfee T, Becherer K, Chen P L, Yeh S H, Yang Y, Kilburn A E, Lee W H, Elledge S J: The retinoblastoma protein associates with the protein phosphatase type 1 catalytic subunit. Genes Dev 7(4):555-569, 1993.

Ellington A D and Szostak J W: In vitro selection of RNA molecules that bind specific ligands. Nature 346(6287): 818-822, 1990.

Fields S and Song O: A novel genetic system to detect protein-protein interactions. Nature 340(6230):245-246, 1989.

Firek S, Draper J, Owen M R, Gandecha A, Cockburn B, Whitelam G C: Secretion of a functional single-chain Fv protein in transgenic tobacco plants and cell suspension cultures. Plant Mol Biol 23(4):861-870, 1993.

Forsblom S, Rigler R, Ehrenberg M, Philipson L: Kinetic studies on the cleavage of adenovirus DNA by restriction endonuclease Eco RI. Nucleic Acids Res 3(12):3255-69, (December) 1976.

Germino F J, Wang Z X, Weissman S M: Screening for in vivo protein-protein interactions. Proc Natl Acad Sci USA 90(3):933-937, 1993.

Gingeras T R, Brooks J E: Cloned restriction/modification system from Pseudomonas aeruginosa. Proc Natl Acad Sci USA 80(2):402-6, January 1983.

Gluzman Y: SV40-transformed simian cells support the replication of early SV40 mutants. Cell 23(1):175-182, 1981.

Gruber M, Schodin B A, Wilson E R, Kranz D M: Efficient tumor cell lysis mediated by a bispecific single chain antibody expressed in Escherichia coli. J Immunol 152 (11): 5368-5374, 1994.

Guarente L: Strategies for the identification of interacting proteins. Proc Natl Acad Sci USA 90(5):1639-1641, 1993.

Guilley H, Dudley R K, Jonard G, Balazs E, Richards K E: Transcription of Cauliflower mosaic virus DNA: detection of promoter sequences, and characterization of transcripts. Cell 30(3):763-73, 1982.

Hardy C F, Sussel L, Shore D: A RAP1-interacting protein involved in transcriptional silencing and telomere length regulation. Genes Dev 6(5):801-814, 1992.

Hawkins R E and Winter G: Cell selection strategies for making antibodies from variable gene libraries: trapping the memory pool. Eur J Immunol 22(3):867-870, 1992.

Holvoet P, Laroche Y, Lijnen H R, Van Hoef B, Brouwers E, De Cock F, Lauwereys M, Gansemans Y, Caen D: Biochemical characterization of single-chain chimeric plasminogen activators consisting of a single-chain Fv fragment of a fibrin-specific antibody and single-chain urokinase. Eur J Biochem 210(3):945-952, 1992.

Honjo T, Alt F W, Rabbitts T H (eds): Immunoglobulin genes. Academic Press: San Diego, Calif., pp. 361-368, ©1989.

Hoogenboom H R, Griffiths A D, Johnson K S, Chiswell D J, Judson P, Winter G: Multi-subunit proteins on the surface of filamentous phage: methodologies for displaying antibody (Fab) heavy and light chains. Nucleic Acids Res 19(15):4133-4137, 1991.

Huse W D, Sastry L, Iverson S A, Kang A S, Alting-Mees M, Burton D R, Benkovic S J, Lerner R A: Generation of a large combinatorial library of the immunoglobulin repertoire in phage lambda. Science 246(4935):1275-1281, 1989.

Huston J S, Levinson D, Mudgett-Hunter M, Tai MS, Novotney J, Margolies M N, Ridge R J, Bruccoleri R E, Haber E, Crea R, et al: Protein engineering of antibody binding sites: recovery of specific activity in an antidigoxin single-chain Fv analogue produced in Escherichia coli. Proc Natl Acad Sci USA 85(16):5879-5883, 1988.

Iwabuchi K, Li B, Bartel P, Fields S: Use of the two-hybrid system to identify the domain of p53 involved in oligomerization. Oncogene 8(6):1693-1696, 1993.

Jackson A L, Pahl P M, Harrison K, Rosamond J, Sclafani R A: Cell cycle regulation of the yeast Cdc7 protein kinase by association with the Dbf4 protein. Mol Cell Biol 13(5): 2899-2908, 1993.

Johnson S and Bird R E: Methods Enzymol 203:88, 1991.

Kabat et al: Sequences of Proteins of Immunological Interest, 4th Ed. U.S. Department of Health and Human Services, Bethesda, Md. (1987)

Kang A S, Barbas C F, Janda K D, Benkovic S J, Lerner R A: Linkage of recognition and replication functions by assembling combinatorial antibody Fab libraries along phage surfaces. Proc Natl Acad Sci USA 88(10): 4363-4366, 1991.

Kettleborough C A, Ansell K H, Allen R W, Rosell-Vives E, Gussow D H, Bendig M M: Isolation of tumor cell-specific single-chain Fv from immunized mice using phage-antibody libraries and the re-construction of whole antibodies from these antibody fragments. Eur J Immunol 24(4):952-958, 1994.

Kruger D H, Barcak G J, Reuter M, Smith H O: EcoRII can be activated to cleave refractory DNA recognition sites. Nucleic Acids Res 16(9):3997-4008, (May 11) 1988.

Lalo D, Caries C, Sentenac A, Thuriaux P: Interactions between three common subunits of yeast RNA polymerases I and III. Proc Natl Acad Sci USA 90(12):5524-5528, 1993.

Laskowski M Sr: Purification and properties of venom phosphodiesterase. Methods Enzymol 65(1):276-84, 1980.

Lefkovits I and Perris B, Editors. Immunological Methods, Vols. I and II. Academic Press, New York, N.Y. Also Vol. III published in Orlando and Vol. IV published in San Diego. ©1979.

Ivan Lefkovits, Editor. Immunology methods manual: the comprehensive sourcebook of techniques. Academic Press, San Diego, ©1997.

Lerner R A, Kang A S, Bain J D, Burton D R, Barbas C F 3d: Antibodies without immunization. Science 258(5086): 1313-1314, 1992.

Leung, D. W., et al, Technique, 1:11-15, 1989.

Li B and Fields S: Identification of mutations in p53 that affect its binding to SV40 large T antigen by using the yeast two-hybrid system. FASEB J 7(10):957-963, 1993.

Lilley G G, Doelzal O, Hillyard C J, Bernard C, Hudson P J: Recombinant single-chain antibody peptide conjugates expressed in Escherichia coli for the rapid diagnosis of HIV. J Immunol Methods 171(2):211-226, 1994.

Lowman H B, Bass S H, Simpson N, Wells J A: Selecting high-affinity binding proteins by monovalent phage display. Biochemistry 30(45):10832-10838, 1991.

Luban J, Bossolt K L, Franke E K, Kalpana G V, Goff S P: Human immunodeficiency virus type 1 Gag protein binds to cyclophilins A and B. Cell 73(6):1067-1078, 1993.

Madura K, Dohmen R J, Varshaysky A: N-recognin/Ubc2 interactions in the N-end rule pathway. J Biol Chem 268 (16):12046-54, (Jun 5) 1993.

Marks J D, Hoogenboom H R, Bonnert T P, McCafferty J, Griffiths A D, Winter G: By-passing immunization. Human antibodies from V-gene libraries displayed on phage. J Mol Biol 222(3):581-597, 1991.

Marks J D, Griffiths A d, Malmqvist M, Clackson T P, Bye J M, Winter G: By-passing immunization: building high affinity human antibodies by chain shuffling. Biotechnology (NY) 10(7):779-783, 1992.

Marks J D, Hoogenboom H R, Griffiths A D, Winter G: Molecular evolution of proteins on filamentous phage. Mimicking the strategy of the immune system. J Biol Chem 267(23):16007-16010, 1992.

Maxam A M, Gilbert W: Sequencing end-labeled DNA with base-specific chemical cleavages. Methods Enzymol 65(1):499-560, 1980.

McCafferty J, Griffiths A D, Winter G, Chiswell D J: Phage antibodies: filamentous phage displaying antibody variable domains. Nature 348(6301):552-554, 1990.

Miller J H. A Short Course in Bacterial Genetics: A Laboratory Manual and Handbook for Escherichia coli and Related Bacteria (see inclusively p. 445). Cold Spring Harbor Laboratory Press, Plainview, N.Y., ©1992.

Milne G T and Weaver D T: Dominant negative alleles of RAD52 reveal a DNA repair/recombination complex including Rad51 and Rad52. Genes Dev 7(9):1755-1765, 1993.

Mullinax R L, Gross E A, Amberg J R, Hay B N, Hogrefe H H, Kubtiz M M, Greener A, Alting-Mees M, Ardourel D, Short J M, et al: Identification of human antibody fragment clones specific for tetanus toxoid in a bacteriophage lambda immunoexpression library. Proc natl Acad Sci USA 87(20):8095-9099, 1990.

Nath K, Azzolina B A: in Gene Amplification and Analysis (ed. Chirikjian J G), vol. 1, p. 113, Elsevier North Holland, Inc., New York, N.Y., ©1981.

Needleman S B and Wunsch C D: A general method applicable to the search for similarities in the amino acid sequence of two proteins. J Mol Biol 48(3):443-453, 1970.

Nelson M, Christ C, Schildkraut I: Alteration of apparent restriction endonuclease recognition specificities by DNA methylases. Nucleic Acids Res 12(13):5165-73, 1984 (Jul 11).

Nicholls P J, Johnson V G, Andrew S M, Hoogenboom H R, Raus J C, Youle R J: Characterization of single-chain antibody (sFv)-toxin fusion proteins produced in vitro in rabbit reticulocyte lysate. J Biol Chem 268(7):5302-5308, 1993.

Oiler A R, Vanden Broek W, Conrad M, Topal M D: Ability of DNA and spermidine to affect the activity of restriction endonucleases from several bacterial species. Biochemistry 30(9):2543-9, (Mar 5) 1991.

Owens R J and Young R J: The genetic engineering of monoclonal antibodies. J Immunol Methods 168(2):149-165, 1994.

Pearson W R and Lipman D J: Improved tools for biological sequence comparison. Proc Natl Acad Sci USA 85(8): 2444-2448, 1988.

Pein C D, Reuter M, Meisel A, Cech D, Kruger D H: Activation of restriction endonuclease EcoRII does not depend on the cleavage of stimulator DNA. Nucleic Acids Res 19(19): 5139-42, (Oct 11) 1991.

Persson M A, Caothien R H, Burton D R: Generation of diverse high-affinity human monoclonal antibodies by repertoire cloning. Proc Natl Acad Sci USA 88(6):2432-2436, 1991.

Queen C, Foster J, Stauber C, Stafford J: Cell-type specific regulation of a kappa immunoglobulin gene by promoter and enhance elements. Immunol Rev 89:49-68, 1986.

Qiang B Q, McClelland M, Poddar S, Spokauskas A, Nelson M: The apparent specificity of NotI (5'-GCGGCCGC-3') is enhanced by M.FnuDII or M.BepI methyltransferases (5'-mCGCG-3'): cutting bacterial chromosomes into a few large pieces. Gene 88(1):101-5, (Mar. 30) 1990.

Raleigh E A, Wilson G: Escherichia coli K-12 restricts DNA containing 5-methylcytosine. Proc Natl Acad Sci USA 83(23):9070-4, (Dec) 1986.

Reidhaar-Olson J F and Sauer R T: Combinatorial cassette mutagenesis as a probe of the informational content of protein sequences. Science 241(4861):53-57, 1988.

Riechmann L and Weill M: Phage display and selection of a site-directed randomized single-chain antibody Fv fragment for its affinity improvement. Biochemistry 32(34): 8848-8855, 1993.

Roberts R J, Macelis D: REBASE—restriction enzymes and methylases. Nucleic Acids Res 24(1):223-35, (Jan. 1) 1996.

Ryan A J, Royal C L, Hutchinson J, Shaw C H: Genomic sequence of a 12S seed storage protein from oilseed rape (Brassica napus c.v. jet neuf). Nucl Acids Res 17(9):3584, 1989.

Sambrook J, Fritsch E F, Maniatis T. Molecular Cloning: A Laboratory Manual. Cold Spring Harbor Laboratory Press, Cold Spring Harbor, N.Y., ©1982.

Sambrook J, Fritsch E F, Maniatis T. Molecular Cloning: A Laboratory Manual. Second Edition. Cold Spring Harbor Laboratory Press, Cold Spring Harbor, N.Y., ©1989.

Scopes R K. Protein Purification: Principles and Practice. Springer-Verlag, New York, N.Y., ©1982.

Silver S C and Hunt S W 3d: Techniques for cloning cDNAs encoding interactive transcriptional regulatory proteins. Mol Biol Rep 17(3):155-165, 1993.

Smith T F, Waterman M S. Adv Appl Math 2:482-end of article, 1981.

Smith T V, Waterman M S: Overlapping genes and information theory. J Theor Biol 91(2):379-80, (Jul. 21) 1981.

Smith T F, Waterman M S: Identification of common molecular subsequences. J Mol Biol 147(1):195-7, (Mar. 25) 1981.

Smith T F, Waterman M S, Fitch W M: Comparative biosequence metrics. J Mol Evol S18(1):38-46, 1981.

Staudinger J, Perry M, Elledge S J, Olson E N: Interactions among vertebrate helix-loop-elix proteins in yeast using the two-hybrid system. J Biol Chem 268(7):4608-4611, 1993.

Stemmer W P, Morris S K, Wilson B S: Selection of an active single chain Fv antibody from a protein linker library prepared by enzymatic inverse PCR. Biotechniques 14(2): 256-265, 1993.

Stemmer W P: DNA shuffling by random fragmentation and reassembly: in vitro recombination for molecular evolution. Proc Natl Acad Sci USA 91(22):10747-10751, 1994.

Sun D, Hurley L H: Effect of the (+)-CC-1065-(N3-adenine) DNA adduct on in vitro DNA synthesis mediated by Escherichia coli DNA polymerase. Biochemistry 31:10, 2822-9, (Mar. 17) 1992, Tague B W, Dickinson C D, Chrispeels M J: A short domain of the plant vacuolar protein phytohemagglutinin targets invertase to the yeast vacuole. Plant Cell 2(6):533-46, (June) 1990.

Takahashi N, Kobayashi I: Evidence for the double-strand break repair model of bacteriophage lambda recombination. Proc Natl Acad Sci U S A 87(7):2790-4, (April) 1990.

Thiesen H J and Bach C: Target Detection Assay (TDA): a versatile procedure to determine DNA binding sites as demonstrated on SP1 protein. Nucleic Acids Res 18(11): 3203-3209, 1990.

Thomas M, Davis R W: Studies on the cleavage of bacteriophage lambda DNA with EcoRI Restriction endonuclease. J Mol Biol 91(3):315-28, (Jan. 25) 1975.

Tingey S V, Walker E L, Corruzzi G M: Glutamine synthetase genes of pea encode distinct polypeptides which are differentially expressed in leaves, roots and nodules. EMBO J 6(1):1-9, 1987.

Topal M D, Thresher R J, Conrad M, Griffith J: Nael endonuclease binding to pBR322 DNA induces looping. Biochemistry 30(7):2006-10, (Feb. 19) 1991.

Tramontano A, Chothia C, Lesk A M: Framework residue 71 is a major determinant of the position and conformation of the second hypervariable region in the VH domains of immunoglobulins. J Mol Biol 215(1):175-182, 1990.

Tuerk C and Gold L: Systematic evolution of ligands by exponential enrichment: RNA ligands to bacteriophage T4 DNA polymerase. Science 249(4968):505-510, 1990.

van de Poll M L, Lafleur M V, van Gog F, Vrieling H, Meerman J H: N-acetylated and deacetylated 4'-fluoro-4-aminobiphenyl and 4-aminobiphenyl adducts differ in their ability to inhibit DNA replication of single-stranded M13 in vitro and of single-stranded phi X174 in Escherichia coli. Carcinogenesis 13(5):751-8, (May) 1992.

Vojtek A B, Hollenberg S M, Cooper J A: Mammalian Ras interacts directly with the serine/threonine kinase Raf. Cell 74(1):205-214, 1993.

Wenzler H, Mignery G, Fisher L, Park W: Sucrose-regulated expression of a chimeric potato tuber gene in leaves of transgenic tobacco plants. Plant Mol Biol 13(4):347-54, 1989.

Williams and Barclay, in Immunoglobulin Genes, The Immunoglobulin Gene Superfamily Winnacker E L. From Genes to Clones: Introduction to Gene Technology. VCH Publishers, New York, N.Y., ©1987.

Winter G and Milstein C: Man-made antibodies. Nature 349 (6307):293 299, 1991.

Yang X, Hubbard E J, Carlson M: A protein kinase substrate identified by the two-hybrid system. Science 257(5070): 680-2, (Jul 31) 1992.

U.S. Pat No. 4,683,195; Filed Feb. 7, 1986, Issued Jul. 28. 1987. Mullis K B, Erlich H A, Arnheim N, Horn G T, Saiki R K, Scharf S J: Process for Amplifying, Detecting, and/or Cloning Nucleic Acid Sequences.

U.S. Pat. No. 4,683,202; Filed Oct. 25, 1985, Issued Jul. 28, 1987. Mullis K B: Process for Amplifying Nucleic Acid Sequences.

U.S. Pat. No. 4,704,362; Filed Nov. 5, 1979, Issued Nov. 3, 1987. Itakura K, Riggs A D: Recombinant Cloning Vehicle Microbial Polypeptide Expression.

WO 88/08453; Filed Apr. 14, 1988, Published Nov. 3, 1988. Alakhov J B, Baranov, V I, Ovodov S J, Ryabova L A, Spirin A S: Method of Obtaining Polypeptides in Cell-Free Translation System.

WO 90/05785; Filed Nov. 15, 1989, Published May 31, 1990. Schultz P: Method for Site-Specifically Incorporating Unnatural Amino Acids into Proteins.

WO 90/07003; Filed Jan. 27, 1989, Published Jun. 28, 1990. Baranov V I, Morozov I J, Spirin A S: Method for Preparative Expression of Genes in a Cell-free System of Conjugated Transcription/translation.

WO 91/02076; Filed Jun. 14, 1990, Published Feb. 21, 1991. Baranov V I, Ryabova L A, Yarchuk O B, Spirin A S: Method for Obtaining Polypeptides in a Cell-free System.

WO 91/05058; Filed Oct. 5, 1989, Published Apr. 18, 1991. Kawasaki G: Cell-free Synthesis and Isolation of Novel Genes and Polypeptides.

WO 91/17271; Filed May 1, 1990, Published Nov. 14, 1991. Dower W J, Cwirla S E: Recombinant Library Screening Methods.

WO 91/18980; Filed May 13, 1991, Published Dec. 12, 1991. Devlin J J: Compositions and Methods for Indentifying Biologically Active Molecules.

WO 91/19818; Filed Jun. 20, 1990, Published Dec. 26, 1991. Dower W J, Cwirla S E, Barrett R W: Peptide Library and Screening Systems.

WO 92/02536; Filed Aug. 1, 1991, Published Feb. 20, 1992. Gold L, Tuerk C: Systematic Polypeptide Evolution by Reverse Translation.

WO 92/03918; Filed Aug. 28, 1991, Published Mar. 19, 1992. Lonberg N, Kay R M: Transgenic Non-human Animals Capable of Producing Heterologous Antibodies.

WO 92/03918; Filed Aug. 28, 1991, Published Mar. 19, 1992. Lonberg N, Kay R M: Transgenic Non-human Animals Capable of Producing Heterologous Antibodies.

WO 92/05258; Filed Sept. 17, 1991, Published Apr. 2, 1992. Fincher G B: Gene Encoding Barley Enzyme.

WO 92/14843; Filed Feb. 21, 1992, Published Sept. 3, 1992. Toole J J, Griffin L C, Bock L C, Latham J A, Muenchau D D, Krawczyk S: Aptamers Specific for Biomolecules and Method of Making.

WO 93/08278; Filed Oct. 15, 1992, Published Apr. 29, 1993. Schatz P J, Cull M G, Miller J F, Stemmer W P: Peptide Library and Screening Method.

WO 93/12227; Filed Dec 17, 1992, Published Jun. 24, 1993. Lonberg, N; Kay R M: Transgenic Non-human Animals Capable of Producing Heterologous Antibodies.

WO 93/12227; Filed Dec. 17, 1992, Published Jun. 24, 1993. Lonberg N, Kay R M: Transgenic Non-human Animals Capable of Producing Heterologous Antibodies.

WO 94/25585; Filed Apr. 25, 1994, Published Nov. 10, 1994. Lonberg, N, Kay R M: Transgenic Non-human Animals Capable of Producing Heterologous Antibodies.

WO 94/25585; Filed Apr. 25, 1994, Published Nov. 10, 1994. Lonberg N, Kay R M: Transgenic Non-human Animals Capable of Producing Heterologous Antibodies.

Arslan T, Abraham A T, Hecht S M: Structurally altered substrates for DNA topoisomerase I. Effects of inclusion of a single 3'-deoxynucleotide within the scissile strand. Nucleosides Nucleotides 1998 January-March;17(1-3): 515-30.

Aupeix K, Toulme J J: Binding of chemically-modified oligonucleotides to the double-stranded stem of an RNA hairpin. Nucleosides Nucleotides 1999 June-July;18 (6-7): 1647-50.

Bazzanini R, Manfredini S, Durini E, Groschel B, Cinatl J, Balzarini J, De Clercq E, Imbach J L, Perigaud C, Gosselin G: Prodrugs of Ara-CMP and Ara-AMP with a S-acyl-2-thioethyl (SATE) biolabile phosphate protecting group: synthesis and biological evaluation. Nucleosides Nucleotides 1999 April-May;18(4-5):971-2. Blackburn G M, Liu X, Rosier A, Brenner C: Two hydrolase resistant analogues of diadenosine 5',5'''-P1, P3-triphosphate for studies with Fhit, the human fragile histidine triad protein. Nucleosides Nucleotides 1998 January-March; 17(1-3): 301-8. Bridson P K, Lin X, Melman N, Ji X D, Jacobson K A: Synthesis and adenosine receptor affinity of 7-beta-D-ribofuiranosylxanthine. Nucleosides Nucleotides 1998 April;17(4):759-68.

Brodin P, Gottikh M, Auclair C, Mouscadet J F: Inhibition of HIV-1 integration by mono- & bi-functionalized triple helix forming oligonucleotides. Nucleosides Nucleotides 1999 June-Juyl; 18(6-7):1717-8.

Creighton T E: Proteins Structures and Molecular Principles. New York: W. H. Freeman and Co., 1984.

De Clercq E: Carbocyclic adenosine analogues as S-adenosylhomocysteine hydrolase inhibitors and antiviral agents: recent advances. Nucleosides Nucleotides 1998 January-March;17(1-3):625-34.

de Zwart M, Link R, von Frijtag Drabbe Kunzel J K, Cristalli G, Jacobson K A, Townsend-Nicholson A, IJzerman A P: A functional screening of adenosine analogues at the adenosine A2B receptor: a search for potent agonists. Nucleosides Nucleotides 1998 June;17(6):969-85.

Egron D, Arzumanov A A, Dyatkina N B, Krayevsky A, Imbach J L, Aubertin A M, Gosselin G, Perigaud C: Synthesis, anti-HIV activity and stability studies of 3'-azido-2',3'-dideoxythymidine 5'-fluorophosphate. Nucleosides Nucleotides 1999 April-May;18(4-5):983-4

Gianolio D A, McLaughlin L W: Synthesis and triplex forming properties of pyrimidine derivative containing extended functionality. Nucleosides Nucleotides 1999 August; 18(8):1751-69.

Gottikh M B, Volkov E M, Romanova E A, Oretskaya T S, Shabarova Z A: Synthesis of oligonucleotide-intercalator conjugates capable to inhibit HIV-1 DNA integration. Nucleosides Nucleotides 1999 June-July; 18(6-7):1645-6.

Hotoda H, Koizumi M, Ohmine T, Furukawa H, Nishigaki T, Abe K, Kosaka T, Tsutsumi S, Sone J, Kaneko M: Biologically active oligodeoxyribonucleotides. 10: anti-HIV-1 activity and stability of modified hexanucleotides containing glycerol-skeleton. Nucleosides Nucleotides 1998 January-March; 17(1-3):243-52.

JP10113194; Filed 19971022, Published 19980506. Donnelly, J J; Dwarki, V J; Liu, M A; Montgomery, D L; Parker, S; Shiver, J W; Ulmer J B: Nucleic Acid Preparation.

Kang S H, Sinhababu A K, Cho M J: Synthesis and biological activity of bis(pivaloyloxymethyl) ester of 2'-azido-2'-deoxyuridine 5'-monophosphate. Nucleosides Nucleotides 1998 June; 17(6):1089-98.

Krayevsky A, Arzumanov A, Shirokova E, Dyatkina N, Victorova L, Jasko M, Alexandrova L: dNTP modified at triphosphate residues: substrate properties towards DNA polymerases and stability in human serum. Nucleosides Nucleotides 1998 January-March; 17(1-3):681-93.

Krayevsky A A, Dyatkina N B, Semizarov D G, Victorova L S, Shirokova E A, Theil F, Von Janta Lipinski M J, Gosselin G, Imbach J L: Reasons and limits of substrate activity of modified L-dNTP in DNA biosynthesis. Nucleosides Nucleotides 1999 April-May;18(4-5): 863-4.

Kvasyuk E I, Mikhailopulo I A, Suhadolnik R J, Henderson E E, Muto N F, Iacono K T, Homon J, Pfleiderer W: Synthesis and biological activity of 2',5'-oligoadenylate trimers containing 5'-terminal 5'-amino-5'-deoxy- and 5'-amino-3',5'- dideoxyadenosine derivatives. Nucleosides Nucleotides 1999 June-July; 18(6-7): 1483-4.

Liu J, Skradis A, Kolar C, Kolath J, Anderson J, Lawson T, Talmadge J, Gmeiner W H: Increased cytotoxicity and decreased in vivo toxicity of FdUMP[10] relative to 5-FU. Nucleosides Nucleotides 1999 August;18(8): 1789-802.

Lutz M J, Will D W, Breipohl G, Benner S A, Uhlmann E: Synthesis of a monocharged peptide nucleic acid (PNA) analog and its recognition as substrate by DNA polymerases. Nucleosides Nucleotides 1999 March;18(3): 393-401. Monaco V, van de Wetering K I, Meeuwenoord N J, van den Elst HA, Stuivenberg H R, Visse R, van der Kaaden J C, Moolenaar G F, Verhoeven E E, Goosen N, van der Marel G A, van Boom J H: Synthesis and biological evaluation of modified DNA fragments for the study of nucleotide excision repair in E. coli. Nucleosides Nucleotides 1999 June-July; 18(6-7):1339-41.

Morozova O V, Kolpashchikov D M, Ivanova T M, Godovikova T S: Synthesis of new photocross-linking 5-C-base-substituted UTP analogs and their application in highly selective affinity labelling of the tick-borne encephalitis virus RNA replicase proteins. Nucleosides Nucleotides 1999 June-July; 18(6-7): 1513-4.

Nguyen-Ba N, Chan L, Quimpere M, Turcotte N, Lee N, Mitchell H, Bedard J: Design and SAR study of a novel class of nucleotide analogues as potent anti-HCMV agents. Nucleosides Nucleotides 1999 April-May; 18(4-5):821-7.

Pandolfi D, Rauzi F, Capobianco M L: Evaluation of different types of end-capping modifications on the stability of oligonucleotides toward 3'- and 5'-exonucleases. Nucleosides Nucleotides 1999 September; 18(9): 2051-69.

Pankiewicz K W, Lesiak-Watanabe K: Novel mycophenolic adenine bis(phosphonate)s as potent anticancer agents and inducers of cells differentiation. Nucleosides Nucleotides 1999 April-May; 18(4-5):927-32.

Perrin D M, Garestier T, Helene C: Expanding the catalytic repertoire of nucleic acid catalysts: simultaneous incorporation of two modified deoxyribonucleoside triphosphates bearing ammonium and imidazolyl functionalities. Nucleosides Nucleotides 1999 March; 18(3):377-91.

Pfundheller H M, Koshkin A A, Olsen C E, Wengel J: Evaluation of oligonucleotides containing two novel 2'-O-methyl modified nucleotide monomers: a 3'-C-allyl and a 2'-O,3'-C-linked bicyclic derivative. Nucleosides Nucleotides 1999 September; 18(9):2017-30.

Ramasamy K S, Stoisavljevic V: Synthesis and biophysical studies of modified oligonucleotides containing acyclic amino alcohol nucleoside analogs. Nucleosides Nucleotides 1999 August;18(8):1845-61.

Schinazi R F, Lesnikowski Z J: Boron containing oligonucleotides. Nucleosides Nucleotides 1998 January-March; 17(1 -3):635-47.

Secrist J A 3rd, Parker W B, Allan P W, Bennett L L Jr, Waud W R, Truss J W, Fowler A T, Montgomery J A, Ealick S E, Wells A H, Gillespie G Y, Gadi V K, Sorscher E J: Gene therapy of cancer: activation of nucleoside prodrugs with E. coli purine nucleoside phosphorylase. Nucleosides Nucleotides 1999 April-May;18(4-5):745-57.

Shirokova E A, Shipitsin A V, Victorova L S, Dyatkina N B, Goryunova L E, Beabealashvilli R S, Hamilton C J, Roberts S M, Krayevsky A A: Modified nucleoside 5'-triphosphonates as a new type of antiviral agents. Nucleosides Nucleotides 1999 April-May; 18(4-5): 1027-8.

Srivastava T K, Friedhoff P, Pingoud A, Katti S B: Application of oligonucleoside methylphosphonates in the studies on phosphodiester hydrolysis by Serratia endonuclease. Nucleosides Nucleotides 1999 September; 18(9): 1945-60.

Stattel J M, Yanachkov I, Wright G E: Synthesis and biocheibical study of N2-(p-n-butylphenyl)-2'-deoxyguanosine 5'-(alpha,beta-imido)triphosphate (BuPdGMPN-HPP): a non-substrate inhibitor of B family DNA polymerases. Nucleosides Nucleotides 1998 August; 17(8): 1505-13.

Terato H, Morita H, Ohyama Y, Ide H: Novel modification of 5-formyluracil by cysteine derivatives in aqueous solution. Nucleosides Nucleotides 1998 January-March; 17(1-3): 131-41.

Tomikawa A, Seno M, Sato-Kiyotaki K, Ohtsuki C, Hirai T, Yamaguchi T, Kawaguchi T, Yoshida S, Saneyoshi M: Synthetic nucleosides and nucleotides. 40. Selective inhibition of eukaryotic DNA polymerase alpha by 9-(beta-D-arabinofuranosyl)-2-(p-n-butylanilino) adenine 5'-triphosphate (BuAaraATP) and its 2'-up azido analog: synthesis and enzymatic evaluations. Nucleosides Nucleotides 1998 January-March; 17(1-3):487-501.

U.S. Pat. No. 5,580,859; Filed 19940318, Issued 19961203. Felgner, P L.; Wolff, J A.; Rhodes, G H.; Malone, R W.; Carson, D A.: Delivery of exogenous DNA sequences in a mammal.

U.S. Pat. No. 5,589,466; Filed 19950126, Issued 19961231. Felgner, P L.; Wolff, J A.; Rhodes, G H.; Malone, R W.; Carson, D A.: Induction of a protective immune response in a mammal by injecting a DNA sequence.

U.S. Pat. No. 5,641,665; Filed 19941128, Issued 19970624. Hobart, P M.; Margalith, M; Parker, S E.; Khatibi, S: Plasmids suitable for IL-2 expression.

U.S. Pat. No. 5,693,622; Filed 19950607, Issued 19971202. Wolff, J A. ;Duke, D J.; Felgner, P L.: Expression of exogenous polynucleotide sequences cardiac muscle of a mammal.

U.S. Pat. No. 5,703,055; Filed 19940126, Issued 19971230. Felgner, P L.; Wolff, J A; Rhodes, G H.; Malone, R W; Carson, D A.: Generation of antibodies through lipid mediated DNA delivery.

U.S. Pat. No. 5,846,946; Filed 19960614, Issued 19981208. Huebner, R C.; Norman, J A.; Liang, X; Camer, K R.; Barbour, A G.; Luke, C J.: Compositions and methods for administering Borrelia DNA.

U.S. Pat. No. 5,910,488; Filed 19951201, Issued 19990608. Nabel, G J.; Nabel, E G.; Lew, D; Marquet, M: Plasmids suitable for gene therapy.

Victorova L S, Semizarov D G, Shirokova E A, Alexandrova L A, Arzumanov A A, Jasko M V, Krayevsky A A: Human DNA polymerases and retroviral reverse transcriptases: selectivity in respect to dNTPs modified at triphosphate residues. Nucleosides Nucleotides 1999 April-May; 18(4-5): 1031-2.

von Janta-Lipinski M, Gaertner K, Lehmann C, Scheer H, Schildt J, Matthes E: Protein and RNA of human telomerase as targets for modified oligonucleotides. Nucleosides Nucleotides 1999 June-July; 18(6-7):1719-20

WO9011092; Filed 19900321, A1 Published 19901004. Felgner, P L. ;Wolff, J A; Rhodes, G H.; Malone, R W; Carson, D A.: Expression Of Exogenus Polynucleotide Sequences In A Vertebrate.

WO9314778; Filed 19930121, A1 Published 19930805. Rhodes, G H.; Dwarki, V J.; Felgner, P L; Wang-Felgner, J; Manthorpe, M: Ex Vivo Gene Transfer.

WO9421797; Filed 19940314, A1 Published 19940929. Donnelly, J J.; Dwarki, V J.; Liu, M A.; Montgomery, D L.; Parker, S E.; Shiver, J W.; Ulmer, J B.: Nucleic Acid Pharmaceuticals.

WO9633736; Filed 19960426, A1 Published 19961031. Baruch D I; Pasloske B L; Howard, R J: Malaria Peptides and Vaccines.

WO9735992; Filed 19970317, A1 Published 19971002. Hobart, P M.; Liang, X: Tetracycline Inducible/Repressible Systems.

WO9926663; Filed 19981120, A2 Published 19990603. Horton, H; Parker, S; Manthorpe, M; Felgner, P: Treatment Of Cancer Using Cytokine-Expressing Polynucleotides And Compositions Therefor.

WO9941368; Filed 19990210, A2 Published 19990819. Punnonen J, Stemmier W P, Whalen R G; Howard, R: Optimization of Immunomodulatory Properties of Genetic Vaccines.

WO9941369; Filed 19990210, A2 Published 19990819. Punnonen J, Stemmer W P, Whalen R G; Howard, R: Genetic Vaccine Vector Engineering.

WO9941383; Filed 19990210, A1 Published 19990819. Punnonen J, Bass, S H, Whalen, R G, Howard, R, Stemmer, W P: Antigen Library Immunization.

WO9941402; Filed 19990210, A2 Published 19990819. Punnonen J, Stemmer, W P, Howard R, Patten P A: Targeting of Genetic Vaccine Vectors.

Structure-Activity considerations are well-known in the art, and the following illustrative but non-limiting examples of references (incorporated by reference in their entirety) are provided:

Dunbrack R L Jr, Gerloff D L, Bower M, Chen X, Lichtarge O, Cohen F E: Meeting review: the Second meeting on the Critical Assessment of Techniques for Protein Structure Prediction (CASP2), Asilomar, Calif., Dec. 13-16, 1996. Fold Des 2(2): R27-42, (1997).

Fischer D, Eisenberg D: Protein fold recognition using sequence-derived predictions. Protein Sci 5(5): 947-55, (May 1996).

Havel T F: An evaluation of computational strategies for use in the determination of protein structure from distance constraints obtained by nuclear magnetic resonance. Prog Biophys Mol Biol 56(1): 43-78, (1991).

Lichtarge O, Yamamoto K R, Cohen F E: Identification of finctional surfaces of the zinc binding domains of intracellular receptors. J Mol Biol 274(3): 325-37, (Dec. 5, 1997).

Matsumoto R, Sali A, Ghildyal N, Karplus M, Stevens R L: Packaging of proteases and proteoglycans in the granules of mast cells and other hematopoietic cells. A cluster of histidines on mouse mast cell protease 7 regulates its binding to heparin serglycin proteoglycans. J Biol Chem 270 (33): 19524-31, (Aug. 18, 1995).

Sali A: Comparative protein modeling by satisfaction of spatial restraints. Mol Med Today 1(6): 270-7, (September 1995).

Sali A, Matsumoto R, McNeil H P, Karplus M, Stevens: R L Three-dimensional models of four mouse mast cell chymases. Identification of proteoglycan binding regions and protease-specific antigenic epitopes. J Biol Chem 268(12): 9023-34, Apr. 25, 1993.

Sali A: Modeling mutations and homologous proteins. Curr Opin Biotechnol 6(4): 437-51, (August 1995).

Sali A, Potterton L, Yuan F, van Vlijmen H, Karplus M: Evaluation of comparative protein modeling by MODELLER. Proteins 23(3): 318-26

SEQUENCE LISTING

```
<160> NUMBER OF SEQ ID NOS: 36

<210> SEQ ID NO 1
<211> LENGTH: 150
<212> TYPE: DNA
<213> ORGANISM: Artificial Sequence
<220> FEATURE:
<223> OTHER INFORMATION: Synthetic Oligonucleotide template 124-2d

<400> SEQUENCE: 1

aatggacaag aaacgtgtcc gtgtgtacaa cgcggagatg gcctatgtcg acacgggcca      60

gggtgattcc gttctgtttc ttcacggcaa cccgacgtcg tcgtatctgt ggaggggcgt     120

aatgcctttt gtgacggacg tcgcccgatg                                      150


<210> SEQ ID NO 2
<211> LENGTH: 149
<212> TYPE: DNA
<213> ORGANISM: Artificial Sequence
<220> FEATURE:
<223> OTHER INFORMATION: Synthetic Oligonucleotide template 12412

<400> SEQUENCE: 2

atggagaaac accgcgtaga agttctcggt tcggagatgg cctacatcga cgtgggagag      60

ggcgacccga tcgtgttcct ccacggaaat cccacgtcgt cgtacctgtg gcggaacgtg     120

attccccacg ttgccggctt gggacgctg                                       149


<210> SEQ ID NO 3
<211> LENGTH: 150
<212> TYPE: DNA
<213> ORGANISM: Artificial Sequence
```

<220> FEATURE:
<223> OTHER INFORMATION: Synthetic Oligonucleotide template 124-1d

<400> SEQUENCE: 3 acacgacaag cgctacatcg aggtgctggg taagcgaatg gcctatgtcg agatgggcga 60 gggtgatccc atcattttcc aacacggcaa tccgacctca tcgtacctgt ggcgcaacat 120 catgccccat gtgcaacagc tcggtcgctg 150

<210> SEQ ID NO 4
<211> LENGTH: 150
<212> TYPE: DNA
<213> ORGANISM: Artificial Sequence
<220> FEATURE:
<223> OTHER INFORMATION: Synthetic Oligonucleotide template mycol

<400> SEQUENCE: 4 cgggcagccg aagtacctag aaatcgccgg gaagcgcatg gcgtatatcg acgaaggcaa 60 gggtgacgcc atcgtctttc agcacggcaa ccccacgtcg tcttacttgt ggcgcaacat 120 catgccgcac ttggaagggc tgggccggct 150

<210> SEQ ID NO 5
<211> LENGTH: 150
<212> TYPE: DNA
<213> ORGANISM: Artificial Sequence
<220> FEATURE:
<223> OTHER INFORMATION: Synthetic Oligonucleotide template b3

<400> SEQUENCE: 5 ctacccaaaa tttcggcggt cggtcttcgg ccgcgagatg gcgtacgtgg aagtgggacg 60 gggcgacccc atcgtactct tgcacggcaa ccccacctcg tcgtacctct ggcgcaacgt 120 gttgccgcac ctggcgccgt taggccgctg 150

<210> SEQ ID NO 6
<211> LENGTH: 150
<212> TYPE: DNA
<213> ORGANISM: Artificial Sequence
<220> FEATURE:
<223> OTHER INFORMATION: Synthetic Oligonucleotide template b1

<400> SEQUENCE: 6 gcatccgaga aagcggatcg ccgtgctcga ttcggagatg agctacgtcg ataccggcga 60 gggagcgccg atcgtgttcc ttcacggcaa cccgacttcc tcctatcttt ggcgcaacat 120 catcccctat ctcgcggatc acggcagatg 150

<210> SEQ ID NO 7
<211> LENGTH: 146
<212> TYPE: DNA
<213> ORGANISM: Artificial Sequence
<220> FEATURE:
<223> OTHER INFORMATION: Synthetic Oligonucleotide template 15112

<400> SEQUENCE: 7 atgccagcga ttgagctatt ggattcgttc atgaactacc gcgacacggg cgtcggcgat 60 cttcccgtcg tgttcctgca cggcaacccc acgtcgtctc acgtctggcg caacgtgatc 120 ccgcacgtcg ctggccagca ccggtg 146

<210> SEQ ID NO 8
<211> LENGTH: 150
<212> TYPE: DNA

<213> ORGANISM: Artificial Sequence
<220> FEATURE:
<223> OTHER INFORMATION: Synthetic Oligonucleotide template rhod2

<400> SEQUENCE: 8 cccccattat gtggaagtcc tgggcgagcg tatgcactac gtcgatgttg gaccgcggga 60 tggcacgcct gtgctgttcc tgcacggtaa cccgacctcg tcctacctgt ggcgcaacat 120 catcccgcat gtagcaccga gtcatcggtg 150

<210> SEQ ID NO 9
<211> LENGTH: 150
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (2)..(3)
<223> OTHER INFORMATION: a, t, c, or g
<220> FEATURE:
<221> NAME/KEY: misc_feature
<222> LOCATION: (7)..(8)
<223> OTHER INFORMATION: a, t, c, or g
<220> FEATURE:
<221> NAME/KEY: misc_feature
<222> LOCATION: (11)..(11)
<223> OTHER INFORMATION: a, t, c, or g
<220> FEATURE:
<221> NAME/KEY: misc_feature
<222> LOCATION: (13)..(13)
<223> OTHER INFORMATION: a, t, c, or g
<220> FEATURE:
<221> NAME/KEY: misc_feature
<222> LOCATION: (16)..(16)
<223> OTHER INFORMATION: a, t, c, or g
<220> FEATURE:
<221> NAME/KEY: misc_feature
<222> LOCATION: (21)..(22)
<223> OTHER INFORMATION: a, t, c, or g
<220> FEATURE:
<221> NAME/KEY: misc_feature
<222> LOCATION: (29)..(29)
<223> OTHER INFORMATION: a, t, c, or g
<220> FEATURE:
<221> NAME/KEY: misc_feature
<222> LOCATION: (32)..(33)
<223> OTHER INFORMATION: a, t, c, or g
<220> FEATURE:
<221> NAME/KEY: misc_feature
<222> LOCATION: (52)..(52)
<223> OTHER INFORMATION: a, t, c, or g
<220> FEATURE:
<221> NAME/KEY: misc_feature
<222> LOCATION: (76)..(76)
<223> OTHER INFORMATION: a, t, c, or g
<220> FEATURE:
<221> NAME/KEY: misc_feature
<222> LOCATION: (82)..(82)
<223> OTHER INFORMATION: a, t, c, or g
<220> FEATURE:
<221> NAME/KEY: misc_feature
<222> LOCATION: (133)..(133)
<223> OTHER INFORMATION: a, t, c, or g
<220> FEATURE:
<221> NAME/KEY: misc_feature
<222> LOCATION: (136)..(136)
<223> OTHER INFORMATION: a, t, c, or g
<220> FEATURE:
<221> NAME/KEY: misc_feature
<222> LOCATION: (140)..(140)
<223> OTHER INFORMATION: a, t, c, or g
<220> FEATURE:
<221> NAME/KEY: misc_feature
<222> LOCATION: (142)..(142)
<223> OTHER INFORMATION: a, t, c, or g

<400> SEQUENCE: 9 vnnbsmnnvd ndnbrnvkvb nnrdbbhsnd bnnsvrvwws vbskayrybg rnvhvsgvvr 60 kgghvhbbcb rtbvtnytyy wncacgghaa yccsacbtcv tcbyayytbt ggmgsrrcrt 120 vwtbccbywy btnvmnsvbn dnsvhmgvyk 150

<210> SEQ ID NO 10
<211> LENGTH: 1044
<212> TYPE: DNA
<213> ORGANISM: Artificial Sequence
<220> FEATURE:
<223> OTHER INFORMATION: Synthetic Oligonucleotide template 150am13_00

<400> SEQUENCE: 10 catgatgcac ggcgatattt catcgagcaa tgacacggtc ggcgttgccg tcgtgaacta 60 caagatgcct cgccttcata ccaaggcgga ggttttagcg aacgccagaa agatcggcga 120 gatgatcgtc ggcatgaaga ccggcctgcc cggaatggat ctggtgatct tcccggaata 180 ttcgacccac ggcatcatgt aggactccaa ggaaatgtac gataccgcgt ccgtcgtgcc 240 cggcgaggag accgagattt ttgccgaagc ctgccgcaag gcgaaagtct ggggcgtgtt 300 ctcgctcacc ggcgaacgtc acgaggaaca tccgaagaag gcgccctaca acacgctgat 360 cctgatgaac gacaagggcg aggtggtcca gaaataccgc aagatcatgc cgtgggttcc 420 gatcgagggc tggtaccccg gcaactgcac ctacgtctcc gacgggccga agggcatgaa 480 ggtttcgctg atcatctgcg atgacggcaa ctatccggaa atctggcgcg actgcgccat 540 gaagggcgcc gagctgatcg tgcgctgcca gggctacatg tatccggcca aggaccagca 600 ggtcatcatg gcgaaggcga tggcgtgggc gaataattgt tacgtcgcgg tttccaatgc 660 cgcgggcttc gatggcgtct attcgtattt cggccactcg gcgatcatcg gcttcgatgg 720 ccgcacgctc ggcgaatgcg gcgaggaaga atacggcatc cagtatgccc agctttcgaa 780 gatgctgatc cgcgacgccc gccgcaccgg acaatcggaa aaccatctct tcaagctggt 840 gcatcgtggc tacaccgggt tgatcaactc cggcgagggc gaccgcggtc tcgcggcctg 900 tccttatgag ttctacaaca aatggatcgc cgatccggaa ggcacccgcg aaatggtcga 960 gtcctttacc cggccgacgg tgggaaccga tgaagcgccc atcgaaggca tcccgaacaa 1020 ggtcgcggtg caccgctgaa agct 1044

<210> SEQ ID NO 11
<211> LENGTH: 1044
<212> TYPE: DNA
<213> ORGANISM: Artificial Sequence
<220> FEATURE:
<223> OTHER INFORMATION: Synthetic Oligonucleotide template 150AM7_001

<400> SEQUENCE: 11 catgcatcac ggcgacattt catcgagcaa tgacacggtc ggcgttgccg tcgtgaacta 60 caagatgccg cggcttcaca ccaaggctga ggtgctggcc aactgccgca agatcgccga 120 catgctggtc ggcatgaaga gcggcctgcc gggaatggat ctggtgatct tcccggaata 180 ttccacccac ggcatcatgt acgactccaa ggagatgtac gacacggcgt cgacggtgcc 240 gggtgaagag accgagattt tcgccgaggc ctgccgcaag gccaaggtct ggggcgtgtt 300 ctcgctgacc ggcgagcgcc acgaggagca tcccaataaa gcgccgtaca acaccctgat 360 cctgatgaac gacaagggtg aagtcgttca gaaatatcgc aagatcatgc cgtgggtgcc 420 gatcgaaggc tggtatcccg gcaactgcac gtacgtctcc gaaggcccga agggcatgaa 480 gatgtcgctg atcatctgcg acgacggcaa ctacccggaa atctggcgtg actgcgcgat 540 gaagggcgcc gaactgatca tccgctgcca gggctacatg tatcccgcca aggatcagca 600 ggtgctgatg gcgaaagcaa tggcctgggc caacaacgtt tatgtcgcgg tcgccaatgc 660 ctcgggcttc gacggcgtct actcgtattt cggccattcg gcgatcatcg gcttcgacgg 720 ccgtaccctc ggcgaatgcg gcgaggagga ttatggcatc cagtatgccg ccatctccaa 780 gtcgctgatc cgcgacgcgc gccgcaccgg ccaatcggaa aaccatctct tcaagctggt 840 gcaccgtggc tacaccggca tgatcaattc cggcgagggc gaccgcggtg tcgcggcttg 900 cccgtatgat ttctattcga aatggatcgc cgatcccgag ggtacacgcg agatggtgga 960 atccttcacg cgtccgacgg tgggtgtgga ggaatgcccg atcgagggca ttccgaacaa 1020 ggccaccacg caccgctgaa agct 1044

<210> SEQ ID NO 12
<211> LENGTH: 1044
<212> TYPE: DNA
<213> ORGANISM: Artificial Sequence
<220> FEATURE:
<223> OTHER INFORMATION: Synthetic Oligonucleotide template 431am7_002

<400> SEQUENCE: 12 catgagacac ggagatatct ccagcagcaa cgattgcgtg ggcgtggccg tcgtgaacta 60 caagatgccg cggctgcata cccgcgcgga ggtgatggag aacgcccgca agatcgccga 120 catggtcgtg ggcatgaagc gcggcctgcc cggcatggac ctggtcatct tccccgagta 180 ctccacccac ggcatcatgt acgacgccaa ggaaatgtac gaaaccgctt cggccattcc 240 gggcgaagag actgctgtgt tcgccgacgc ctgccgcaag gccaacgtat ggggcgtgtt 300 ttcgctgacg ggcgagcgcc acgaagagca cccgaacaag gcgccgtaca acacgctcat 360 cctgatgaac aacaagggcg agatcgtgca gaagtaccgc aagatcatgc cctgggtgcc 420 gatcgaaggc tggtatccgg gcgattgcac ctatgtgtcg gaaggcccca agggactgaa 480 gatcagcctc atcatctgcg acgacggcaa ttaccccgag atctggcgcg attgcgccat 540 gcgcggcgcc gagctgatcg tgcgttgcca gggatacatg tacccggcca aggaccagca 600 ggtcatggtg tccaaggcca tggcgtggat gaacaacgtc tacgtggcgg tggccaatgc 660 cgcgggcttc gacggcgtgt attcctactt cggccattcg gccatcatcg gcttcgacgg 720 ccgcacgctg ggcgaatgcg gtgaagaaga catgggcgtg cagtacgccg agctctccac 780 cagcctgatc cgcgacgcgc gcaagaacat gcagtcgcag aaccacttgt tcaagctggt 840 gcaccgcggc tacaccggca agatcaattc cggcgaagag gccaccggcg tcgcggcatg 900 cccgtacaac ttctacgcca actggatcaa cgatccggag ggcacgcgca agatggtcga 960 atccttcacc cggtccaccg tgggcacgcc ggagtgcccc atggacggca tccccaacga 1020 ggacgccaag caccgctaga agct 1044

<210> SEQ ID NO 13
<211> LENGTH: 1998
<212> TYPE: DNA
<213> ORGANISM: Cercopithecine herpesvirus 8

<400> SEQUENCE: 13 atcgatttaa actgcccgat tgaggttgtc gctgaacact ttgtgagtct tttcgaaggt 60 agatatgaca ctgctttcca gaagtgccgc tgaagcctgg ggtacatatc tgaagcagcg 120 agatgagcgt cccgaggacg tgatacgctg cgactacggc gtcttcagtt tgcgtaatct 180 cgtgttccaa cgttgtctga ctatgttaca gggtgtttat ctgcgacaat acgatcaacc 240 gtgtttacga gaatatatta aaaagaattc tggtactatc attccgttgc gcaacccctg 300 tagctggttt ctcgtccttc gctctggtat agatattccc caggtagaaa cccgttcgtt 360 cgacgagtat ctttgctgca aagagaaatt ggaagcactg ggaatattgg gggtgcagtt 420 gcgtgatggc agtgatcgca aaaaaatcca ggagactacg tgtgtggttc tgctgggaag 480 ctatggattt gtgtacgtgt atgactggga cagtgacgga ctctttcaga taggtacctc 540 actcaaagaa ctcgcgcacc acggtttact gacatgtgaa tcggtatatc gccatccgca 600 aacgcccttc tccagcaccg agcctcgttt tcaagtcgag aaattgttgt gtctcgatcc 660 gacagacgca cgtggtctag ctaagaccgc agaagagttt catggcgtta acgtagtagt 720 gaaaacccct gggcgatcgg aggccgatcc cttgctcctt ctgggtactg tggagaagct 780 acgtcaaatg tatccctttg ctaaaatgag agctgataac tttagtaatc tcataaagta 840 tattaatcaa cgcatgtgtt gccgatggta cgtacttggt gttactggcc gttacgctaa 900 ttttggaatt ttgctgacct gtggaataat tctgttggac gagtgcggcg tgtgttatgt 960 gctgagaatc gacgaaagcg acgtgtttcg tctagccgat aacatccaaa tgttgttcag 1020 atgcggcttt cttaagctcc gtggcattac gcgatttgac cgcggattgc gtggcgaggc 1080 tcgtctggag agtgagtgct actgctatca cggtgcccgt aagcaagatc tctcttggtg 1140 gtctatggtc aacacagtta ccgccgagca gctctgtggt gcgtacgact ggctcacgcg 1200 cagtaatcgc gctcatgata aaatacgtac cagttgttgt tggggacgta gtgatttgat 1260 gcctaccgga gtattgcaag agaatcagaa ttggtgcttt ccgtggagca gtgtcacggt 1320 tctacaaggg ccccaaagcg gtgcgtggca agaaaatgat gagttaacgg agaaaacgtc 1380 tgatggtact gtgatgtttc gtgtagacag aggtttttct cccagaaccg taaagttcga 1440 gggtgaaagc gatgactaca cagaagagga ggaagatgat gataaccagt cagaagaaac 1500 ccctcagcat cagcctgttg tcattgtttc acatgaaaca aacggcagtg ttgattctta 1560 tgatgatgag agtgagtcat ctctgtcctc agatacccat gatccaccac ccccagacat 1620 tatggccata atccaaaagg aatggcaaaa cgaagagccg gttaccaatg aaagagaatt 1680 gttactgcgg cgtgcacgac gagctaaaca tatgaaaaag tggcattgtt ccctggaaag 1740 ggttagcatt tatgacccct tgaatgctaa tattcagtgc tttgattaaa caatgcattt 1800 gtattcaatt atctaattcc ggtgtaccgt gtcatttctc catgcagtgg tgggaaacag 1860 attacatatt tagacacacg tatcacttgt gaaagctgag tcaacatcat gcaattgtcg 1920 gacgaggtcc gggtcgttcg ttctgtgttt ctgttacgag tttacatttt attatggttc 1980 aaagtcttct atttctaa 1998

<210> SEQ ID NO 14
<211> LENGTH: 1932
<212> TYPE: DNA
<213> ORGANISM: Human herpesvirus type 5

<400> SEQUENCE: 14 gccatggcat ccgtactggg tcccatttcg gggcacgtgc tgaaagccgt gtttagtcgc 60 ggcgacacgc cggtgctgcc gcacgagacg cgactcctgc agacgggtat ccacgtgcgc 120 gtgagccagc cctcgctgat cctggtgtcg cagtacacgc ccgactcgac gccatgccac 180

```
cgcggcgaca atcagctgca ggtgcagcac acgtacttta cgggcagcga ggtggagaac    240
gtgtcggtca acgtgcacaa ccccacgggc cggagcatct gccccagcca agagcccatg    300
tcgatctatg tgtacgcgct gccgctcaag atgctgaaca tccccagcat caacgtgcac    360
cactacgcgt cgggggccga gcgcaaacac cgacacctgc ccgtagctga cgctgtgatt    420
cacgcgtcgg gcaaccagat gtggcaggcg cgtctcacgg tctcgggact ggcctggacg    480
cgtcagcaga accagtggaa agagcccgac gtctactaca cgtcagcgtt cgtgtttccg    540
accaaggacg tggcactgcg gcacgtggtg tgcgcgcacg agctggtttg ctccatggag    600
aacacgcgcg caaccaagat gcaggtgata ggtgaccagt acgtcaaggt gtacctggag    660
tccttctgcg aggacgtgcc ctccggcaag ctctttatgc acgtcacgct gggctctgac    720
gtggaagagg acctgacgat gacccgcaac ccgcaaccct tcatgcgccc ccacgagcgc    780
aacggcttta cggtgttgtg tcccaaaaat atgataatca aaccgggcaa gatctcgcac    840
atcatgctgg atgtggcttt tacctcacac gagcattttg ggctgctgtg tcccaagagc    900
atcccgggcc tgagcatctc aggtaaccta ttgatgaacg ggcagcagat cttcctggag    960
gtgcaagcga tacgcgagac cgtggaactg cgtcagtacg atcccgtggc tgcgctcttc   1020
tttttcgata tcgacttgct gctgcagcgc gggcctcagt acagcgaaca ccccaccttc   1080
accagccagt atcgcatcca gggcaagctt gagtaccgac acacctggga ccggcacgac   1140
gagggtgccg cccagggcga cgacgacgtc tggaccagcg gatcggactc cgacgaggaa   1200
ctcgtaacca ccgagcgcaa gacgccccgc gttaccggcg gcggcgccat gggggcgcc    1260
tccacttccg cgggccggaa acgcaaatca gcatcctcgg cgacggcgtg cacggcgggc   1320
gttatgacac gcggccgcct taaggccgag tccaccgtcg cgcccgaaga ggacaccgac   1380
gaggattccg acaacgaaat ccacaatccg gccgtgttca cctggccgcc ctggcaggcc   1440
ggcatcctgg cccgcaacct ggtgcccatg gttgctacgg ttcagggtca gaatctgaag   1500
taccaggagt tcttctggga cgccaacgac atctaccgca tcttcgccga attggaaggc   1560
gtatggcagc ccgctgcgca acccaaacgt cgccgccacc ggcaagacgc cttgcccggg   1620
ccatgcatcg cctcgacgcc caaaaagcac cgaggttgag ccacccgccg cgcacgctta   1680
ggacgactct ataaaaaccc acgtccactc agacacgcga cttttggccg ccacacctgt   1740
cgccgctgct atatttgcga cagttgccgg aacccttccc gacctcccac gaagacccgt   1800
tcacctttgc gcatcccctg accccccccc tcatcccggc ttcgcgatgt ctcaggcatc   1860
gtcctcgccc ggtgagggac cctcgtcgga agcggccgcg atcagcgagg ccgaagccgc   1920
cagcggaagc tt                                                       1932
```

<210> SEQ ID NO 15
<211> LENGTH: 538
<212> TYPE: DNA
<213> ORGANISM: Marmota monax

<400> SEQUENCE: 15

```
ggcctaactc tctctgaaac gatgaaatac acaagttatt tcttggcttt tcagctctgc     60
atcattttgg gttcttctag ctgttactcc caggacacag ttaataaaga aatagaagat    120
ttaaaaggat attttaatgc aagtaattca aatgtatcag atggcgggtc tctcttcttg    180
gatattttgg ataaatggaa agaggagagt gacaaaaaag taatccagag ccaaattgtc    240
tctttctact tcaaactctt tgaacactta aaagacaaca agatcatcca aaggagcatg    300
gacaccatca agggggatct ttttgctaag ttcttcaaca gcagtaccaa taagctgcag    360
```

gacttcctaa aggtgtctca agttcaggta aatgacctga agatccagcg taaagcagtg 420 agtgaactca agaaagtgat gaatgatctg ttaccacact ctaccctaag gaagcgaaaa 480 aggagtcagt cttcgattcg gggtcggaga gcatccaaat aacagtcctc atgcctgc 538

<210> SEQ ID NO 16
<211> LENGTH: 567
<212> TYPE: DNA
<213> ORGANISM: Felis catus

<400> SEQUENCE: 16 ctactgattt caacttcttt ggcctaactc tccgaaacga tgaattacac aagttttatt 60 ttcgctttcc agctttgcat aattttgtgt tcttctggtt attactgtca ggccatgttt 120 tttaaagaaa tagaagagct aaagggatat tttaatgcaa gtaatccaga tgtagcagat 180 ggtgggtcgc ttttcgtaga cattttgaag aactggaaag aggagagtga taaaacaata 240 attcaaagcc aaattgtctc cttctacctg aaaatgtttg aaaacctgaa agatgatgac 300 cagcgcattc aaaggagcat ggacaccatc aaggaagaca tgcttgataa gttgttaaat 360 accagctcca gtaaacggga tgacttcctc aagctgattc aaatccctgt gaatgatctg 420 caggtccagc gcaaagcaat aaatgaactc ttcaaagtga tgaatgatct ctcaccaaga 480 tctaacctga ggaagcggaa aaggagccag aatctgtttc gaggccgtag agcatcgaaa 540 taatggttgt cctgcctgca atatttg 567

<210> SEQ ID NO 17
<211> LENGTH: 438
<212> TYPE: DNA
<213> ORGANISM: Homo sapien

<400> SEQUENCE: 17 tgttactgcc aggacccata tgtaaaagaa gcagaaaacc ttaagaaata ttttaatgca 60 ggtcattcag atgtagcgga taatggaact cttttcttag gcattttgga gaattggaaa 120 gaggagagtg acagaaaaat aatgcagagc caaattgtct ccttttactt caaacttttt 180 agaaacttta aagatgacca gagcatccaa aagagtgtgg agaccatcaa ggaagacatg 240 aatgtcaagt ttttcaatag caacaaaaag aaacgagatg acttcgaaaa gctgactaat 300 tattcggtaa ctgacttgaa tgtccaacgc aaagcaatac atgaactcat ccaagtgatg 360 gctgaactgt cgccagcagc taaaacaggg aagcggaaaa ggagtcagat gctgtttcga 420 ggtcgaagag catcccag 438

<210> SEQ ID NO 18
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 18 ggccttccgg accgc 15

<210> SEQ ID NO 19
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 19 ttcatcgagc aggtgct 17

<210> SEQ ID NO 20
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 20 ccgcttacgg aggtcgag 18

<210> SEQ ID NO 21
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 21 cctgttgacc gagagccact g 21

<210> SEQ ID NO 22
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 22 cgggctcacc ggc 13

<210> SEQ ID NO 23
<211> LENGTH: 6
<212> TYPE: PRT
<213> ORGANISM: Artificial Sequence
<220> FEATURE:
<223> OTHER INFORMATION: 6-His tag

<400> SEQUENCE: 23

His His His His His His
1 5

<210> SEQ ID NO 24
<211> LENGTH: 22
<212> TYPE: DNA
<213> ORGANISM: Artificial Sequence
<220> FEATURE:
<223> OTHER INFORMATION: Illustrative Restriction Enzyme Recognition
Site
<220> FEATURE:
<221> NAME/KEY: misc_feature
<222> LOCATION: (7)..(22)
<223> OTHER INFORMATION: a, t, c, or g; this range may encompass 14 or
16 nucleotides

<400> SEQUENCE: 24 ctgaagnnnn nnnnnnnnnn nn 22

<210> SEQ ID NO 25
<211> LENGTH: 5
<212> TYPE: PRT
<213> ORGANISM: Artificial Sequence
<220> FEATURE:
<223> OTHER INFORMATION: linker peptide

<400> SEQUENCE: 25

Gly Gly Gly Gly Ser
1 5

<210> SEQ ID NO 26
<211> LENGTH: 15
<212> TYPE: PRT
<213> ORGANISM: Artificial Sequence
<220> FEATURE:
<223> OTHER INFORMATION: linker peptide

<400> SEQUENCE: 26

Gly Gly Gly Gly Ser Gly Gly Gly Gly Ser Gly Gly Gly Gly Ser
1 5 10 15

<210> SEQ ID NO 27
<211> LENGTH: 10
<212> TYPE: DNA
<213> ORGANISM: Artificial Sequence
<220> FEATURE:
<223> OTHER INFORMATION: Illustrative Restriction Enzyme Recognition
Site
<220> FEATURE:
<221> NAME/KEY: modified_base
<222> LOCATION: (6)..(10)
<223> OTHER INFORMATION: a, t, c or g

<400> SEQUENCE: 27 gagtcnnnnn 10

<210> SEQ ID NO 28
<211> LENGTH: 10
<212> TYPE: DNA
<213> ORGANISM: Artificial Sequence
<220> FEATURE:
<223> OTHER INFORMATION: Illustrative Restriction Enzyme Recognition
Site

<400> SEQUENCE: 28 cgcgctggac 10

<210> SEQ ID NO 29
<211> LENGTH: 223
<212> TYPE: DNA
<213> ORGANISM: Artificial Sequence
<220> FEATURE:
<223> OTHER INFORMATION: Formula Sequence
<220> FEATURE:
<221> NAME/KEY: modified_base
<222> LOCATION: (1)..(10)
<223> OTHER INFORMATION: a, t, c or g; this range may encompass 1-10
nucleotides
<220> FEATURE:
<221> NAME/KEY: modified_base
<222> LOCATION: (21)..(120)
<223> OTHER INFORMATION: a, t, c or g; this range may encompass 1-100
nucleotides
<220> FEATURE:
<221> NAME/KEY: modified_base
<222> LOCATION: (124)..(223)
<223> OTHER INFORMATION: a, t, c or g; this range may encompass 0-100
nucleotides

<400> SEQUENCE: 29 nnnnnnnnnn aagggaggag nnnnnnnnnn nnnnnnnnnn nnnnnnnnnn nnnnnnnnnn 60 nnnnnnnnnn nnnnnnnnnn nnnnnnnnnn nnnnnnnnnn nnnnnnnnnn nnnnnnnnnn 120 atgnnnnnnn nnnnnnnnnn nnnnnnnnnn nnnnnnnnnn nnnnnnnnnn nnnnnnnnnn 180 nnnnnnnnnn nnnnnnnnnn nnnnnnnnnn nnnnnnnnnn nnn 223

<210> SEQ ID NO 30
<211> LENGTH: 215
<212> TYPE: DNA
<213> ORGANISM: Artificial Sequence
<220> FEATURE:
<223> OTHER INFORMATION: Formula Sequence
<220> FEATURE:
<221> NAME/KEY: modified_base
<222> LOCATION: (1)..(10)
<223> OTHER INFORMATION: a, t, c or g; this range may encompass 1-10
nucleotides
<220> FEATURE:
<221> NAME/KEY: modified_base
<222> LOCATION: (16)..(115)
<223> OTHER INFORMATION: a, t, c or g; this range may encompass 1-100
nucleotides
<220> FEATURE:
<221> NAME/KEY: modified_base
<222> LOCATION: (116)..(215)
<223> OTHER INFORMATION: a, t, c or g; this range may encompass 0-100
nucleotides

<400> SEQUENCE: 30 nnnnnnnnnn aagggnnnnn nnnnnnnnnn nnnnnnnnnn nnnnnnnnnn nnnnnnnnnn 60 nnnnnnnnnn nnnnnnnnnn nnnnnnnnnn nnnnnnnnnn nnnnnnnnnn nnnnnnnnnn 120 nnnnnnnnnn nnnnnnnnnn nnnnnnnnnn nnnnnnnnnn nnnnnnnnnn nnnnnnnnnn 180 nnnnnnnnnn nnnnnnnnnn nnnnnnnnnn nnnnn 215

<210> SEQ ID NO 31
<211> LENGTH: 123
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (24)..(123)
<223> OTHER INFORMATION: a, t, c or g; this range may encompass 10-100
nucleotides

<400> SEQUENCE: 31 ctagaagaga ggagaaaacc atgnnnnnnn nnnnnnnnnn nnnnnnnnnn nnnnnnnnnn 60 nnnnnnnnnn nnnnnnnnnn nnnnnnnnnn nnnnnnnnnn nnnnnnnnnn nnnnnnnnnn 120 nnn 123

<210> SEQ ID NO 32
<211> LENGTH: 121
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (22)..(121)
<223> OTHER INFORMATION: a, t, c or g; this range may encompass 10-100
nucleotides

<400> SEQUENCE: 32 gatcaaaggc gcgcctgcag gnnnnnnnnn nnnnnnnnnn nnnnnnnnnn nnnnnnnnnn 60 nnnnnnnnnn nnnnnnnnnn nnnnnnnnnn nnnnnnnnnn nnnnnnnnnn nnnnnnnnnn 120 n 121

<210> SEQ ID NO 33

-continued

```
<211> LENGTH: 23
<212> TYPE: DNA
<213> ORGANISM: Artificial Sequence
<220> FEATURE:
<223> OTHER INFORMATION: primer

<400> SEQUENCE: 33

ctagaaggga ggagaaaacc atg                                          23


<210> SEQ ID NO 34
<211> LENGTH: 21
<212> TYPE: DNA
<213> ORGANISM: Artificial Sequence
<220> FEATURE:
<223> OTHER INFORMATION: primer

<400> SEQUENCE: 34

gatcaaaggc gcgcctgcag g                                            21


<210> SEQ ID NO 35
<211> LENGTH: 39
<212> TYPE: DNA
<213> ORGANISM: Artificial Sequence
<220> FEATURE:
<223> OTHER INFORMATION: primer

<400> SEQUENCE: 35

ctagaaggga ggagaattac atgaagcggc ttttagccc                         39


<210> SEQ ID NO 36
<211> LENGTH: 27
<212> TYPE: DNA
<213> ORGANISM: Artificial Sequence
<220> FEATURE:
<223> OTHER INFORMATION: primer

<400> SEQUENCE: 36

agctaagggt caaggccgca cccgagg                                      27
```

What is claimed is:

[1. A method of producing a progeny library comprised of chimerized but pre-determined polynucleotide sequences each of which is comprised of a pre-determined number of building block sequences that are assembled in non-random order, the method comprising:

(a) generating a plurality of pre-determined nucleic acid building block sequences comprised of sequences delineated by demarcation points selected from aligned progenitor nucleic acid sequences; and (b) non-stochastically assembling said nucleic acid building block sequences to produce said chimerized but pre-determined polynucleotide sequences, such that a designed overall assembly order is achieved for each of said chimerized but pre-determined polynucleotide sequence.]

[2. The method of claim 1 where the progenitor nucleic acid sequences comprise sequences derived from an uncultivated organism or an environmental sample.]

[3. The method of claim 1 where the progenitor nucleic acid sequences are comprised of genomic nucleic acid sequences.]

[4. The method of claim 1, where the progeny library is comprised of at least $10^{10}$ different pre-determined progeny molecular sequences.]

[5. The method of claim 1, where the progeny library is comprised of at least $10^{15}$ different pre-determined progeny molecular sequences.]

[6. The method of any of claims 1-5, where the nucleic acid building block sequences are obtained from polynucleotide sequences that encode enzymes or fragments thereof.]

[7. The method of any of claims 1-5, where the nucleic acid building block sequences are assembled to produce polynucleotide encoding biochemical pathways from one or more operons or gene clusters of portions thereof.]

[8. The method of any of claims 1-5, where the nucleic acid building block sequences are obtained from polynucleotide encoding polyketides or fragments thereof.]

[9. The method of any of claims 1-5, where the nucleic acid building block sequences are obtained from polynucleotide encoding antibodies or antibody fragments or other peptides or polypeptides.]

[10. The method of any of claims 1-5, where the step of (b) non-stochastically assembling said nucleic acid building blocks is performed to generate a display library comprised of polypeptides or antibodies or peptidomimetic antibodies or antibody variable region sequences suitable for affinity interaction screening.]

[11. The method of any of claims 1-5, further comprising the step of (c) screening said progeny library to identify an evolved molecular property.]

[12. The method of claim 1, where step of (c) is comprised of expression screening to identify an evolved molecular property.]

*13. A method of producing a progeny library comprised of chimerized but pre-determined polynucleotide sequences each of which is comprised of a pre-determined number of building block sequences that are assembled in non-random order, the method comprising: (a) generating a plurality of pre-determined nucleic acid building block sequences comprised of sequences delineated by demarcation points selected to create nucleic acid building blocks of a pre-determined size from aligned progenitor nucleic acid sequences, wherein each of said plurality of pre-determined nucleic acid building blocks is a double stranded building block with two nucleotide overhangs generated by a method comprising the steps of (i) generating overlapping blunt-ended amplification products; (ii) melting the blunt-ended amplification products to produce single stranded nucleic acids; (iii) annealing the single stranded nucleic acids to produce a population of double stranded nucleic acids; and (iv) selecting for double stranded nucleic acids with two nucleotide overhangs; wherein selecting for double stranded nucleic acids with two nucleotide overhangs comprises degrading other nucleic acids in the population with a 3' acting nuclease; and (b) non-stochastically assembling said nucleic acid building block sequences to produce said chimerized but pre-determined polynucleotide sequences, such that a designed overall assembly order is achieved for each of said chimerized but pre-determined polynucleotide sequence.*

*14. The method of claim 13 where the progenitor nucleic acid sequences comprise sequences derived from an uncultivated organism or an environmental sample.*

*15. The method of claim 13 where the progenitor nucleic acid sequences are comprised of genomic nucleic acid sequences.*

*16. The method of claim 13, where the progeny library is comprised of at least $10^{10}$ different pre-determined progeny molecular sequences.*

*17. The method of claim 13, where the progeny library is comprised of at least $10^{15}$ different pre-determined progeny molecular sequences.*

*18. The method of any of claims 13 to 17, where the nucleic acid building block sequences are obtained from polynucleotide sequences that encode enzymes or fragments thereof.*

*19. The method of any of claims 13 to 17, where the nucleic acid building block sequences are assembled to produce polynucleotide encoding biochemical pathways from one or more operons or gene clusters of portions thereof.*

*20. The method of any of claims 13 to 17, where the nucleic acid building block sequences are obtained from polynucleotide encoding polyketides or fragments thereof.*

*21. The method of any of claims 13 to 17, where the nucleic acid building block sequences are obtained from polynucleotide encoding antibodies or antibody fragments or other peptides or polypeptides.*

*22. The method of any of claims 13 to 17, where the step of (b) non-stochastically assembling said nucleic acid building blocks is performed to generate a display library comprised of polypeptides or antibodies or peptidomimetic antibodies or antibody variable region sequences suitable for affinity interaction screening.*

*23. The method of any of claims 13 to 17, further comprising the step of (c) screening said progeny library to identify an evolved molecular property.*

*24. The method of claim 13, where step of (c) is comprised of expression screening to identify an evolved molecular property.*

*25. The method of claim 13, wherein the 3' acting nuclease is exonuclease III.*

* * * * *